US012201631B2

(12) United States Patent
Orefice et al.

(10) Patent No.: US 12,201,631 B2
(45) Date of Patent: Jan. 21, 2025

(54) METHODS AND COMPOSITIONS FOR REDUCING TACTILE DYSFUNCTION AND ANXIETY ASSOCIATED WITH AUTISM SPECTRUM DISORDER, RETT SYNDROME, AND FRAGILE X SYNDROME

(71) Applicant: President and Fellows of Harvard College, Cambridge, MA (US)

(72) Inventors: Lauren L. Orefice, Cambridge, MA (US); David D. Ginty, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 105 days.

(21) Appl. No.: 17/845,961

(22) Filed: Jun. 21, 2022

(65) Prior Publication Data

US 2023/0031479 A1   Feb. 2, 2023

Related U.S. Application Data

(63) Continuation of application No. 16/308,422, filed as application No. PCT/US2017/036621 on Jun. 8, 2017, now Pat. No. 11,547,706.

(60) Provisional application No. 62/421,807, filed on Nov. 14, 2016, provisional application No. 62/347,260, filed on Jun. 8, 2016.

(51) Int. Cl.
*A61K 31/495* (2006.01)
*A61K 31/196* (2006.01)
*A61K 31/36* (2006.01)
*A61K 31/4196* (2006.01)
*A61K 31/437* (2006.01)
*A61K 31/4465* (2006.01)
*A61K 31/4535* (2006.01)
*A61P 25/00* (2006.01)
*C12N 15/86* (2006.01)
*A61K 9/00* (2006.01)
*A61K 45/06* (2006.01)

(52) U.S. Cl.
CPC .......... *A61K 31/495* (2013.01); *A61K 31/196* (2013.01); *A61K 31/36* (2013.01); *A61K 31/4196* (2013.01); *A61K 31/437* (2013.01); *A61K 31/4465* (2013.01); *A61K 31/4535* (2013.01); *A61P 25/00* (2018.01); *C12N 15/86* (2013.01); *A61K 9/0019* (2013.01); *A61K 45/06* (2013.01)

(58) Field of Classification Search
CPC .................................................. A61K 31/495
See application file for complete search history.

(56) References Cited

U.S. PATENT DOCUMENTS

| | | |
|---|---|---|
| 3,243,427 A | 3/1966 | Recder et al. |
| 3,516,988 A | 6/1970 | Schmitt |
| 3,862,149 A | 1/1975 | Cortel et al. |
| 4,065,451 A | 12/1977 | McCaully et al. |
| 4,122,265 A | 10/1978 | Jaunin |
| 4,382,938 A | 5/1983 | Kaplan et al. |
| 4,460,592 A | 7/1984 | Kaplan et al. |
| 4,492,695 A | 1/1985 | Kaplan et al. |
| 4,820,834 A | 4/1989 | Evans et al. |
| 4,879,293 A | 11/1989 | Hiraga et al. |
| 5,618,824 A | 4/1997 | Schmidt et al. |
| 5,776,930 A | 7/1998 | Lynch, Jr. et al. |
| 5,786,357 A | 7/1998 | Young et al. |
| 6,927,290 B2 | 8/2005 | Miki et al. |
| 7,456,173 B2 | 11/2008 | Jerussi et al. |
| 8,980,887 B2 | 3/2015 | Yang et al. |
| 9,586,890 B2 | 3/2017 | Statsyuk et al. |
| 11,434,244 B2 | 9/2022 | Ginty et al. |
| 11,547,706 B2 | 1/2023 | Orefice et al. |
| 12,077,512 B2 | 9/2024 | Ginty et al. |
| 12,084,451 B2 | 9/2024 | Ginty et al. |
| 2006/0084806 A1 | 4/2006 | Sridharan et al. |
| 2007/0015810 A1 | 1/2007 | Cuberes |
| 2008/0312279 A1* | 12/2008 | Warren ............... A61K 31/4462 514/315 |
| 2010/0150944 A1 | 6/2010 | Hilbush et al. |

(Continued)

FOREIGN PATENT DOCUMENTS

| | | |
|---|---|---|
| CN | 103933036 A | 7/2014 |
| EP | 0167919 A2 | 1/1986 |

(Continued)

OTHER PUBLICATIONS

More GABA for Autism and Epilepsy? Not so Simple, Epiphany, An Alternative Reality for Classic Autism—Based on Today's Science, Wednesday Dec. 23, 2015, available at https://www.epiphanyasd.com/2015/12/more-gaba-for-autism-and-epilepsy-not.html.*
Braat et al., Neuron 86, Jun. 3, 2015, 1119-1130.*
Cascio et al., Somatosensory processing in neurodevelopmental disorders, J. Neurodevelop. Disord. (2010) 2:62-69.*
Orefice et al., Peripheral Mechanosensory Neuron Dysfunction Underlies Tactile and Behavioral Deficits in Mouse Models of ASDs, Cell, Jul. 14, 2016;166(2):299-313.*
Drasbek et al., THIP, a hypnotic and antinociceptive drug, enhances an extrasynaptic GABAA receptor-mediated conductance in mouse neocortex. Cereb Cortex. Aug. 2006;16(8):1134-41. doi: 10.1093/cercor/bhj055. Epub Oct. 12, 2005.

(Continued)

*Primary Examiner* — Svetlana M Ivanova
(74) *Attorney, Agent, or Firm* — Wolf, Greenfield & Sacks, P.C.

(57) ABSTRACT

The present invention features a method of reducing tactile dysfunction or anxiety in a subject diagnosed with Autism Spectrum Disorder, Rett Syndrome, or Fragile X syndrome by administering a $GABA_A$ agent having reduced blood brain barrier or by expressing a nucleic acid encoding an exogenous alpha or beta subunit of a $GABA_A$ receptor in dorsal root ganglion neurons in the subject using a vector.

13 Claims, 72 Drawing Sheets

Specification includes a Sequence Listing.

(56) References Cited

U.S. PATENT DOCUMENTS

| | | | |
|---|---|---|---|
| 2011/0046090 A1* | 2/2011 | Barlow | A61K 31/137 514/91 |
| 2012/0095217 A1 | 4/2012 | Ritter et al. | |
| 2014/0066504 A1 | 3/2014 | Hochman | |
| 2015/0051151 A1 | 2/2015 | Eisenbach-Schwartz et al. | |
| 2015/0203486 A1 | 7/2015 | Bently et al. | |
| 2015/0313913 A1 | 11/2015 | Catterall et al. | |
| 2016/0193169 A1 | 7/2016 | Hoffman | |
| 2017/0197967 A1 | 7/2017 | Pasricha et al. | |
| 2020/0179374 A1 | 6/2020 | Orefice et al. | |
| 2021/0128508 A1 | 5/2021 | Hoffman et al. | |
| 2021/0206714 A1 | 7/2021 | Ginty et al. | |
| 2021/0206771 A1 | 7/2021 | Ginty et al. | |
| 2022/0162173 A1 | 5/2022 | Ginty et al. | |
| 2022/0233133 A1 | 7/2022 | Ginty et al. | |
| 2023/0051850 A1 | 2/2023 | Ginty et al. | |

FOREIGN PATENT DOCUMENTS

| | | | |
|---|---|---|---|
| WO | WO 1996/031210 A1 | 4/1996 | |
| WO | WO 97/49690 A1 | 12/1997 | |
| WO | WO 1999/051594 A1 | 10/1999 | |
| WO | WO 2002/028831 A1 | 4/2002 | |
| WO | WO 03/051274 A2 | 6/2003 | |
| WO | WO 2004/106310 A1 | 12/2004 | |
| WO | WO 2008/003044 A2 | 1/2008 | |
| WO | WO 2008/022396 A1 | 2/2008 | |
| WO | WO 2010/017047 A1 | 2/2010 | |
| WO | WO 2013/154712 A1 | 10/2013 | |
| WO | WO 2014/100438 A1 | 6/2014 | |
| WO | WO-2014123909 A1 * | 8/2014 | A61K 31/4355 |
| WO | WO 2014/138791 A1 | 9/2014 | |
| WO | WO 2015/013715 A2 | 1/2015 | |
| WO | WO 2015/052076 A1 | 4/2015 | |
| WO | WO 2017/214442 A1 | 12/2017 | |
| WO | WO 2018/114663 A1 | 6/2018 | |
| WO | WO 2019/103658 A2 | 5/2019 | |
| WO | WO 2020/237043 A1 | 11/2020 | |

OTHER PUBLICATIONS

Hoehn-Saric, Effects of THIP on chronic anxiety. Psychopharmacology (Berl). 1983;80(4):338-41. doi: 10.1007/BF00432116.
Olmos-Serrano et al., The GABA(A) receptor agonist THIP ameliorates specific behavioral deficits in the mouse model of fragile X syndrome. Dev Neurosci. 2011;33(5):395-403. doi: 10.1159/000332884. Epub Nov. 8, 2011.
Pardridge, Drug transport across the blood-brain barrier. J Cereb Blood Flow Metab. Nov. 2012;32(11):1959-72. doi: 10.1038/jcbfm.2012.126. Epub Aug. 29, 2012.
Paulson et al., Blood-brain barrier transfer and cerebral uptake of antiepileptic drugs. Clin Pharmacol Ther. Oct. 1982;32(4):466-77. doi: 10.1038/clpt.1982.190.
Extended European Search Report for Application No. 20779891.9, mailed Nov. 21, 2022.
Extended European Search Report for Application No. 20810565.0, mailed Jun. 29, 2023.
Boitano et al., Structure activity studies of a novel cytotoxic benzodiazepine. Bioorg Med Chem Lett. Oct. 6, 2003;13(19):3327-30. doi: 10.1016/s0960-894x(03)00683-8.
No Author Listed, Pubchem CID 3393. Flurazepam compound summary. Entered Mar. 25, 2005. 81 pages.
No Author Listed, Caplus Chemical Abstracts Service for U.S. Pat. No. 9,586,890. 2017. 3 pages.
Ogata et al., 5-Aryl-1,5-dihydro-2H-1,4-benzodiazepin-2-one derivatives as antianxiety agents. J Med Chem. Jun. 1977;20(6):776-81. doi: 10.1021/jm00216a008.
Pavlovsky et al., Synthesis and anticonvulsant activity of 3-alkoxy-1,2-dihydro-3H-1,4-benzodiazepin-2-ones. Pharmaceutical Chemistry Journal. 2012; 46(9): 540-545. DOI: 10.1007/s11094-012-0842-9.

Roland et al., Quinazolines et benzodiazépines-1,4. LX1) Imidazo[5,1-c]benzodiazépines-1,4. 1973; 56(7):2569-2583. Helvetica Chimica Acta. Retrieved from the Internet: URL: https://api.wiley.com/onlinelibrary/tdm/v1/articles/10.1002%2Fhlca.19730560742>.
Waszczak et al., GABAergic actions of THIP in vivo and vitro: a comparison with muscimol and GABA. Eur J Pharmacol. Jul. 11, 1980;65(1):21-9. doi: 10.1016/0014-2999(80)90204-6.
Partial Supplementary European Search Report, mailed Jan. 24, 2020, in connection with Application No. EP 17811036.7.
European Search Report, mailed Jun. 24, 2020, in connection with Application No. EP 17811036.7.
Invitation to Pay Additional Fees, mailed Sep. 11, 2017, in connection with Application No. PCT/US2017/036621.
International Search Report and Written Opinion, mailed Nov. 9, 2017, in connection with Application No. Application No. PCT/US2017/036621.
International Preliminary Report on Patentability, mailed Oct. 29, 2018, in connection with Application No. PCT/US2017/036621.
Extended European Search Report for Application No. 19806972.6, mailed Feb. 9, 2022.
International Search Report and Written Opinion, mailed Jul. 25, 2019, in connection with Application No. PCT/US2019/033581.
International Preliminary Report on Patentability, mailed Dec. 3, 2020, in connection with Application No. PCT/US2019/033581.
Partial European Search Report, mailed Sep. 16, 2021, in connection with Application No. 19810786.4.
Extended European Search Report, mailed Dec. 20, 2021, in connection with Application No. 19810786.4.
Invitation to Pay Additional Fees, mailed Jul. 19, 2019, in connection with Application No. PCT/US2019/034390.
International Search Report and Written Opinion, mailed Sep. 19, 2019, in connection with Application No. PCT/US2019/034390.
International Preliminary Report on Patentability, mailed Dec. 10, 2020, in connection with Application No. PCT/US2019/034390.
Invitation to Pay Additional Fees, mailed Jun. 4, 2020, in connection with Application No. PCT/US2020/024564.
International Search Report aand Written Opinion, mailed Jul. 28, 2020, in connection with Application No. PCT/US2020/024564.
International Preliminary Report on Patentability, mailed Oct. 7, 2021, in connection with Application No. PCT/US2020/024564.
International Search Report aand Written Opinion, mailed Aug. 17, 2020, in connection with Application No. PCT/US2020/033984.
International Preliminary Report on Patentability, mailed Dec. 2, 2021, in connection with Application No. PCT/US2020/033984.
[No Author Listed] Caplus Registry No. 1616667-55-0. Carbamic acid, N,N-diethyl-, 6-(5-chloro-2-pyridinyl)-6,7-dihydro-7-oxo-5H-pyrrolo[3,4-b]pyrazin-5-yl ester entered STN: Jul. 23, 2014.
[No Author Listed] Caplus Registry No. 952499-50-2. [1,2-a]pyridine-3-acetamide, 6,8-dichloro-2-(4-chlorophenyl)-N-[2-[(7-nitro-2,1,3-benzoxadiazol-4-yl)amino]ethyl]-N-(phenylmethyl)- Entered STN: Nov. 6, 2007.
[No Author Listed] Caplus Registry No. 952499-71-7. Carbamic acid, N-[2-[[2-[6,8-dichloro-2-(4-chlorophenyl)imidazo[1,2-a]pyridin-3-yl]acetyl](phenylmethyl)amino]ethyl]-, 1,1-dimethylethyl ester. Entered STN: Nov. 6, 2007.
[No Author Listed] Caplus Registry No. 952499-78-4. 1,2-a]pyridine-3-acetamide, N-(2-aminoethyl)-6,8-dichloro-2-(4-chlorophenyl)-N-(phenylmethyl). Entered STN: Nov. 6, 2007.
[No Author Listed] PubChem. 4-Methyl-1-{[2-(4-chlorophenyl)-imidazo[1,2-a]pyridin-3-yl]-methylcarbonyl}-piperazine. Accessed Jul. 11, 2019; created Feb. 8, 2017; modified Jul. 10, 2019. https://pubchem.ncbi.nlm.nih.gov/compound/13068199. 7 pages.
[No Author Listed] PubChem. Compound Summary for SID 319566201. Available Date Dec. 8, 2016; [Retrieved on Jul. 2, 2019]. Retrieved from the internet. https://pubchem.ncbi.nlm.nih.gov/substance/319566201.
[No Author Listed] Pubmed-CID: 13068199. Create Date: Feb. 8, 2007. pp. 1-7.
[No Author Listed] Pubmed-CID: 19842214. Create Date: Dec. 5, 2007. pp. 1-7.
[No Author Listed] Pubmed-CID: 4506. Create Date: Mar. 25, 2005. pp. 1-47.

(56) References Cited

OTHER PUBLICATIONS

[No Author Listed] Pubmed-CID: 614001. Create Date: Mar. 27, 2005. pp. 1-11.
[No Author Listed], Cas RN: 2098817-47-9. 2017. 3 pages.
Abrahams et al., Advances in autism genetics: on the threshold of a new neurobiology. Nat Rev Genet. May 2008;9(5):341-55. doi: 10.1038/nrg2346.
Agudo et al., Achieving regio- and enantioselectivity of P450-catalyzed oxidative CH activation of small functionalized molecules by structure-guided directed evolution. Chembiochem. Jul. 9, 2012;13(10):1465-73. doi: 10.1002/cbic.201200244. Epub Jun. 18, 2012.
Akyol et al., Generating somatic mosaicism with a Cre recombinase-microsatellite sequence transgene. Nat Methods. Mar. 2008;5(3):231-3.
Amaral et al., The amygdala and autism: implications from non-human primate studies. Genes Brain Behav. Oct. 2003;2(5):295-302.
Amaral, The amygdala, social behavior, and danger detection. Ann N Y Acad Sci. Dec. 2003;1000(1):337-47.
Anagnostou et al., Intranasal oxytocin versus placebo in the treatment of adults with autism spectrum disorders: a randomized controlled trial. Mol Autism. Dec. 2012;3(1):16.
Antoine et al., Increased Excitation-Inhibition Ratio Stabilizes Synapse and Circuit Excitability in Four Autism Mouse Models. Neuron. Feb. 20, 2019;101(4):648-61.
Bader et al., Neurophysiological findings in the Rett syndrome, I: Emg, conduction velocity, EEG and somatosensory-evoked potential studies. Brain Dev. Jan. 1, 1989;11(2):102-9.
Baio et al., Prevalence of Autism Spectrum Disorder Among Children Aged 8 Years—Autism and Developmental Disabilities Monitoring Network, 11 Sites, United States, 2014. MMWR Surveill Summ. Apr. 27, 2018; 67(6): 1-23.
Banerjee et al., Impairment of cortical GABAergic synaptic transmission in an environmental rat model of autism. Int J Neuropsychopharmacol. Jul. 2013;16(6):1309-18. doi: 10.1017/S1461145712001216. Epub Dec. 11, 2012.
Berge et al., Pharmaceutical salts. J Pharm Sci. Jan. 1977;66(1):1-19.
Bhattacherjee et al., Neuronal cytoskeletal gene dysregulation and mechanical hypersensitivity in a rat model of Rett syndrome. Proceedings of the National Academy of Sciences. Aug. 15, 2017; 114(33): E6952-E6961.
Bowery et al., Isoguvacine, isonipecotic acid, muscimol and N-methyl isoguvacine on the GABA receptor in rat sympathetic ganglia. Experientia. Sep. 15, 1978;34(9):1193-5. doi: 10.1007/BF01922953.
Bowery et al., Characteristics of GABAB receptor binding sites on rat whole brain synaptic membranes. Br J Pharmacol. Jan. 1983; 78(1): 191-206.
Boyle et al., The behavioral phenotype of FMR1 mutations. Am J Med Genet C Semin Med Genet. Nov. 15, 2010; 154(4): 469-76.
Braat et al., The GABAA Receptor as a Therapeutic Target for Neurodevelopmental Disorders. Neuron. Jun. 3, 2015;86(5):1119-30.
Braff et al., Human studies of prepulse inhibition of startle: normal subjects, patient groups, and pharmacological studies. Psychopharmacology (Berl.). Jul. 2001;156(2-3):234-58. doi: 10.1007/s002130100810.
Brandt et al., Impaired peripheral somatosensory function in children with Prader-Willi syndrome. Neuropediatrics. Jun. 1998; 29(30): 124-6.
Carlton et al., Peripheral GABA(A) receptors: evidence for peripheral primary afferent depolarization. Neuroscience. Jul. 1, 1999; 93(2): 713-22.
Cascio et al., Tactile Perception in Adults with Autism: a Multidimensional Psychophysical Study. J Autism Dev Disord. Jan. 2008;38(1):127-37. doi: 10.1007/s10803-007-0370-8. Epub Apr. 6, 2007.
Cascio, Somatosensory processing in neurodevelopmental disorders. J Neurodev Disord. Jun. 2010;2(2):62-9.
Cellot et al., GABAergic signaling as therapeutic target for autism spectrum disorders. Front Pediatr. Jul. 8, 2014;2:70.
Chen et al., Presynaptic GABAergic inhibition regulated by BDNF contributes to neuropathic pain induction. Nature communications. Oct. 30, 2014; 5: 5331.
Cheng et al., Relationship between the inhibition constant (KI) and the concentration of inhibitor which causes 50 per cent inhibition (I50) of an enzymatic reaction. Biochem. Pharmacol. Dec. 1973; 22(23):3099-3108.
Choi et al., The maternal interleukin-17a pathway in mice promotes autism-like phenotypes in offspring. Science. Feb. 26, 2016; 351(6276): 933-9.
Coury et al., Use of psychotropic medication in children and adolescents with autism spectrum disorders. Pediatrics. Nov. 1, 2012; 130(Suppl 2): S69-76.
Crozier et al.,MrgD activation inhibits KCNQ/M-currents and contributes to enhanced neuronal excitability. The Journal of neuroscience : the official journal of the Society for Neuroscience. Apr. 18, 2007; 27(16): 4492-6.
Dalai et al., Exploring selectivity requirements for peripheral versus central benzodiazepine receptor binding affinity: QSAR modeling of 2-phenylimidazo[1,2-a]pyridine acetamides using topological and physicochemical descriptors. Indian J Biochem Biophys. Apr. 2006;43(2):105-18.
Dawes et al., Immune or Genetic-Mediated Disruption of CASPR2 Causes Pain Hypersensitivity Due to Enhanced Primary Afferent Excitability. Neuron. Feb. 21, 2018; 97(4):806-22.
Denora et al., 2-Phenyl-imidazo[1,2-a]pyridine compounds containing hydrophilic groups as potent and selective ligands for peripheral benzodiazepine receptors: synthesis, binding affinity and electrophysiological studies. J Med Chem. Nov. 13, 2008;51(21):6876-88. doi: 10.1021/jm8006728. Epub Oct. 4, 2008.
Dorrn et al.,Developmental sensory experience balances cortical excitation and inhibition. Nature. Jun. 2010; 465(7300): 932-6.
Downs et al., Linking MECP2 and pain sensitivity: the example of Rett syndrome. Am J Med Genet A. May 2010; 152(5): 1197-205.
Du et al., Local GABAergic signaling within sensory ganglia controls peripheral nociceptive transmission. J Clin Invest. May 1, 2017; 127(5): 1741-56.
Enna et al., The role of GABA in the mediation and perception of pain. Adv Pharmacol. Jan. 1, 2006; 54: 1-27.
Erickson et al.,STX209 (arbaclofen) for autism spectrum disorders: an 8-week open-label study. J Autism Dev Disord. Apr. 1, 2014; 44(4): 958-64.
Fier et al., Synthesis and late-stage functionalization of complex molecules through C-H fluorination and nucleophilic aromatic substitution. J Am Chem Soc. Jul. 16, 2014;136(28):10139-47. doi: 10.1021/ja5049303. Epub Jul. 1, 2014.
Filice et al. Reduction in parvalbumin expression not loss of the parvalbumin-expressing GABA interneuron subpopulation in genetic parvalbumin and shank mouse models of autism. Mol Brain. Dec. 2016; 9: 10.
Flegel et al., RNA-Seq Analysis of Human Trigeminal and Dorsal Root Ganglia with a Focus on Chemoreceptors. PLoS One. Jun. 12, 2015; 10(6): e0128951.
Fukuda et al.,Delayed maturation of neuronal architecture and synaptogenesis in cerebral cortex of Mecp2-deficient mice. J Neuropathol Exp Neurol. Jun. 1, 2005; 64(6): 537-44.
Gebhardt et al., Maturation of prepulse inhibition (PPI) in childhood: Maturation of PPI in childhood. Psychophysiology. Apr. 2012;49(4):484-8. doi: 10.1111/j.1469-8986.2011.01323.x. Epub Dec. 16, 2011.
Golombok et al.,Cognitive impairment in long-term benzodiazepine users. Psychol Med. May 1988; 18(2): 365-74.
Groeneveld et al., Measuring blood-brain barrier penetration using the NeuroCart, a CNS test battery. Drug Discov Today Technol. Jun. 1, 2016; 20: 27-34.
Guastella et al. The effects of a course of intranasal oxytocin on social behaviors in youth diagnosed with autism spectrum disorders: a randomized controlled trial. J Child Psychol Psychiatry. Apr. 2015; 56(4): 444-52.

(56) References Cited

OTHER PUBLICATIONS

Gudex, Adverse effects of benzodiazepines. Soc Sci Med. Jan. 1, 1991; 33(5): 587-96.
Guetzoyan et al., Flow chemistry synthesis of zolpidem, alpidem and other GABA agonists and their iological evaluation through the use of in-line frontal affinity chromatography. Chemical Science. 2013; 4(2): 764-69.
Gupta et al., Quantitative structure-activity relationship studies on some nonbenzodiazepine series of compounds acting at the benzodiazepine receptor. Bioorg Med Chem. Nov. 1998;6(11):2213-8. doi: 10.1016/s0968-0896(98)00169-2.
Guy et al., A mouse Mecp2-null mutation causes neurological symptoms that mimic Rett syndrome. Nat Genet. Mar. 2001;27(3):322-6.
Haas et al., Peripheral nerve findings in Rett syndrome. J Child Neurol. Jan. 1988; 3(1_Suppl): S25-30.
Hadjikhani et al., Bumetanide for autism: more eye contact, less amygdala activation. Sci Rep. Feb. 26, 2018; 8(1): 3602.
Hagerman et al., Neuropathy as a presenting feature in fragile X-associated tremor/ataxia syndrome. Am J Med Genet A. Oct. 1, 2007; 143(19): 2256-60.
Han et al. SHANK3 Deficiency Impairs Heat Hyperalgesia and TRPV1 Signaling in Primary Sensory Neurons. Neuron. Dec. 21, 2016; 92(6): 1279-93.
Hanack et al., GABA blocks pathological but not acute TRPV1 pain signals. Cell. Feb. 12, 2015; 160(4): 759-770.
Hanson et al., Structural requirements for eszopiclone and zolpidem binding to the gamma-aminobutyric acid type-A (GABAA) receptor are different. J Med Chem. Nov. 27, 2008;51(22):7243-52. doi: 10.1021/jm800889m.
Hasegawa et al., Analyzing somatosensory axon projections with the sensory neuron-specific Advillin gene. The Journal of neuroscience : the official journal of the Society for Neuroscience. Dec. 26, 2007; 27(52): 14404-14.
Hashemi et al., The Number of Parvalbumin-Expressing Interneurons Is Decreased in the Medial Prefrontal Cortex in Autism. Cereb Cortex. Mar. 1, 2017; 27(3): 1931-43.
He et al.,Critical period inhibition of NKCC1 rectifies synapse plasticity in the somatosensory cortex and restores adult tactile response maps in fragile X mice. Mol Psychiatry. Nov. 2019; 24(11):1732-47.
Hill et al.,3H-baclofen and 3H-GABA bind to bicuculline-insensitive GABA B sites in rat brain. Nature. Mar. 1981; 290(5802): 149-152.
Howes et al., Autism spectrum disorder: Consensus guidelines on assessment, treatment and research from the British Association for Psychopharmacology. J Psychopharmacol. Jan. 2018; 32(1): 3-29.
Hubel et al., The period of susceptibility to the physiological effects of unilateral eye closure in kittens. The Journal of physiology. Feb. 1, 1970; 206(2): 419-36.
Janak et al.,From circuits to behaviour in the amygdala. Nature. Jan. 2015; 517(7534): 284-92.
Jaramillo et al., Novel Shank3 mutant exhibits behaviors with face validity for autism and altered striatal and hippocampal function. Autism Res. Jan. 2017; 10(1): 42-65.
Jellinger et al.,Neuropathology of Rett syndrome. Acta Neuropathol. Mar. 1, 1988; 76(2): 142-58.
Jevtovic-Todorovic et al., Early exposure to common anesthetic agents causes widespread neurodegeneration in the developing rat brain and persistent learning deficits. The Journal of neuroscience: the official journal of the Society for Neuroscience. Feb. 1, 2003; 23(3): 876-82.
Jiao et al. A key mechanism underlying sensory experience-dependent maturation of neocortical GABAergic circuits in vivo. Proceedings of the National Academy of Sciences. Jul. 19, 2011; 108(29): 12131-6.
Kanner, Autistic disturbances of affective contact. Nerv Child. 1943; 2: 217-250.
Khalfa et al., Peripheral auditory asymmetry in infantile autism. Eur J Neurosci. Feb. 2001; 13(3): 628-32.

King et al.,Lack of efficacy of citalopram in children with autism spectrum disorders and high levels of repetitive behavior: citalopram ineffective in children with autism. Arch Gen Psychiatry. Jun. 1, 2009; 66(6): 583-90.
Kodish et al., Pharmacotherapy for anxiety disorders in children and adolescents. Dialogues in clinical neuroscience. Dec. 2011; 13(4): 439-452.
Kohl et al., Prepulse Inhibition of the Acoustic Startle Reflex in High Functioning Autism. PLoS One. Mar. 18, 2014;9(3):e92372. doi: 10.1371/journal.pone.0092372. eCollection 2014.
Konig et al., Integrator or coincidence detector? The role of the cortical neuron revisited. Trends Neurosci. Apr. 1, 1996; 19(4): 130-7.
Krishnan et al., MeCP2 regulates the timing of critical period plasticity that shapes functional connectivity in primary visual cortex. Proceedings of the National Academy of Sciences. Aug. 25, 2015; 112(34): E4782-91.
Krogsgaard-Larsen et al., A new class of GABA agonist. Nature. 1977; 268: 53-55.
Krogsgaard-Larsen et al., Structure-activity studies on the inhibition of GABA binding to rat brain membranes by muscimol and related compounds. J Neurochem. Jun. 1978; 30(6): 1377-82.
Krogsgaard-Larsen et al., THIP, isoguvacine, isoguvacine oxide, and related GABA agonists. Adv Biochem Psychopharmacol. 1981; 29: 69-76.
Kuznetsov et al., Synthesis of cyclic |1-5,7 amino alcohols with cholinolytic properties. Zhurnal Obshchei Khimii [Russian Journal Of Organic Chemistry]. Jan. 1, 1959; 29: 2421-2428.
Laquintana et al., N-Benzyl-2-(6,8-dichloro-2-(4-chlorophenyl)imidazo[1,2-a]pyridin-3-yl)-N-(6-(7-nitrobenzo[c][1,2,5]oxadiazol-4-ylamino)hexyl)acetamide as a New Fluorescent Probe for Peripheral Benzodiazepine Receptor and Microglial Cell Visualization†. Bioconjugate Chem. 2007;18(5):1397-1407.
Lau et al., Temporal control of gene deletion in sensory ganglia using a tamoxifen-inducible Advillin-Cre-ERT2 recombinase mouse. Mol Pain. Dec. 21, 2011; 7: 1744-8069.
Lemonnier et al., Effects of bumetanide on neurobehavioral function in children and adolescents with autism spectrum disorders. Transl Psychiatry. Mar. 2017; 7(3): e1056.
Levy et al., The effect of the GABA antagonists bicuculline and picrotoxin on primary afferent terminal excitability. Brain research. Aug. 11, 1972; 43(1): 171-80.
Lopez-Mendoza et al., Visible light/Ir(III) photocatalytic initiation of xanthate-based radical-chain reactions: Xanthate group transfer and oxidative addition to aromatic systems. Tetrahedron. Apr. 2018; 74(38):5494-5502.
Lozano et al., Modulation of the GABAergic pathway for the treatment of fragile X syndrome. Neuropsychiatr Dis Treat. Sep. 16, 2014;10:1769-79. doi: 10.2147/NDT.S42919. eCollection 2014.
Lyst et al., Rett syndrome mutations abolish the interaction of MeCP2 with the NCoR/SMRT co-repressor. Nature neuroscience. Jul. 2013; 16(7): 898-902.
Maddox et al., The Accuracy of the ADOS-2 in Identifying Autism among Adults with Complex Psychiatric Conditions. J Autism Dev Disord. Sep. 2017;47(9):2703-2709. doi: 10.1007/s10803-017-3188-z.
Madsen et al., Increased Prepulse Inhibition and Sensitization of the Startle Reflex in Autistic Children: Sensorimotor gating in autistic children. Autism Res. Feb. 2014;7(1):94-103. doi: 10.1002/aur.1337. Epub Oct. 4, 2013.
Mammen et al., Infant Avoidance during a Tactile Task Predicts Autism Spectrum Behaviors in Toddlerhood. Infant Ment Health J. Nov. 2015; 36(6): 575-87.
Marin, Interneuron dysfunction in psychiatric disorders. Nat Rev Neurosci. Feb. 2012; 13(2): 107-120.
Mazurek et al., Anxiety, sensory over-responsivity, and gastrointestinal problems in children with autism spectrum disorders. J Abnorm Child Psychol. Jan. 1, 2013; 41(1): 165-76.
Mei et al., Adult restoration of Shank3 expression rescues selective autistic-like phenotypes. Nature. Feb. 2016; 530(7591): 481-4.
Nadeau et al., Treatment of comorbid anxiety and autism spectrum disorders. Neuropsychiatry. Dec. 2011;1(6):567-78.

(56) References Cited

OTHER PUBLICATIONS

Nelson et al., Excitatory/Inhibitory Balance and Circuit Homeostasis in Autism Spectrum Disorders. Neuron. Aug. 19, 2015; 87(4): 684-98.
No Author Listed, Annex to ESOP (EP19810786). Jan. 1, 2021. 84 pages.
Obradovic et al., Silencing the alpha2 subunit of gamma-aminobutyric acid type A receptors in rat dorsal root ganglia reveals its major role in antinociception posttraumatic nerve injury. Anesthesiology. Sep. 1, 2015; 123(3): 654-67.
Oginsky et al., Hyperexcitability of Mesencephalic Trigeminal Neurons and Reorganization of Ion Channel Expression in a Rett Syndrome Model. J Cell Physiol. May 2017; 232(5): 1151-64.
Orefice et al., Targeting Peripheral Somatosensory Neurons to Improve Tactile-Related Phenotypes in ASD Models. Cell. Aug. 8, 2019;178(4):867-886.e24. doi: 10.1016/j.cell.2019.07.024.
Orefice, Peripheral Somatosensory Neuron Dysfunction: Emerging Roles in Autism Spectrum Disorders. Neuroscience. Oct. 1, 2020;445:120-129. doi: 10.1016/j.neuroscience.2020.01.039. Epub Feb. 6, 2020.
Page et al.,GABA(B) receptors inhibit mechanosensitivity of primary afferent endings. The Journal of neuroscience : the official journal of the Society for Neuroscience. Oct. 1, 1999; 19(19): 8597-8602.
Pajouhesh et al., Medicinal chemical properties of successful central nervous system drugs. NeuroRx. Oct. 1, 2005; 2(4): 541-553.
Peca et al., Shank3 mutant mice display autistic-like behaviours and striatal dysfunction. Nature. Apr. 2011; 472(7344): 437-442.
Peixoto et al., Early hyperactivity and precocious maturation of corticostriatal circuits in Shank3B(−/−) mice. Nature neuroscience. May 2016; 19(5): 716-24.
Perche et al., Early Retinal Defects in Fmr1(−/y) Mice: Toward a Critical Role of Visual Dys-Sensitivity in the Fragile X Syndrome Phenotype? Front Cell Neurosci. Apr. 6, 2018; 12: 96.
Phelan et al., The 22q13.3 Deletion Syndrome (Phelan-McDermid Syndrome). Mol Syndromol. 2011; 2(3-5): 186-201.
Price et al., Fragile X mental retardation protein (FMRP) and the spinal sensory system. Results Probl Cell Differ. 2012; 54, 41-59.
Ray et al., Comparative transcriptome profiling of the human and mouse dorsal root ganglia: an RNA-seq-based resource for pain and sensory neuroscience research. Pain. Jul. 2018; 159(7): 1325-1345.
Romermann et al., Multiple blood-brain barrier transport mechanisms limit bumetanide accumulation, and therapeutic potential, in the mammalian brain. Neuropharmacology. May 1, 2017; 117: 182-94.
Roy et al., QSAR modeling of peripheral versus central benzodiazepine receptor binding affinity of 2-phenylimidazo[1,2-a]pyridineacetamides using optimal descriptors calculated with Smiles. QSAR Comb Sci. 2007; 26(4): 460-468.
Rudolph et al., Beyond classical benzodiazepines: novel therapeutic potential of GABAA receptor subtypes. Nat Rev Drug Discov. Sep. 2011; 10(9): 685-97.
Salamon, Conners Scale for ADHD Assessment. WebMD. Jul. 12, 2020. available at https://www.webmd.com/add-adhd/childhood-adhd/conners-rating-scale#:text=The%20Conners%20rating%20scale%20is, %2C%20home%20life%2C%20and%20relationships. 2 pages.
Samanta et al., Search for Structural Requirements of2-Phenylimidazo[1,2-a]pyridineacetamide Analogs to Im prove Affinity and Selectivity towards Central and/or Peripheral Benzodiazepine Receptors. Internet Electronic Journal of Molecular Design. Jul. 2007; 6(7): 183-99.
Schultz et al., Sensory hypersensitivity predicts repetitive behaviours in autistic and typically-developing children. Autism : the international journal of research and practice. May 2019; 23(4): 1028-41.
Shank et al., Ion and temperature effects on the binding of gamma-aminobutyrate to its receptors and the high-affinity transport system. J. Neurochem. Jun. 1990;54(6):2007-15.
Silverman et al., Behavioural phenotyping assays for mouse models of autism. Nat Rev Neurosci. Jul. 2010;11(7):490-502. doi: 10.1038/nrn2851.
Simons et al., Early experience of tactile stimulation influences organization of somatic sensory cortex. Nature. Apr. 1987; 326(6114): 694-7.
Sohal et al., Parvalbumin neurons and gamma rhythms enhance cortical circuit performance. Nature. Jun. 2009; 459(7247): 698-702.
Swerdlow et al., Sensorimotor gating of the startle reflex: what we said 25 years ago, what has happened since then, and what comes next. J Psychopharmacol. Nov. 2016;30(11):1072-1081. doi: 10.1177/0269881116661075. Epub Aug. 18, 2016.
Tata et al., Lack of cognitive recovery following withdrawal from long-term benzodiazepine use. Psychol Med. Feb. 1994; 24(1): 203-13.
Tomassy et al. Developmental abnormalities of cortical interneurons precede symptoms onset in a mouse model of Rett syndrome. J Neurochem. Oct. 2014; 131(1): 115-27.
Tomchek et al., Sensory processing in children with and without autism: a comparative study using the short sensory profile. Am J Occup Ther. Mar. 1, 2007; 61(2): 190-200.
Torres et al., Autism: the micro-movement perspective. Front Integr Neurosci. Jul. 24, 2013;7: 32.
Trapani et al., Structure-activity relationships and effects on neuroactive steroid synthesis in a series of 2-phenylimidazo[1,2-a]pyridineacetamide peripheral benzodiazepine receptors ligands. J Med Chem. Jan. 13, 2005;48(1):292-305. doi: 10.1021/jm049610q.
Trapani et al., Synthesis and binding affinity of 2-phenylimidazo[1,2-alpha]pyridine derivatives for both central and peripheral benzodiazepine receptors. A new series of high-affinity and selective ligands for the peripheral type. J Med Chem. Sep. 12, 1997;40(19):3109-18. doi: 10.1021/jm970112+.
Tuccinardi et al., A virtual screening study of the 18 kDa translocator protein using pharmacophore models combined with 3D-QSAR studies. ChemMedChem. Oct. 2009;4(10):1686-94. doi: 10.1002/cmdc.200900254.
Usoskin et al., Unbiased classification of sensory neuron types by large-scale single-cell RNA sequencing. Nature neuroscience. Jan. 2015; 18(1): 145-53.
Veenstra-Danderweele et al., Arbaclofen in Children and Adolescents with Autism Spectrum Disorder: A Randomized, Controlled, Phase 2 Trial. Neuropsychopharmacology. Jun. 2017; 42(7): 1390-8.
Voos et al., Autistic traits are associated with diminished neural response to affective touch. Soc Cogn Affect Neurosci. Apr. 2013;8(4):378-86. doi: 10.1093/scan/nss009. Epub Jan. 20, 2012.
Wang et al., Striatopallidal dysfunction underlies repetitive behavior in Shank3-deficient model of autism. The Journal of Clinical Investigation. May 1, 2017; 127(5): 1978-90.
Watanabe et al., Disruption of the epilepsy KCNQ2 gene results in neural hyperexcitability. J Neurochem. Jul. 2000; 75(1): 28-33.
Wiesel et al., Extent of recovery from the effects of visual deprivation in kittens. Journal of neurophysiology. Nov. 1, 1965; 28(6): 1060-72.
Wiggins et al., Brief report: sensory abnormalities as distinguishing symptoms of autism spectrum disorders in young children. J Autism Dev Disord. Jul. 1, 2009; 39(7): 1087-91.
Womelsdorf et al., Dynamic circuit motifs underlying rhythmic gain control, gating and integration. Nature neuroscience. Aug. 2014; 17(8): 1031-9.
Wright, Cognition and behavior: Sensory sensitivity tied to autism, Oct. 10, 2012, available at https://www.spectrumnews.org/news/cognition-and-behavior-sensory-sensitivity-tied-to-autism/.
Yatawara et al., The effect of oxytocin nasal spray on social interaction deficits observed in young children with autism: a randomized clinical crossover trial. Mol Psychiatry. Sep. 2016; 21(9): 1225-31.
Yi et al., Autism-associated SHANK3 haploinsufficiency causes Ih channelopathy in human neurons. Science. May 6, 2016; 352(6286): aaf2669.
Zeilhofer et al., Fast synaptic inhibition in spinal sensory processing and pain control. Physiological reviews. Jan. 2012; 92(1): 193-235.

(56) References Cited

OTHER PUBLICATIONS

Zheng et al., Suppression of KCNQ/M (Kv7) potassium channels in dorsal root ganglion neurons contributes to the development of bone cancer pain in a rat model. Pain. Mar. 1, 2013; 154(3): 434-48.
Zikopoulos et al., Altered neural connectivity in excitatory and inhibitory cortical circuits in autism. Front Hum Neurosci. Sep. 27, 2013; 7: 609.
U.S. Appl. No. 18/790,038, filed Jul. 31, 2024, Ginty et al.
U.S. Appl. No. 18/782,829, filed Jul. 24, 2024, Ginty et al.

\* cited by examiner

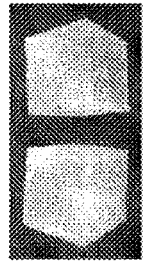
Fig. 1A
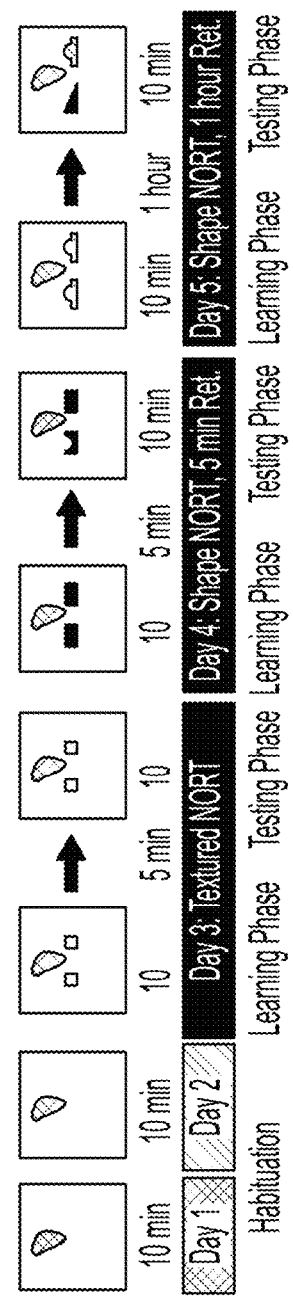
Fig. 1B
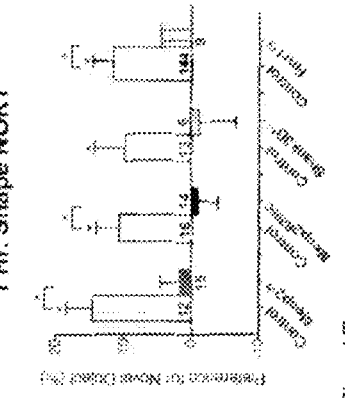
Fig. 1E
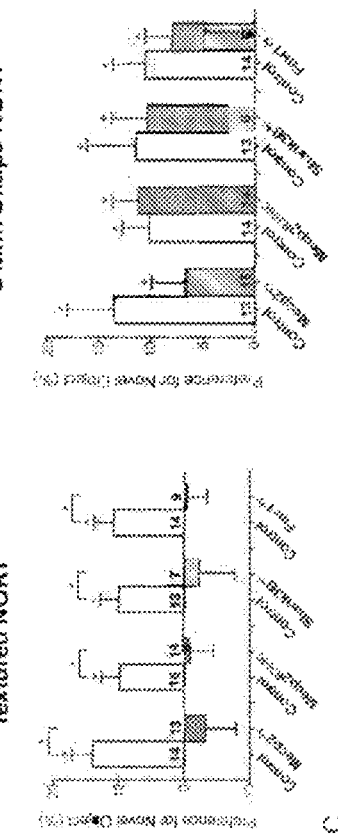
Fig. 1C
Fig. 1D

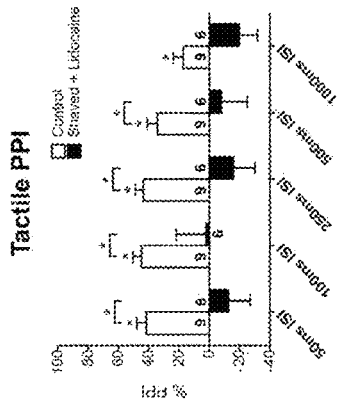
Fig. 1F
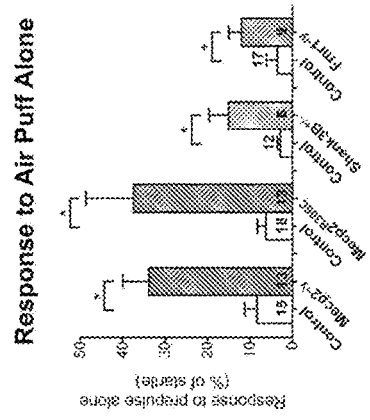
Fig. 1G
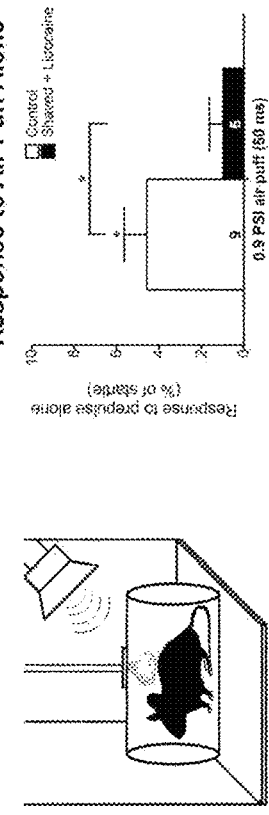
Fig. 1H
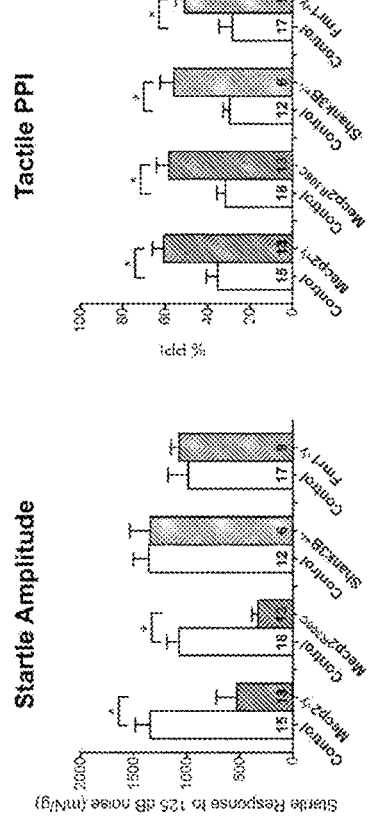
Fig. 1I
Fig. 1J
Fig. 1K

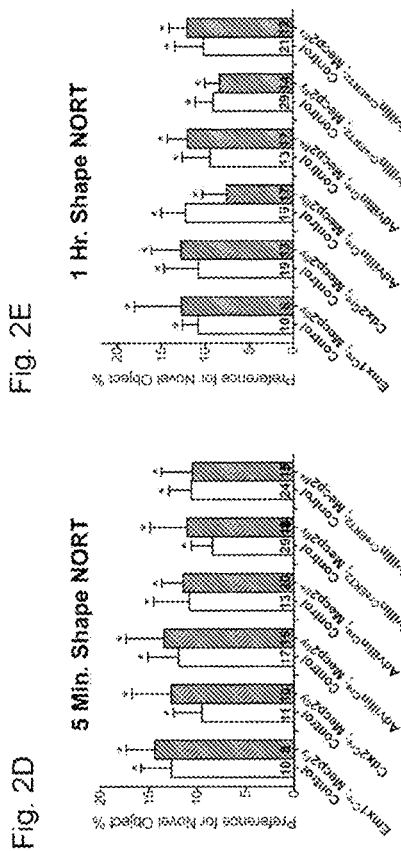
Fig. 2C
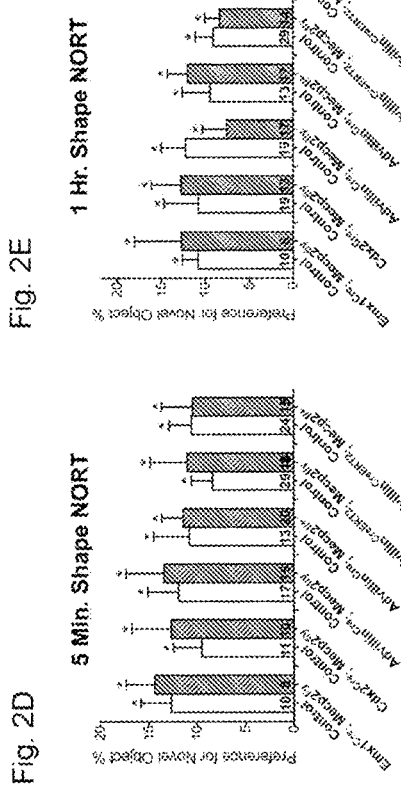
Fig. 2D
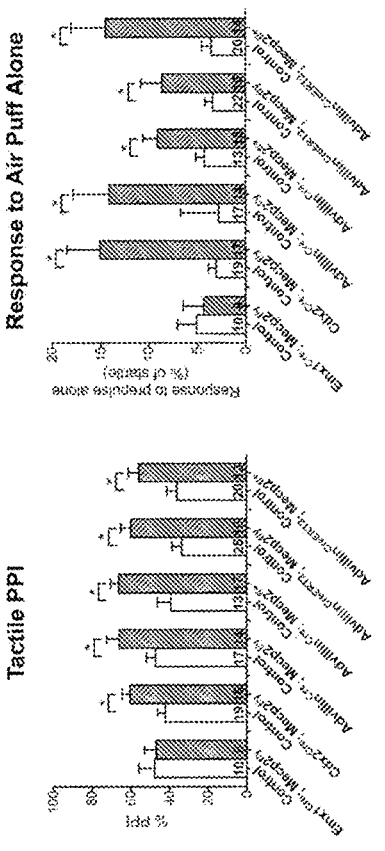
Fig. 2E
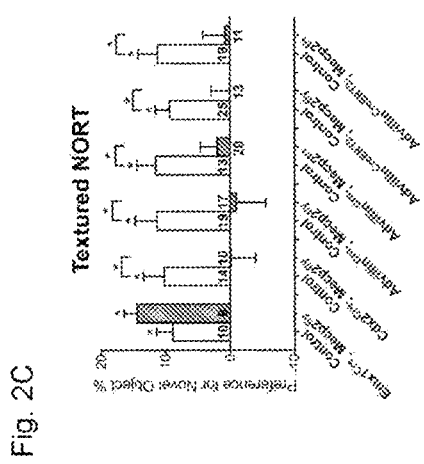
Fig. 2F
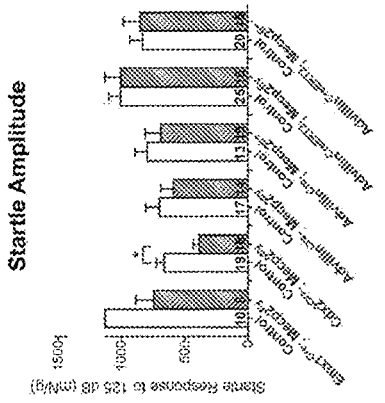
Fig. 2G
Fig. 2H

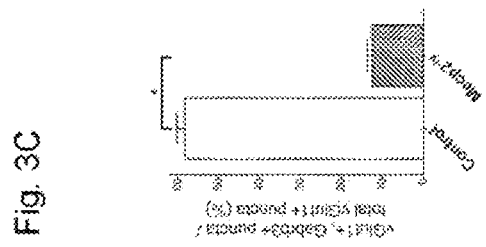
Fig. 3A
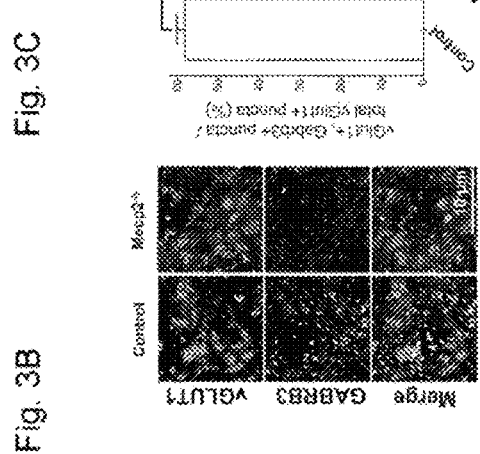
Fig. 3B
Fig. 3C
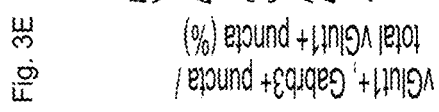
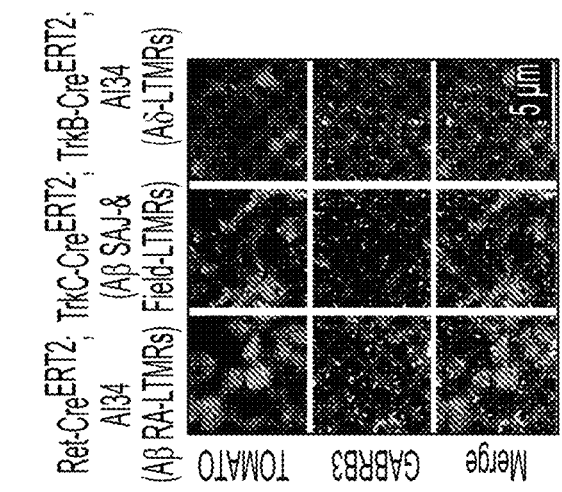
Fig. 3D
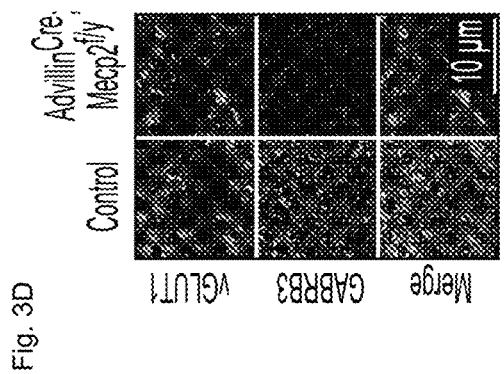
Fig. 3E

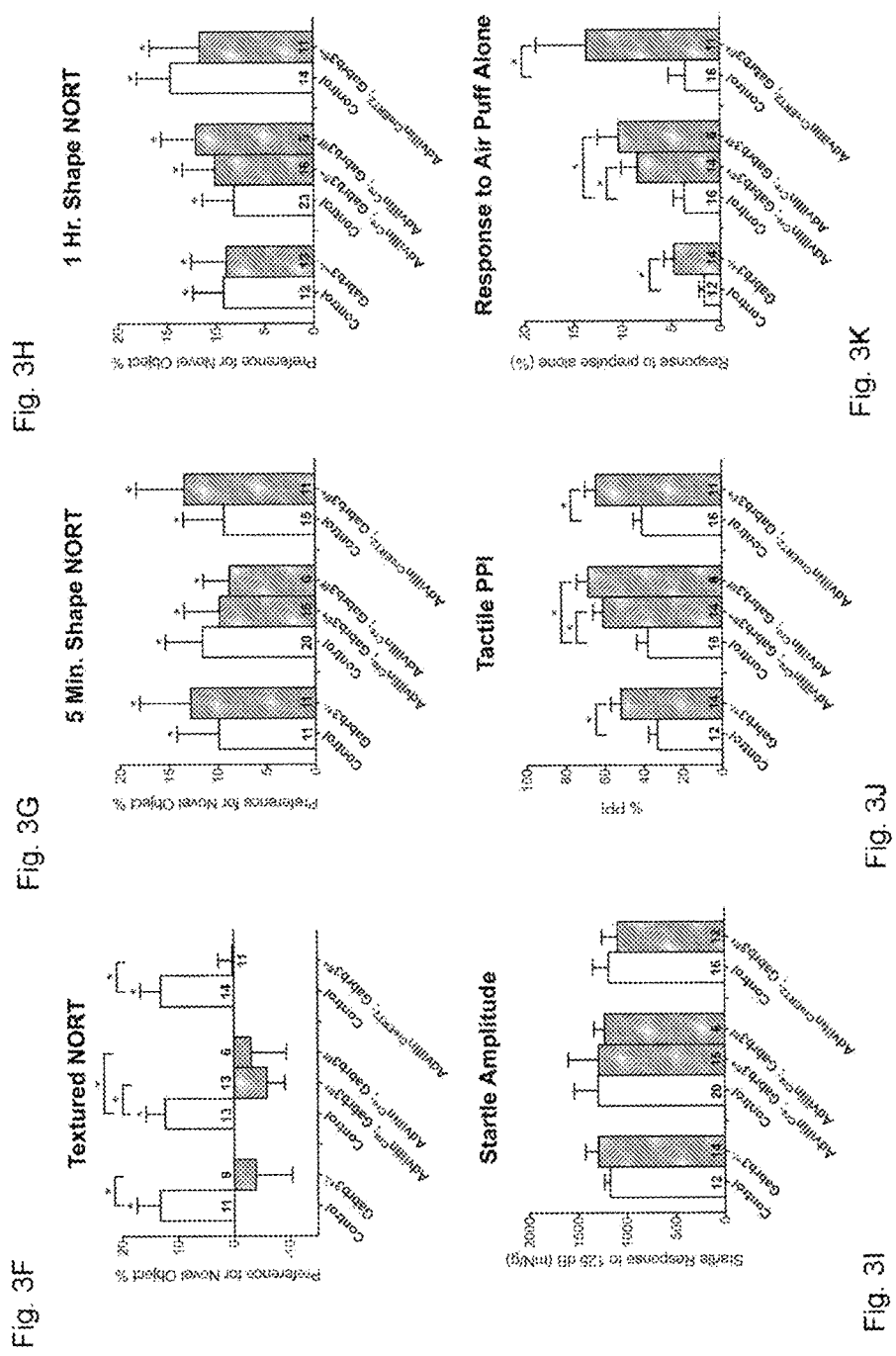

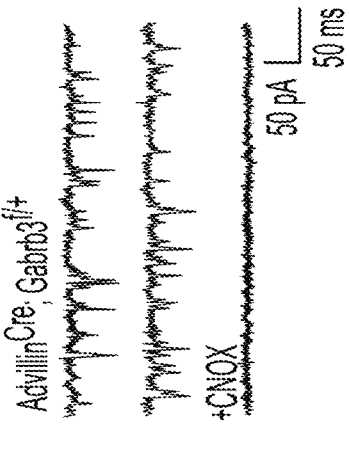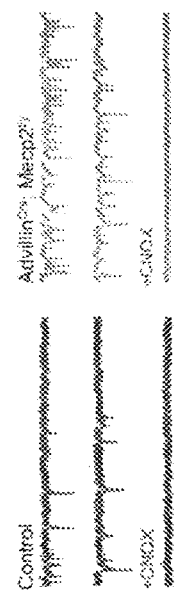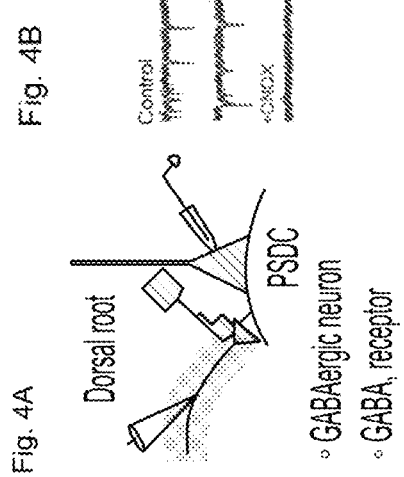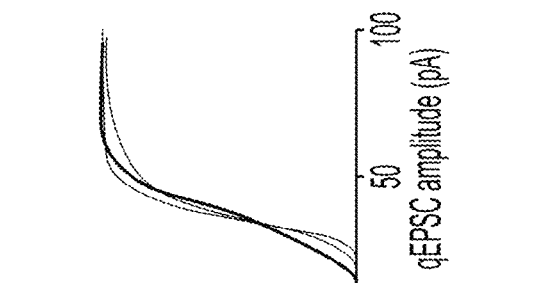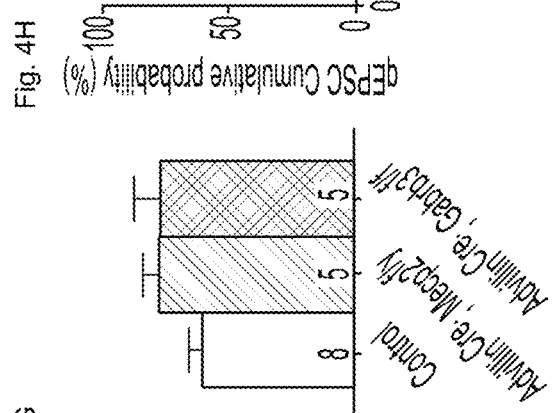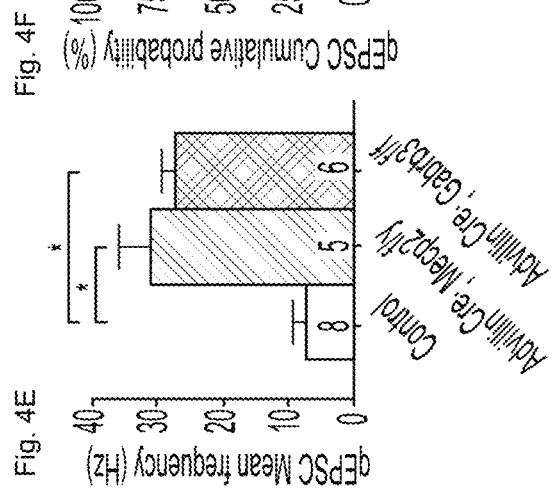

Baseline
+20 µM Bicuculline

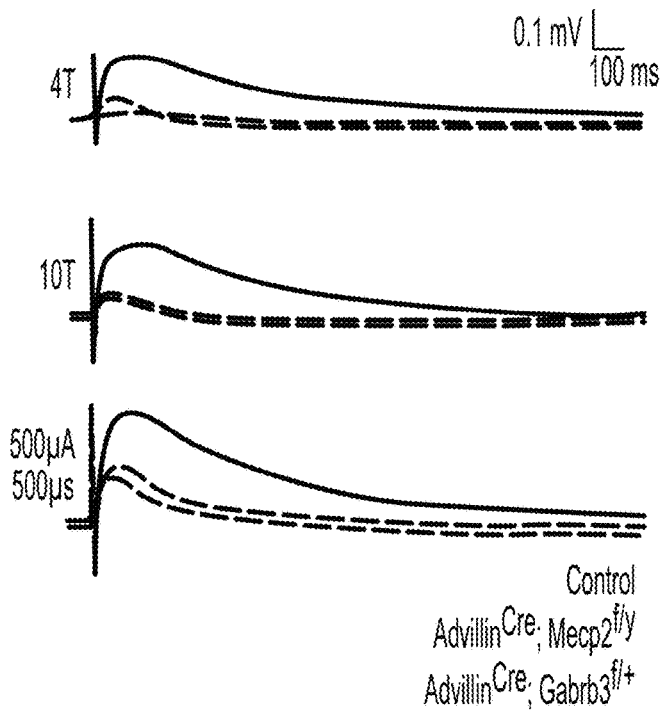
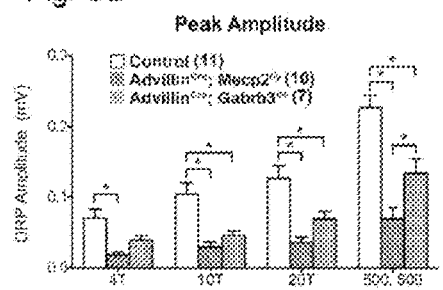
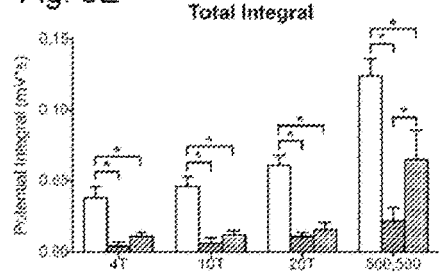
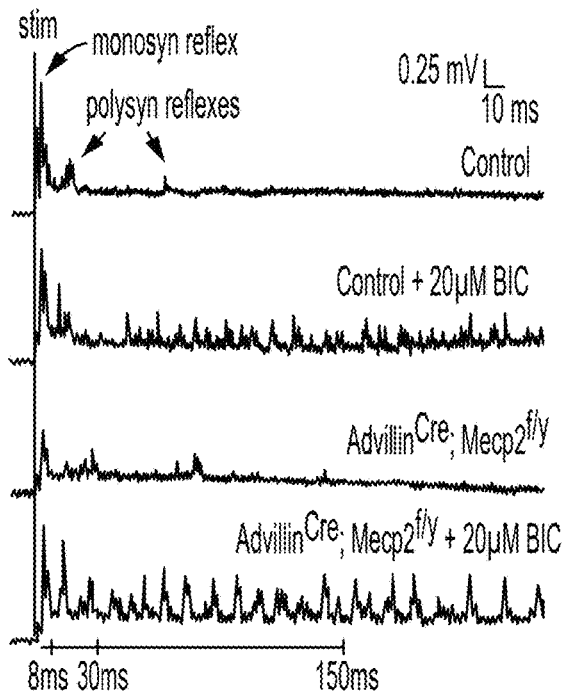
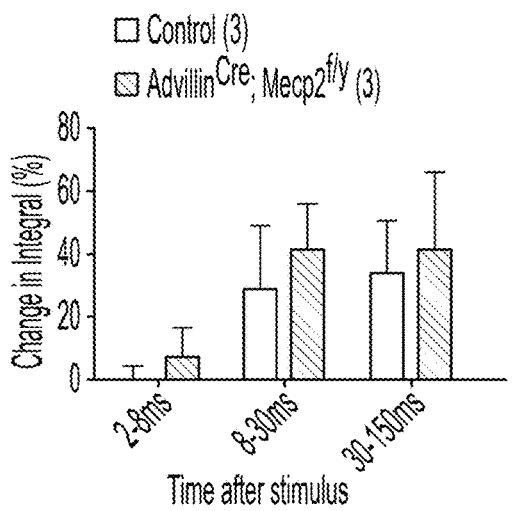

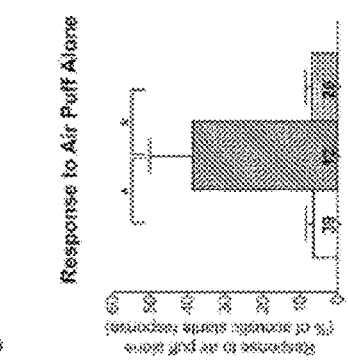
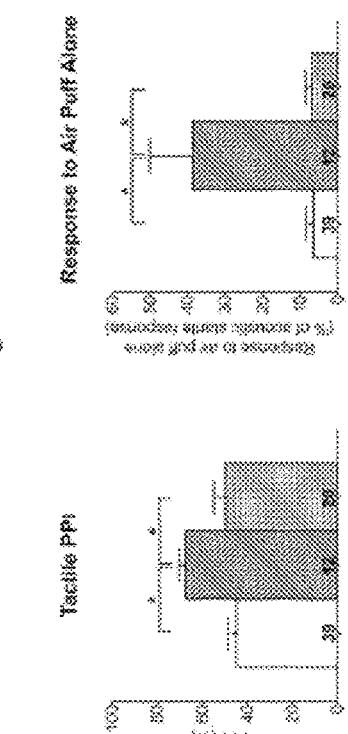
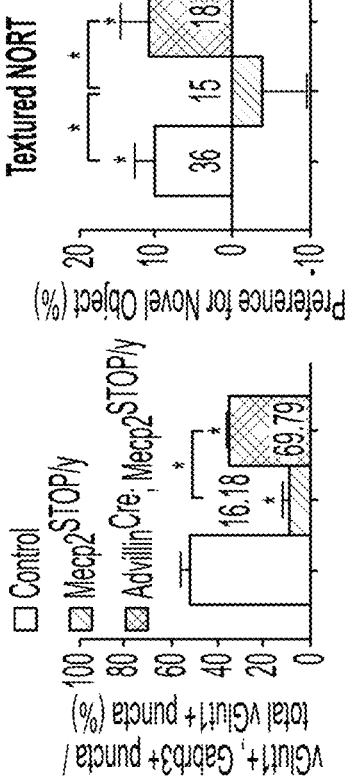
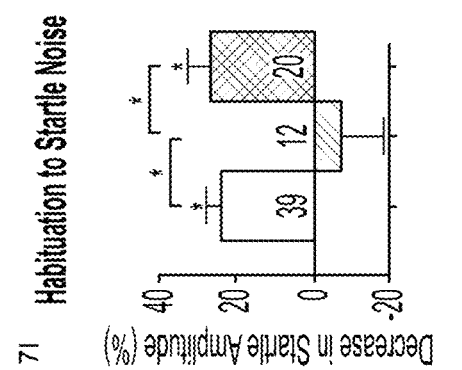
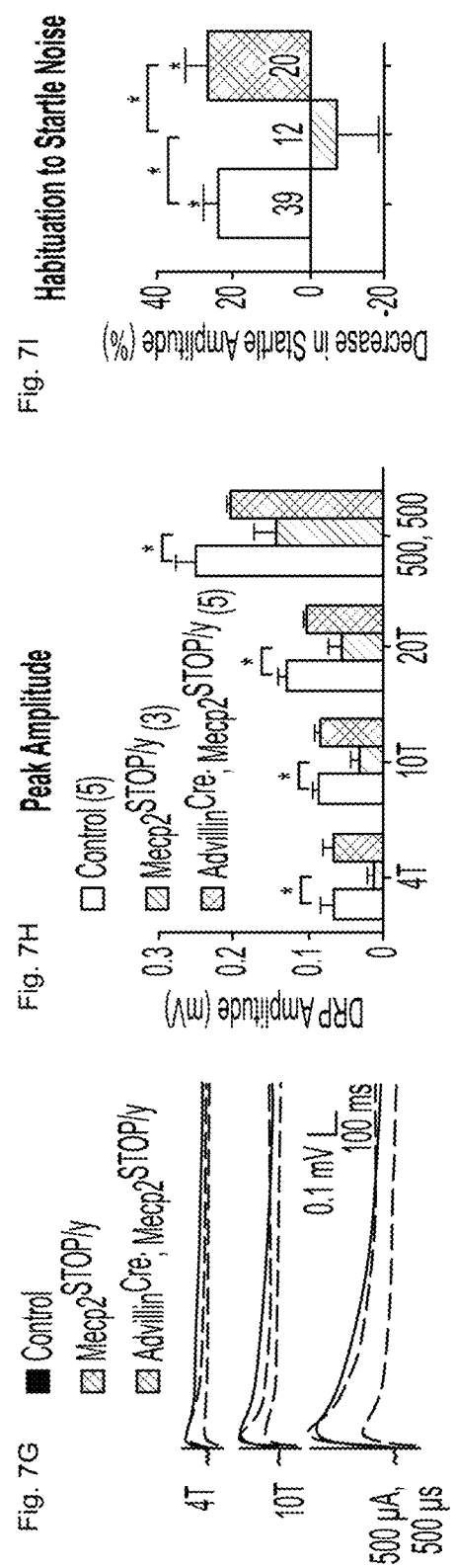

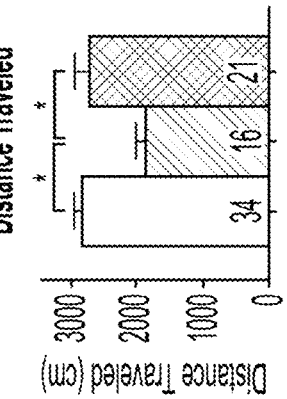
Fig. 7L
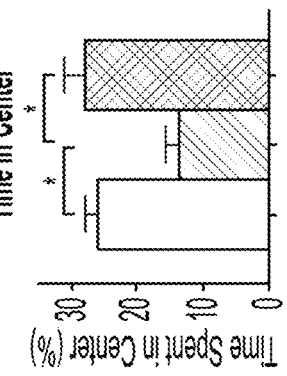
Fig. 7K
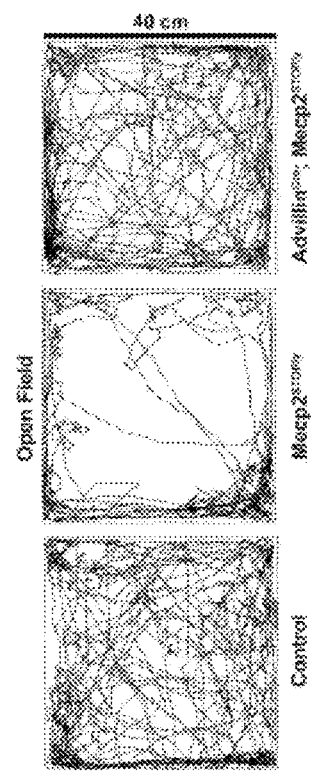
Fig. 7J
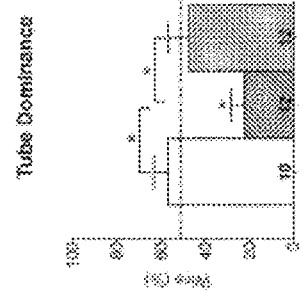
Fig. 7P
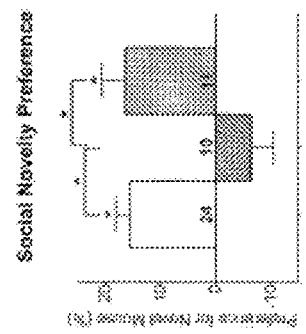
Fig. 7O
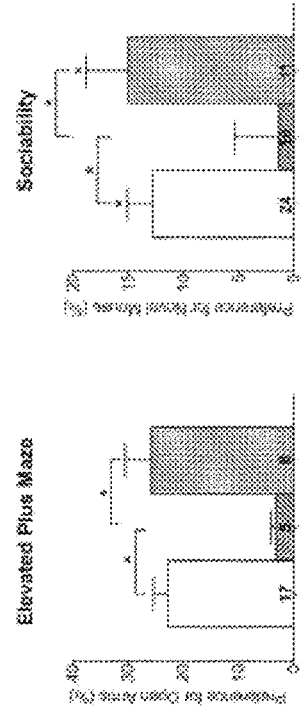
Fig. 7N
Fig. 7M

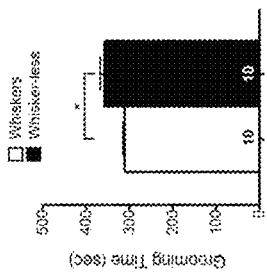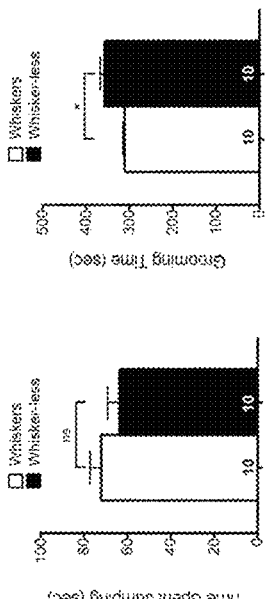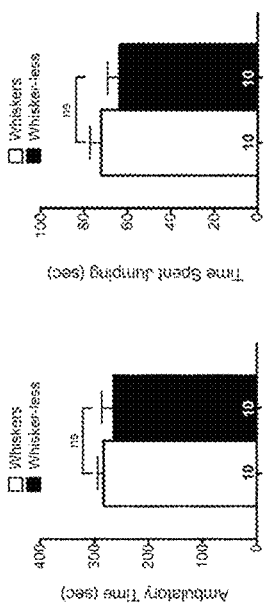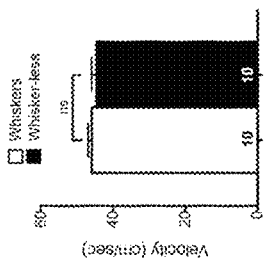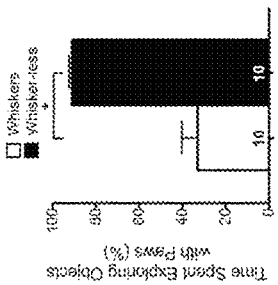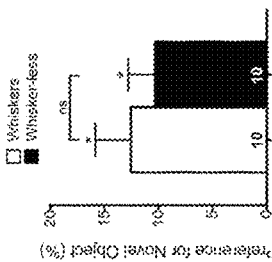
Fig. 8A  Fig. 8B  Fig. 8C  Fig. 8D
Fig. 8E  Fig. 8F  Fig. 8G

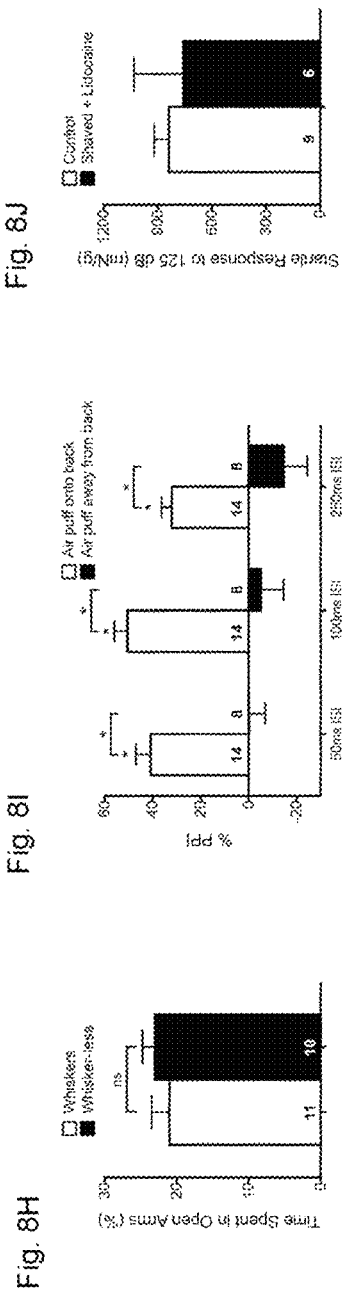

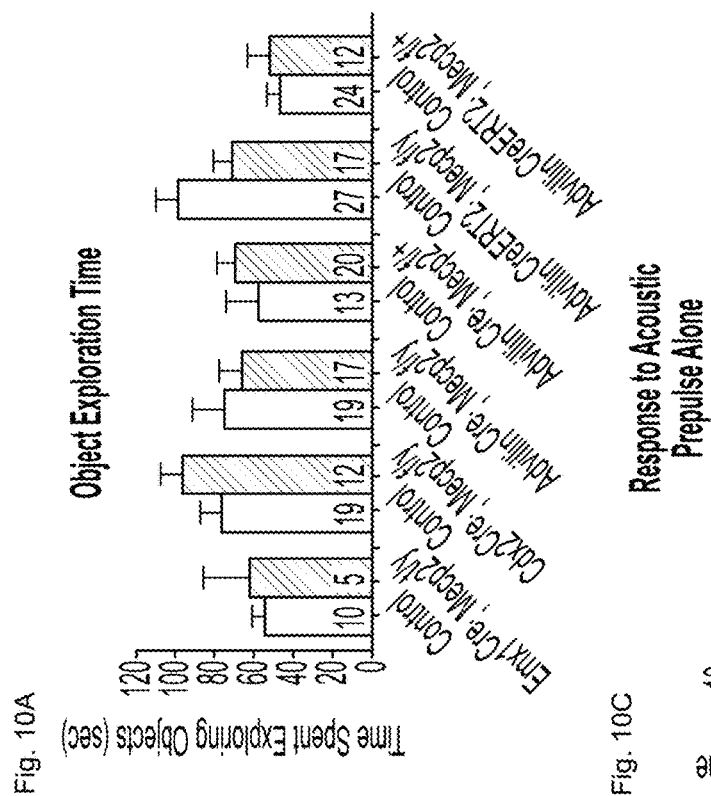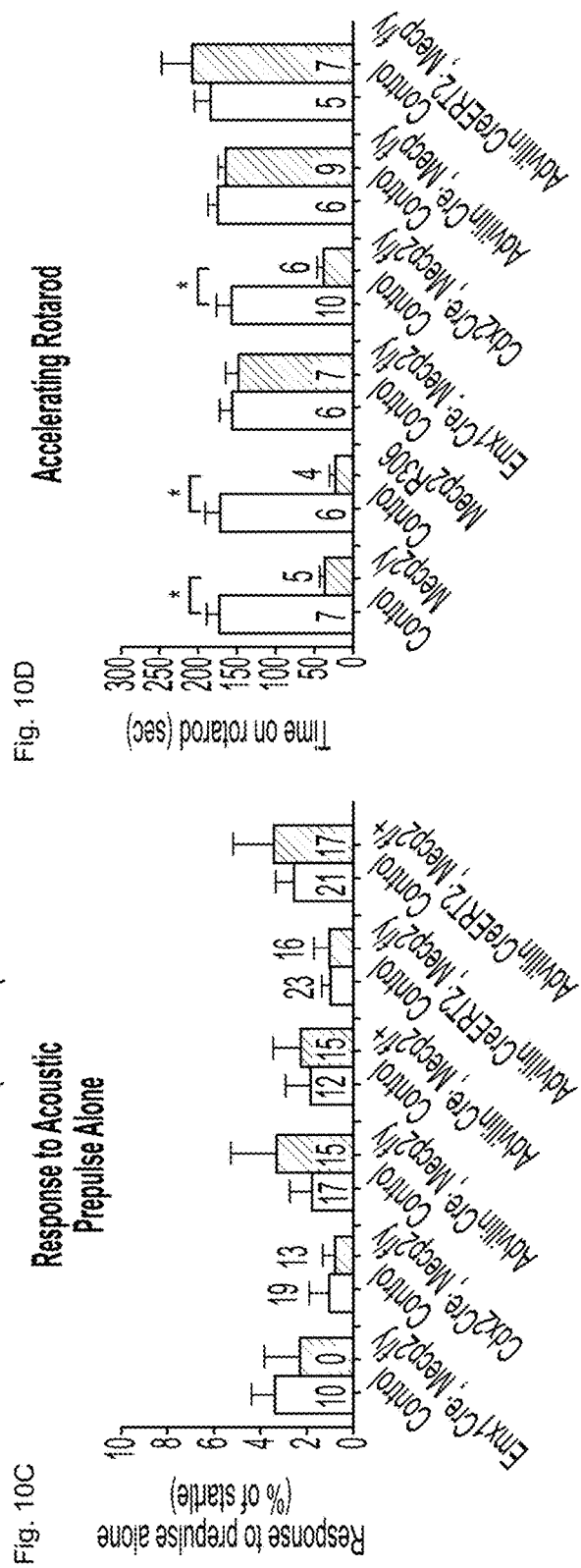

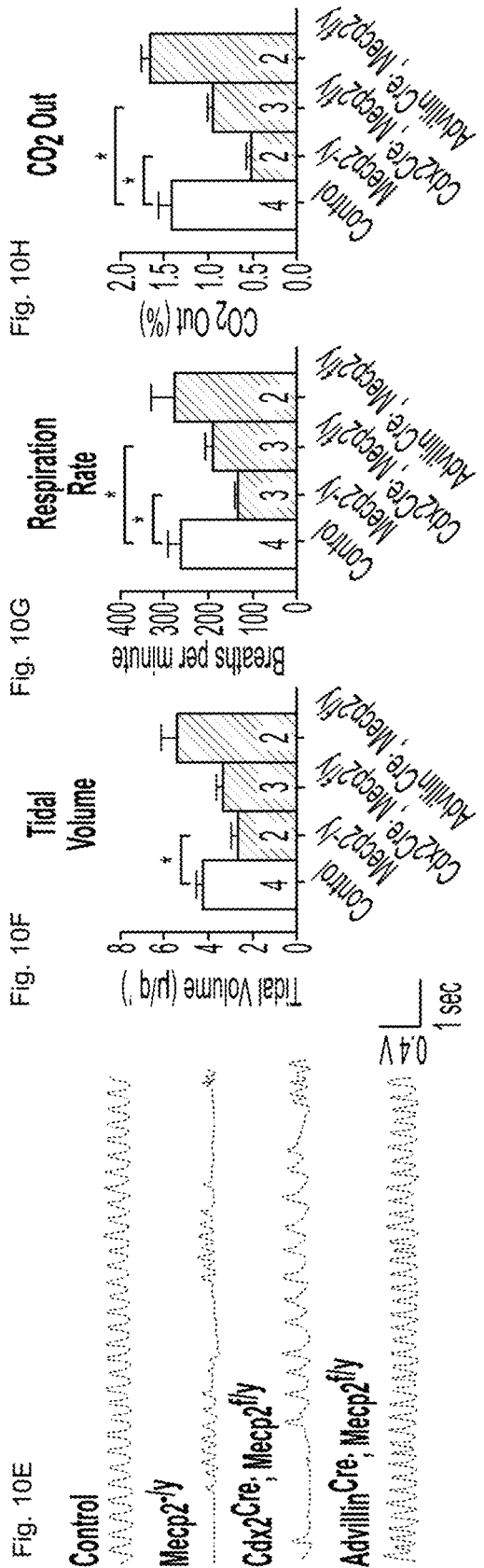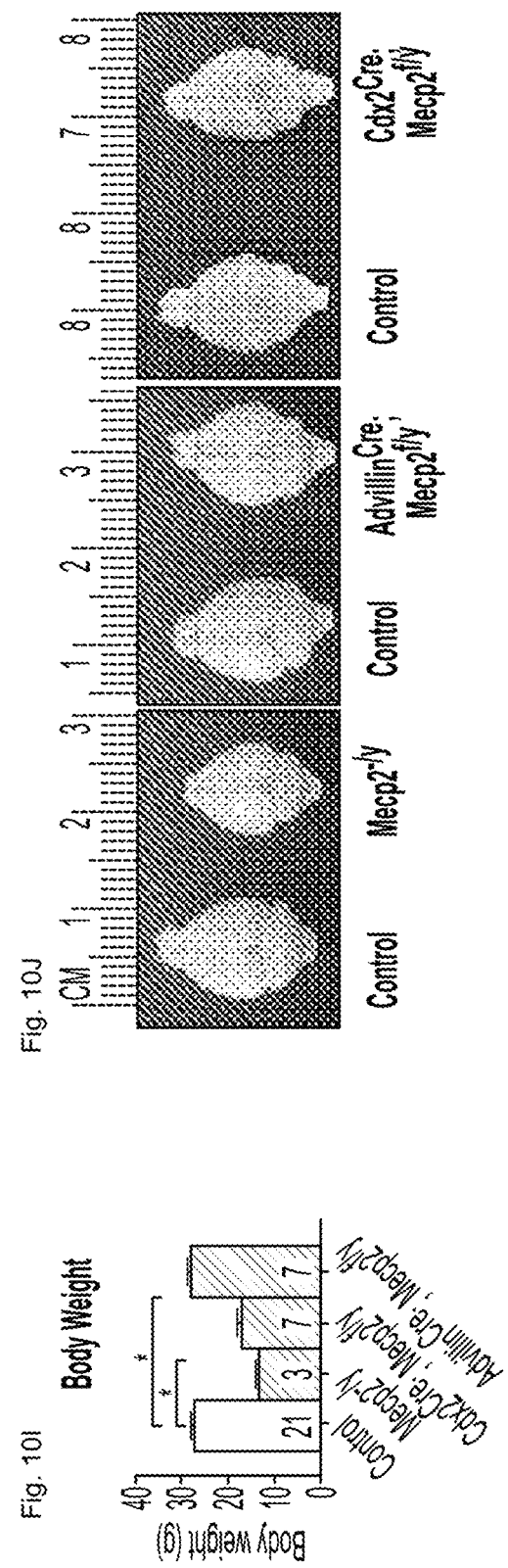

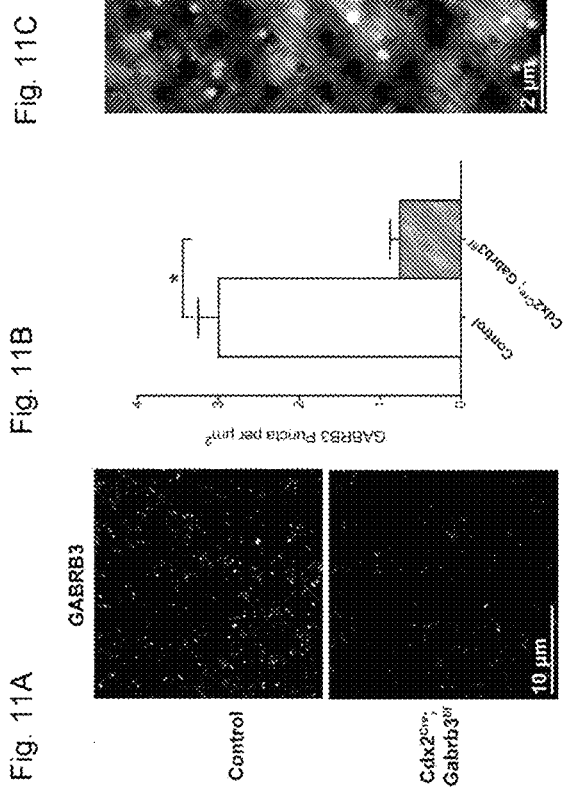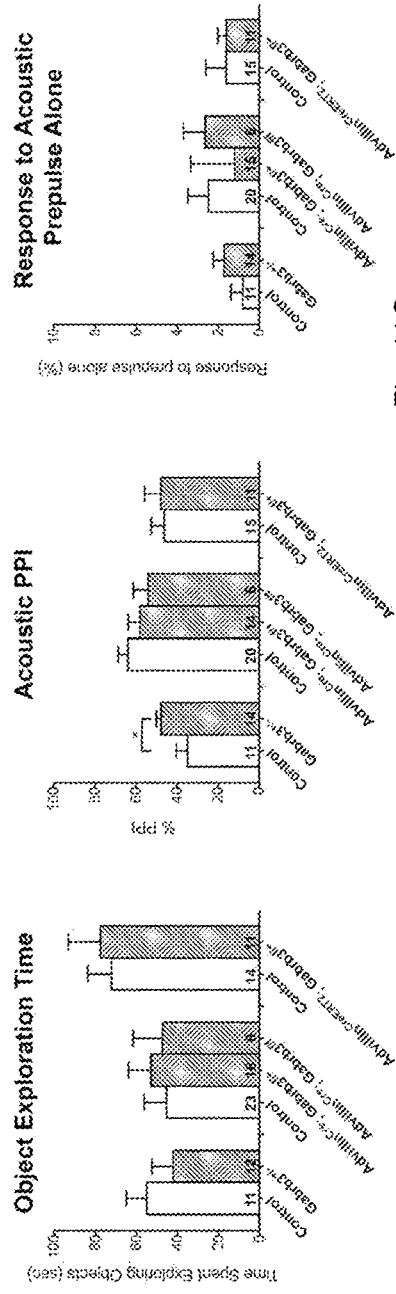

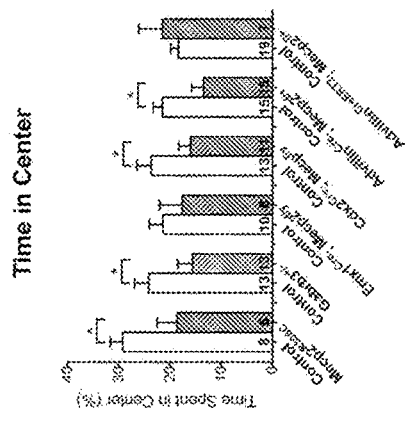
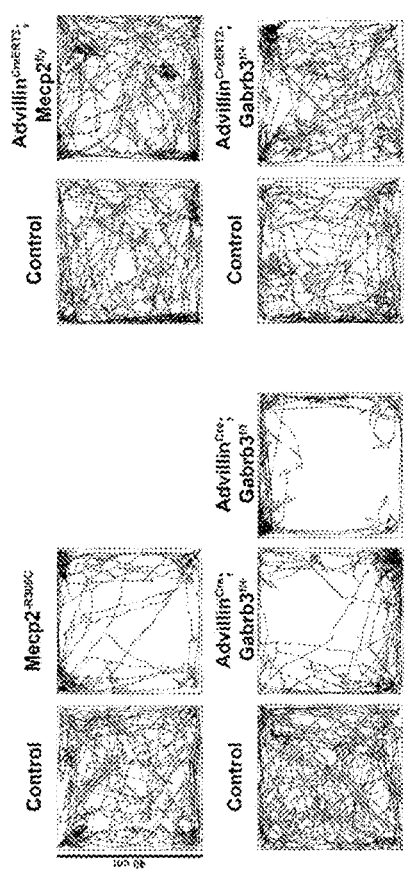
Fig. 12A
Fig. 12B
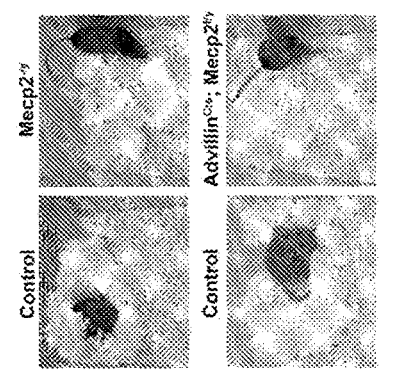
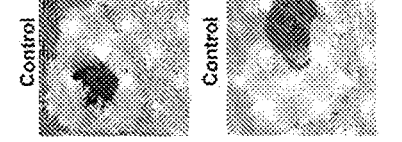
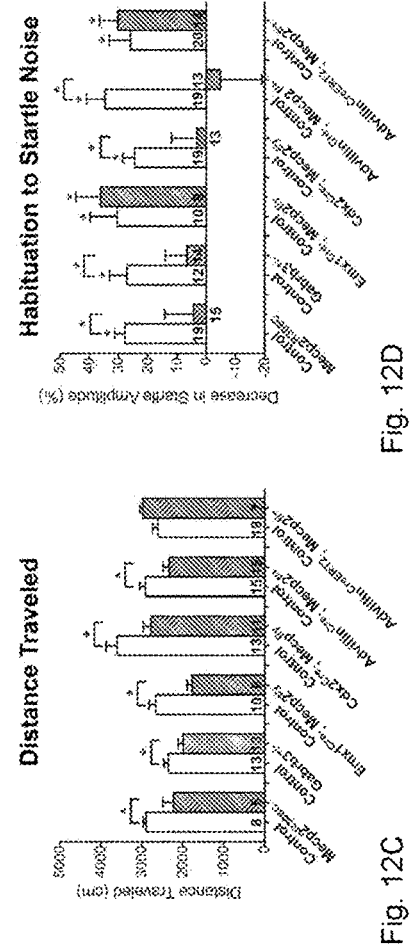
Fig. 12C
Fig. 12D
Fig. 12E

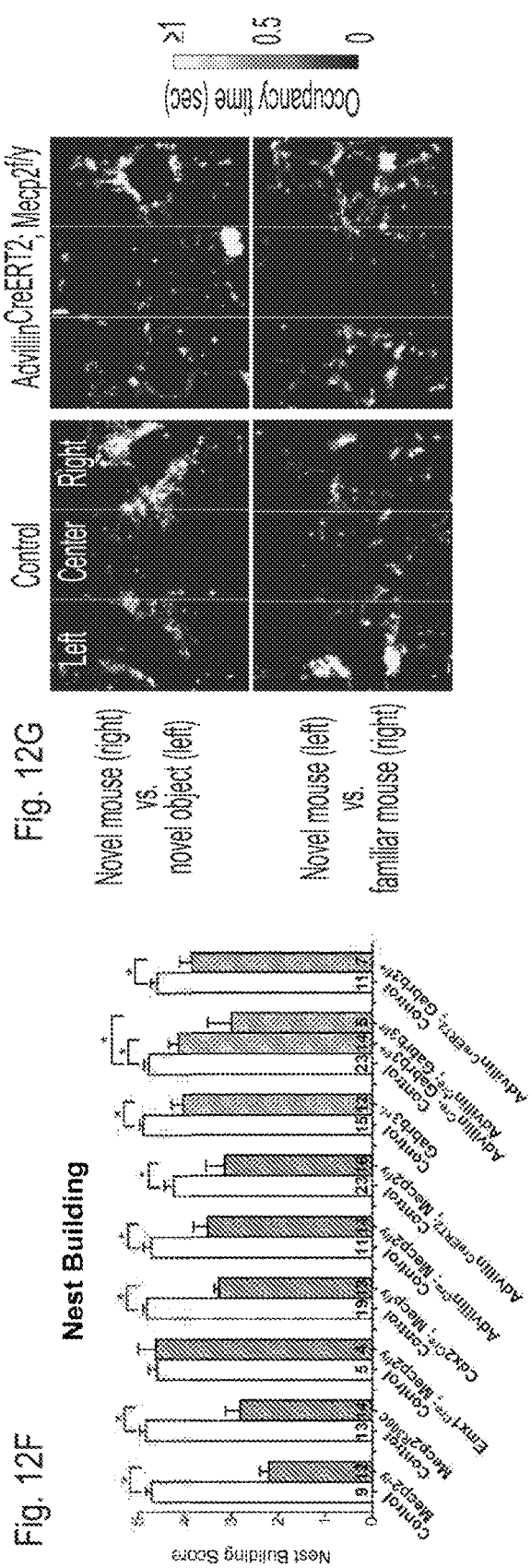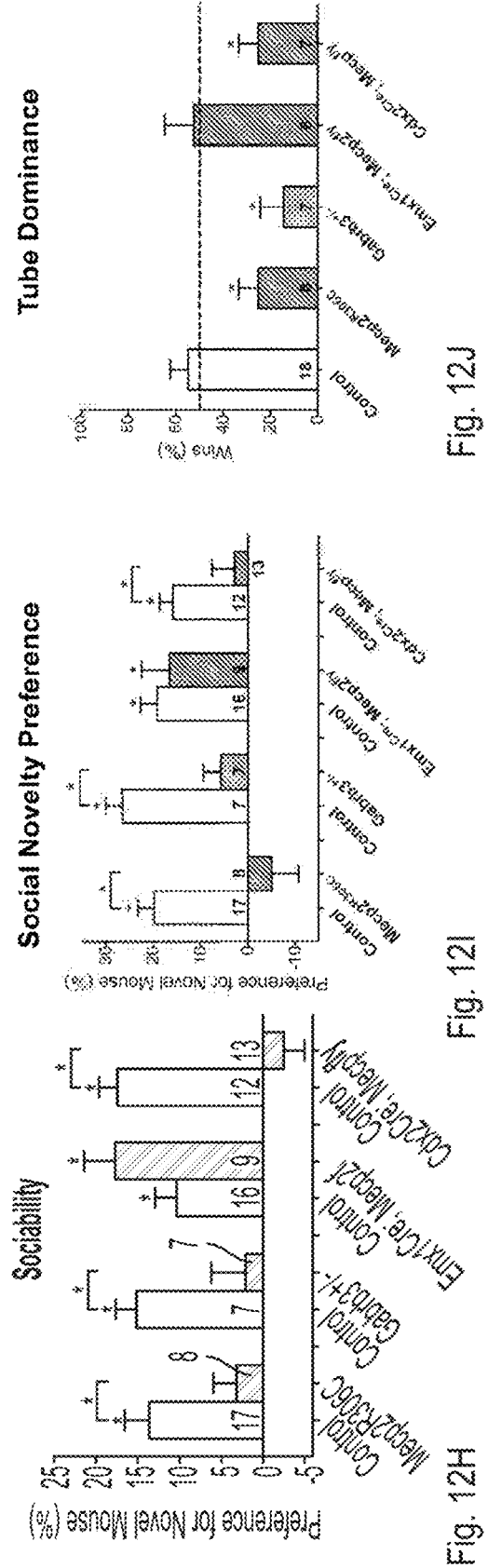
Fig. 12F Nest Building
Fig. 12G
Fig. 12H Sociability
Fig. 12I Social Novelty Preference
Fig. 12J Tube Dominance

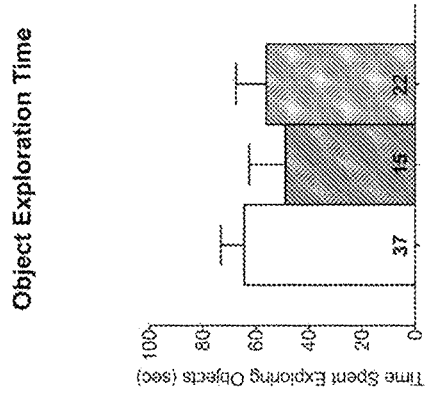
Fig. 13A
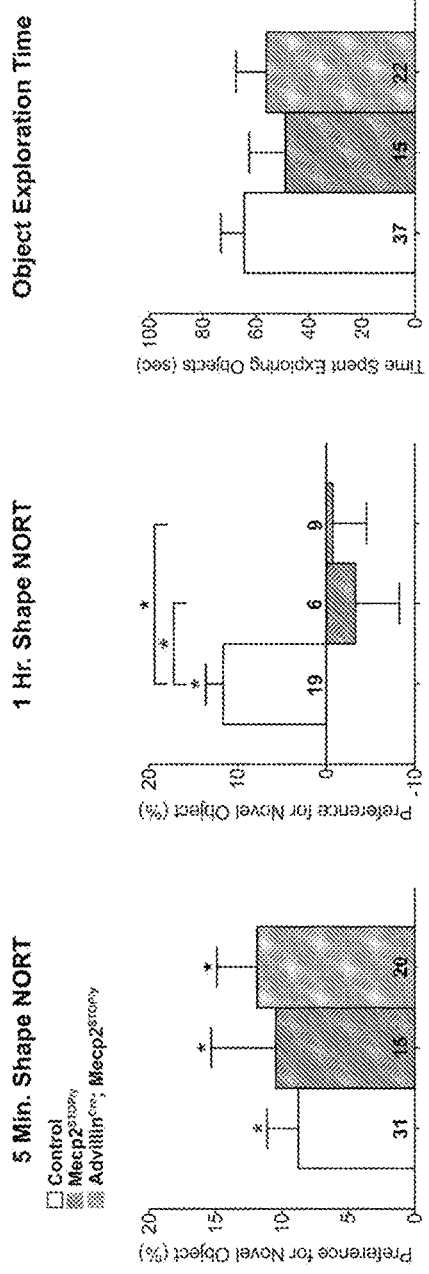
Fig. 13B
Fig. 13C
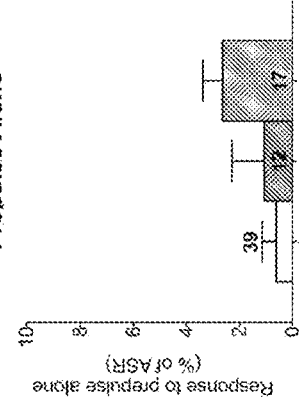
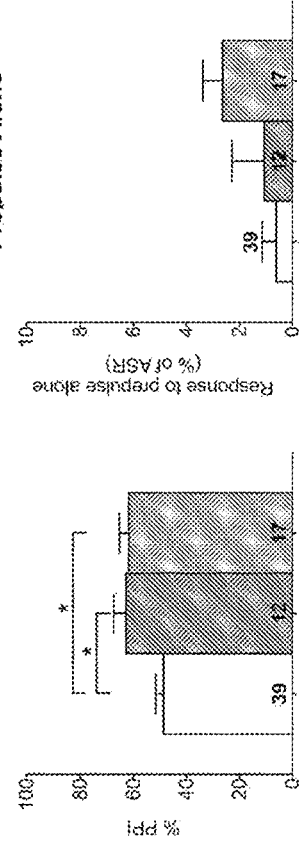
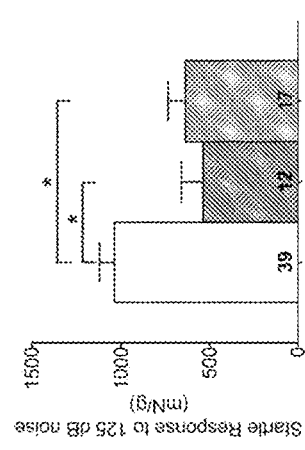
Fig. 13D
Fig. 13E
Fig. 13F

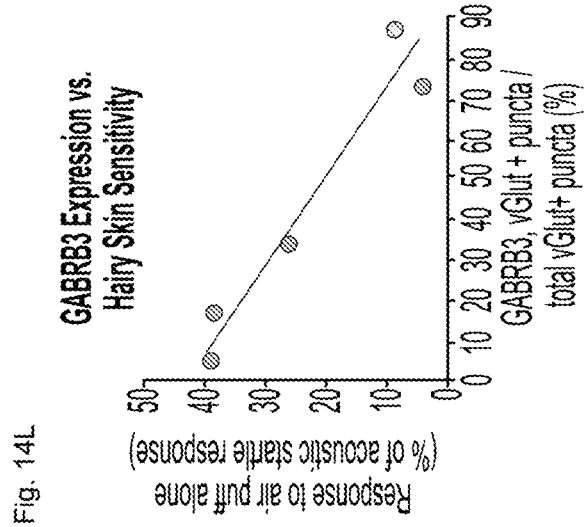
Fig. 14J
Fig. 14K
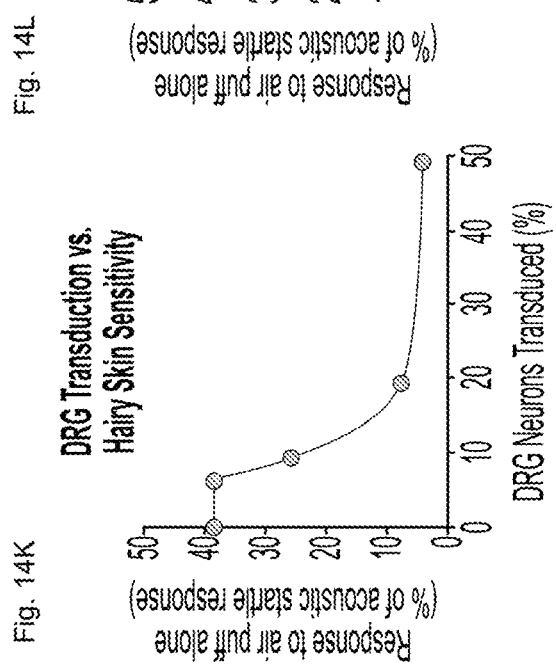
Fig. 14L
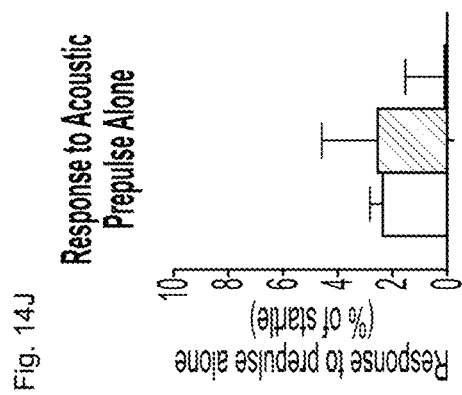
Fig. 14M
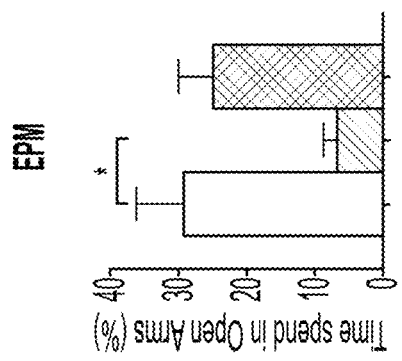
Fig. 14P
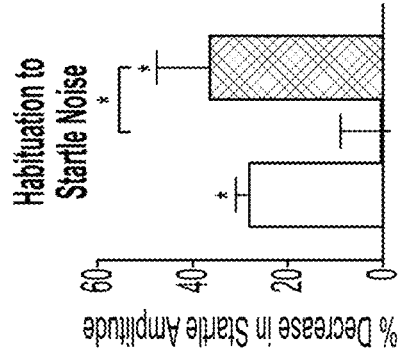
Fig. 14O
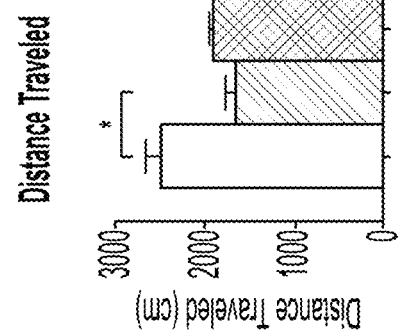
Fig. 14N
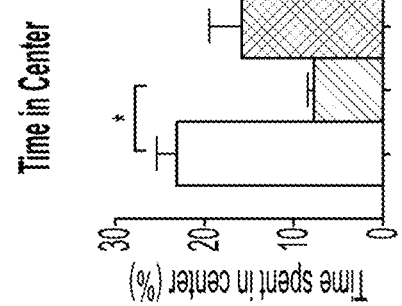

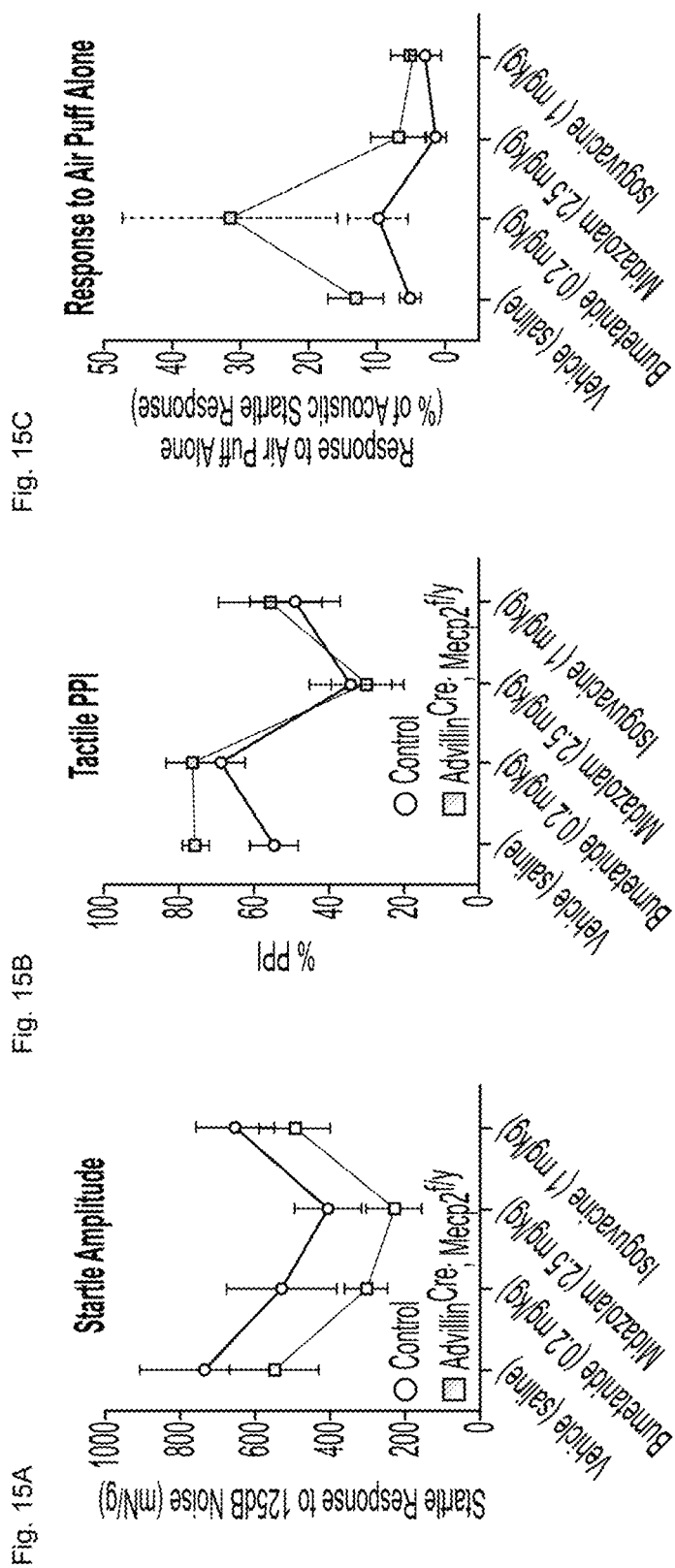

Textured NORT

5 min. Control NORT

1 hr. Control NORT

Object Exploration Time

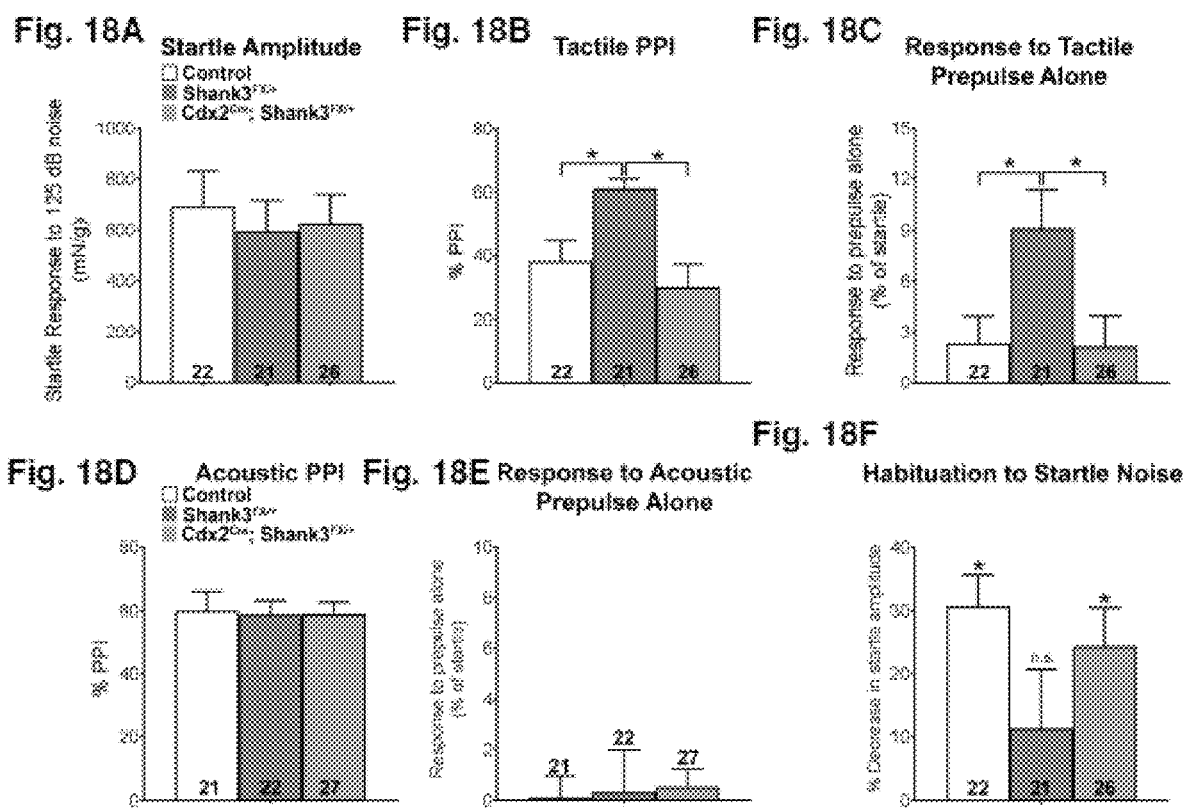

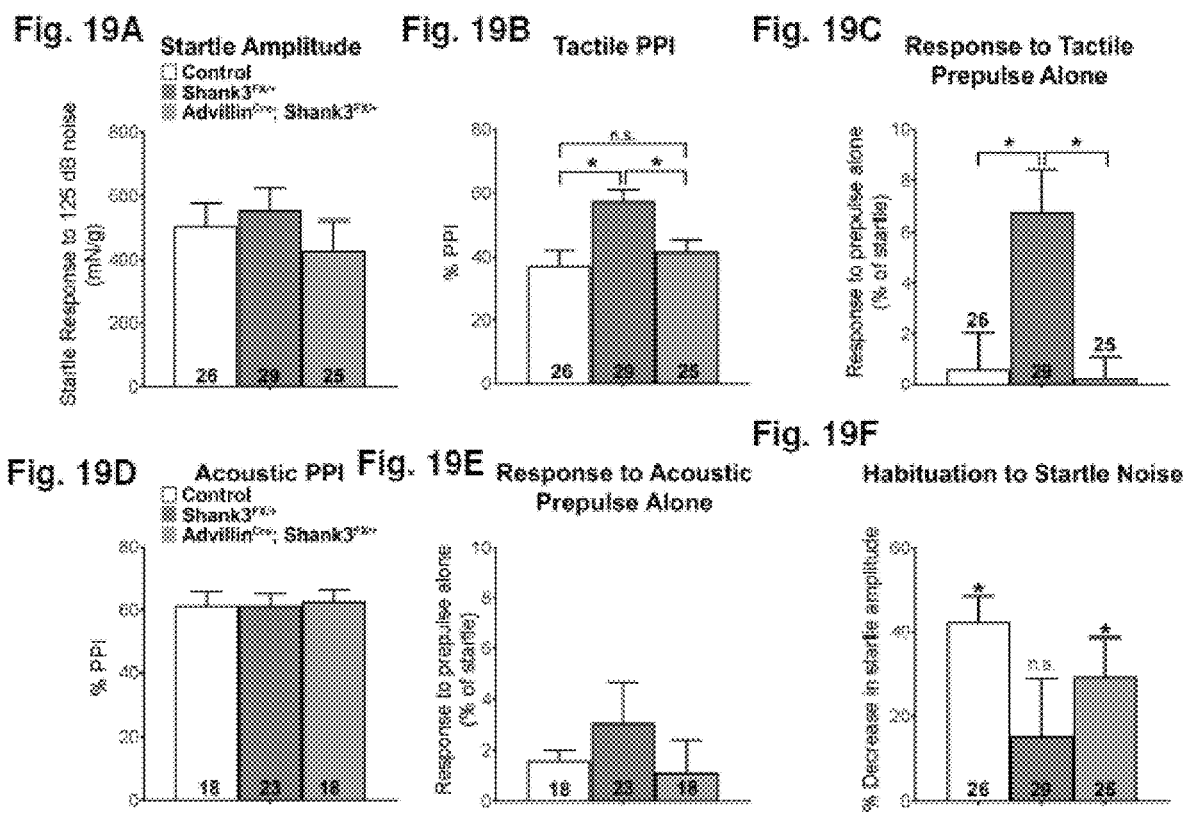

Fig. 22A
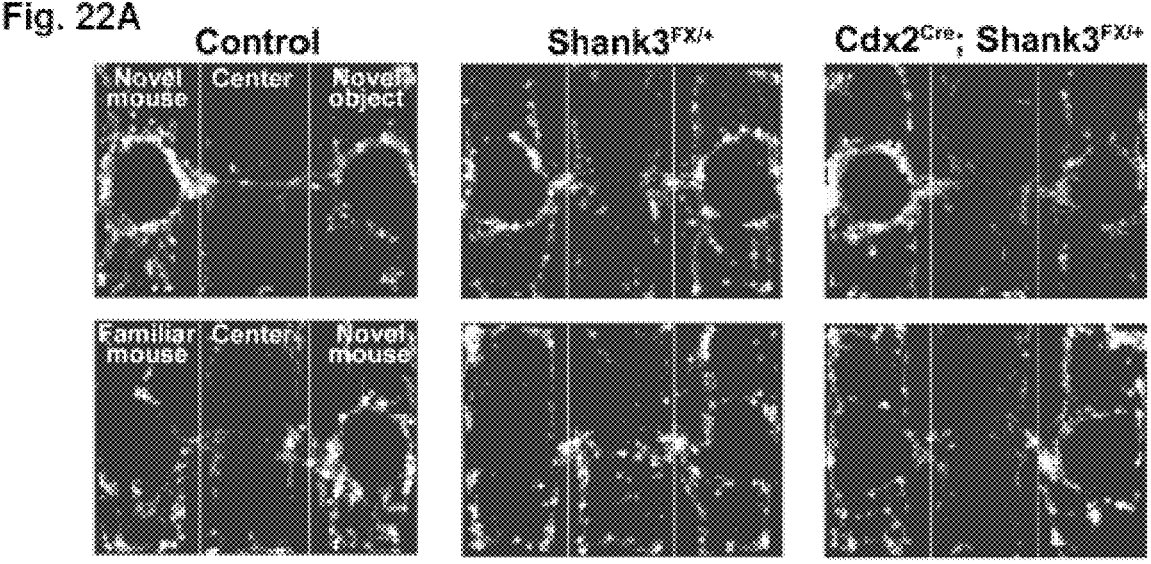
Fig. 22B Sociability
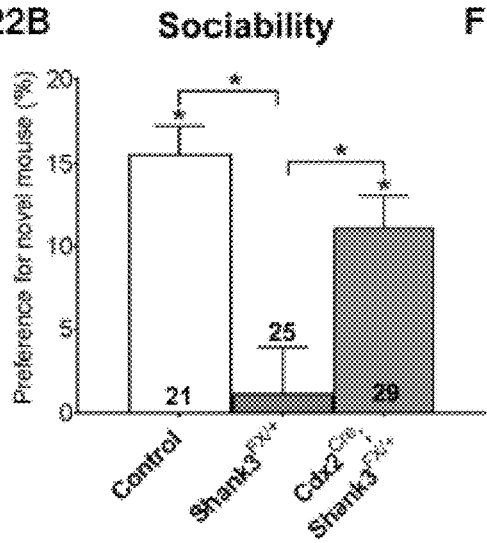
Fig. 22C Social Novelty Preference
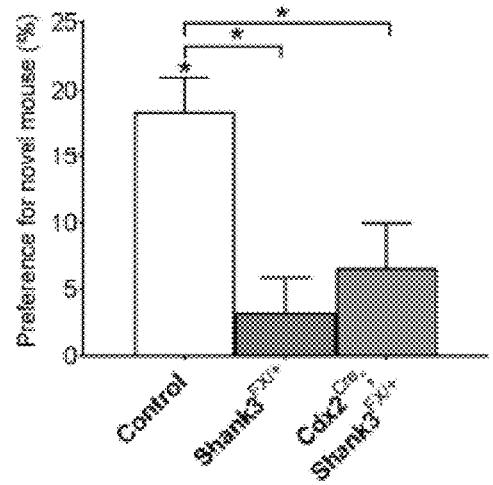

Fig. 22D Sociability
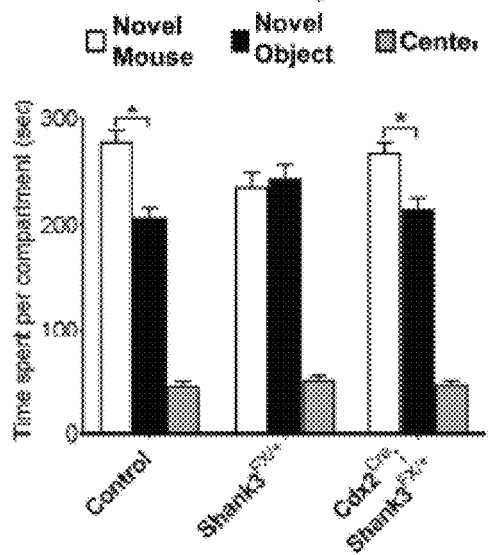
Fig. 22E Social Novelty Preference
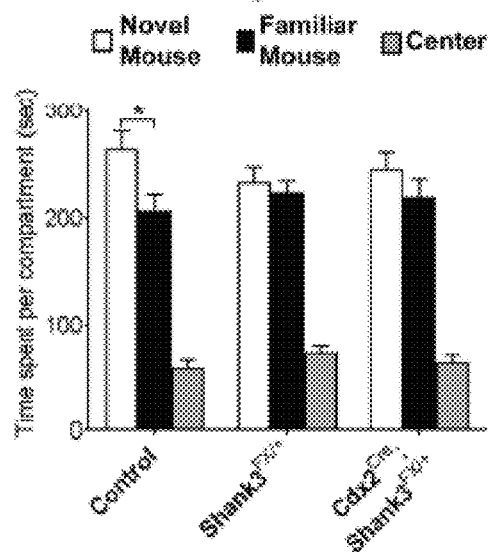

Fig. 23A
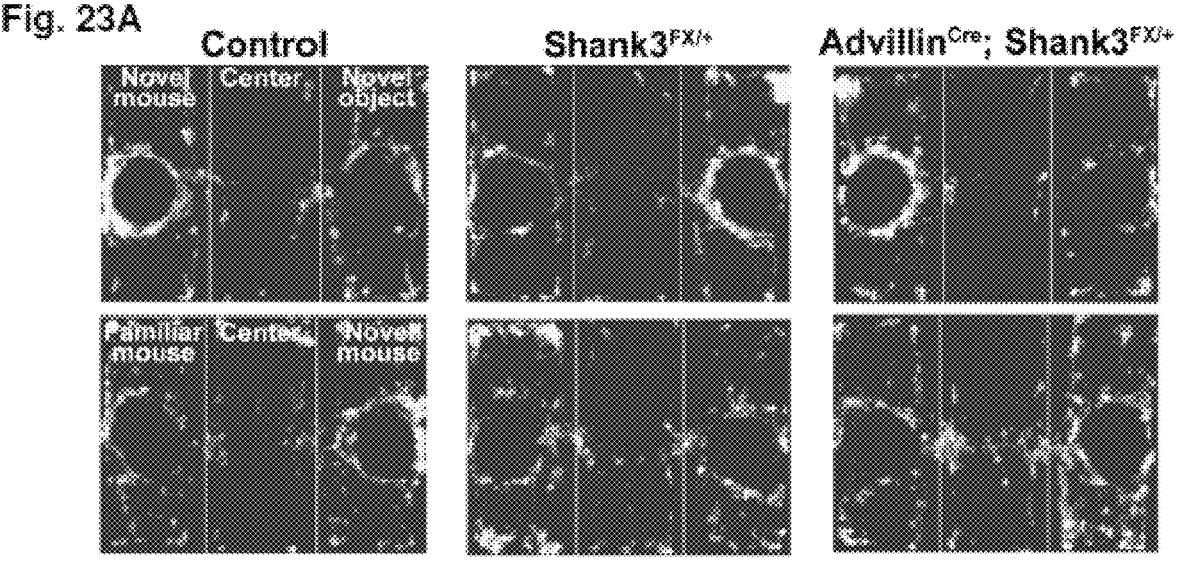
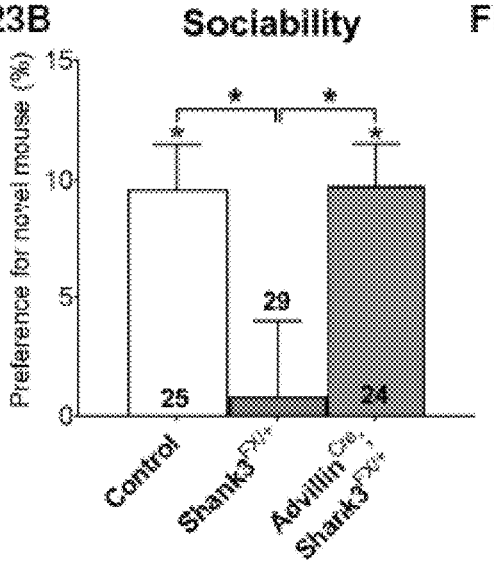
Fig. 23B Sociability
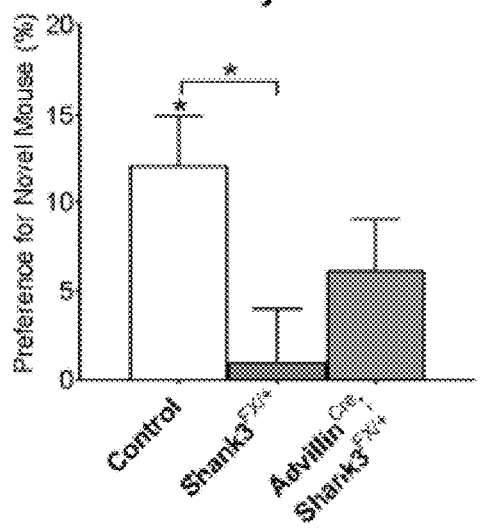
Fig. 23C Social Novelty Preference

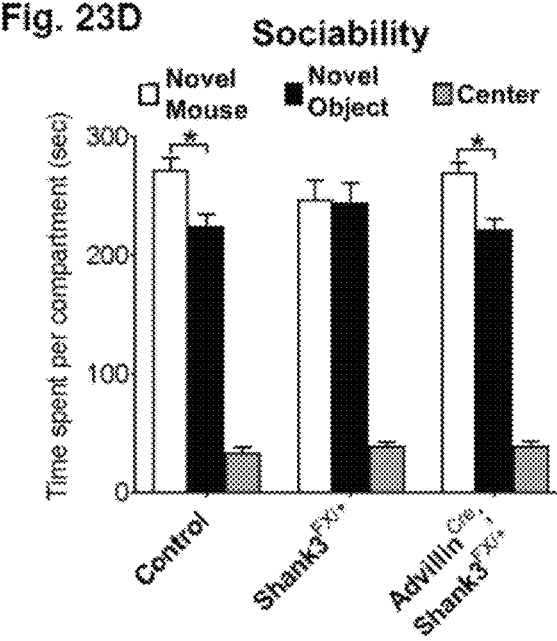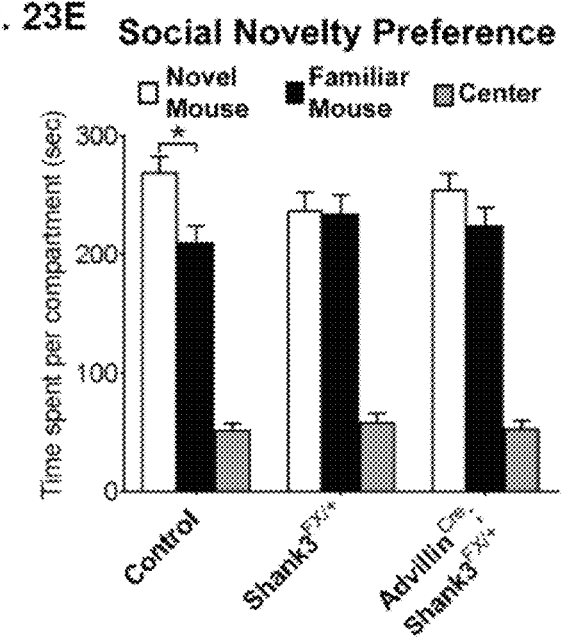

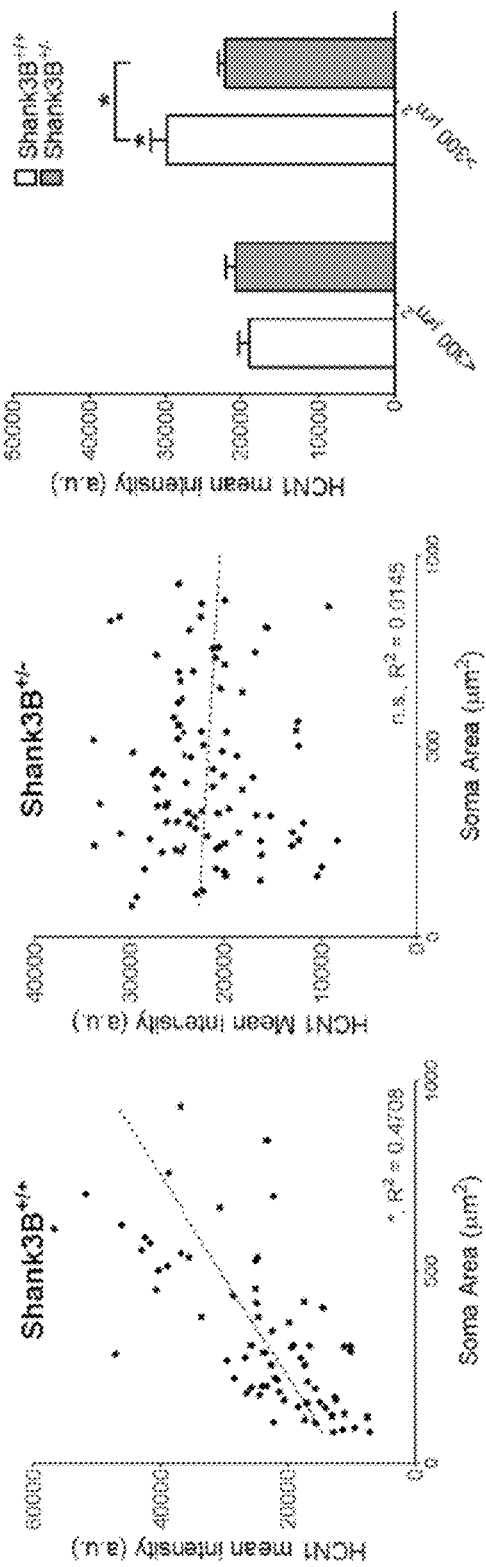

Fig. 27A
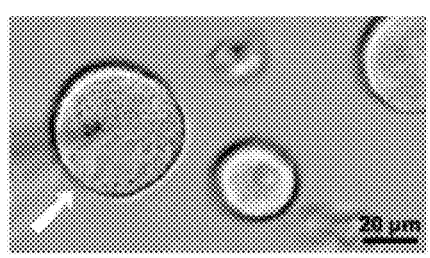
Fig. 27B  Protocol:
Fig. 27C  Shank3B+/+
Fig. 27D  Shank3B-/-
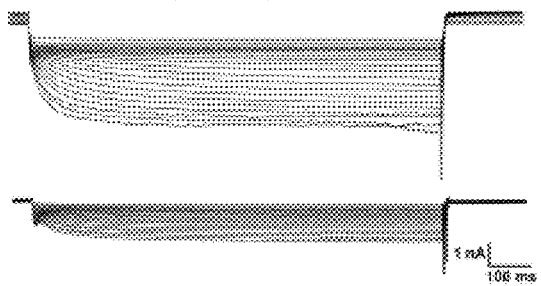
Fig. 27E
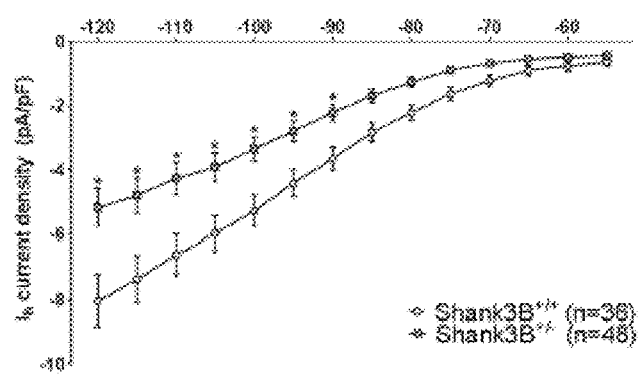

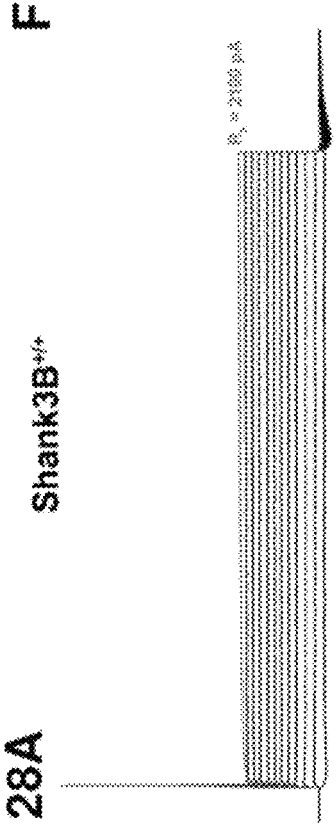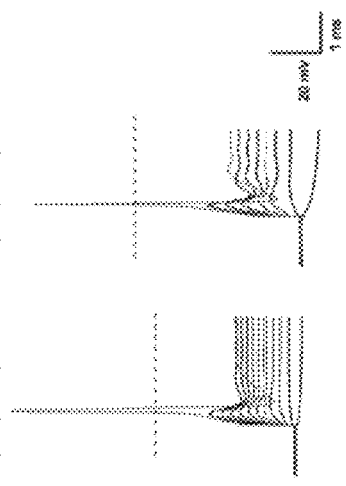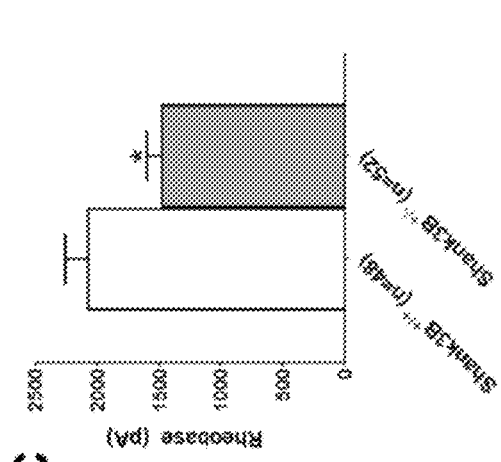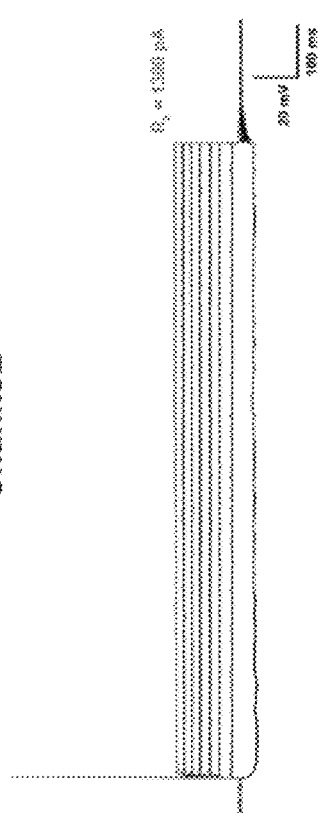
Fig. 28A      Fig. 28B      Fig. 28C Fig. 29A
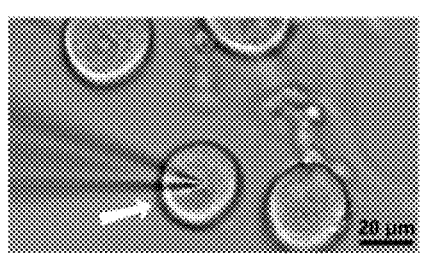
Fig. 29B Protocol:
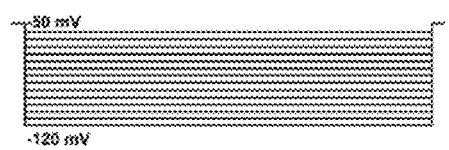
Fig. 29C Shank3B+/+
Fig. 29D Shank3B+/-
Fig. 29E
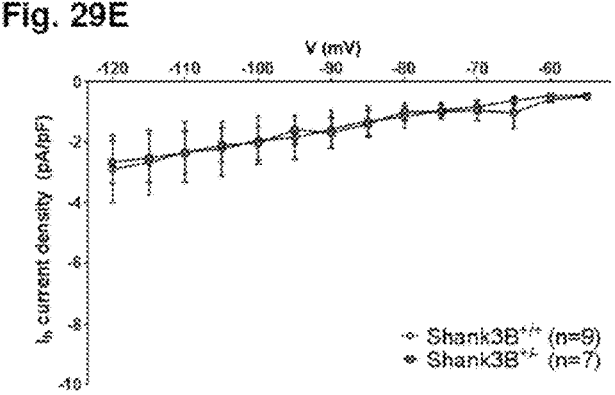

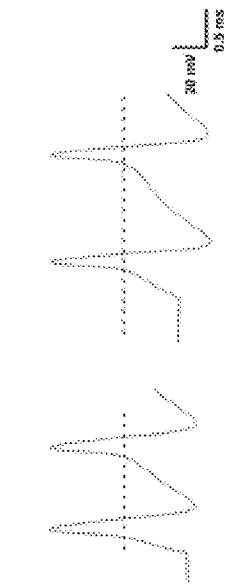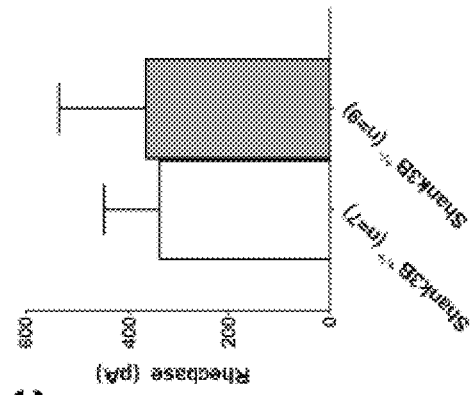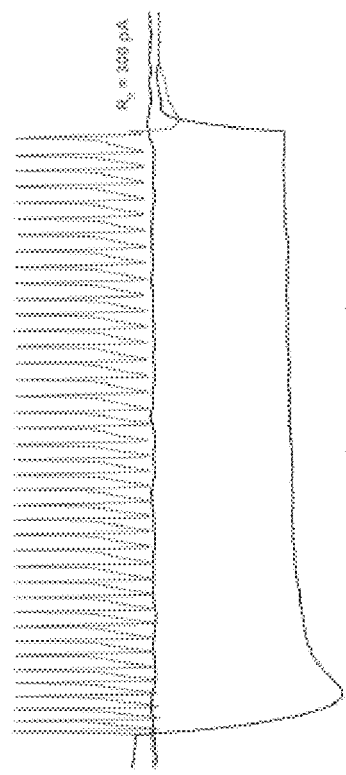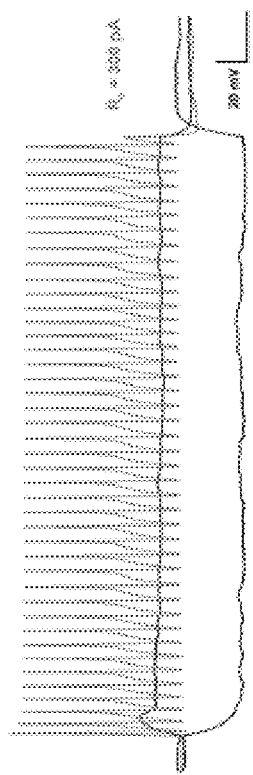
Fig. 30A  Fig. 30B  Fig. 30C

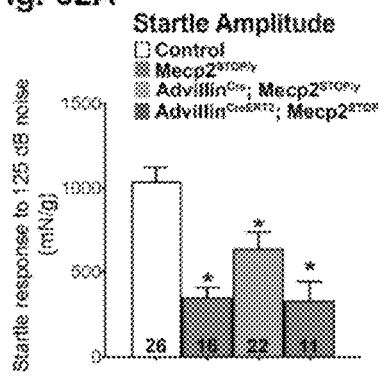
Fig. 32A Startle Amplitude
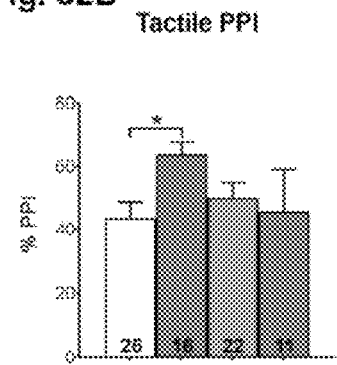
Fig. 32B Tactile PPI
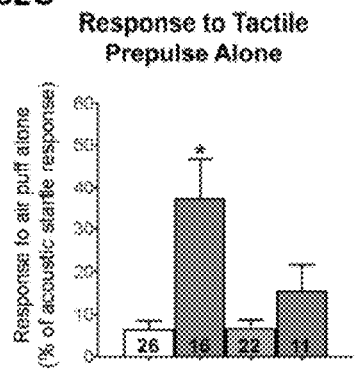
Fig. 32C Response to Tactile Prepulse Alone
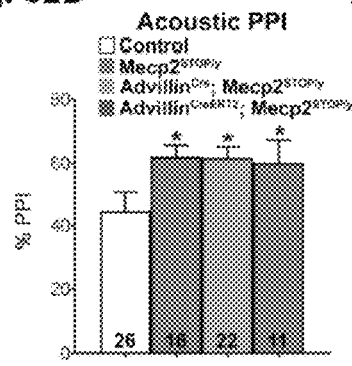
Fig. 32D Acoustic PPI
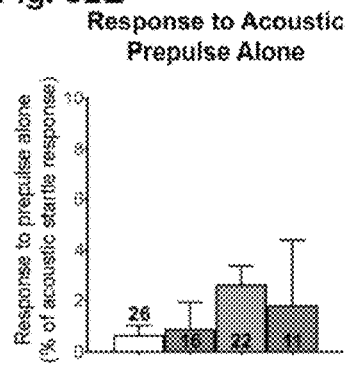
Fig. 32E Response to Acoustic Prepulse Alone
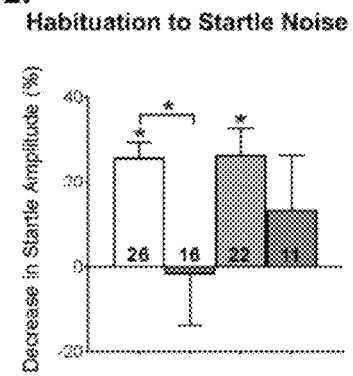
Fig. 32F Habituation to Startle Noise

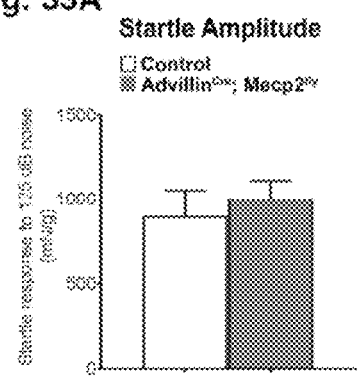 Fig. 33A Startle Amplitude
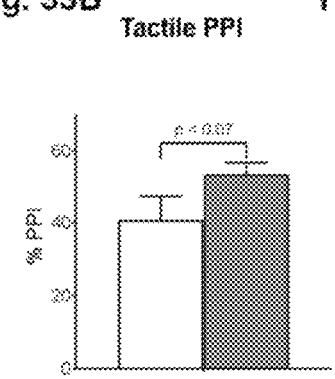 Fig. 33B Tactile PPI
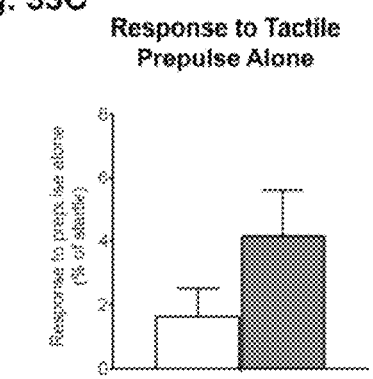 Fig. 33C Response to Tactile Prepulse Alone
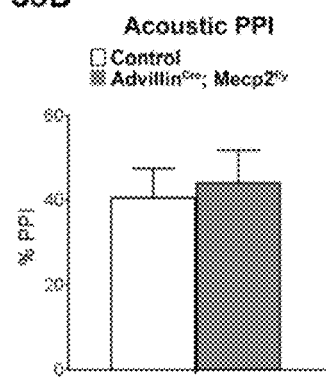 Fig. 33D Acoustic PPI
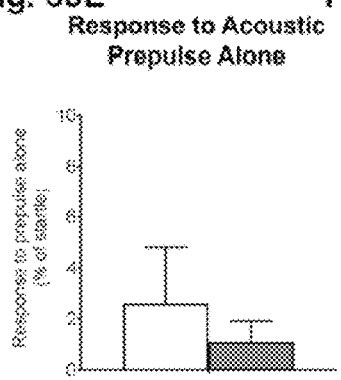 Fig. 33E Response to Acoustic Prepulse Alone
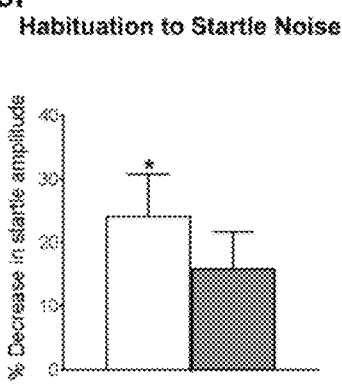 Fig. 33F Habituation to Startle Noise

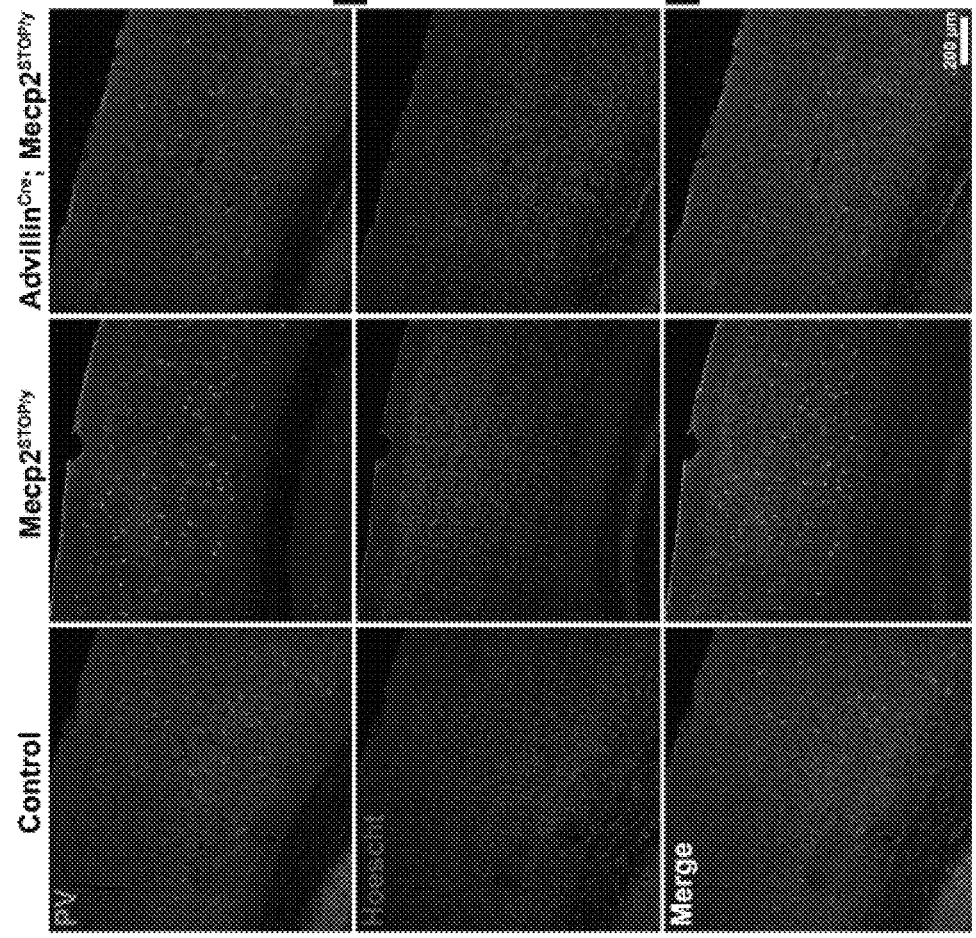

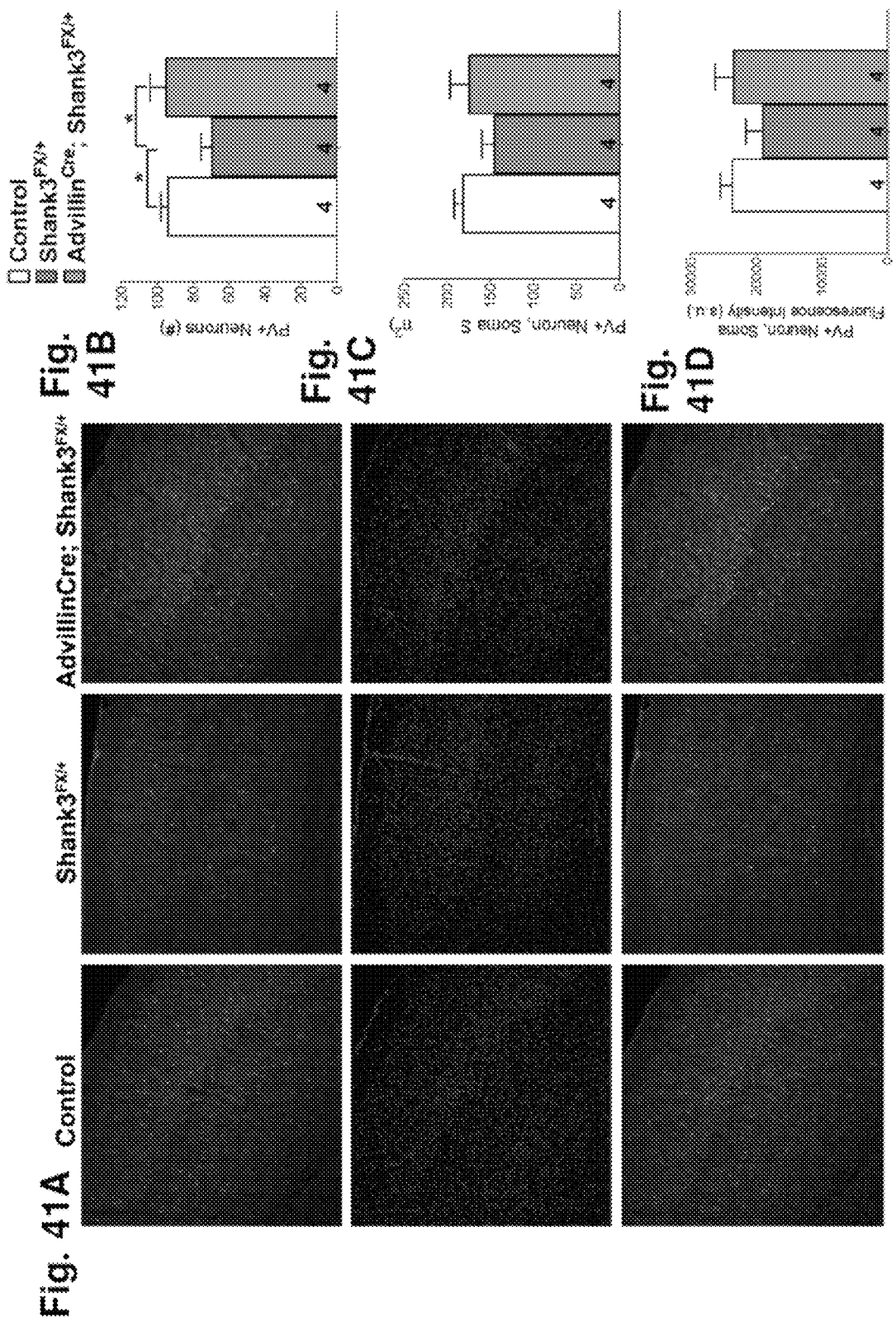

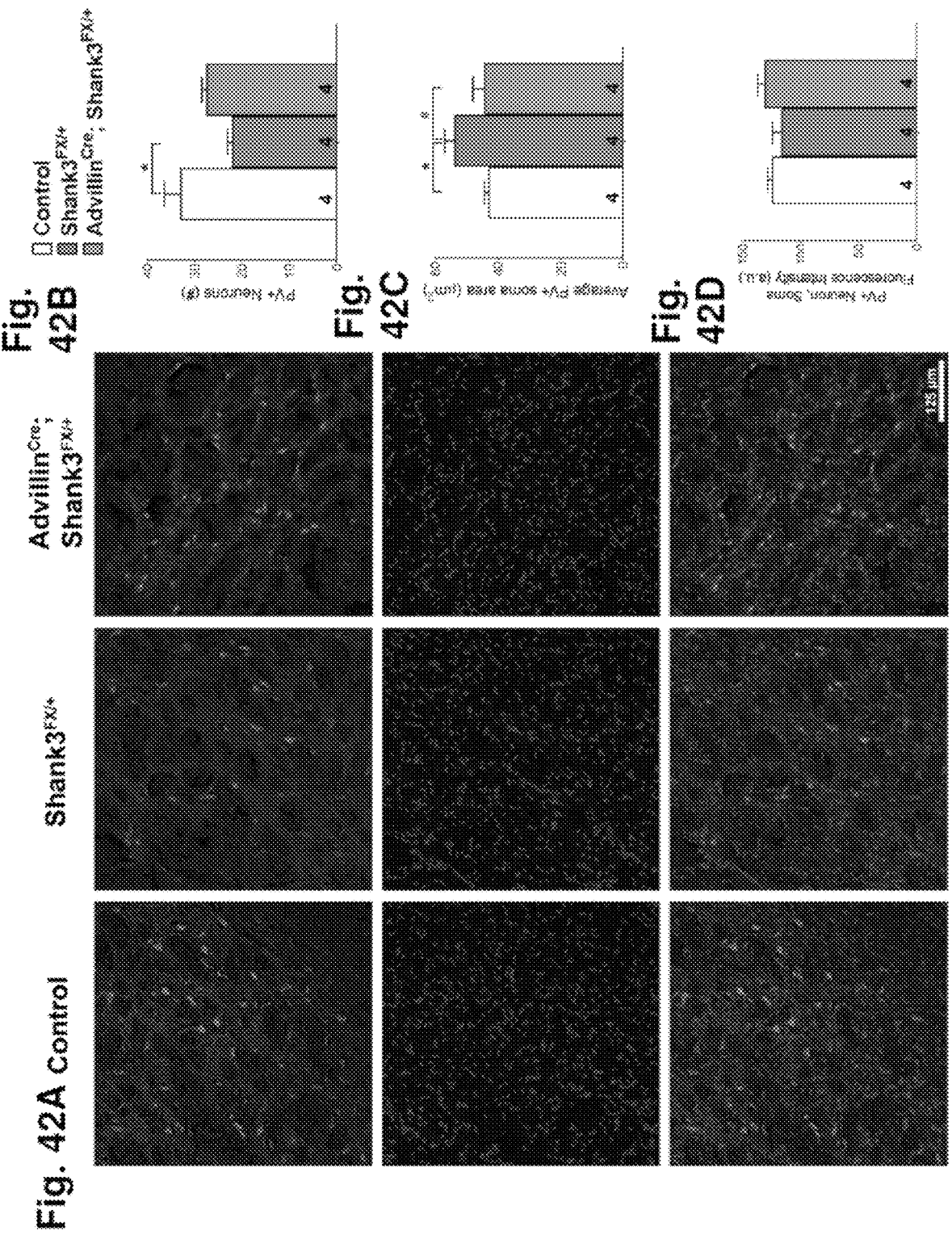

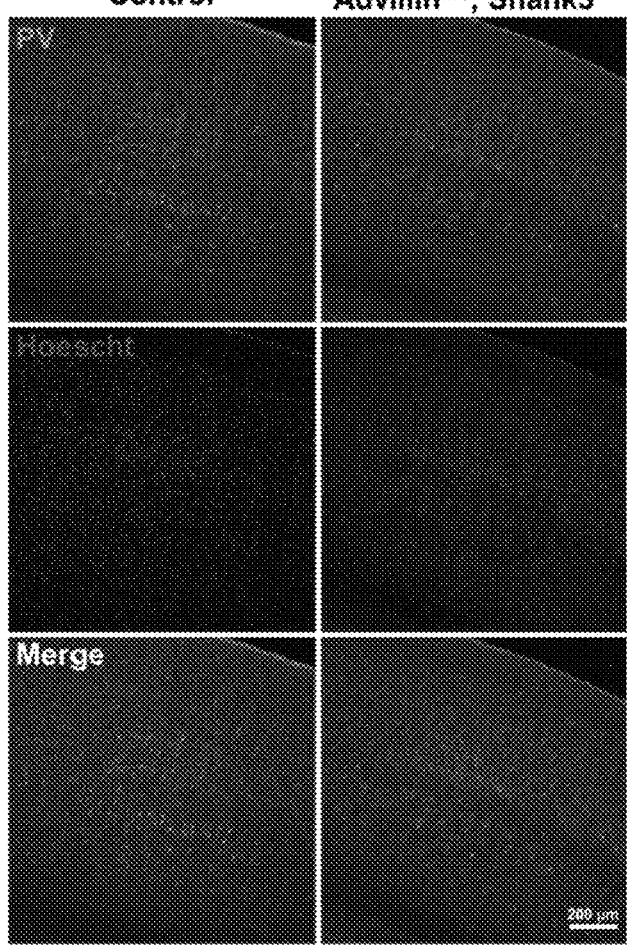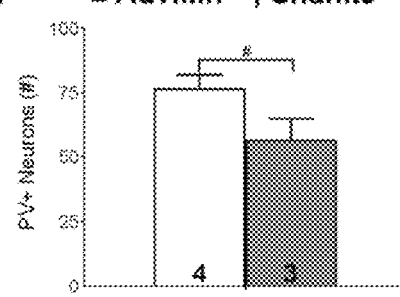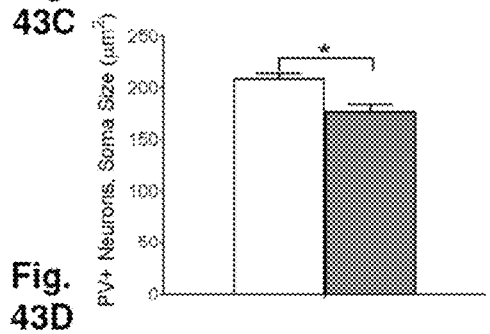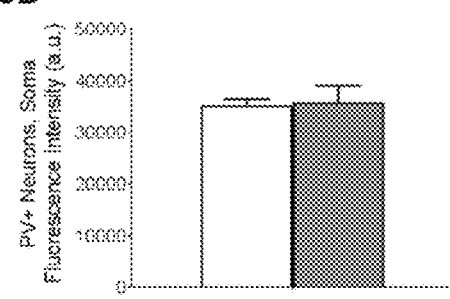

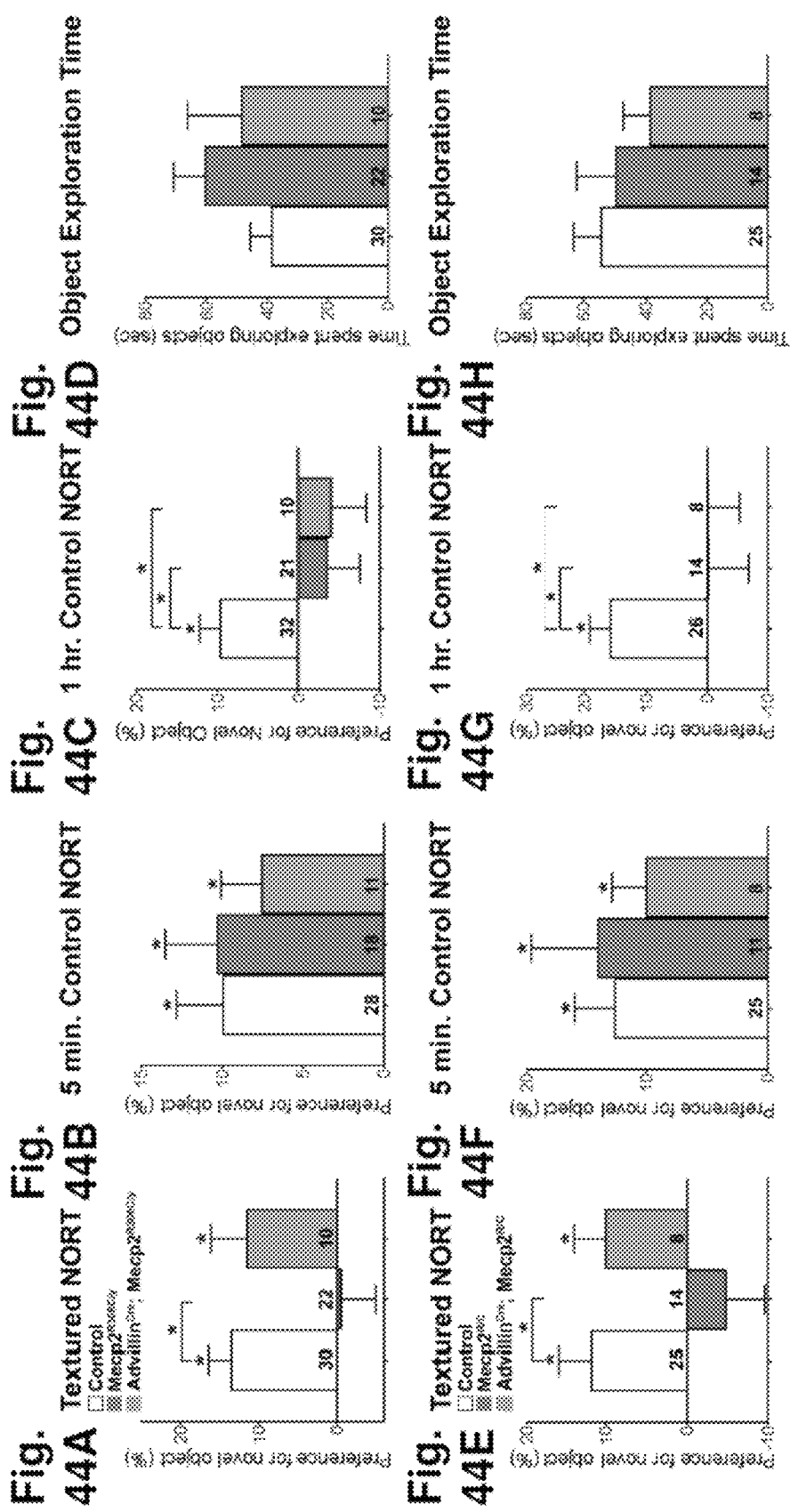

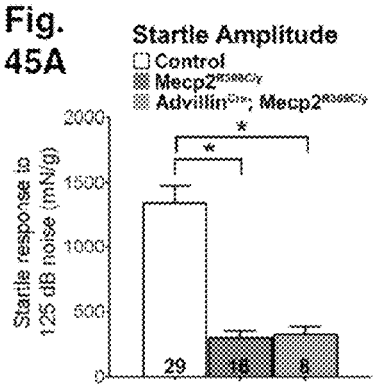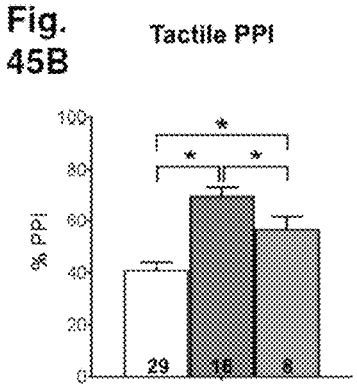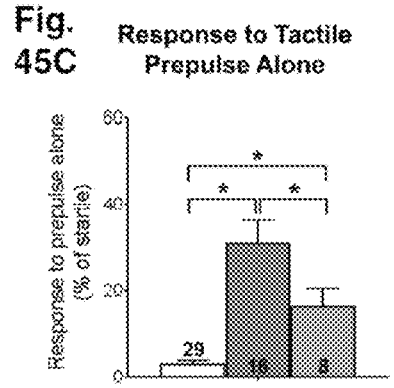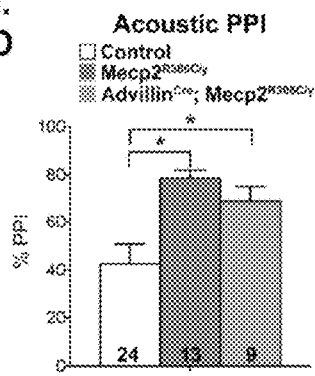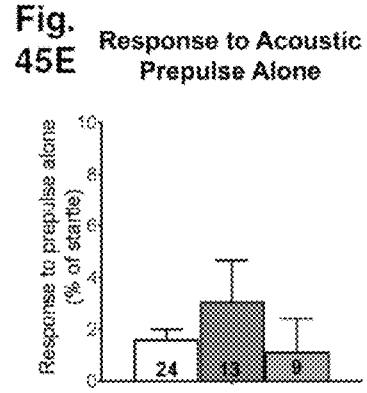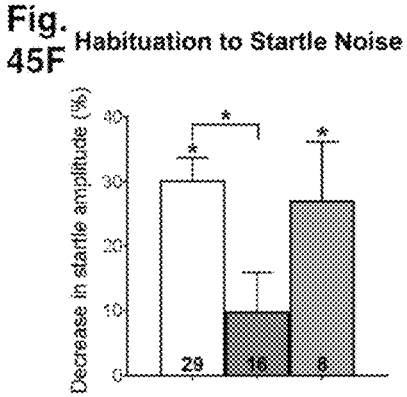

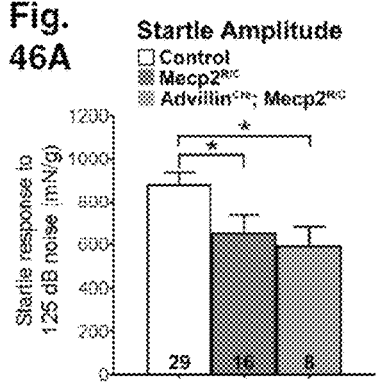
Fig. 46A Startle Amplitude
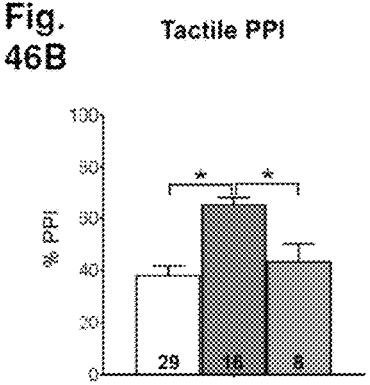
Fig. 46B Tactile PPI
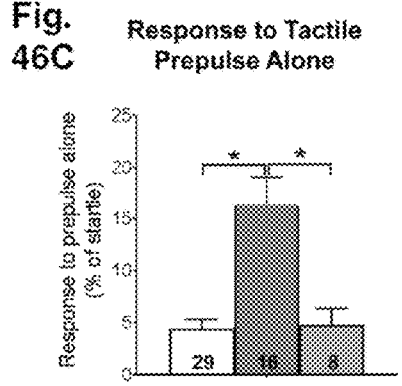
Fig. 46C Response to Tactile Prepulse Alone
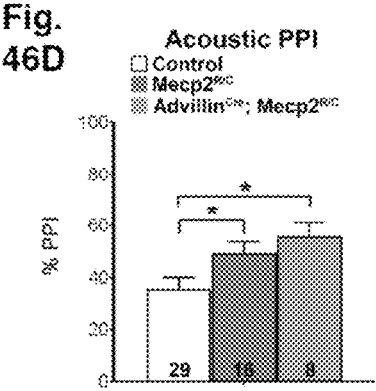
Fig. 46D Acoustic PPI
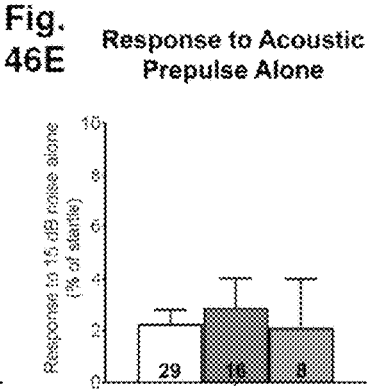
Fig. 46E Response to Acoustic Prepulse Alone
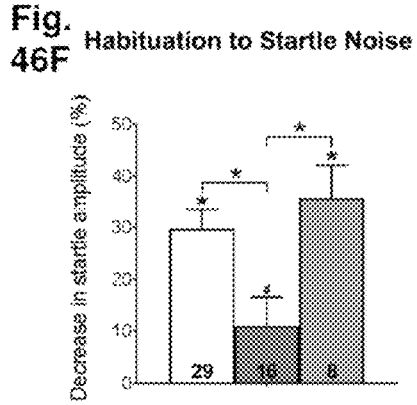
Fig. 46F Habituation to Startle Noise

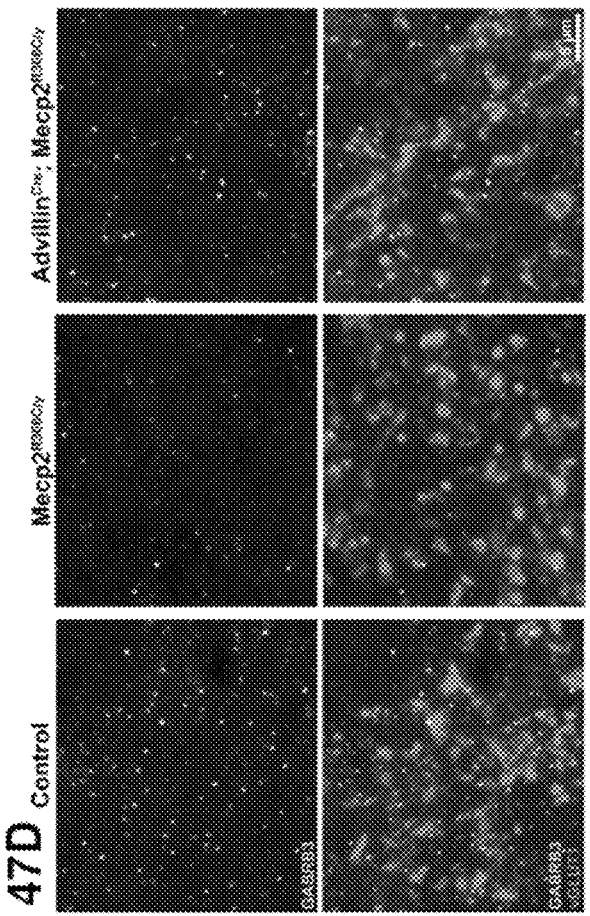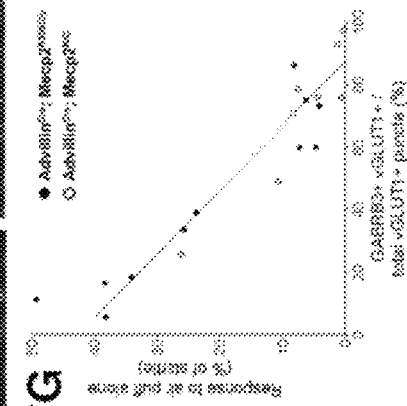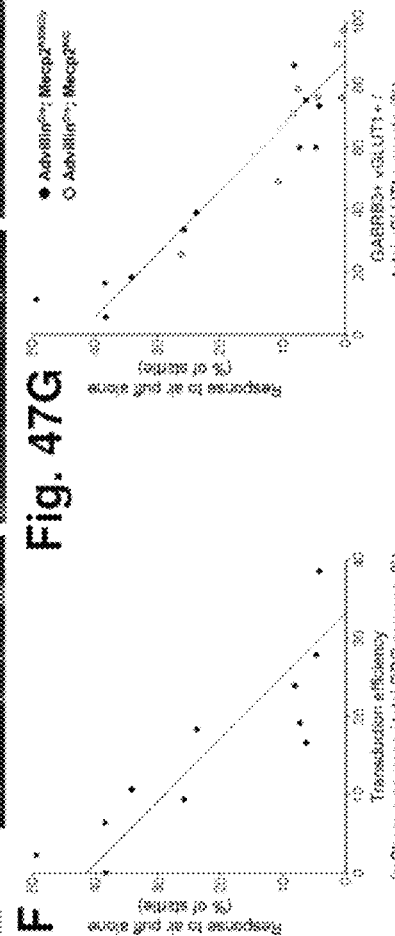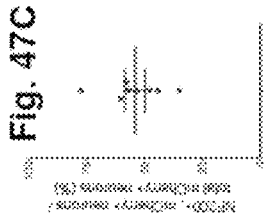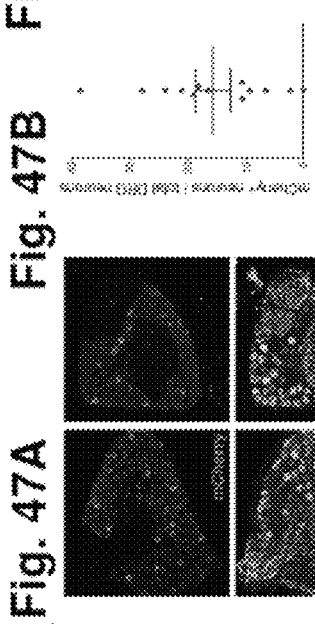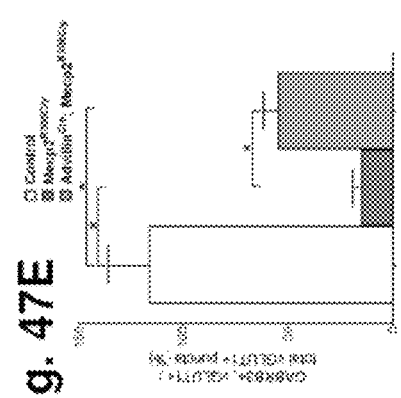
Fig. 47A  Fig. 47B  Fig. 47C  Fig. 47D  Fig. 47E  Fig. 47F  Fig. 47G Fig. 48A Control    Mecp2$^{R306C/y}$    Advillin$^{Cre}$; Mecp2$^{R306C/y}$
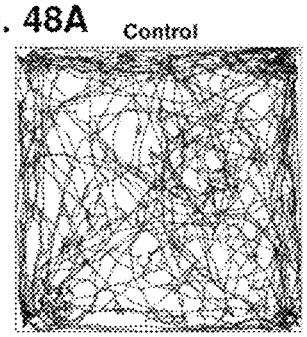 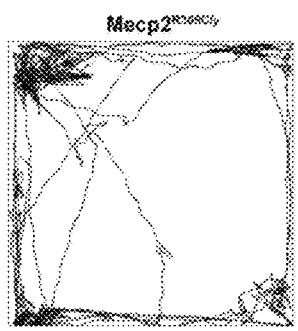 
Fig. 48B □ Control ▨ Mecp2$^{R306C/y}$ ▨ Advillin$^{Cre}$; Mecp2$^{R306C/y}$ (P5 Virus)
Fig. 48C
Fig. 48D Elevated Plus Maze
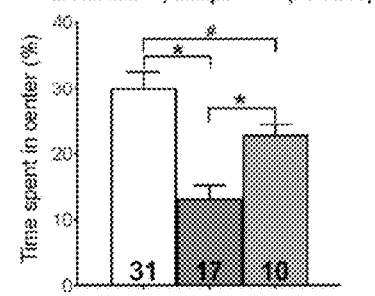 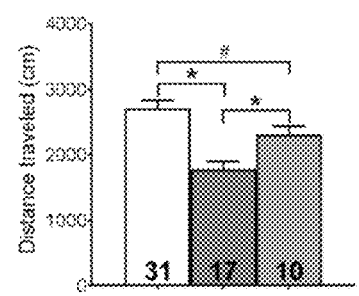 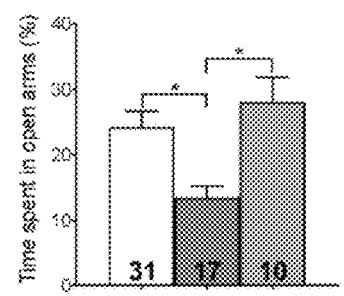

Fig. 49A
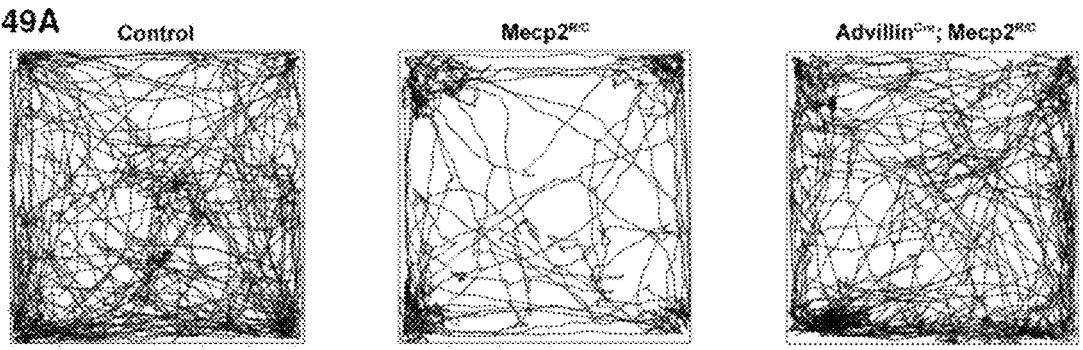
Control      Mecp2^{R/C}      Advillin^{Cre}; Mecp2^{R/C}

Fig. 49D Elevated Plus Maze 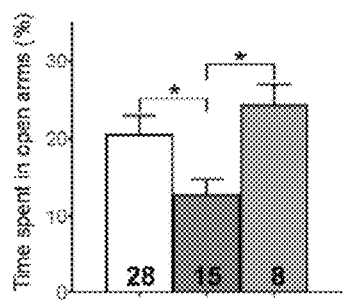

□ Control
▨ Mecp2^{R/C}
▨ Advillin^{Cre}; Mecp2^{R/C} (P5 Virus)

METHODS AND COMPOSITIONS FOR REDUCING TACTILE DYSFUNCTION AND ANXIETY ASSOCIATED WITH AUTISM SPECTRUM DISORDER, RETT SYNDROME, AND FRAGILE X SYNDROME

Related Applications

This application is a continuation of and claims priority under 35 U.S.C. § 120 to U.S. Patent Application, U.S. Ser. No. 16/308,422, filed Dec. 7, 2018, which is a national stage filing under 35 U.S.C. § 371 of international PCT application, PCT/US2017/036621, filed Jun. 8, 2017, which claims priority under 35 U.S.C. § 119(e) to U.S. Provisional Application, U.S. Ser. No. 62/421,807, filed on Nov. 14, 2016, and to U.S. Provisional Application, U.S. Ser. No. 62/347,260, filed on Jun. 8, 2016, each of which is incorporated herein by reference in its entirety.

GOVERNMENT SUPPORT

This invention was made with government support under NS007484 and NS034814 and DE022750 awarded by National Institutes of Health (NIH). The government has certain rights in this invention.

BACKGROUND OF THE INVENTION

Autism spectrum disorders (ASD) are a highly prevalent class of neurodevelopmental disorders characterized by impairments in social communication and interactions, as well as restricted and repetitive behaviors. 95% of individuals with ASD also exhibit aberrant reactivity to sensory stimuli, including tactile stimuli. A majority of ASD patients (60.9%) report altered tactile sensitivity in both glabrous (smooth) and hairy skin, and increased sensitivity to vibration and thermal pain. As with idiopathic or non-syndromic ASD, pervasive developmental disorders that cause syndromic forms of ASD are also associated with altered somatosensation. For example, tactile hypersensitivity is common in patients with Rett Syndrome, which is caused by mutations in the X-linked methyl-CpG-binding protein 2 (Mecp2) gene. Similarly, abnormalities in tactile perception are observed in patients with Fragile X syndrome, which is highly associated with ASD and caused by mutations in Fmr1. There is an inverse correlation between the presence of ASD traits in human subjects and their neural responses to C-low-threshold mechanoreceptor (LTMR)-targeted affective touch.

SUMMARY OF THE INVENTION

In one aspect, the invention features a method of reducing tactile dysfunction in a subject diagnosed with ASD, Rett Syndrome (RTT), or Fragile X Syndrome, by administering a $GABA_A$ agent having reduced blood brain barrier permeability.

In another aspect, the invention features a method for reducing anxiety in a subject diagnosed with ASD, RTT, or Fragile X Syndrome by administering a $GABA_A$ agent having reduced blood brain barrier permeability.

In some embodiments of either aspect, the $GABA_A$ agent is an agonist selected from the group consisting of isoguvacine, N-methyl isoguvacine, isoguvacine hydrochloride, homotaurine, acetylaminopropane sulfonate, acetylaminopropane sulfonate salt, homohypotaurine, β-guanidinopropionic acid, TACA, trans-amino-4-crotonic acid, trans-aminocyclopentane-3-3carboxylic acid, or GABA.

In some embodiments of either aspect, the $GABA_A$ agent is a positive allosteric modulator selected from the group consisting of 4,5,6,7-tetrahydroisoxazolo[5,4-c]pyridine-3-ol (THIP), TCS 1205, 5-nitro-alpha-oxo-N-(1R)-phenylethyl]-1H-indole-3-acetamide, 5-oxo-zaleplon, homo-6-proline, Isonipecotic acid, tiagabine, ZAPA, 3-((aminoiminomethyl)thio)-2-propenoic acid, ZAPA sulfate, L-838,417, THIP hydrochloride, TP 003 (5-fluoro-2-[4-fluoro-3-[8-fluoro-7-(2-hydroxypropan-2-y0imidazo[1,2-a]pyridin-3-yl]phenyl]benzonitrile), stiripentol, or loreclezole [1-[(Z)-2-chloro-2-(2,4-dichlorophenyl)vinyl]-1H-1,2,4-triazole].

In some embodiments, the $GABA_A$ agent is THIP, a salt of THIP, a functional analog of THIP, or a salt of a functional analog of THIP. As used herein, functional analogs of THIP are compounds that share certain chemical structural features with THIP but comprise one or more structural differences. Functional analogs of THIP exhibit the same general biological activity as THIP but may exhibit such activity to a different extent.

For example, in some embodiments, the $GABA_A$ agent is an agonist having Formula (I):

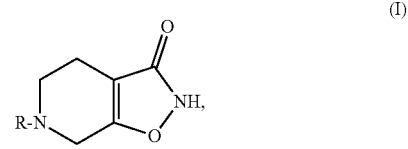

where R is selected from the group consisting of hydrogen, acetyl, or a group of the general Formula (Ia):

where R' is $C_1$-$C_8$ alkyl, phenyl, phenyl substituted in the 4 position with halogen, $C_1$-$C_4$ alkoxy, or $C_1$-$C_4$ alkyl; or phenylalkyl such as benzyl or phenylethyl in which the phenyl group may be substituted in the 4-position with halogen, $C_1$-$C_4$ alkoxy, or $C_1$-$C_4$ alkyl; and salts thereof. The compounds of Formula (I) may exist in tautomeric form, as shown in Formula (I'):

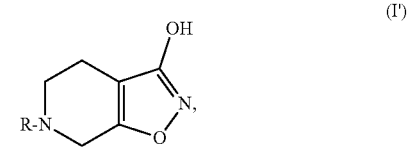

where Formula I is to be understood as covering tautomeric form (I') and mixtures of the two tautomeric forms.

In another aspect, the invention features a method of reducing tactile dysfunction or reducing anxiety in a subject diagnosed with ASD, RTT, or Fragile X Syndrome by expressing a nucleic acid encoding an exogenous alpha or beta subunit of a $GABA_A$ receptor in dorsal root ganglion (DRG) neurons in the subject.

In some embodiments of this aspect, the nucleic acid is expressed using an AAV vector or a lentiviral vector. In specific embodiments, the nucleic acid is expressed using an AAV 2/9 vector. In other embodiments, the nucleic acid is operably linked to a neuron specific promoter. In specific embodiments, the neuron-specific promoter is a DRG-specific promoter. In certain embodiments, the promoter is an advillin, synapsin I, mouse calcium/calmodulin-dependent protein kinase II, tubulin alpha I, neuron-specific enolase, platelet-derived growth factor-beta chain promoter (PDGF β), neurofilament, receptor tyrosine kinase (RET), G-protein-coupled receptor MRGPRB4, tyrosine-hydroxylase (TH), tropomyosin receptor kinase B (TrkB), or tropomyosin receptor kinase C. In other embodiments, the nucleic acid is an mRNA. In specific embodiments, the subunit is β1, β2, β3, α1, α2, α3, α4, α5, or α6.

In some embodiments, the method features expressing a first nucleic acid encoding an exogenous alpha subunit of a $GABA_A$ receptor and a second nucleic acid encoding an exogenous beta subunit of a $GABA_A$ receptor. In certain embodiments, the subunit compositions are as follows: (i) α1, β3, γ2; (ii) α2, β3, γ2; (iii) α3, β3, γ2; (iv) α4, β3, γ2; (v) α5, β3, γ2; (vi) α6, β3, γ2; (vii) α1, β1, γ2; (viii) α1, β2, γ2; (ix) α4, β3; (x) α4, β3, δ; (xi) α6, β3; (xii) α6, β3, δ; (xiii) α1, β2; (xiv) α3, β3; (xv) α1, β2, δ; (xvi) α4, β2, δ; (xvii) α3, β3, ⊖; or (xviii) α3, β3, ε. In some embodiments, the nucleic acid is administered via intrathecal delivery or intraperitoneal delivery.

In another aspect, the invention features a gene therapy vector encoding an alpha or beta subunit operably linked to a promoter for expression in DRG neurons. In some embodiments, the vector is AAV. In other embodiments, the vector is AAV 2/9.

In another aspect, the invention features a method of reducing tactile dysfunction in a subject diagnosed with ASD, Rett Syndrome (RTT), or Fragile X Syndrome, by administering a HCN agonist.

In another aspect, the invention features a method for reducing anxiety in a subject diagnosed with ASD, RTT, or Fragile X Syndrome by administering an HCN agonist.

In some embodiments of either aspect, the HCN agonist is lamotrigine or gabapentin.

In some embodiments of either aspect, the HCN agonist is an HCN1 agonist. The term "reducing" means treating or decreasing the symptoms of patients diagnosed with ASD, Rett Syndrome, or Fragile X Syndrome.

The term "tactile dysfunction" refers to exhibiting symptoms such as withdrawing when being touched, refusing to eat certain 'textured' foods and/or to wear certain types of clothing, complaining about having hair or face washed, avoiding getting hands dirty (e.g., glue, sand, mud, fingerpaint), and using finger tips rather than whole hands to manipulate objects. Tactile dysfunction may lead to a misperception of touch and/or pain (hyper- or hyposensitive) and may lead to self-imposed isolation, general irritability, distractibility, and hyperactivity.

The term "Autism Spectrum Disorder (ASD)" refers to a heterogeneous group of neurodevelopmental disorders as classified in the fifth revision of the American Psychiatric Association's Diagnostic and Statistical Manual of Mental Disorders $5^{th}$ edition (DSM-5). The DSM-5 redefined the autism spectrum to encompass the prior (DSM-IV-TR) diagnosis of autism, Asperger syndrome, pervasive developmental disorder not otherwise specified, childhood disintegrative disorder, and Rett syndrome. The autism spectrum disorders are characterized by social deficits and communication difficulties, stereotyped or repetitive behaviors and interests, and in some cases, cognitive delays. For example, an ASD is defined in the DSM-5 as exhibiting (i) deficits in social communication and interaction not caused by general developmental delays (must exhibit three criteria including deficits in social-emotional reciprocity, deficits in nonverbal communication, and deficits in creating and maintaining relationships appropriate to developmental level), (ii) demonstration of restricted and repetitive patterns of behavior, interest or activities (must exhibit two of the following four criteria: repetitive speech, repetitive motor movements or repetitive use of objects, adherence to routines, ritualized patterns of verbal or nonverbal, or strong resistance to change, fixated interests that are abnormally intense of focus, and over or under reactivity to sensory input or abnormal interest in sensory aspects of environment), (iii) symptoms must be present in early childhood, and (iv) symptoms collectively limit and hinder everyday functioning. The term "ASD" is also contemplated herein to include Dravet's syndrome and autistic-like behavior in non-human animals.

The term "Rett Syndrome" refers to an X-linked disorder which affects approximately one in ten-thousand girls. Patients go through four stages: Stage I) Following a period of apparently normal development from birth, the child begins to display social and communication deficits, similar to those seen in other autism spectrum disorders, between six and eighteen months of age. The child shows delays in their developmental milestones, particularly for motor ability, such as sitting and crawling. Stage II) Beginning between one and four years of age, the child goes through a period of regression in which they lose speech and motor abilities, developing stereotypical midline hand movements and gait impairments. Breathing irregularities, including apnea and hyperventilation also develop during this stage. Autistic symptoms are still prevalent at this stage. Stage III) Between age two and ten, the period of regression ends and symptoms plateau. Social and communication skills may show small improvements during this plateau period, which may last for most of the patients' lives. Stage IV) Motor ability and muscle deterioration continues. Many girls develop severe scoliosis and lose the ability to walk.

The term "Fragile X Syndrome" refers to an X chromosome-linked condition that is characterized by a visible constriction near the end of the X chromosome, at locus q27.3 that causes intellectual disability, behavioral and learning challenges and various physical characteristics Fragile X syndrome is the most common inherited form of mental retardation and developmental disability. Males with Fragile X syndrome usually have mental retardation and often exhibit characteristic physical features and behavior. Fragile X syndrome is characterized by behavior similar to autism and attention deficit disorder, obsessive-compulsive tendencies, hyperactivity, slow development of motor skills and anxiety fear disorder. When these disabilities are severe and occur simultaneously, the condition is sometimes described as autism, and may be associated with any degree of intelligence. Other characteristics are a likable, happy, friendly personality with a limited number of autistic-like features such as hand-flapping, finding direct eye contact unpleasant, and some speech and language problems. Physical features may include large ears, long face, soft skin and large testicles (called "macroorchidism") in post-pubertal males. Connective tissue problems may include ear infections, flat feet, high arched palate, double-jointed fingers and hyper-flexible joints.

The term "blood brain barrier" refers to a transvascular permeability barrier that tightly controls entry of substances into the brain. The capillaries that perfuse the brain are lined with special endothelial cells that lack fenestrations and are sealed by endothelial tight junctions. The tight endothelium provides a physical barrier that together with metabolic barriers forms the basis of the BBB.

The term "reduced permeability" refers to peripherally acting compositions of $GABA_A$ agents that are less able to cross the blood brain barrier.

The term "anxiety" refers to an emotion characterized by feelings of tension, worried thoughts and physical changes like increased blood pressure. Anxiety can be characterized by having recurring intrusive thoughts or concerns, avoiding certain situations out of worry, and physical symptoms such as sweating, trembling, dizziness or a rapid heartbeat.

The term "nucleic acid" refers to an oligonucleotide, nucleotide, or polynucleotide, and fragments or portions thereof, and to DNA or RNA of genomic or synthetic origin which may be single- or double-stranded, and represent the sense or antisense strand.

The term "exogenous" refers to a subunit of a $GABA_A$ receptor in DRG neurons that is exogenously introduced to the subject by way of a nucleic acid encoding the subunit.

The term "$GABA_A$ receptor" refers to a heterogeneous family of ligand-gated ion channels responsible for mediating inhibitory neurotransmission. These receptors are composed of five subunits that can belong to eight different subunit classes.

The term "$GABA_A$ agent" refers to an agent that increases GABAergic signaling by opening of the GABA receptor chloride channel thereby inducing hyperpolarization of the post-synaptic neuron. In some embodiments, the agent is a $GABA_A$ receptor agonist. In other embodiments, the agent is a positive allosteric modulator of the $GABA_A$ receptor.

The term "agonist" refers to an agent that binds to a receptor (e.g., the GABA receptor) and thereby alters the proportion of receptors in the active conformation, resulting in a biologic response, for example, by increasing the frequency of opening of the GABA chloride channel resulting in an increase of the chloride ion conductance of the post-synaptic membrane to produce an inhibition of neuronal firing. A full agonist results in a maximal response by occupying all or a fraction of receptors. A partial agonist results in less than a maximal response even when the drug occupies all of the receptors.

The term "positive allosteric modulator" refers to an agent that binds a receptor (e.g., the $GABA_A$ receptor), at a site other than that bound by the natural ligand (e.g., GABA) and enhances the activity of the receptor in response to the natural ligand e.g., GABA, for example, by increasing the frequency of opening of the GABA chloride channel. A positive allosteric modulator need not activate the chloride channel of the GABA receptor directly (e.g., does not substitute for the neurotransmitter GABA), but rather allosterically enhances the effects of GABA at the receptor level.

The term "alpha ($\alpha$) subunit" refers to a type of the $GABA_A$ receptor subunit isoform. Alpha subunit isoforms include alpha 1, alpha 2, alpha 3, alpha 4, alpha 5, and alpha 6.

The term "beta ($\beta$) subunit" refers to a type of the $GABA_A$ receptor subunit isoform. Beta subunit isoforms include beta 1, beta 2, and beta 3.

The term "gamma ($\gamma$) subunit" refers to a type of the $GABA_A$ receptor subunit isoform. Gamma subunits include gamma 1, gamma 2, and gamma 3.

The term "theta ($\theta$) subunit" refers to a type of the $GABA_A$ receptor subunit.

The term "sigma ($\delta$) subunit" refers to a type of the $GABA_A$ receptor subunit isoform.

The term "epsilon ($\epsilon$) subunit" refers to a type of the $GABA_A$ receptor subunit isoform.

The term "neuron-specific promoter" means that the promoter includes at least one nucleotide sequence capable of activating neuronal cell specific expression of operably linked sequences.

The term "operably linked" refers to a physical or functional juxtaposition of the components so described as to permit them to function in their intended manner. More specifically, for example, two DNA sequences operably linked means that the two DNAs are arranged (cis or trans) in such a relationship that at least one of the DNA sequences is able to exert a physiological effect upon the other sequence. For example, a muscle-specific promoter can be operably linked with a gene to promote neuron-specific transcription of the gene.

The term "vector" means any plasmid or virus encoding a nucleic acid. The vector may be a viral vector which is suitable as a delivery vehicle for delivery of a nucleic acid that encodes a protein of the invention, to the patient, or the vector may be a non-viral vector which is suitable for the same purpose. Examples of viral and non-viral vectors for delivery of DNA to cells and tissues are well known in the art. Examples of viral vectors include, but are not limited to, a recombinant adenovirus, a recombinant retrovirus, a recombinant adeno-associated virus, a recombinant avian pox virus, and the like. Examples of non-viral vectors include, but are not limited to, liposomes, polyamine derivatives of DNA, and the like.

The term "adeno-associated vector (AAV)" refers to a recombinantly produced virus or viral particle that comprises a polynucleotide to be delivered into a host cell, either in vivo, ex vivo or in vitro. AAV is a nonpathogenic human parvovirus which is commonly used for gene transfer in mammals. The AAV genome is built of single stranded DNA, and comprises inverted terminal repeats at both ends of the DNA strand, and two open reading frames: rep and cap, encoding replication and capsid 30 proteins, respectively. A foreign polynucleotide can replace the native rep and cap genes. AAVs can be made with a variety of different serotype capsids which have varying transduction profiles or as used herein "tropism" for different tissue types. Examples of AAV serotypes include but are not limited to AAV1, AAV2, AAV3, AAV4, AAV5, AAV6, AAV7, AAV8, AAV9, and AAVrh10. AAV vectors can be produced, for example, by triple transfection of subconfluent HEK293 cells by three plasmids: AAV cis-plasmid 35 containing the gene of interest, AAV trans-plasmid containing AAV rep and cap genes, and an adenovirus helper plasmid, for example, pDF6.

The term "LogP" is the partition coefficient reflecting the relative solubility of a drug in octanol versus water. The higher the value, the lower the water solubility. Generally a reduction in the LogP is associated with reduced permeability across the blood brain barrier. LogP can be predicted from the structure of a $GABA_A$ agent using standard physiochemical prediction software.

The term "polar surface area (PSA)" refers to the polar surface area of a molecule and is a reflection of the polarity of the molecule. Generally, higher PSA is associated with reduced permeability across the blood brain barrier. PSA can be predicted from the structure of a $GABA_A$ agent using standard physiochemical prediction software.

The term "freely rotatable bonds (FRBs)" refer to the number of freely rotatable bonds a $GABA_A$ agent has. A greater number of freely rotatable bonds generally correlates with lower blood brain permeability. FRB's can be determined from the structure of a $GABA_A$ agent using standard physiochemical prediction software.

The terms "effective amount" or "amount effective to" or "therapeutically effective amount" mean an amount of a $GABA_A$ agent of the invention sufficient to produce a desired result, for example, reducing tactile dysfunction or anxiety in a subject upon administration of a composition containing a $GABA_A$ agent having reduced BBB permeability. The increases and decreases related to administration an effective amount of a $GABA_A$ agent are relative to levels or symptoms, as applicable, in a subject that has not been administered a $GABA_A$ agent of the invention or relative to the subject prior to administration of a $GABA_A$ agent of the invention.

The term "intrathecal delivery" refers to an injection into the spinal canal.

The term "intraperitoneal delivery" refers to an injection into the peritoneum.

The term "subject," as used herein, refer to any animal (e.g., a mammal, e.g., a human). A subject to be treated according to the methods described herein may be one who has been diagnosed with a developmental disorder (e.g., ASD, Rett Syndrome, and Fragile X Syndrome) as having such a condition or one at risk of developing the condition. Diagnosis may be performed by any method or technique known in the art. One skilled in the art will understand that a subject to be treated according to the present invention may have been subjected to standard tests or may have been identified, without examination, as one at high risk due to the presence of one or more risk factors.

The term "pharmaceutical composition," as used herein, represents a composition containing a GABAA agent, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal administration (e.g., as a sterile preservative-free composition in a solvent system suitable for intrathecal use); or in any other formulation described herein.

The term "pharmaceutically acceptable excipient" or "pharmaceutically acceptable carrier," as used interchangeably herein, refers to any ingredient other than the $GABA_A$ agents described herein (e.g., a vehicle capable of suspending or dissolving the active $GABA_A$ agent) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene, calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P.H. Stahl and C.G. Wermuth), Wiley-VCH, 2008. The salts can be prepared in situ during the final isolation and purification of the $GABA_A$ agents by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

BRIEF DESCRIPTION OF THE DRAWINGS

FIGS. 1A-1K show mouse models of ASD exhibit aberrant innocuous touch sensitivity. FIG. 1A is an image showing a smooth textured object (left) and a rough textured object (right) used in the textured NORT. FIG. 1B is a schematic outlining the protocol for the three NORT assays. FIG. 1C is a graph showing the discrimination indices for textured NORT. A positive value indicates preference for the novel object, compared to the familiar object. *, p<0.05. FIG. 1D is a graph showing the discrimination indices for 5 minute control NORT. A positive value indicates preference for the novel object, compared to the familiar object. *, p<0.05. FIG. 1E is a graph showing the discrimination indices for 1 hour control NORT. A positive value indicates preference for the novel object, compared to the familiar object. *, p<0.05. FIG. 1F is a schematic showing the tactile PPI assay. FIG. 1G is a graph showing the response to a light air puff (0.9 PSI, 50 ms) applied to the back hairy skin, in either naïve mice or mice in which the back hairy skin was shaved and lidocaine was locally applied to block cutaneous sensory neuron activation. Responses are expressed as percent of startle response to a 125 dB noise. *, p<0.01. FIG. 1H is a graph showing the percent inhibition of the startle response to a 125 dB noise (pulse), when the startle noise was preceded by a light air puff (prepulse) at multiple interstimulus intervals (ISIs) between the prepulse and the pulse. [2-way ANOVA: P<0.001, $F(1,65)=51.27$] Post-hoc Bonferroni test: *, p<0.05. FIG. 1I is a graph showing the magnitude of startle response to a 125 dB noise in mutant mice and control littermates. *, p<0.001. FIG. 1J is a graph showing the percent inhibition of the startle response to a 125 dB noise, when the startle noise is preceded by a light air puff (250 ms ISI). *, p<0.05. FIG. 1K is a graph showing the response to a light air puff alone, in mutant mice and control littermates. Responses are expressed as percent of startle response to a 125 dB noise. *, p<0.05.

FIGS. 2A-2H show Mecp2 expression in primary somatosensory neurons is required for normal tactile behaviors. FIG. 2A is a series of IHC images of DRG, transverse SC or trunk primary somatosensory cortex (Brain) showing Mecp2 protein expression in control mice or mice with conditional deletion of Mecp2 generated by crossing an Mecp2 floxed mouse line to various Cre recombinase mouse lines, as indicated. IB4 labels lamina IIi of the dorsal horn. FIG. 2B is a series of Kaplan-Meier curves showing the percentage of mutant mice in each line surviving up to 40 weeks of age. FIGS. 2C is a graph showing discrimination indices for textured NORT in mutant mice and control littermates. *, p<0.05. FIG. 2D is a graph showing discrimination indices for 5 minute control NORT in mutant mice and control littermates. *, p<0.05. FIG. 2E is a graph showing discrimination indices for 1 hour control NORT in mutant mice and control littermates. *, p<0.05. FIG. 2F is a graph showing the magnitude of startle response to a 125 dB noise. *, p<0.05. FIG. 2G is a graph showing the percent inhibition of the startle response to a 125 dB noise, when the startle noise was preceded by a light air puff (250 ms ISI). *, p<0.05. FIG. 2H is a graph showing the response to a light air puff alone. *, p<0.05.

FIGS. 3A-3K show sensory neuron deletion of Mecp2 causes a decrease in GABRB3 puncta associated with sensory neuron terminals in the SC, and Gabrb3 in primary somatosensory neurons is required for tactile sensitivity. FIG. 3A is a series of IHC images of SC dorsal horn lamina III from Ai34 (Rosa26$^{LSL-Synaptophysin-tdTomato}$) mice crossed to Ret$^{CreERT2}$, TrkB$^{CreERT2}$ mice, to label Aβ RAI-LTMRs, Aβ Field- and Aβ SAI-LTMRs, or Aδ-LTMRs, respectively. Sections were immunostained for tdTOMATO (TOMATO) and GABRB3 to mark the presence of GABRB3 puncta in proximity to Aβ- and Aδ-LTMR presynaptic terminals. FIG. 3B is a series of IHC images of SC dorsal horn lamina III from Mecp2$^{-/y}$ mutant mice and control littermates, co-labeled for vGLUT1 (presynaptic terminals for Aβ and Aδ LTMRs) and GABRB3 to mark the presence of GABRB3 puncta at Aβ and Aδ LTMR presynaptic terminals. FIG. 3C is a graph showing the quantification of vGLUT1+puncta co-labeled with GABRB3, relative to the total number of vGLUT1+puncta visualized per image. *, p<0.001. FIG. 3D is a series of IHC images of SC dorsal horn lamina III from Advillin$^{Cre}$; Mecp2$^{f/y}$ mutant mice and control littermates, co-labeled for vGLUT1 and GABRB3 to mark the presence of GABRB3 puncta at Aβ and Aδ LTMR presynaptic terminals. FIG. 3E is a graph showing the quantification of vGLUT1+puncta co-labeled with GABRB3, relative to the total number of vGLUT1+ puncta visualized per image. *, p<0.001. FIG. 3F is a graph showing the discrimination index for textured NORT. *, p<0.05. For Advillin$^{CR}$ group: [1-way ANOVA: P<0.001, F(2,29)=7.287] Post-hoc Bonferroni's test: *, p<0.05. FIG. 3G is a graph showing the discrimination index for 5 minute control NORT. FIG. 3H is a graph showing the discrimination index for 1 hour control NORT. *, p<0.05. FIG. 3I is a graph showing the magnitude of startle response to a 125 dB noise. FIG. 3J is a graph showing the percent inhibition of the startle response to a 125 dB noise, when the startle noise was preceded by a light air puff (250 ms ISI). *, p<0.05. For Advillin$^{Cre}$ group: [1-way ANOVA: P<0.001, F(2,33)=7.238] Post-hoc Tukey's test: *, p<0.05. FIG. 3K is a graph showing the response to a light air puff alone. *, p<0.05. For Advillin$^{Cre}$ group: [1-way ANOVA: P<0.05, F(2,33)=4.821] Post-hoc Tukey's test:*, p<0.05.

FIGS. 4A-4H show primary somatosensory neuron deletion of either Mecp2 or Gabrb3 induces A-fiber synapse hyperexcitability. FIG. 4A is a diagram depicting whole-cell patch clamp recording configuration of PSDC projection neurons while stimulating dorsal roots. FIG. 4B is a schematic showing representative quantal EPSC (qEPSC) traces from SC slices of control mice. FIG. 4C is a schematic showing representative qEPSC traces from SC slices of Advillin$^{Cre}$; Mecp2$^{f/y}$ mutant mice. FIG. 4D is a schematic showing representative qEPSC traces from SC slices of Advillin$^{Cre}$; Gabrb3$^{f/+}$ mutant mice. FIG. 4E is a bar graph showing the mean frequency of qEPSCs recorded from SC slices of control or mutant mice. [1-way ANOVA: P<0.0001, F(2,15)=20.8] Post-hoc Tukey's test: *, p<0.001. FIG. 4F is a graph showing the cumulative probability for inter-event interval of qEPSCs recorded from SC slices of control or mutant mice. [Kruskal-Wallis test: P<0.0001, H=864.1] Post-hoc Dunn's test: all three groups significantly different, p<0.0001. FIG. 4G is a bar graph showing the mean amplitude of qEPSCs recorded from SC slices of control or mutant mice. FIG. 4H is a graph showing the cumulative probability of qEPSCs recorded from SC slices of control or mutant mice.

FIGS. 5A-5G show primary somatosensory neuron deletion of either Mecp2 or Gabrb3 leads to loss of PSI in the SC dorsal horn. FIG. 5A is a schematic showing the recording configuration, with location of 3 recording electrodes and one stimulating electrode. FIG. 5B is a series of traces representing an average of 10 sweeps, low pass filtered at 1 kHz showing bicuculline inhibits the low-threshold evoked DRP while facilitating high-threshold DRPs in control mice. FIG. 5C is a series of representative traces for evoked DRP recordings at varying stimulus intensities from Advillin$^{Cre}$; Mecp2$^{f/y}$, Advillin$^{Cre}$; Gabrb3$^{f/+}$ mutant or age-matched control mice. FIG. 5D is a series of bar graphs quantifying the average peak amplitude for evoked DRP recordings at varying stimulus intensities from mutant or control mice. [2-way ANOVA: P<0.0001, F(2,100)=45.23] Post-hoc Holm-Sidak's test: *, p<0.05. FIG. 5E is a series of bar graphs quantifying the total integral for evoked DRP recordings at varying stimulus intensities from mutant or control mice. [2-way ANOVA: P<0.0001, F(2,100)=44.58] Post-hoc Holm-Sidak's test: *, p<0.05. FIG. 5F is a sample trace of a ventral root reflex recorded with maximum intensity stimulation, both alone and with bicuculline from mutant or control mice where integral windows are marked to include monosynaptic, short latency polysynaptic, and long latency polysynaptic responses. FIG. 5G is a series of bar graphs quantifying the percent change in integral for reflexes in mutant or control mice at maximum intensity stimulation.

FIG. 6A is a series of representative activity traces in the OF test for Mecp2$^{-/y}$ and Advillin$^{Cre}$; Mecp2$_{f/y}$ mutant mice, and control littermates. FIG. 6B is a series of bar graphs showing the time spent in the center of the OF chamber. *, p<0.05. For Advillin$^{Cre}$; Gabrb3 floxed group: [1-way ANOVA: P<0.05, F(2,36)=4.325] Post-hoc Bonferroni's test: *, p<0.05. FIG. 6C is a series of bar graphs showing the total distance traveled in the OF chamber. *, $p<0.05$. For Advillin$^{Cre}$; Gabrb3 floxed group: [1-way ANOVA: $P<0.05$, $F(2,36)=3.499$] Post-hoc Bonferroni's test: *, $p<0.05$. FIG. 6D is a series of bar graphs showing the percent decrease in startle response to a 125 dB noise during a 30-minute tactile PPI session, when comparing the first five startle responses to the last five responses to a 125 dB noise. *, $p<0.05$. For Advillin$^{Cre}$; Gabrb3 floxed group: [1-way ANOVA: $P<0.001$, $F(2,38)=5.354$] Post-hoc Bonferroni's test: *, $p<0.05$. FIG. 6E is a series of bar graphs showing the percent time spent in the open arms of the EPM. *, $p<0.05$. FIG. 6F is a series of representative heat maps of activity in the 3-chamber social interaction test during the "Sociability" (top panels) and "Social Novelty Preference" (bottom panels) portions of the assay, for control, Mecp2$^{-/y}$ and Advillin$^{Cre}$; Mecp2$^{f/y}$ mice. FIG. 6G is a series of bar graphs showing the preference index for the percentage of time spent investigating the novel mouse in the "Sociability" portion of the 3-chamber social interaction test. *, $p<0.05$. For Advillin$^{Cre}$; Gabrb3 floxed group: [1-way ANOVA: $P<0.0001$, $F(2,40)=11.17$] Post-hoc Bonferroni's test: *, $p<0.001$. FIG. 6H is a series of bar graphs showing the preference index for the percentage of time spent investigating the novel mouse in the "Social Novelty Preference" portion of the 3-chamber social interaction test. *, $p<0.05$. For Advillin$^{Cre}$; Gabrb3 floxed group: [1-way ANOVA: $P<0.05$, $F(2,40)=3.882$] Post-hoc Bonferroni's test: *, $p<0.05$. FIG. 6I is a series of bar graphs showing the win percentage in the tube dominance test for mutant mice or control littermates, when tested against control mice from the same crosses. *, $p<0.05$.

FIGS. 7A-7P show Mecp2 expression exclusively in primary somatosensory neurons is sufficient for normal tactile sensitivity, GABRB3 expression, PSI, and certain cognitive behaviors. FIG. 7A is a series of IHC images of DRG, transverse SC or primary somatosensory cortex (Brain) showing MECP2 protein expression in control, Mecp2 null (Mecp2$^{STOP/y}$) or mice in which Mecp2 is expressed only in primary somatosensory neurons (Advillin$^{Cre}$; Mecp2$^{STOP/y}$). FIG. 7C is a series of bar graphs quantifying vGLUT1+puncta co-labeled with GABRB3, relative to the total number of vGLUT1+ puncta visualized per image with the percent GABRB3 puncta in images from mutant mice relative to control values being indicated in white text within bars. [1-way ANOVA: $P<0.0001$, $F(2,7)=44.97$] Post-hoc Tukey's test: *, $p<0.05$. FIG. 7D is a bar graph showing the discrimination index for textured NORT. [1-way ANOVA: $P<0.05$, $F(2,62)=4.322$] Post-hoc Tukey's test: *, $p<0.05$. FIG. 7E is a series of bar graphs showing the percent inhibition of the startle response to a 125 dB noise, when the startle noise is preceded by a light air puff (250 ms [1-way ANOVA: $P<0.05$, $F(2,68)=5.392$] Post-hoc Holm-Sidak's test: *, $p<0.05$. FIG. 7F is a series of bar graphs showing the response to a light air puff alone. [1-way ANOVA: $P<0.0001$, $F(2,68)=14.47$] Post-hoc Tukey's test: *, $p<0.0001$. FIG. 7G is a series of representative traces for evoked DRP recordings at varying stimulus intensities from mutant mice and control littermates. FIG. 7H is a series of bar graphs showing the peak amplitude for evoked DRP recordings at varying stimulus intensities. [2-way ANOVA: $P<0.0001$, $F(2,40)=16.12$] Post-hoc uncorrected Fisher's LSD test: *, $p<0.05$. FIG. 7I is a series of bar graphs showing the percent decrease in startle response to a 125 dB noise during a 30-minute tactile PPI session, when comparing the first five startle responses to the last five responses to a 125 dB noise. [1-way ANOVA:$P<0.05$, $F(2,37)=4.919$ Post-hoc Holm-Sidak's test: *, $p<0.05$. FIG. 7J is a schematic showing the representative traces of activity in the OF test. FIG. 7K is a series of bar graphs showing the time spent in the center of the OF chamber. [1-way ANOVA: $P<0.05$, $F(2,35)=4.539$] Post-hoc Holm-Sidak's test: *, $p<0.05$; #, $p<0.10$. FIG. 7L is a series of bar graphs showing the total distance traveled in the OF chamber. [1-way ANOVA: $P<0.001$, $F(2,35)=6.836$] Post-hoc Holm-Sidak's test: *, $p<0.05$. FIG. 7M is a series of bar graphs showing the percentage of time spent in the open arms of the EPM. [1-way ANOVA: $P<0.01$, $F(2,27)=7.463$] Post-hoc Tukey's test: *, $p<0.01$. FIG. 7N is a series of bar graphs showing the preference index for the "Sociability" portion of the 3-chamber social interaction test. [1-way ANOVA: $P<0.05$, $F(2,42)=4.141$] Post-hoc Tukey's test:*, $p<0.05$. FIG. 7O is a series of bar graphs showing the preference index for the "Social Novelty Preference" portion of the 3-chamber social interaction test. [1-way ANOVA: $P<0.0001$, $F(2,42)=11.18$] Post-hoc Tukey's test: *, $p<0.001$. FIG. 7P is a series of graphs showing the win percentage in the tube dominance test *, $p<0.05$.

FIGS. 8A-8J show characterization of tactile behavioral assays. FIG. 8A is a bar graph showing the average velocity for control mice during a 20 minute open field test, that were either naïve or had their whiskers removed one day prior to testing. FIG. 8B is a bar graph showing the average ambulatory time for wild type mice during a 20 minute open field test, that were either naïve or had their whiskers removed one day prior to testing. FIG. 8C is a bar graph average time spent jumping for wild type mice during a 20 minute open field test, that were either naïve or had their whiskers removed one day prior to testing. FIG. 8D is a bar graph showing the average time spent grooming for wild type mice during a 20 minute open field test, that were either naïve or had their whiskers removed one day prior to testing. *, $p<0.05$. FIG. 8E is a bar graph showing the discrimination index for textured NORT, for wild type mice that were either naïve or had their whiskers removed three days prior to testing, where a positive value indicates preference for the novel object, compared to the familiar object. Values shown are for the explore portion of the test. *, $p<0.05$. FIG. 8F is a series of bar graphs quantifying and categorizing methods used by mice to investigate objects during textured NORT, for wild type mice that were either naïve or had their whiskers removed three days prior to testing. Method of investigation was categorized as whisking/nose pokes or use of the glabrous skin on paws. [2-way ANOVA: $P<0.0001$, $F(2,54)=16.96$] Post-hoc Sidak's test: *, $p<0.05$. FIG. 8G is a bar graph showing the percentage of time mice used the glabrous skin on their paws to investigate objects during textured NORT, for wild type mice that were either naïve or had their whiskers removed three days prior to testing. Values shown are for the explore portion of the test, as a proportion of the total object investigation time. *, $p<0.05$. FIG. 8H is a bar graph showing the average time spent in the open arms of an elevated plus maze, for wild type mice that were either naïve or had their whiskers removed one day prior to testing. FIG. 8I is a bar graph showing the magnitude of startle response to a 125 dB noise in either naïve animals or with the back hairy skin shaved and lidocaine application. FIG. 8J is a bar graph showing the percent inhibition of the startle response to a 125 dB noise (pulse), when the startle noise is preceded by a light air puff (prepulse) at multiple ISIs between the prepulse and the pulse. Animals either had the air puff stimulus directed at the back hairy skin, or pointed away from the body. [2-way ANOVA: P<0.001, F(1,60)=72.31] Post-hoc Bonferroni test:*, p<0.001.

FIG. 9A is a series of bar graphs showing the amount of time spent physically interacting with both the familiar and novel object in the testing session of textured NORT in Mecp2$^{-/y}$, Mecp2$^{R306C}$, Shank3B$^{+/-}$, Fmr1$^{-/y}$ mutant mice and their control littermates. FIG. 9B is a series of bar graphs showing the percent inhibition of the startle response to a 125 dB noise (pulse), when the startle noise is preceded by tone prepulse (80 dB) in Mecp2$^{-/y}$Mecp2$^{R306C}$, Shank3B$^{+/-}$, Fmr1$^{-/y}$ mutant mice and their control littermates. *, p<0.05. FIG. 9C is a series of bar graphs showing the response to a non-startling acoustic noise (80 dB, 20 ms), in Mecp2$^{-/y}$, Mecp2$^{R306C}$, Shank3B$^{+/-}$, Fmr1$^{-/y}$ mutant mice and their control littermates, where responses are expressed as percent of startle response to a 125 dB startle noise.

FIGS. 10A-10J shows additional behavioral and respiratory analyses of Mecp2 mutant mice. FIG. 10A is a series of bar graphs showing the amount of time spent physically interacting with both the familiar and novel object in the textured NORT in Emx1$^{Cre}$; Mecp2$^{f/y}$, Cdx2$^{Cre}$; Mecp2$^{f/y}$, Advillin$^{Cre}$; Mecp2$^{f/+}$, Advillin$^{Cre}$; Mecp2$^{f/y}$, Advillin$^{CreERT2}$; Mecp2$^{f/y}$ and Advillin$^{CreERT2}$; Mecp2$^{f/+}$ mutant mice and their control littermates. FIG. 10B is a series of bar graphs showing the percent inhibition of the startle response to a 125 dB noise (pulse), when the startle noise is preceded by tone prepulse (80 dB) in Emx1$^{Cre}$; Mecp2$^{f/y}$, Cdx2$^{Cre}$; Mecp2$^{f/y}$, Advillin$^{Cre}$; Mecp2$^{f/+}$, Advillin$^{Cre}$; Mecp2$^{f/y}$, Advillin$^{CreERT2}$; Mecp2$^{f/y}$ and Advillin$^{CreERT2}$; Mecp2$^{f/+}$ mutant mice and their control littermates. n.s., not significant. FIG. 10C is a series of bar graphs showing the response to a non-startling acoustic noise (80 dB, 20 ms), in Emx1$^{Cre}$; Mecp2$^{f/y}$, Cdx2$^{Cre}$; Mecp2$^{f/y}$, Advillin$^{Cre}$; Mecp2$^{f/+}$, Advillin$^{Cre}$; Mecp2$^{f/y}$, Advillin$^{CreERT2}$; Mecp2$^{f/y}$ and Advillin$^{CreERT2}$; Mecp2$^{f/+}$ mutant mice and their control littermates, where responses are expressed as percent of startle response to a 125 dB startle noise. FIG. 10D is a series of bar graphs showing the average time spent on an accelerating rotarod in Mecp2$^{-/y}$, Mecp2$^{R306C}$, Emx1$^{Cre}$; Mecp2$^{f/y}$, Cdx2$^{Cre}$; Mecp2$^{f/y}$W, Advillin$^{Cre}$; Mecp2$^{f/y}$ and Advillin$^{CreER2}$; Mecp2$^{f/y}$ mutant mice and their control littermates. *, p<0.001. FIG. 10E is a schematic showing representative plethysmography traces for control mice, Mecp2$^{-/y}$, Cdx2$^{Cre}$; Mecp2$^{f/y}$ and Advillin$^{Cre}$; Mecp2$^{f/y}$ mutant mice. FIG. 10F is a bar graph showing average tidal volume for control mice, Mecp2$^{-/y}$, Cdx2$^{Cre}$; Mecp2$^{f/y}$ and Advillin$^{Cre}$; Mecp2$^{f/y}$ mutant mice. [1-way ANOVA: P<0.001, F(3,7)=8.785] Post-hoc Holm-Sidak's test:*, p<0.05. FIG. 10G is a bar graph showing the average breath frequency for control mice, Mecp2$^{-/y}$, Cdx2$^{Cre}$; Mecp2$^{f/y}$ and Advillin$^{Cre}$; Mecp2$^{f/y}$ mutant mice. [1-way ANOVA: P<0.05, F(3,7)=4.365] Post-hoc Holm-Sidak's test: *, p<0.05.

FIG. 10H is a bar graph showing the average expiration volume for control mice, Mecp2$^{-/y}$, Cdx2$^{Cre}$; Mecp2$^{f/y}$ and Advillin$^{Cre}$; Mecp2$^{f/y}$ mutant mice. [1-way ANOVA: P<0.001, F(3,7)=13.52] Post-hoc Holm-Sidak's test: *, p<0.05. FIG. 10I is a bar graph showing the average body weight (g) for control mice, Mecp2$^{-/y}$, Cdx2$^{Cre}$; Mecp2$^{f/y}$ and Advillin$^{Cre}$; Mecp2$^{f/y}$ mutant mice at 8 weeks of age. [1-way ANOVA: P<0.0001, F(3,40)=183.8] Post-hoc Bonferroni test: *, p<0.001. FIG. 10J is a picture showing representative whole brain images of 3 month old Mecp2$^{-/y}$, Cdx2$^{Cre}$; Mecp2$^{f/y}$ and Advillin$^{Cre}$; Mecp2$^{f/y}$ mutant mice and control littermates, where only Mecp2$^{-}$/Y mutant mice exhibit reduced brain size compared to control littermates.

FIGS. 11A-11G show the characterization of GABRB3 expression and antibody specificity, and Gabrb3 functions in behavior. FIG. 11A is a series of IHC images of spinal cord slices from a Cdx2cre; Gabrb3$^{f/f}$ mutant and control littermate, showing GABRB3 puncta in lamina III of the dorsal horn, where tissue was harvested from 3-5 month old animals. Scale bar: 10 μm. FIG. 11B is a bar graph quantifying the number of GABRB3 puncta in lamina III of the dorsal horn of Cdx2$^{Cre}$; Gabrb3$^{f/f}$ mutants and control littermates. *, p<0.01. FIG. 11C is an IHC image of a spinal cord slice from control tissue, showing co-localization of GABRB3 with vGLUT1-postive terminals in lamina III of the dorsal horn. Scale bar: 2 μm. FIG. 11D is a series of IHC images of spinal cord slices from an Advillin$^{Cre}$; Gabrb3$^{f/f}$ mutant and control littermate, expression of vGLUT1 and GABRB3 in lamina III of the dorsal horn. Scale bar: 5 μm. Tissue was harvested from 3-5 month old animals. FIG. 11E is a series of bar graphs showing the amount of time (sec) spent physically interacting with both the familiar and novel object in the textured NORT in Gabrb3$^{+/-}$, Advillin$^{Cre}$; Gabrb3$^{f/f}$, Advillin$^{Cre}$; Gabrb3$^{f/+}$ and Advillin$^{CreERT2}$; Gabrb3$^{f/+}$ mutant mice and their control littermates. FIG. 11F is a series of bar graphs showing the percent inhibition of the startle response to a 125 dB noise (pulse), when the startle noise is preceded by tone prepulse (80 dB) in Gabrb3$^{+/-}$, Advillin$^{Cre}$; Gabrb3$^{f/f}$, Advillin$^{Cre}$; Gabrb3$^{f/+}$ and Advillin$^{creERT2}$; Gabrb3$^{f/+}$ mutant mice and their control littermates. *, p<0.05. FIG. 11G is a series of bar graphs showing the response to a non-startling acoustic noise (80 dB, 20 ms), in Gabrb3$^{+/-}$, Advillin$^{Cre}$; Gabrb3$^{f/f}$, Advillin$^{Cre}$; Gabrb3$^{f/+}$ and Advillin$^{CreERT2}$; Gabrb3$^{f/+}$ mutant mice and their control littermates, where responses are expressed as percent of startle response to a 125 dB noise.

FIGS. 12A-12J show additional behavioral analyses of Mecp2 and Gabrb3 mutant mice. FIG. 12A is a schematic showing representative traces of activity in the open field test for Mecp2$^{R306C}$, Advillin$^{CreERT2}$; Mecp2$^{f/y}$, Advillin$^{Cre}$; Gabrb3$^{f/f}$, Advillin$^{Cre}$; Gabrb3$^{f/+}$ and Advillin$^{creERT2}$; Gabrb3$^{f/+}$ mutant mice and their control littermates. FIG. 12B is a series of bar graphs showing average time spent in the center of the open field chamber for Mecp2$^{R306C}$, Gabrb3$^{+/-}$, Emx1$^{Cre}$; Mecp2$^{f/y}$, Cdx2$^{Cre}$; Mecp2$^{f/y}$, Advillin$^{Cre}$; Mecp2$^{f/+}$ and Advillin$^{CreERT2}$; Mecp2$^{f/+}$ mutant mice and their control littermates *, p<0.05. FIG. 12C is a series of bar graphs showing the average total distance traveled in the open field chamber for Mecp2$^{R306C}$, Gabrb3$^{+/-}$, Emx1$^{Cre}$; Mecp2$^{f/y}$, Cdx2$^{Cre}$; Mecp2$^{f/y}$, Advillin$^{Cre}$; Mecp2$^{f/+}$ and Advillin$^{CreERT2}$; Mecp2$^{f/+}$ mutant mice and their control littermates *, p<0.05. FIG. 12D is a series of bar graphs showing the percent decrease in startle response to a 125 dB noise during a 30-minute tactile PPI session, when comparing the first five startle responses to the last five responses to a 125 dB noise for Mecp2$^{R306C}$, Gabrb3$^{+/-}$, Emx1$^{Cre}$; Mecp2$^{f/y}$, Cdx2$^{Cre}$; Mecp2$^{f/y}$, Advillin$^{Cre}$; Mecp2$^{f/+}$ and Advillin$^{creERT2}$; Mecp2$^{f/+}$ mutant mice and their control littermates *, p<0.05. FIG. 12E is a series of representative images of nest building behavior for Mecp2$^{-/y}$ and Advillin$^{Cre}$; Mecp2$^{f/y}$ mutant mice and control littermates. FIG. 12F is a series of bar graphs showing average nest building scores for Mecp2$^{R306C}$, Gabrb3$^{+/-}$, Emx1$^{Cre}$; Mecp2$^{f/y}$ and Cdx2$^{Cre}$; Mecp2$^{f/y}$ mutant mice and their control littermates. *, p<0.05. FIG. 12G is a series of representative heat maps of activity in the 3-chamber social interaction test during the "Sociability" (top panels) and "Social Novelty Preference" (bottom panels) portions of the assay, for an Advillin$^{CreERT2}$; Mecp2$^{f/y}$ mutant mouse and a control littermate. FIG. 12H is a series of bar graphs showing the preference index for the percentage of time spent investigating the novel mouse in "Sociability" portions of the 3-chamber social interaction test, for Mecp2$^{R306C}$, Gabrb3$^{+/-}$, Emx1$^{Cre}$; Mecp2$^{f/y}$ and Cdx2$^{Cre}$; Mecp2$^{f/y}$ mutant mice and their control littermates. *, p<0.05. FIG. 12I is a series of bar graphs showing the preference index for the percentage of time spent investigating the novel mouse in "Social Novelty Preference" portions of the 3-chamber social interaction test, for Mecp2$^{R306C}$, Gabrb3$^{+/-}$, Emx1$^{Cre}$; Mecp2$^{f/y}$ and Cdx2$^{Cre}$; Mecp2$^{f/y}$ mutant mice and their control littermates. *, p<0.05. FIG. 12J is a series of bar graphs showing average win percentage in the tube dominance test for Mecp2$^{R306C}$, Gabrb3$^{+/-}$, Emx1$^{Cre}$; Mecp2$^{f/y}$ and Cdx2$^{Cre}$; Mecp2$^{f/y}$ mutant mice, when tested against control mice of the same line. *, p<0.05.

FIGS. 13A-13J show additional behavioral analyses of Advillin$^{Cre}$; Mecp2$^{STOP/y}$ mutant mice. FIG. 13A is a bar graph showing the discrimination index for 5 minute control NORT [1-way ANOVA: P<0.01, F(2,66)=7.427] Post-hoc Tukey's test: *, p<0.05. FIG. 13B is a bar graph showing the discrimination index for 1 hour control NORT [1-way ANOVA: P<0.01, F(2,66)=7.427] Post-hoc Tukey's test: *, p<0.05. FIG. 13C is a bar graph showing the amount of time (sec) spent physically interacting with both the familiar and novel object in the textured NORT for Mecp2$^{STOP/y}$ and Advillin$^{Cre}$; Mecp2$^{STOP/y}$ mutant mice and their control littermates. FIG. 13D is a bar graph showing the magnitude of startle response to a 125 dB noise for Mecp2$^{STOP/y}$ and Advillin$^{Cre}$; Mecp2$^{STOP/y}$ mutant mice and their control littermates. [1-way ANOVA: P<0.01, F(2,65)=7.145] Post-hoc Bonferroni's test: *, p<0.05. FIG. 13E is a bar graph showing percent inhibition of the startle response to a 125 dB noise (pulse), when the startle noise is preceded by tone prepulse (80 dB) for Mecp2$^{STOP/y}$ and Advillin$^{Cre}$; Mecp2$^{STOP/y}$ mutant mice and their control littermates. [1-way ANOVA: P<0.01, F(2,65)=5.298] Post-hoc Bonferroni's test: *, p<0.05. FIG. 13F is a bar graph showing response to a non-startling acoustic noise (80 dB, 20 ms), in Mecp2$^{STOP/y}$ and Advillin$^{Cre}$; Mecp2$^{STOP/y}$ mutant mice and their control littermates, where responses are expressed as percent of startle response to a 125 dB startle noise. FIG. 13G is a bar graph showing average time spent on an accelerating rotarod for Mecp2$^{SOP/y}$, Advillin$^{Cre}$; Mecp2$^{STOP/y}$ mutant mice and their control littermates. [1-way ANOVA: P<0.0001, F(2,34)=48.69] Post-hoc Bonferroni's test: *, p<0.0001. FIG. 13H is pictures of representative whole brain images of 3 month old Mecp2$^{STOP/y}$ and Advillin$^{Cre}$; Mecp2$^{STOP/y}$ mutant mice and a control littermate. Both Mecp2$^{STOP/y}$ and Advillin$^{Cre}$; Mecp2$^{STOP/y}$ mutant mice exhibit reduced brain size compared to control littermates. FIG. 13I is a bar graph showing the average nest building scores. *, p<0.01. FIG. 13J is a schematic showing representative heat maps of activity in the 3-chamber social interaction test during the "Sociability" (top panels) and "Social Novelty Preference" (bottom panels) portions of the assay, for control, Mecp2$^{STOP/y}$ and Advillin$^{Cre}$; Mecp2$^{STOP/y}$ mice.

FIG. 14O is a bar graph showing postnatal expression of Gabrb3 in peripheral somatosensory neurons significantly improves anxiety-like behaviors as measured by habituation to startle noise.

FIG. 15A is a graph showing the startle response of Advillin$^{Cre}$; Mecp2$^{f/y}$ mutant mice and control littermates following injection of: vehicle (saline), Bumetanide (0.2 mg/kg), Midazolam (2.5 mg/kg) or isoguvacine (1 mg/kg). Midazolam injected animals show a trend toward decreased startle amplitude, compared to animals treated with vehicle. FIG. 15B is a graph showing the response to tactile PPI of Advillin$^{Cre}$; Mecp2$^{f/y}$ mutant mice and control littermates following injection of: vehicle (saline), Bumetanide (0.2 mg/kg), Midazolam (2.5 mg/kg) or isoguvacine (1 mg/kg). Vehicle-treated Advillin$^{Cre}$; Mecp2$^{f/y}$ mutant mice exhibit increased performance on the tactile PPI assay, compared to vehicle treated control littermates. Both Midazolam- and isoguvacine injected Advillin$^{Cre}$; Mecp2$^{f/y}$ mutant mice exhibit a trend toward normalized responses in the tactile PPI assay, and are not different than control littermates with the same drug treatment. FIG. 15C is a graph showing the response to air puff alone of Advillin$^{Cre}$; Mecp2$^{f/y}$ mutant mice and control littermates following injection of: vehicle (saline), Bumetanide (0.2 mg/kg), Midazolam (2.5 mg/kg) or isoguvacine (1 mg/kg). Vehicle-treated Advillin$^{Cre}$; Mecp2$^{f/y}$ mutant mice exhibit increased response to an air puff stimulus alone, compared to vehicle treated control littermates. Both Midazolam or isoguvacine treatment in Advillin$^{Cre}$; Mecp2$^{f/y}$ mutant mice decreased response to an air puff stimulus alone, and animals with these treatments did not increased responses compared to control littermates.

FIG. 16A is a bar graph of discrimination index for a textured NORT, comparing texture discrimination performance in control mice, mice with heterozygous mutations in Shank3 (Shank3$^{FX/+}$) or mice with conditional restoration of Shank3 in all cells below the neck (Cdx2$^{Cre}$; Shank3$^{FX/+}$). The Cdx2$^{Cre}$; Shank3$^{FX/+}$ mice are heterozygous for the Shank3 mutation in the brain, but both alleles for Shank3 are functional in cells below cervical level 2 of the spinal cord. A positive value indicates preference for the novel object, compared to the familiar object, with *, p<0.05. Comparisons between groups are noted by brackets; one-way ANOVA with post-hoc Tukey's test: *, p<0.05. Animal numbers per group are shown in the bars of each panel. FIG. 16B is a bar graph of discrimination index for a 5-minute control NORT. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 16C is a bar graph of discrimination index for a 1-hour control NORT. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 16D is a bar graph of amount of time spent physically interacting with both the familiar and novel object in the testing session of the textured NORT in mutant mice and their control littermates. One-way ANOVA with post-hoc Tukey's test, not significant.

FIG. 17A is a bar graph of discrimination index for textured NORT, comparing texture discrimination performance in control mice, mice with heterozygous mutations in Shank3 (Shank3$^{FX/+}$) or mice with conditional restoration of Shank3 in all cells below the neck (Advillin$^{Cre}$; Shank3$^{FX/+}$). Advillin$^{Cre}$; Shank3$^{FX+}$ mice are heterozygous for the Shank3 mutation, except in peripheral somatosensory neurons, both alleles for Shank3 are normal. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 17B is a bar graph of discrimination index for a 5-minute control NORT. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 17C is a bar graph of the discrimination index for a 1-hour control NORT. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 17D is a bar graph of the amount of time spent physically interacting with both the familiar and novel object in the testing session of textured NORT in mutant mice and their control littermates. One-way ANOVA with post-hoc Tukey's test, not significant. Animal numbers per group are shown in the bars of each panel.

FIGS. 18A-18F show improvements observed in hairy skin sensitivity in Shank3 heterozygous mutant mice having restored Shank3 expression in all cells below the neck. FIG. 18A is a bar graph showing the magnitude of startle response to a 125 dB noise in mutant mice and control littermates. One-way ANOVA with post-hoc Tukey's test, not significant. Animal numbers per group are shown in the bars of each panel. FIG. 18B is a bar graph showing the percent inhibition of the startle response to a 125 dB noise (pulse), when the startle noise was preceded by a light air puff (prepulse, 0.9 PSI) at an interstimulus interval of 250 ms between the prepulse and the pulse. One-way ANOVA with post-hoc Tukey's test: *, p<0.05. FIG. 18C is a bar graph showing the response to a light air puff alone, administered to the back hairy skin (0.9 PSI). Responses are expressed as percent of startle response to a 125 dB noise. One-way ANOVA with post-hoc Tukey's test: *, p<0.05. FIG. 18D is a bar graph showing the percent inhibition of the startle response to a 125 dB noise (pulse), when the startle noise is preceded by tone prepulse (80 dB) in mutant mice and their control littermates. One-way ANOVA with post-hoc Tukey's test, not significant. FIG. 18E is a bar graph showing response to a non-startling acoustic noise (80 dB, 20 ms), in mutant mice and their control littermates. Responses are expressed as percent of startle response to a 125 dB startle noise. One-way ANOVA with post-hoc Tukey's test, not significant. FIG. 18F is a bar graph showing percent decrease in startle response to a 125 dB noise during a 30-minute tactile PPI session, when comparing the first five startle responses to the last five responses of the session, to a 125 dB noise. Asterisks indicate a significant decrease in startle response over time; one-sample t-test, *, p<0.05; n.s., not significant.

FIGS. 19A-19F show improvements observed in hairy skin sensitivity in Shank3 heterozygous mutant mice havening restored Shank3 expression in peripheral sensory neurons. FIG. 19A is a bar graph showing magnitude of startle response to a 125 dB noise in mutant mice and control littermates. One-way ANOVA with post-hoc Tukey's test, not significant. Animal numbers per group are shown in the bars of each panel. FIG. 19B is a bar graph showing percent inhibition of the startle response to a 125 dB noise (pulse), when the startle noise was preceded by a light air puff (prepulse, 0.9 PSI) at an interstimulus interval of 250 ms between the prepulse and the pulse. One-way ANOVA with post-hoc Tukey's test: *, p<0.05. FIG. 19C is a bar graph showing response to a light air puff alone, administered to the back hairy skin (0.9 PSI). Responses are expressed as percent of startle response to a 125 dB noise. One-way ANOVA with post-hoc Tukey's test: *, p<0.05. FIG. 19D is a bar graph showing percent inhibition of the startle response to a 125 dB noise (pulse), when the startle noise is preceded by tone prepulse (80 dB) in mutant mice and their control littermates. One-way ANOVA with post-hoc Tukey's test, not significant. FIG. 19E is a bar graph showing response to a non-startling acoustic noise (80 dB, 20 ms), in mutant mice and their control littermates. Responses are expressed as percent of startle response to a 125 dB startle noise. One-way ANOVA with post-hoc Tukey's test, not significant. FIG. 19F is a bar graph showing percent decrease in startle response to a 125 dB noise during a 30-minute tactile PPI session, when comparing the first five startle responses to the last five responses of the session, to a 125 dB noise. Asterisks indicate a significant decrease in startle response over time; one-sample t-test, *, p<0.05; n.s., not significant.

FIG. 20A shows representative activity traces in the OF test for mutant mice and control littermates. FIG. 20B is a bar graph showing time spent in the center of the OF chamber. Comparisons between groups: one-way ANOVA with post-hoc Tukey's test: *, p<0.05. Animal numbers per group are shown in the bars of each panel. FIG. 20C is a bar graph showing total distance traveled in the OF chamber. One-way ANOVA with post-hoc Tukey's test, not significant.

FIG. 21A shows representative activity traces in the OF test for mutant mice and control littermates. FIG. 21B is a bar graph showing time spent in the center of the OF chamber. Comparisons between groups: one-way ANOVA with post-hoc Tukey's test: *, p<0.05. Animal numbers per group are shown in the bars of each panel. FIG. 21C is a bar graph showing total distance traveled in the OF chamber. One-way ANOVA with post-hoc Tukey's test, not significant.

FIGS. 22A-22E show improvements in some aspects of social behavior impairments observed in Shank3 heterozygous mutant mice having restored Shank3 expression in all cells below the neck. FIG. 22A shows representative heat maps of activity in the 3-chamber social interaction test during the "Sociability" (top panels) and "Social Novelty Preference" (bottom panels) portions of the assay, for control, Shank3$^{FX/+}$ and Cdx2$^{Cre}$; Shank3$^{FX/+}$ mice. FIG. 22B is a bar graph of preference index for the percentage of time spent investigating the novel mouse in the "Sociability" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 22C is a bar graph of preference index for the percentage of time spent investigating the novel mouse in the "Social Novelty Preference" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 22D is a bar graph of average time spent (in seconds) in each of the three chambers during the "Sociability" and "Social Novelty Preference" portion of the 3-chamber social interaction test for the indicated groups. Comparisons between time spent in each chamber, per genotype: repeated measures two-way ANOVA with post-hoc Tukey's test: *, p<0.05. FIG. 22E is a bar graph of average time spent (in seconds) in each of the three chambers during the "Social Novelty Preference" portion of the 3-chamber social interaction test for the indicated groups. Comparisons between time spent in each chamber, per genotype: repeated measures two-way ANOVA with post-hoc Tukey's test: *, p<0.05.

FIGS. 23A-23E show improvements in some aspects of social behavior impairments observed in Shank3 heterozygous mutant mice having restored Shank3 expression in peripheral sensory neurons. FIG. 23A shows representative heat maps of activity in the 3-chamber social interaction test during the "Sociability" (top panels) and "Social Novelty Preference" (bottom panels) portions of the assay, for control, Shank3$^{FX/+}$ and Advillin$^{Cre}$; Shank3$^{FX/+}$ mice. FIG. 23B is a bar graph of preference index for the percentage of time spent investigating the novel mouse in the "Sociability" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 23C is a bar graph of reference index for the percentage of time spent investigating the novel mouse in the "Social Novelty Preference" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 23D is a bar graph of average time spent (in seconds) in each of the three chambers during the "Sociability" and "Social Novelty Preference" portion of the 3-chamber social interaction test for the indicated groups. Comparisons between time spent in each chamber, per genotype: repeated measures two-way ANOVA with post-hoc Tukey's test: *, p<0.05. FIG. 23E is a bar graph of average time spent (in seconds) in each of the three chambers during the "Social Novelty Preference" portion of the 3-chamber social interaction test for the indicated groups. Comparisons between time spent in each chamber, per genotype: repeated measures two-way ANOVA with post-hoc Tukey's test: *, p<0.05.

FIG. 24A shows Immunohistochemistry (IHC) images of spinal cord (SC) dorsal horn lamina III/IV from control, Advillin$^{Cre}$; Mecp2$^{f/y}$, Advillin$^{Cre}$; Gabrb3$^{f/f}$, or Shank3B$^{-/-}$ mutant mice. Sections were immunostained for vGLUT1 (presynaptic terminals for A↑ and Aδ LTMRs) and GABRB3 to mark the presence of GABRB3 puncta at Aβ and Aδ LTMR presynaptic terminals. FIG. 24B is a bar graph of quantification of vGLUT1+puncta co-labeled with GABRB3, relative to the total number of vGLUT1+ puncta visualized per image. *, p<0.01. Puncta numbers are compared between mutant animals and their control littermates, Student's unpaired t-test: *, p<0.01. FIG. 24C is a bar graph of percentage of vGLUT1+puncta co-labeled with GABRB3, relative to the total number of vGLUT1+puncta visualized per image, as compared to values of control littermates (controls set as 100%). *, p<0.001. Percentages are compared between mutant animals and their control littermates, Student's unpaired t-test: *, p<0.001.

FIG. 25A shows immunohistochemistry (IHC) images of spinal cord (SC) dorsal horn lamina III/IV from control, Advillin$^{Cre}$; Mecp2$^{f/y}$, Advillin$^{Cre}$; Gabrb3$^{f/f}$, or Shank3B$^{-/-}$ mutant mice. Sections were immunostained for vGLUT1 (presynaptic terminals for Aβ and Aδ LTMRs) and HCN1 to mark the presence of HCN1 puncta at Aβ and Aδ LTMR presynaptic terminals. FIG. 25B is a bar graph of quantification of vGLUT1+puncta co-labeled with HCN1, relative to the total number of vGLUT1+puncta visualized per image. *, p<0.01. Puncta numbers are compared between mutant animals and their control littermates, Student's unpaired t-test: *, p<0.01. FIG. 25C is a bar graph of percentage of vGLUT1+puncta co-labeled with HCN1, relative to the total number of vGLUT1+puncta visualized per image, as compared to values of control littermates (controls set as 100%). *, p<0.001. Percentages are compared between mutant animals and their control littermates, Student's unpaired t-test: *, p<0.01.

FIGS. 26A-26F show that HCN1 expression is decreased in large diameter peripheral somatosensory neurons, but not small diameter neurons, of Shank3B mutant mice. FIG. 26A is a scatter plot showing average HCN1 fluorescence intensity per cultured DRG sensory neuron, as a function of cell body size ($\mu m^2$), in control neurons cultured from DRGs of Shank3B$^{+/+}$ mice. Linear regression analysis, *, p<0.001. FIG. 26B is a scatter plot showing average HCN1 fluorescence intensity per cultured DRG sensory neuron, as a function of cell body size ($\mu m^2$), in control neurons cultured from DRGs of Shank3B$^{+/-}$ mice. Linear regression analysis, not significant. FIG. 26C is a bar graph showing average HCN1 fluorescence intensity of small diameter (<300 $\mu m^2$) primary somatosensory neurons compared to large diameter (>300 $\mu m^2$) primary somatosensory neurons, cultured from control (Shank3B$^{+/+}$) and mutant (Shank3B$^{+/-}$) mice. Two-way ANOVA with post-hoc Tukey's test: asterisk above bar indicates significant difference between small and large diameter neurons within the same genotype, *, p<0.05. Asterisk over bracket denotes significant difference between genotypes for large diameter neurons. FIG. 26D is a scatter plot showing average GABRB3 fluorescence intensity per cultured DRG sensory neuron, as a function of cell body size ($\mu m^2$), in control neurons cultured from DRGs of Shank3B+$^4$ mice. Linear regression analysis, *, p<0.001. FIG. 26E is a scatter plot showing average GABRB3 fluorescence intensity per cultured DRG sensory neuron, as a function of cell body size ($\mu m^2$), in control neurons cultured from DRGs of Shank3B$^{+/-}$ mice. Linear regression analysis, *, p<0.001. FIG. 26F is a bar graph showing average GABRB3 fluorescence intensity of small diameter (<300 $\mu m^2$) primary somatosensory neurons compared to large diameter (>300 $\mu m^2$) primary somatosensory neurons, cultured from control (Shank3B$^{+/+}$) and mutant (Shank3B$^{+/-}$) mice. Two-way ANOVA with post-hoc Tukey's test: asterisk above bar indicates significant difference between small and large diameter neurons within the same genotype, *, p<0.05. N.s. over bracket denotes no significant difference between genotypes when comparing the same size neuron groups.

FIGS. 27A-27E show that large diameter primary sensory neurons from Shank3B mutant mice exhibit deficits in In currents. FIG. 27A is an example image of cultured DRG neurons in whole cell patch clamp recording configuration. The white arrow denotes a large diameter neuron, which is defined as >40 $\mu m$ in diameter. FIG. 27B shows the voltage step protocol used to activate HCN channels and elicit In during whole cell voltage clamp recordings. FIG. 27C shows representative traces showing In during a hyperpolarizing voltage step protocol in a large diameter neuron cultured from DRGs of a control mouse (Shank3B$^{+/+}$). FIG. 27D shows representative traces with diminished In during a hyperpolarizing voltage step protocol in a large diameter neuron cultured from DRGs of a mutant mouse (Shank3B$^{+/-}$). FIG. 27E is graph showing the quantification of total current density at each voltage step for large diameter neurons cultured from DRGs of control and mutant mice. N=36 neurons, 5 mice for control and 48 neurons, 5 mice for mutant condition. Two-way ANOVA with post-hoc Sidak's test, *, p<0.05.

FIGS. 28A-28C show that large diameter primary sensory neurons from Shank3B mutant mice exhibit hyperexcitability. FIG. 28A shows representative traces from large diameter neurons cultured from DRGs of control (Shank3B$^{+/+}$) and mutant (Shank3B$^{+/-}$) mice during whole cell current clamp recordings, in which the minimal amount of current required to elicit an action potential in each neuron (rheobase, Rn), was determined. FIG. 28B shows magnified images of representative traces from large diameter neurons cultured from DRGs of control (Shank3B$^{+/+}$) and mutant (Shank3B$^{+/-}$) mice during whole cell current clamp previousrecordings, in which the minimal amount of current required to elicit an action potential in each neuron (rheobase, Rn), was determined. FIG. 28C is a bar graph of quantification of average rheobase in large diameter neurons cultured from DRGs of control (Shank3B$^{+/+}$) and mutant (Shank3B$^{+/-}$) mice during whole cell current clamp recordings. N=48 neurons, 5 mice for control and 52 neurons, 5 mice for mutant condition. Student's unpaired t-test, *, p<0.005.

FIGS. 29A-29E show that small diameter primary sensory neurons from Shank3B mutant mice do not exhibit deficits in In currents. FIG. 29A is an example image of cultured DRG neurons in whole cell patch clamp recording configuration. The white arrow denotes a small diameter neuron, which is defined as<30 $\mu m$ in diameter. FIG. 29B shows the voltage step protocol used to activate HCN channels and elicit In during whole cell voltage clamp recordings. FIG. 29C shows representative traces showing In during a hyperpolarizing voltage step protocol in a small diameter neuron cultured from DRGs of a control mouse (Shank3B$^{+/+}$). FIG. 29D shows representative traces with diminished In during a hyperpolarizing voltage step protocol in a small diameter neuron cultured from DRGs of a mutant mouse (Shank3B$^{+/-}$). FIG. 29E is a graph of quantification of total current density at each voltage step for small diameter neurons cultured from control and mutant mice. N=9 neurons, 2 mice for control and 7 neurons, 2 mice for mutant condition. Repeated measures two-way ANOVA, not significant.

FIGS. 30A-30C show small diameter primary sensory neurons from Shank3B mutant mice exhibit normal excitability. FIG. 30A shows representative traces from small diameter neurons cultured from DRGs of control (Shank3B$^{+/+}$) and mutant (Shank3B$^{+/-}$) mice during whole cell current clamp recordings, in which the minimal amount of current required to elicit an action potential in each neuron (rheobase, $R_h$), was determined. FIG. 30B shows magnified images of representative traces from small diameter neurons cultured from DRGs of control (Shank3B$^{+/+}$) and mutant (Shank3B$^{+/-}$) mice during whole cell current clamp recordings, in which the minimal amount of current required to elicit an action potential in each neuron (rheobase, $R_h$), was determined. FIG. 30C is a bar graph of quantification of average rheobase in small diameter neurons cultured from DRGs of control (Shank3B$^{+/+}$) and mutant (Shank3B$^{+/-}$) mice during whole cell current clamp recordings. N=7 neurons, 2 mice for control and 9 neurons, 2 mice for mutant. Student's unpaired t-test, not significant.

FIG. 31A is a graph of quantification of total current density at each voltage step during a hyperpolarizing voltage step protocol for large diameter neurons cultured from DRGs of control and Mecp2$^{STOP/y}$ mutant mice. Repeated measures two-way ANOVA, not significant. FIG. 31B is a bar graph of quantification of average rheobase in large diameter neurons cultured from DRGs of control (Mecp2$^{+/y}$) and mutant (Mecp2$^{STOP/y}$) mice during whole cell current clamp recordings. N=32 neurons, 4 mice for control and 43 neurons, 4 mice for mutant condition. Student's unpaired t-test, *, p<0.05. FIG. 31C is a graph of quantification of total current density at each voltage step during a hyperpolarizing voltage step protocol for small diameter neurons cultured from DRGs of control and Mecp2$^{STOP/y}$ mutant mice. Repeated measures two-way ANOVA, main effect of genotype, p<0.05. FIG. 31D is a bar graph of quantification of average rheobase in small diameter neurons cultured from DRGs of control (Mecp2$^{+/y}$) and mutant (Mecp2$^{STOP/y}$) mice during whole cell current clamp recordings. N=10 neurons, 2 mice for control and 9 neurons, 2 mice for mutant condition. Student's unpaired t-test, not significant.

FIGS. 32A-32F demonstrate that Mecp2 expression exclusively in peripheral sensory neurons, beginning at P28, is sufficient for normal hairy skin sensitivity. FIG. 32A is a bar graph showing magnitude of startle response to a 125 dB noise in Mecp2 mutant mice (Mecp2$^{STOP/y}$), mice with Mecp2 expressed only in peripheral somatosensory neurons (Advillin$^{Cre}$; Mecp2$^{STOP/y}$), mice with Mecp2 expressed only in peripheral somatosensory neurons beginning at P28 (Advillin$^{CreERT2}$; Mecp2$^{STOP/y}$) or control littermates Mice were administered 1 mg tamoxifen per day for 5 days beginning at P28, which resulted in expression of Mecp2 in >90% of DRG neurons of Advillin$^{CreERT2}$; Mecp2$^{STOP/y}$ mice, whereas Mecp2 expression in the SC and brain was unaltered. One-way ANOVA with post-hoc Tukey's test, *, p<0.05. Animal numbers per group are shown in the bars of each panel. FIG. 32B is a bar graph showing percent inhibition of the startle response to a 125 dB noise (pulse), when the startle noise was preceded by a light air puff (prepulse, 0.9 PSI) at an interstimulus interval of 250 ms between the prepulse and the pulse. One-way ANOVA with post-hoc Tukey's test: *, p<0.05. FIG. 32C is a bar graph showing response to a light air puff alone, administered to the back hairy skin (0.9 PSI). Responses are expressed as percent of startle response to a 125 dB noise. One-way ANOVA with post-hoc Tukey's test: *, p<0.05. FIG. 32D is a bar graph showing percent inhibition of the startle response to a 125 dB noise (pulse), when the startle noise is preceded by tone prepulse (80 dB) in mutant mice and their control littermates. One-way ANOVA with post-hoc Tukey's test: *, p<0.05. FIG. 32E is a bar graph showing response to a non-startling acoustic noise (80 dB, 20 ms), in mutant mice and their control littermates. Responses are expressed as percent of startle response to a 125 dB startle noise. One-way ANOVA with post-hoc Tukey's test, not significant. FIG. 32F is a bar graph showing percent decrease in startle response to a 125 dB noise during a 30-minute tactile PPI session, when comparing the first five startle responses to the last five responses of the session, to a 125 dB noise. Asterisks above bars indicate a significant decrease in startle response over time; one-sample t-test, *, p<0.05. Asterisk above bracket indicates a significant difference between the indicated genotypes, one-way ANOVA with post-hoc Tukey's test: *, p<0.05.

FIGS. 33A-33F show that peripheral sensory neuron deletion of Mecp2 at P10-P14 leads to increased hairy skin sensitivity. FIG. 33A is a bar graph of magnitude of startle response to a 125 dB noise in control mice or mice with conditional deletion of Mecp2 in peripheral sensory neurons, following administration of tamoxifen (Advillin$^{CreERT2}$; Mecp2$^{f/y}$) Mice were administered 1 mg tamoxifen per day on P10, P12 and P14, which resulted in loss of Mecp2 expression in >90% of DRG neurons, whereas Mecp2 expression in the SC and brain was unaltered. Unpaired Student's t-test, not significant. N=11 mice per control and mutant genotype group. FIG. 33B is a bar graph of percent inhibition of the startle response to a 125 dB noise (pulse), when the startle noise was preceded by a light air puff (prepulse, 0.9 PSI) at an interstimulus interval of 250 ms between the prepulse and the pulse. Unpaired Student's t-test, not significant: p<0.07. FIG. 33C is a bar graph showing response to a light air puff alone, administered to the back hairy skin (0.9 PSI). Responses are expressed as percent of startle response to a 125 dB noise. FIG. 33D is a bar graph showing percent inhibition of the startle response to a 125 dB noise (pulse), when the startle noise is preceded by tone prepulse (80 dB) in mutant mice and their control littermates. Unpaired Student's t-test, not significant. FIG. 33E is a bar graph showing response to a non-startling acoustic noise (80 dB, 20 ms), in mutant mice and their control littermates. Responses are expressed as percent of startle response to a 125 dB startle noise. Unpaired Student's t-test, not significant. FIG. 33F is a bar graph of percent decrease in startle response to a 125 dB noise during a 30-minute tactile PPI session, when comparing the first five startle responses to the last five responses of the session, to a 125 dB noise. Asterisks above bars indicate a significant decrease in startle response over time; one-sample t-test, *, p<0.05.

FIG. 34A shows a bar graph of percentage of time spent in the open arms of the elevated plus maze (EPM) for Mecp2 mutant mice (Mecp2$^{STOP/y}$) mice with Mecp2 expressed only in peripheral somatosensory neurons (Advillin$^{Cre}$; Mecp2$^{STOP/y}$), mice with Mecp2 expressed only in peripheral somatosensory neurons beginning at P28 (Advillin$^{CreERT2}$; Mecp2$^{STOP/y}$) or control littermates. Mice were administered 1 mg tamoxifen per day for 5 days beginning at P28, which resulted in expression of Mecp2 in >90% of DRG neurons of Advillin$^{CreERT2}$;Mecp2$^{STOP/y}$ mice, whereas Mecp2 expression in the SC and brain was unaltered. One-way ANOVA with post-hoc Tukey's test, *, p<0.05. FIG. 34B is a bar graph of percentage of time spent in the open arms of the elevated plus maze (EPM) for control mice or mice with conditional deletion of Mecp2 in peripheral sensory neurons, following administration of tamoxifen (Advillin$^{CreERT2}$; Mecp2$^{f/y}$). Mice were administered 1 mg tamoxifen per day on P10, P12 and P14, which resulted in loss of Mecp2 expression in >90% of DRG neurons, whereas Mecp2 expression in the SC and brain was unaltered. Unpaired Student's t-test: *, p<0.05. FIG. 34C is a bar graph of percentage of time spent in the open arms of the elevated plus maze (EPM) for both male and female mice with conditional deletion of Mecp2 in peripheral sensory neurons (Advillin$^{Cre}$; Mecp2$^{f/y}$ or Advillin$^{Cre}$; Mecp2$^{f/+}$), compared to control littermates of the same sex. One-way ANOVA with post-hoc Tukey's test, *, p<0.05; #, p<0.10.

FIG. 35A shows representative activity traces in the OF test for Mecp2 mutant mice (Mecp2$^{STOP/y}$), mice with Mecp2 expressed only in peripheral somatosensory neurons (Advillin$^{Cre}$; Mecp2$^{STOP/y}$), mice with Mecp2 expressed only in peripheral somatosensory neurons beginning at P28 (Advillin$^{CreERT2}$; Mecp2$^{STOP/y}$) or control littermates. Mice were administered 1 mg tamoxifen per day for 5 days beginning at P28, which resulted in expression of Mecp2 in >90% of DRG neurons of Advillin$^{CreERT2}$; Mecp2$^{STOP/y}$ mice, whereas Mecp2 expression in the SC and brain was unaltered. FIG. 35B shows a bar graph of percentage of time spent in the center of the chamber during the open field test, for Mecp2 mutant mice (Mecp2$^{STOP/y}$), mice with Mecp2 expressed only in peripheral somatosensory neurons (Advillin$^{Cre}$; Mecp2$^{STOP/y}$), mice with Mecp2 expressed only in peripheral somatosensory neurons beginning at P28 (Advillin$^{CreERT2}$; Mecp2$^{STOP/y}$) or control littermates. One-way ANOVA with post-hoc Tukey's test, *, p<0.05. FIG. 35C is a bar graph of total distance travelled during the open field test, for Mecp2 mutant mice (Mecp2$^{STOP/y}$), mice with Mecp2 expressed only in peripheral somatosensory neurons (Advillin$^{Cre}$; Mecp2$^{STOP/y}$) mice, with Mecp2 expressed only in peripheral somatosensory neurons beginning at P28 (Advillin$^{CreERT2}$; Mecp2$^{STOP/y}$) or control littermates. One-way ANOVA with post-hoc Tukey's test, *, p<0.05. FIG. 35D is a bar graph of preference index for the percentage of time spent investigating the novel mouse in the "Sociability" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 35E is a bar graph of preference index for the percentage of time spent investigating the novel mouse in the "Social Novelty Preference" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel.

FIGS. 36A-36D shows that restoration of Mecp2 only in peripheral sensory neurons of Mecp2 mutant mice improves PV-positive neuronal impairments in the primary somatosensory cortex. FIG. 36A is immunohistochemical (IHC) images of trunk region of primary somatosensory cortex of control, mutant (mecp2$^{sTOP/y}$), and mutant rescue (Advillin$^{Cre}$; Mecp2$^{STOP/y}$) mice, showing expression patterns for parvalbumin (PV) and Hoechst. FIG. 36B is a bar graph of quantification of the number of PV-positive neurons within a 1 mm$^2$ region of trunk primary somatosensory cortex. N=12 controls, 7 mutant and 7 mutant rescue mice, with 3 sections analyzed per mouse. One-way ANOVA with post-hoc Tukey's test, *, p<0.0001. FIG. 36C is a bar graph of average soma size of PV-positive neurons within a 1 mm$^2$ region of trunk primary somatosensory cortex. N=12 controls, 7 mutant and 7 mutant rescue mice, with 3 sections analyzed per mouse. One-way ANOVA with post-hoc Tukey's test, *, p<0.05. FIG. 36D is a bar graph of average soma fluorescence intensity of PV-positive neurons within a 1 mm$^2$ region of trunk primary somatosensory cortex. N=12 controls, 7 mutant and 7 mutant rescue mice, with 3 sections analyzed per mouse. One-way ANOVA with post-hoc Tukey's test, *, p<0.05.

FIG. 37A shows immunohistochemical (IHC) images of basolateral amygdala (BLA) of control, mutant (Mecp2$^{STOP/y}$), and mutant rescue (Advillin$^{Cre}$; Mecp2$^{STOP/y}$) mice, showing expression patterns for PV and Hoechst. FIG. 37B is a bar graph of total BLA area in control, mutant (Mecp2$^{STOP/y}$ and mutant rescue (Advillin$^{Cre}$; Mecp2$^{STOP/y}$) mice N=10 controls, 7 mutant and 6 mutant rescue mice, with 2 sections analyzed per mouse. One-way ANOVA with post-hoc Tukey's test, *, p<0.05; n.s., not significant. FIG. 37C is a bar graph of average fluorescence intensity of PV-positive neurons in the BLA of control, mutant (Mecp2$^{STOP/y}$), and mutant rescue (Advillin$^{Cre}$; Mecp2$^{STOP/y}$) mice N=10 controls, 7 mutant and 6 mutant rescue mice, with 2 sections analyzed per mouse. One-way ANOVA with post-hoc Tukey's test, not significant. FIG. 37D is a bar graph of average soma fluorescence intensity of PV-positive neurons in the BLA of control, mutant (Mecp2$^{STOP/y}$), and mutant rescue (Advillin$^{Cre}$; Mecp2$^{STOP/y}$) mice N=10 controls, 7 mutant and 6 mutant rescue mice, with 2 sections analyzed per mouse. One-way ANOVA with post-hoc Tukey's test, not significant.

FIG. 38A shows immunohistochemical (IHC) images of reticular nucleus of the thalamus from control, mutant (Mecp2$^{STOP/y}$), and mutant rescue (Advillin$^{Cre}$; Mecp2$^{STOP/y}$) mice, showing expression patterns for PV (and Hoechst. FIG. 38B is a bar graph of quantification of total area of PV-positive neurons within the thalamic reticular nucleus region. N=10 controls, 7 mutant and 6 mutant rescue mice, with 3 sections analyzed per mouse. One-way ANOVA with post-hoc Tukey's test, not significant. FIG. 38C is a bar graph of average soma fluorescence intensity of PV-positive neurons within the thalamic reticular nucleus region. N=10 controls, 7 mutant and 6 mutant rescue mice, with 3 sections analyzed per mouse. One-way ANOVA with post-hoc Tukey's test, not significant.

FIG. 39A shows immunohistochemical (IHC) images of hippocampus from control, mutant (Mecp2$^{STOP/y}$), and mutant rescue (Advillin$^{Cre}$; Mecp2$^{STOP/y}$mice, showing expression patterns for PV and Hoechst. FIG. 39B shows a bar graph of quantification of the number of PV-positive neurons within the hippocampal region. N=12 controls, 7 mutant and 7 mutant rescue mice, with 3 sections analyzed per mouse. One-way ANOVA with post-hoc Tukey's test, *, p<0.05. FIG. 39C shows a bar graph of average soma size of PV-positive neurons within the hippocampal region. N=12 controls, 7 mutant and 7 mutant rescue mice, with 3 sections analyzed per mouse. One-way ANOVA with post-hoc Tukey's test, *, p<0.001. FIG. 39D shows a bar graph of average soma fluorescence intensity of PV-positive within the hippocampal region. N=12 controls, 7 mutant and 7 mutant rescue mice, with 3 sections analyzed per mouse. One-way ANOVA with post-hoc Tukey's test, not significant.

FIG. 40A shows immunohistochemical (IHC) images of the trunk region of the primary somatosensory cortex of control and mutant (Advillin$^{Sre}$; Mecp2$^{f/y}$) mice, showing expression patterns for PVand Hoechst. FIG. 40B is a bar graph of quantification of the number of PV-positive neurons within a 1 mm$^2$ region of trunk primary somatosensory cortex. N=3 controls and 2 mutant mice, with 3 sections analyzed per mouse. Student's unpaired t-test, *, p<0.005. FIG. 40C is a bar graph of average soma size of PV-positive neurons within a 1 mm$^2$ region of trunk primary somatosensory cortex. N=3 controls and 2 mutant mice, with 3 sections analyzed per mouse. FIG. 40D is a bar graph of average soma fluorescence intensity of PV-positive neurons within a 1 mm² region of trunk primary somatosensory cortex. N=3 controls and 2 mutant mice, with 3 sections analyzed per mouse. One-way ANOVA with post-hoc Tukey's test, not significant.

FIGS. 41A-41D show that restoration of Shank3 only in peripheral sensory neurons of Shank3 mutant mice improves PV-positive neuronal impairments in the primary somatosensory cortex. FIG. 41A is immunohistochemical (IHC) images of trunk region of primary somatosensory cortex of control, mutant (Shank3$^{FX/+}$), and mutant rescue (Advillin$^{Cre}$; Shank3$^{FX+}$) mice, showing expression patterns for parvalbumin (PV) and Hoechst. FIG. 41B is a bar graph of quantification of the number of PV-positive neurons within a 1 mm² region of trunk primary somatosensory cortex. N=4 controls, 4 mutant and 4 mutant rescue mice, with 3 sections analyzed per mouse. One-way ANOVA with post-hoc Tukey's test, *, p<0.05. FIG. 41O is a bar graph of average soma size of PV-positive neurons within a 1 mm² region of trunk primary somatosensory cortex. N=12 controls, 7 mutant and 7 mutant rescue mice, with 3 sections analyzed per mouse. One-way ANOVA with post-hoc Tukey's test, not significant. FIG. 41D is a bar graph of average soma fluorescence intensity of PV-positive neurons within a 1 mm² region of trunk primary somatosensory cortex. N=12 controls, 7 mutant and 7 mutant rescue mice, with 3 sections analyzed per mouse. One-way ANOVA with post-hoc Tukey's test, not significant.

FIGS. 42A-42D show that restoration of Shank3 only in peripheral sensory neurons of Shank3 mutant mice improves PV-positive neuronal impairments in the basolateral amygdala. FIG. 42A shows immunohistochemical (IHC) images of basolateral amygdala (BLA) of control, mutant (Shank3$^{FX/+}$), and mutant rescue (Advillin$^{Cre}$; Shank3$^{FX/+}$) mice, showing expression patterns for PV and Hoechst. FIG. 42B is a bar graph of total BLA area in control, mutant (Shank3$^{FX/+}$), and mutant rescue (Advillin$^{Cre}$; Shank3$^{FX/+}$) mice N=4 controls, 4 mutant and 4 mutant rescue mice, with 2 sections analyzed per mouse. One-way ANOVA with post-hoc Tukey's test, *, p<0.05; #, p<0.10. FIG. 42C is a bar graph of average fluorescence intensity of PV-positive neurons in the BLA of control, mutant (Shank3$^{FX/+}$), and mutant rescue (Advillin$^{Cre}$; Shank3$^{FX/+}$) mice N=4 controls, 4 mutant and 4 mutant rescue mice, with 2 sections analyzed per mouse. FIG. 42D is a bar graph of average soma fluorescence intensity of PV-positive neurons in the BLA of control, mutant (Shank3$^{FX/+}$), and mutant rescue (Advillin$^{Cre}$; Shank3$^{FX/+}$) mice N=4 controls, 4 mutant and 4 mutant rescue mice, with 2 sections analyzed per mouse.

FIGS. 43A-43D show that deletion of Shank3 only in peripheral sensory neurons leads to fewer PV-positive neurons in the primary somatosensory cortex. FIG. 43A shows immunohistochemical (IHC) images of the trunk region of the primary somatosensory cortex of control and mutant (Advillin$^{Cre}$; Shank3$^{f/+}$) mice, showing expression patterns for PV and Hoechst. FIG. 43B is a bar graph of quantification of the number of PV-positive neurons within a 1 mm² region of trunk primary somatosensory cortex. N=4 controls and 3 mutant mice, with 3 sections analyzed per mouse. Student's unpaired t-test, #, p<0.10. FIG. 43C is a bar graph of average soma size of PV-positive neurons within a 1 mm² region of trunk primary somatosensory cortex. N=4 controls and 3 mutant mice, with 3 sections analyzed per mouse. Student's unpaired t-test, *, p<0.05. FIG. 43D is a bar graph of average soma fluorescence intensity of PV-positive neurons within a 1 mm² region of trunk primary somatosensory cortex. N=4 controls and 3 mutant mice, with 3 sections analyzed per mouse. One-way ANOVA with post-hoc Tukey's test, not significant.

FIGS. 44A-44H show that viral expression of GABRB3 in peripheral sensory neurons, beginning at P5, improves texture discrimination deficits observed in Mecp2$^{R306C}$ mutant mice. FIG. 44A is a bar graph of discrimination index for textured NORT, comparing texture discrimination performance in control mice, male mice with hemizygous mutations in Mecp2 (Mecp2$^{R306C/y}$) or male Advillin$^{Cre}$; Mecp2$^{R306C/y}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. A positive value indicates preference for the novel object, compared to the familiar object, *, p<0.05. Comparisons between groups are noted by brackets; one-way ANOVA with post-hoc Tukey's test: *, p<0.05. Animal numbers per group are shown in the bars of each panel. FIG. 44B is a bar graph of discrimination index for a 5-minute control NORT. A positive value indicates preference for the novel object, compared to the familiar object, *, p<0.05. Animal numbers per group are shown in the bars of each panel. FIG. 44C is a bar graph of discrimination index for a 1-hour control NORT. A positive value indicates preference for the novel object, compared to the familiar object, *, p<0.05. Comparisons between groups are noted by brackets; one-way ANOVA with post-hoc Tukey's test: *, p<0.05. Animal numbers per group are shown in the bars of each panel. FIG. 44D is a bar graph of amount of time spent physically interacting with both the familiar and novel object in the testing session of textured NORT in mutant mice and their control littermates. One-way ANOVA with post-hoc Tukey's test, not significant. FIG. 44E is a bar graph of discrimination index for textured NORT, comparing texture discrimination performance in female control mice, female mice with heterozygous mutations in Mecp2 (Mecp2$^{R/C}$ or female Advillin$^{Cre}$; Mecp2$^{R/C}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. A positive value indicates preference for the novel object, compared to the familiar object, *, p<0.05. Comparisons between groups are noted by brackets; one-way ANOVA with post-hoc Tukey's test: *, p<0.05. Animal numbers per group are shown in the bars of each panel.

FIG. 44F is a bar graph of discrimination index for a 5-minute control NORT. A positive value indicates preference for the novel object, compared to the familiar object, *, p<0.05. Animal numbers per group are shown in the bars of each panel. FIG. 44G is bar graph for discrimination index for a 1-hour control NORT. A positive value indicates preference for the novel object, compared to the familiar object, *, p<0.05. Comparisons between groups are noted by brackets; one-way ANOVA with post-hoc Tukey's test: *, p<0.05. Animal numbers per group are shown in the bars of each panel. FIG. 44H is a bar graph of amount of time spent physically interacting with both the familiar and the novel object in the testing session of textured NORT in mutant mice and their control littermates. One-way ANOVA with post-hoc Tukey's test, not significant.

FIGS. 45A-45F show that viral expression of GABRB3 in peripheral sensory neurons, beginning at P5, improves hairy skin hypersensitivity observed in male Mecp2$^{R306C/y}$ mutant mice. FIG. 45A is a bar graph of magnitude of startle response to a 125 dB noise in control mice, male mice with hemizygous mutations in Mecp2 (Mecp2$^{R306C/y}$) or male Advillin$^{Cre}$; Mecp2$^{R306C/y}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. One-way ANOVA with post-hoc Tukey's test, *, $p<0.05$. Animal numbers per group are shown in the bars of each panel. FIG. 45B is a bar graph of percent inhibition of the startle response to a 125 dB noise (pulse), when the startle noise was preceded by a light air puff (prepulse, 0.9 PSI) at an interstimulus interval of 250 ms between the prepulse and the pulse. One-way ANOVA with post-hoc Tukey's test: *, $p<0.05$. FIG. 45C is a bar graph of response to a light air puff alone, administered to the back hairy skin (0.9 PSI). Responses are expressed as percent of startle response to a 125 dB noise. One-way ANOVA with post-hoc Tukey's test: *, $p<0.05$. FIG. 45D is a bar graph of percent inhibition of the startle response to a 125 dB noise (pulse), when the startle noise is preceded by tone prepulse (80 dB) in mutant mice and their control littermates. One-way ANOVA with post-hoc Tukey's test, *, $p<0.05$. FIG. 45E is a bar graph of response to a non-startling acoustic noise (80 dB, 20 ms), in mutant mice and their control littermates. Responses are expressed as percent of startle response to a 125 dB startle noise. One-way ANOVA with post-hoc Tukey's test, not significant. FIG. 45F is a bar graph of percent decrease in startle response to a 125 dB noise during a 30-minute tactile PPI session, when comparing the first five startle responses to the last five responses of the session, to a 125 dB noise. Asterisks above bars indicate a significant decrease in startle response over time; one-sample t-test, *, $p<0.05$. Asterisks above brackets indicate significant differences between groups, one-way ANOVA with post-hoc Tukey's test, *, $p<0.05$.

FIGS. 46A-46F show that viral expression of GABRB3 in peripheral sensory neurons, beginning at P5, improves hairy skin hypersensitivity observed in female Mecp2$^{R/C}$ mutant mice. FIG. 46A is a bar graph of magnitude of startle response to a 125 dB noise in control mice, female mice with heterozygous mutations in Mecp2 (Mecp2$^{R/C}$ or female Advillin$^{Cre}$; Mecp2$^{R/C}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. One-way ANOVA with post-hoc Tukey's test, *, $p<0.05$. Animal numbers per group are shown in the bars of each panel. FIG. 46B is a bar graph of percent inhibition of the startle response to a 125 dB noise (pulse), when the startle noise was preceded by a light air puff (prepulse, 0.9 PSI) at an interstimulus interval of 250 ms between the prepulse and the pulse. One-way ANOVA with post-hoc Tukey's test: *, $p<0.05$. FIG. 46C is a bar graph of response to a light air puff alone, administered to the back hairy skin (0.9 PSI). Responses are expressed as percent of startle response to a 125 dB noise. One-way ANOVA with post-hoc Tukey's test: *, $p<0.05$. FIG. 46D is a bar graph of percent inhibition of the startle response to a 125 dB noise (pulse), when the startle noise is preceded by tone prepulse (80 dB) in mutant mice and their control littermates. One-way ANOVA with post-hoc Tukey's test, *, $p<0.05$. FIG. 46E is a bar graph of response to a non-startling acoustic noise (80 dB, 20 ms), in mutant mice and their control littermates. Responses are expressed as percent of startle response to a 125 dB startle noise. One-way ANOVA with post-hoc Tukey's test, not significant. FIG. 46F is a bar graph of percent decrease in startle response to a 125 dB noise during a 30-minute tactile PPI session, when comparing the first five startle responses to the last five responses of the session, to a 125 dB noise. Asterisks above bars indicate a significant decrease in startle response over time; one-sample t-test, *, $p<0.05$; #, $p<0.10$. Asterisks above brackets indicate significant differences between groups, one-way ANOVA with post-hoc Tukey's test, *, $p<0.05$.

FIGS. 47A-47G show that increased expression of GABRB3 in peripheral sensory neurons negatively correlates with hairy skin sensitivity in Mecp2 mutant mice. FIG. 47A shows intraperitoneal (i.p.) injection of AAV.FLEX.Gabrb3.mCherry into Advillin$^{Cre}$; Mecp2$^{R306C}$ mutant mice at P5 causes transduction of peripheral sensory neurons, as evidenced by positive staining for mCherry. Transduced large diameter neurons are co-stained with mCherry and NF200. FIG. 47B shows quantification of the percentage of neurons transduced per dorsal root ganglion (DRG) of animals i.p. injected with AAV.FLEX.Gabrb3.mCherry. Three different DRGs were analyzed per animal. FIG. 47C shows quantification of the percentage of large diameter primary sensory neurons that were transduced with AAV.FLEX.Gabrb3.mCherry. Three different DRGs were analyzed per animal. FIG. 47D shows i.p. injection of AAV.FLEX.Gabrb3.mCherry into Advillin$^{Cre}$; Mecp2$^{R306C}$ mutant mice at P5 increases GABRB3 expression in lamina III of the SC dorsal horn. Immunohistochemistry (IHC) images of spinal cord (SC) dorsal horn lamina III/IV from control, Mecp2$^{R306C/y}$ or Advillin$^{Cre}$; Mecp2$^{R306C/y}$ mice. Sections were immunostained for vGLUT1 (presynaptic terminals for Aβ and Aδ LTMRs) and GABRB3 to mark the presence of GABRB3 puncta at Aβ and Aδ LTMR presynaptic terminals. FIG. 47E shows quantification of vGLUT1+puncta co-labeled with GABRB3, relative to the total number of vGLUT1+puncta visualized per image. *, $p<0.01$. Puncta numbers are compared between mutant animals and their control littermates, one-way ANOVA with post-hoc Tukey's test: *, $p<0.05$. FIG. 47F is a graph of the percentage of primary somatosensory neurons transduced with AAV.FLEX.Gabrb3.mCherry is negatively correlated with hairy skin sensitivity. Comparison of individual animals' average transduction efficiency to their responses to a light air puff stimulus (50 ms, 0.9 PSI). Linear regression analysis, $R^2=0.752$. FIG. 47G is a graph of the percentage of vGLUT1+puncta co-labeled with GABRB3, relative to the total number of vGLUT1+puncta is negatively correlated with hairy skin sensitivity. Comparison of individual animals' expression levels of GABRB3 at Aβ and Aδ LTMR presynaptic terminals (vGLUT1+terminals), to their responses to a light air puff stimulus (50 ms, 0.9 PSI). Linear regression analysis, $R^2=0.8792$.

FIGS. 48A-48D show that an increased expression of GABRB3 in peripheral sensory neurons beginning at P5 improves anxiety-like behavior in male Mecp2$^{R306C}$ mutant mice. FIG. 48A shows representative traces of activity during the open field test for control mice, male mice with hemizygous mutations in Mecp2 (Mecp2$^{R306C/y}$) or male Advillin$^{Cre}$; Mecp2$^{R306C/y}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. FIG. 48B shows a bar graph of percentage of time spent in the center of the chamber during the open field test. One-way ANOVA with post-hoc Tukey's test, *, $p<0.05$; #, $p<0.10$. FIG. 48C shows a bar graph of total distance travelled during the open field test. One-way ANOVA with post-hoc Tukey's test, *, $p<0.05$; #, $p<0.10$. FIG. 48D shows a bar graph of percentage of time spent in the open arms of the elevate plus maze. One-way ANOVA with post-hoc Tukey's test, *, p<0.05.

FIGS. 49A-49D show that an increased expression of GABRB3 in peripheral sensory neurons beginning at P5 rescues anxiety-like behavior in female Mecp2$^{R306C}$ mutant mice. FIG. 49A shows representative traces of activity during the open field test for control mice, female mice with heterozygous mutations in Mecp2 (Mecp2$^{R/C}$) or female Advillin$^{Cre}$; Mecp2$^{R/C}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. FIG. 49B is a bar graph of percentage of time spent in the center of the chamber during the open field test. One-way ANOVA with post-hoc Tukey's test, *, p<0.05. FIG. 49C is a bar graph of total distance travelled during the open field test. One-way ANOVA with post-hoc Tukey's test, *, p<0.05. FIG. 49D Percentage of time spent in the open arms of the elevate plus maze. One-way ANOVA with post-hoc Tukey's test, *, p<0.05.

FIG. 50A shows representative heat maps of activity in the 3-chamber social interaction test during the "Sociability" (top panels) and "Social Novelty Preference" (bottom panels) portions of the assay, for control mice, male mice with hemizygous mutations in Mecp2 (Mecp2$^{R306C/y}$) or male Advillin$^{Cre}$; Mecp2$^{R306C/y}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. FIG. 50B shows a bar graph of preference index for the percentage of time spent investigating the novel mouse in the "Sociability" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 50C shows a bar graph of preference index for the percentage of time spent investigating the novel mouse in the "Social Novelty Preference" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 50D is a bar graph of average time spent (in seconds) in each of the three chambers during the "Sociability" and "Social Novelty Preference" portion of the 3-chamber social interaction test for the indicated groups. Comparisons between time spent in each chamber, per genotype: repeated measures two-way ANOVA with post-hoc Tukey's test: *, p<0.05.

FIG. 51A shows representative heat maps of activity in the 3-chamber social interaction test during the "Sociability" (top panels) and "Social Novelty Preference" (bottom panels) portions of the assay, for control mice, female mice with heterozygous mutations in Mecp2 (Mecp2$^{R/C}$) or female Advillin$^{Cre}$; Mecp2$^{R/C}$ mutant rescue mice. Mice were intraperitoneally injected at P5 with AAV.FLEX.Gabrb3.mCherry, which allows for expression of GABRB3 in peripheral sensory neurons of mice with the Advillin$^{Cre}$ transgene. FIG. 51B is a bar graph of preference index for the percentage of time spent investigating the novel mouse in the "Sociability" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 51C is a bar graph of preference index for the percentage of time spent investigating the novel mouse in the "Social Novelty Preference" portion of the 3-chamber social interaction test. A positive value indicates preference for the novel object, compared to the familiar object. *, p<0.05. Comparisons between groups are noted by brackets; one-way ANOVA with post-hoc Tukey's test: *, p<0.05. Animal numbers per group are shown in the bars of each panel. FIG. 51 D is a bar graph of average time spent (in seconds) in each of the three chambers during the "Sociability" and "Social Novelty Preference" portion of the 3-chamber social interaction test for the indicated groups. Comparisons between time spent in each chamber, per genotype: repeated measures two-way ANOVA with post-hoc Tukey's test: *, p<0.05. FIG. 51E is a bar graph of average time spent (in seconds) in each of the three chambers during the "Social Novelty Preference" portion of the 3-chamber social interaction test for the indicated groups. Comparisons between time spent in each chamber, per genotype: repeated measures two-way ANOVA with post-hoc Tukey's test: *, p<0.05.

FIG. 52A shows immunohistochemical (IHC) images of the trunk region of peripheral somatosensory cortex of control, mutant (Mecp2$^{R306C/y}$), and mutant rescue (Advillin$^{Cre}$; mecp2$^{R306C/y}$) mice, showing expression patterns for parvalbumin (PV) and Hoechst. Mice were intraperitoneally injected at P5 with AAV.FLEX.Gabrb3.mCherry, which allows for expression of GABRB3 in peripheral sensory neurons of mice with the Advillin$^{Cre}$ transgene. FIG. 52B is a bar graph of quantification of the number of PV-positive neurons within a 1 mm$^2$ region of trunk primary somatosensory cortex. N=6 controls, 6 mutant and 6 mutant rescue mice, with 3 sections analyzed per mouse. One-way ANOVA with post-hoc Tukey's test, *, p<0.0001. FIG. 52C is a bar graph of average soma size of PV-positive neurons within a 1 mm$^2$ region of trunk primary somatosensory cortex. N=6 controls, 6 mutant and 6 mutant rescue mice, with 3 sections analyzed per mouse. One-way ANOVA with post-hoc Tukey's test, *, p<0.05. FIG. 52D is bar graph of average soma fluorescence intensity of PV-positive neurons within a 1 mm$^2$ region of trunk primary somatosensory cortex. N=6 controls, 6 mutant and 6 mutant rescue mice, with 3 sections analyzed per mouse. One-way ANOVA with post-hoc Tukey's test, not significant.

FIG. 53A shows immunohistochemical (IHC) images of trunk region of primary somatosensory cortex of control, mutant (Mecp2$^{R306C/y}$) and mutant rescue (Advillin$^{Cre}$; Mecp2$^{R306C/y}$) mice, showing expression patterns for parvalbumin (PV) and Hoechst. Mice were intraperitoneally injected at P5 with AAV.FLEX.Gabrb3.mCherry, which allows for expression of GABRB3 in peripheral sensory neurons of mice with the Advillin$^{Cre}$ transgene. FIG. 53B shows a bar graph of quantification of the number of PV-positive neurons within a 1 mm$^2$ region of trunk primary somatosensory cortex. N=6 controls, 6 mutant and 6 mutant rescue mice, with 3 sections analyzed per mouse. One-way ANOVA with post-hoc Tukey's test, *, p<0.0001. FIG. 53C is a bar graph of average soma size of PV-positive neurons within a 1 mm$^2$ region of trunk primary somatosensory cortex. N=6 controls, 6 mutant and 6 mutant rescue mice, with 3 sections analyzed per mouse. One-way ANOVA with post-hoc Tukey's test, *, p<0.05. FIG. 53D is a bar graph of average soma fluorescence intensity of PV-positive neurons within a 1 mm$^2$ region of trunk primary somatosensory cortex. N=6 controls, 6 mutant and 6 mutant rescue mice, with 3 sections analyzed per mouse. One-way ANOVA with post-hoc Tukey's test, not significant.

FIG. 54A shows resting membrane potential of large diameter neurons cultured from DRGs of control mice in whole cell voltage clamp configuration, during a baseline period, 5 minutes after the application of 10 µM isoguvacine and 5 minutes after washout of 10 µM isoguvacine. Repeated measures one-way ANOVA, *, p<0.05. FIG. 54B shows resting membrane potential of large diameter neurons cultured from DRGs of control mice in whole cell voltage clamp configuration, during a baseline period or 5 minutes after the application of 10 µM isoguvacine. Student's paired t-test, p<0.05. FIG. 54C shows quantification of the minimal amount of current required to elicit an action potential in large diameter neurons in whole cell current clamp configuration, during a baseline period or 5 minutes after the application of 10 µM isoguvacine and 5 minutes after washout of 10 µM isoguvacine. Repeated measures one-way ANOVA, *, p<0.05. FIG. 54D shows quantification of the minimal amount of current required to elicit an action potential in large diameter neurons in whole cell current clamp configuration, during a baseline period or 5 minutes after the application of 10 µM isoguvacine. Student's paired t-test, p<0.05.

FIG. 55A shows resting membrane potential of large diameter neurons cultured from DRGs of control mice or Shank3B$^{+/-}$ mutant mice in whole cell voltage clamp configuration, during a baseline period or 5 minutes after the application of 10 µM isoguvacine. Repeated measures two-way ANOVA with post-hoc Tukey's test: *, p<0.05. FIG. 55B shows quantification of the minimal amount of current required to elicit an action potential in large diameter neurons cultured from DRGs of control mice or Shank3B$^{+/-}$ mutant mice in whole cell current clamp configuration, during a baseline period or 5 minutes after the application of 10 µM isoguvacine. Repeated measures two-way ANOVA with post-hoc Tukey's test: *, p<0.05. FIG. 55C shows resting membrane potential of large diameter neurons cultured from DRGs of control mice or Mecp2$^{STOP/y}$ mutant mice in whole cell voltage clamp configuration, during a baseline period or 5 minutes after the application of 10 µM isoguvacine. Repeated measures two-way ANOVA with post-hoc Tukey's test: *, p<0.05. FIG. 55D shows quantification of the minimal amount of current required to elicit an action potential in large diameter neurons cultured from DRGs of control mice or Mecp2$^{STOP/y}$ mutant mice in whole cell current clamp configuration, during a baseline period or 5 minutes after the application of 10 µM isoguvacine. Repeated measures two-way ANOVA with post-hoc Tukey's test: *, p<0.05.

FIG. 56A shows a graph of percent inhibition of the startle response (PPI) to a 125-dB noise (pulse), when the startle noise was preceded by a light air puff (prepulse, 0.9 PSI, 50 ms) at an interstimulus interval of 250 ms. Values are expressed as percent of control littermates' performance. Experiments were performed in mutant mice (Advillin$^{Cre}$; Mecp2$^{fl/y}$, Shank3B$^{+/-}$ or Fmr1$^{-/y}$) and control littermates, 30 minutes after an intraperitoneal (i.p.) of either saline (vehicle) or Isoguvacine (1 mg/kg). Two-way ANOVA, with post-hoc Holm-Sidak's test, *, p<0.05, when comparing mutants to control within same treatment; #, p<0.05, when comparing the same genotype across different treatments. FIG. 56B is a graph of response to a light air puff stimulus alone (0.9 PSI, 50 ms). Responses are expressed as a percent of startle response to a 125-B noise. Experiments were performed in mutant mice (Advillin$^{Cre}$; Mecp2$^{fl/y}$, Shank3B$^{+/-}$ or Fmr1$^{-/y}$) and control littermates, 30 minutes after an intraperitoneal (i.p.) of either saline (vehicle) or isoguvacine (1 mg/kg). Two-way ANOVA, with post-hoc Holm-Sidak's test, *, p<0.05, and †, p<0.10, when comparing mutants to control within same treatment; p<0.05, when comparing the same genotype across different treatments. FIG. 56C is a graph of magnitude of startle response to a 125-dB noise. Experiments were performed in mutant mice (Advillin$^{Cre}$; Mecp2$^{fl/y}$, Shank3B$^{+/-}$ or Fmr1$^{-/y}$) and control littermates, 30 minutes after an intraperitoneal (i.p.) of either saline (vehicle) or isoguvacine (1 mg/kg). FIG. 56D is a graph of magnitude of startle response to a 125-dB noise. Experiments were performed in control mice, 30 minutes after an intraperitoneal (i.p.) of either saline (vehicle), isoguvacine (1 mg/kg), or Midazolam (2.5 mg/kg). Two-way ANOVA, with post-hoc Holm-Sidak's test, *, p<0.05, when comparing the same genotype across different treatments.

DETAILED DESCRIPTION

Figure 2A:
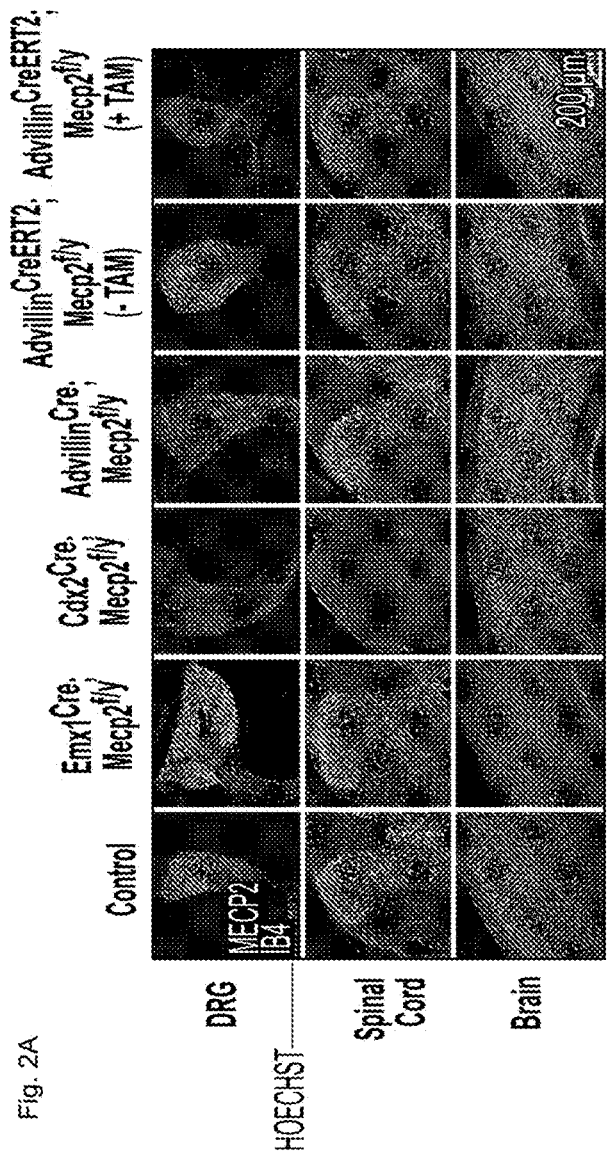

Although abnormalities in touch perception are commonly reported in ASD, the underlying neural mechanisms are not known. The first step leading to normal touch perception is activation of low-threshold mechanosensory neurons (LTMRs) with highly specialized endings in the skin. LTMRs respond to innocuous mechanical stimuli and mediate perception of object shape, texture, skin stroking, skin indentation, hair movement, and vibration. As with all mammalian somatosensory neurons, cutaneous LTMRs are pseudo-unipolar neurons with one peripheral axonal branch that innervates the skin and another branch that innervates the central nervous system (CNS). While LTMR central projections terminate in a somatotopic manner within the spinal cord (SC) dorsal horn, forming synaptic contacts onto both locally projecting interneurons and postsynaptic dorsal column projection neurons (PSDCs), a large subset of myelinated LTMRs also send an axonal branch via the dorsal column that terminates in the dorsal column nuclei (DCN) of the brainstem. Thus, the SC dorsal horn and DCN are initial sites of integration and processing of innocuous touch information that is then conveyed to higher brain centers. LTMRs, the SC dorsal horn, DCN, thalamus, and cortex represent potential loci of dysfunction underlying impairments in touch perception in ASD patients.

The great majority of ASD research has focused on brain-specific mechanisms and circuits, with little attention to potential contributions of the peripheral nervous system and SC to ASD phenotypes. Systemic virally-mediated replacement of Mecp2 in Mecp2 hemizygous (Mecp2$^{-/y}$) male mice effectively rescues behavioral deficits that are relevant to some ASD phenotypes. In contrast, intracranial viral delivery of Mecp2 only mildly improves behavioral phenotypes. Peripheral nervous system and SC deficiencies caused by disruption of Mecp2 or other ASD-associated genes play an important role in cutaneous tactile sensitivity. Early childhood tactile experiences are critical for the acquisition of normal social behavior and communication skills in humans and rodents. Tactile processing deficits in ASD contribute to aberrant cognitive and social behaviors.

A range of mouse ASD genetic models combined with behavioral testing, synaptic analyses, and electrophysiology were used to define both the etiology of aberrant tactile sensitivity in ASD and the contribution of somatosensory dysfunction to the expression of ASD-like traits. An SC locus of mechanosensory neuron synaptic dysfunction underlies aberrant tactile perception in ASD and a tactile processing deficiency during development contributes to anxiety-like behavior and social interaction deficits in adulthood.

Based on the work described here, we propose that small molecule-based and gene therapy can be used to reducing tactile dysfunction or anxiety. Accordingly, the present invention features a method of reducing tactile dysfunction or anxiety in a subject diagnosed with Autism Spectrum Disorder, Rett Syndrome, or Fragile X syndrome by administering a GABA$_A$ agent having reduced blood brain barrier or by expressing a nucleic acid encoding an exogenous alpha or beta subunit of a GABA$_A$ receptor in dorsal root ganglion neurons in the subject using a vector.

Small Molecule Therapy

ABA$_A$ agents having reduced BBB permeability can be used to reduce tactile dysfunction and anxiety. Suitable GABA$_A$ agents include agonists and positive allosteric modulators.

Gamma-aminobutyrate (GABA) is synthesized primarily by the enzyme glutamate decarboxylase (GAD), which catalyzes the conversion of the excitatory neurotransmitter glutamate to GABA mediates a wide range of physiological functions, both in the CNS and in external tissues and organs, via binding to GABA receptor subtypes, termed GABA$_B$, and GABA$_A$ receptors are the most abundant subtype of GABA$_A$ receptors are ionotropic receptors comprised of multiple subunits that form ligand-gated chloride ion channels. Activation of GABA$_A$ receptor subunits have been cloned (alpha, beta, gamma, delta, epsilon, pi, and theta subunits), each encoded by a separate gene. In addition, many subunits have multiple isoforms and/or splice variants, giving rise to a large degree of structural diversity GABA$_A$ Agents In some embodiments, a GABA$_A$ agent having reduced blood brain barrier permeability is administered to reduce tactile dysfunction or anxiety in patients diagnosed with ASD, Rett Syndrome, or Fragile X Syndrome. In some embodiments, the GABA$_A$ agent is an agonist selected from the group consisting of Isoguvacine, N-methyl isoguvacine, Isoguvacine hydrochloride, homotaurine, acetylaminopropane sulfonate, acetylaminopropane sulfonate salt, Homohypotaurine, β-guanidinopropionic acid, TACA, Trans-amino-4-crotonic acid, Trans-aminocyclopentane-3-3carboxylic acid, or GABA. In other embodiments, the GABA$_A$ agent is a positive allosteric modulator selected from the group consisting of 4,5,6,7-tetrahydroisoxazolo[5,4-c]pyridine-3-ol (THIP) and functional analogs thereof, TCS 1205, 5-nitro-alpha-oxo-N-(1R)-phenylethyl]-1H-indole-3-acetamide, 5-oxo-zaleplon, homo-β-proline, Isonipecotic acid, Tiagabine, ZAPA, 3-((aminoiminomethyl) thio)-2- propenoic acid, ZAPA sulfate, L-838,417, THIP salts, including but not limited to THIP hydrochloride, TP 003 (5-fluoro-2-[4-fluoro-3-[8-fluoro-7-(2-hydroxypropan-2-y0imidazo[1,2-a]pyridin-3-yl]phenyl]benzonitrile), Stiripentol, or Loreclezole [1-[(Z)-2-chloro-2-(2,4-dichlorophenyl)vinyl]-1H-1,2,4-triazole].

In some embodiments, the GABA$_A$ agent may be THIP, a salt of THIP, a functional analog of THIP, or a salt of a functional analog of THIP. As used herein, functional analogs of THIP are compounds that share certain chemical structural features with THIP but comprise one or more structural differences. Functional analogs of THIP exhibit the same general biological activity as THIP but may exhibit such activity to a different extent.

For example, in some embodiments, the GABA$_A$ agent may be an agonist having Formula (I):

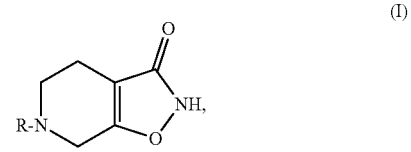

(I)

where R is selected from the group consistina of hvdroaen. acetyl. or a group of the general Formula (Ia):

(Ia)

where R' is $C_1$-$C_8$ alkyl, phenyl, phenyl substituted in the 4 position with halogen, $C_1$-$C_4$ alkoxy, or $C_1$-$C_4$ alkyl; or phenylalkyl such as benzyl or phenylethyl in which the phenyl group may be substituted in the 4-position with halogen, $C_1$-$C_4$ alkoxy, or $C_1$-$C_4$ alkyl; and salts thereof.

The compounds of Formula (I) may exist in tautomeric form, as shown in Formula (I'):

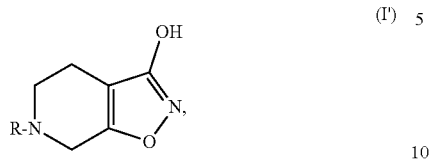

(I')

where Formula I is to be understood as covering tautomeric form (I') and mixtures of the two tautomeric forms.

Compounds of Formula (I) and salts thereof include the compounds depicted in Table 1.

TABLE 1

| Name | Structure |
| --- | --- |
| 4,5,6,7-tetrahydroisoxazolo(5,4-c)pyridin-3-ol (THIP) | 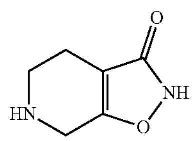 |
| 4,5,6,7-tetrahydroisoxazolo(5,4-c)pyridin-3-ol zwitterion | 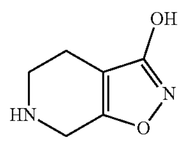 |
| 6-acetyl-4,5,6,7-tetrahydroisoxazolo[5,4-c]pyridine-3-ol | 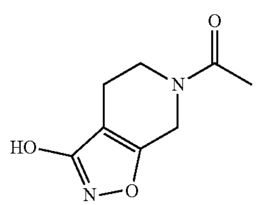 |
| methyl 3-hydroxy-4,5,6,7-tetrahydroisoxazolo[5,4-c]pyridine-6-carboxylate | 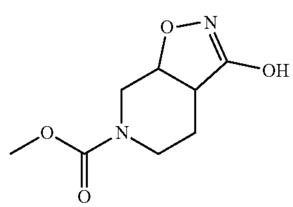 |
| ethyl 3-hydroxy-4,5,6,7-tetrahydroisoxazolo[5,4-c]pyridine-6-carboxylate | 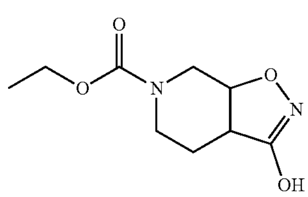 |
| tert-butyl 3-hydroxy-4,5,6,7-tetrahydroisoxazolo[5,4-c]pyridine-6-carboxylate | 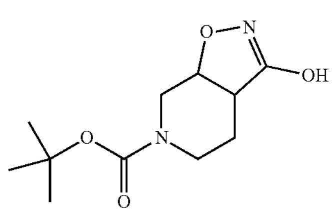 [SMILES: CC(C)(C)OC(=O)N1CCC2C(O)=NOC2C1] |

TABLE 1-continued

| Name | Structure |
|---|---|
| phenyl 3-hydroxy-4,5,6,7-tetrahydroisoxazolo[5,4-c]pyridine-6-carboxylate | 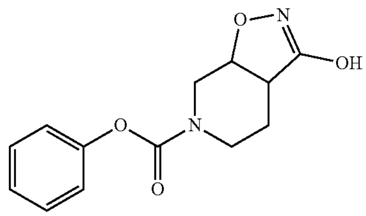 [SMILES: O=C(Oc1ccccc1)N1CCC2C(O)=NOC2C1] |
| 4-chlorophenyl 3-hydroxy-4,5,6,7-tetrahydroisoxazolo[5,4-c]pyridine-6-carboxylate | 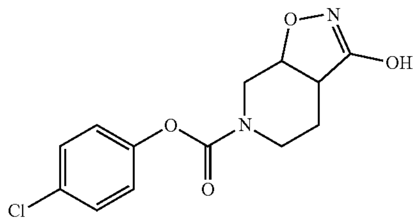 [SMILES: O=C(Oc1ccc(Cl)cc1)N1CCC2C(O)=NOC2C1] |
| 4-methoxyphenyl 3-hydroxy-4,5,6,7-tetrahydroisoxazolo[5,4-c]pyridine-6-carboxylate | 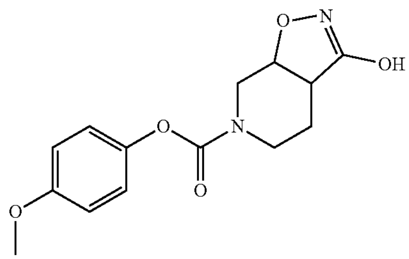 [SMILES: COc1ccc(OC(=O)N2CCC3C(O)=NOC3C2)cc1] |
| benzyl 3-hydroxy-4,5,6,7-tetrahydroisoxazolo[5,4-c]pyridine-6-carboxylate | 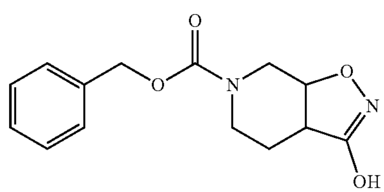 [SMILES: O=C(OCc1ccccc1)N1CCC2C(O)=NOC2C1] |
| 3-hydroxy-4,5,6,7-tetrahydroisoxazolo[5,4-c]pyridinium bromide | 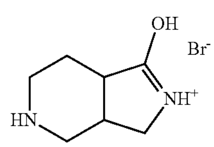 |
| 3-hydroxy-4,5,6,7-tetrahydroisoxazolo[5,4-c]pyridinium hydrochloride | 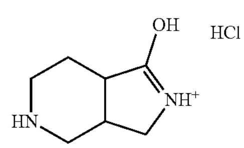 |

Pharmaceutical Compositions

GABA$_A$ agents are preferably formulated into pharmaceutical compositions for administration to human subjects in a biologically compatible form suitable for administration in vivo. Pharmaceutical compositions typically include a GABA$_A$ agent and a pharmaceutically acceptable excipient.

The GABA$_A$ agent can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The GABA$_A$ agent may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, a GABA$_A$ agent can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of $GABA_A$ agents into preparations which can be used pharmaceutically.

The excipient or carrier is selected on the basis of the mode and route of administration. Suitable pharmaceutical carriers, as well as pharmaceutical necessities for use in pharmaceutical formulations, are described in Remington: The Science and Practice of Pharmacy, 22nd Ed., Allen, Ed. (2012), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in Handbook of Pharmaceutical Excipients, 6th Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in Remington: The Science and Practice of Pharmacy, 22nd Ed., Allen, Ed. (2012), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the $GABA_A$ agent, or pharmaceutically acceptable salts or prodrugs thereof, or pharmaceutical compositions thereof, can vary depending on many factors, e.g., the pharmacodynamic properties of the $GABA_A$ agent; the mode of administration; the age, health, and weight of the recipient; the nature and extent of the symptoms; the frequency of the treatment, and the type of concurrent treatment, if any; and the clearance rate of the $GABA_A$ agent in the animal to be treated. One of skill in the art can determine the appropriate dosage based on the above factors. The $GABA_A$ agent may be administered initially in a suitable dosage that may be adjusted as required, depending on the clinical response. In general, a suitable daily dose of a $GABA_A$ agent will be that amount of the $GABA_A$ agent that is the lowest dose effective to produce a therapeutic effect. Such an effective dose will generally depend upon the factors described above.

A $GABA_A$ agent may be administered to the patient in a single dose or in multiple doses. When multiple doses are administered, the doses may be separated from one another by, for example, 1-24 hours, 1-7 days, 1-4 weeks, or 1-12 months. The $GABA_A$ agent may be administered according to a schedule or the $GABA_A$ agent may be administered without a predetermined schedule. An active $GABA_A$ agent may be administered, for example, 1, 2, 3, 4, 5, 6, 7, 8, 9, 10, 11, or 12 times per day, every 2nd, 3rd, 4th, 5th, or 6th day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions.

While the attending physician ultimately will decide the appropriate amount and dosage regimen, an effective amount of a $GABA_A$ agent may be, for example, a total daily dosage of, e.g., between 0.05 mg and 3000 mg of any of the $GABA_A$ agents described herein. Alternatively, the dosage amount can be calculated using the body weight of the patient. Such dose ranges may include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the $GABA_A$ agent is administered.

In the methods of the invention, the time period during which multiple doses of a $GABA_A$ agent are administered to a patient can vary. For example, in some embodiments doses of the $GABA_A$ agents are administered to a patient over a time period that is 1-7 days; 1-12 weeks; or 1-3 months. In other embodiments, the $GABA_A$ agents are administered to the patient over a time period that is, for example, 4-11 months or 1-30 years. In other embodiments, the $GABA_A$ agents are administered to a patient at the onset of symptoms. In any of these embodiments, the amount of $GABA_A$ agent that is administered may vary during the time period of administration. When a $GABA_A$ agent is administered daily, administration may occur, for example, 1, 2, 3, 4, 5, 6, 7, 8, 9, 10, 11, or 12 times per day.

Formulations

A $GABA_A$ agent may be administered to patients or animals with a pharmaceutically-acceptable diluent, carrier, or excipient, in unit dosage form. The $GABA_A$ agents for use in treatment of ASD, Rett Syndrome, or Fragile X Syndrome may be produced and isolated by any standard technique known to those in the field of medicinal chemistry. Conventional pharmaceutical practice may be employed to provide suitable formulations or compositions to administer the identified $GABA_A$ agent to patients diagnosed with ASD, Rett Syndrome, or Fragile X Syndrome.

Exemplary routes of administration of the $GABA_A$ agent, or pharmaceutical compositions thereof, used in the present invention include oral, sublingual, buccal, transdermal, intradermal, intramuscular, parenteral, intravenous, intraarterial, intracranial, subcutaneous, intraorbital, intraventricular, intraspinal, intraperitoneal, intranasal, inhalation, intrathecal and topical administration. The $GABA_A$ agents desirably are administered with a pharmaceutically acceptable carrier. Pharmaceutical formulations of the $GABA_A$ agents formulated for treatment of ASD, Rett Syndrome, and Fragile X Syndrome are also part of the present invention.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of $GABA_A$ agents, or by incorporating the $GABA_A$ agent into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the $GABA_A$ agents and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Parenteral Administration

The $GABA_A$ agents can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the $GABA_A$ agents may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

Exemplary formulations for parenteral administration include solutions of the $GABA_A$ agent prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, 22nd Ed., Allen, Ed. (2012) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the $GABA_A$ agents. Other potentially useful parenteral delivery systems for $GABA_A$ agents include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the $GABA_A$ agent. Exemplary formulations for parenteral release of the $GABA_A$ agent include: aqueous solutions, powders for reconstitution, cosolvent solutions, oil/water emulsions, suspensions, oil-based solutions, liposomes, microspheres, and polymeric gels.

Reducing $GABA_A$ Agent BBB Permeability

In some embodiments, a $GABA_A$ agent that crosses the blood brain barrier can be modified such that it retains its $GABA_A$ activity but has reduced blood brain barrier permeability. When modified to have reduced blood brain barrier permeability, it is essential for the GABAA agents not to lose their functionality critical to maintaining intrinsic activity for their utility as potential drugs. In some embodiments, the GABAA agents have the suitable structures and physiochemical properties that maintain or improve their therapeutic activity, but limit their exposure to the CNS. In some embodiments, GABAA agents have physiochemical properties, such as Log P (water- octanol partition coefficient) values, PSA and/or FRBs, which limit the ability of these agents to penetrate the blood brain barrier and enter the CNS. In some embodiments, these agents have equivalent activity.

In some embodiments, the GABAA agents comprise substituents that increase the molecular weight of the $GABA_A$ agents in order to render them less penetrant of the blood brain barrier. The substituents could result in additional increases in PSA and or decreases in lipophilicity in order to further decrease permeability. Alternatively blocking groups could be added to sterically hinder sites of metabolic attack.

Gene Therapy

In some embodiments, a nucleic acid encoding an exogenous alpha or beta subunit of a $GABA_A$ receptor in DRG neurons may be used to reduce tactile dysfunction or anxiety in a subject diagnosed with ASD, Rett Syndrome, or Fragile X Syndrome. In another embodiment, a first nucleic acid encoding an exogenous alpha subunit of a $GABA_A$ receptor and a second nucleic acid encoding an exogenous beta subunit of a $GABA_A$ receptor may be used to reduce tactile dysfunction or anxiety in a subject diagnosed with ASD, Rett syndrome, or Fragile X. In some embodiments the nucleic acid is expressed using an AAV vector or a lentiviral vector. In some embodiments, the nucleic acid is expressed using an AAV 2/9 vector.

The $GABA_A$ receptor is derived form a family of different genes which generates a large degree of receptor diversity, with different combinations of subunits giving rise to receptors with specific properties. $GABA_A$ receptors are ligand-gated receptors, composed of five subunits arranged around a central pore, permeable to chloride and bicarbonate. Functional receptors consist of five subunits selected from 19 known receptor subunits: $\alpha 1$-6, $\beta 1$-3, $\gamma 1$-3, $\delta$, $\epsilon$, $\theta$, $\pi$, and $\rho 1$-3. This non-random assembly results in a complex heterogeneity of $GABA_A$ receptor subtypes, and each subtype has a distinct physiological and pharmacological profile. Subunits of all superfamily members share the same predicted transmembrane topology. These subunit polypeptides contain four transmembrane domains with a large extracellular N-terminal region, a large intracellular loop between transmembrane domains 3 and 4, and a small, extracellular C-terminal domain. When assembled, the native $GABA_A$ receptor subunits are arranged in a pentameric array such that the second transmembrane region of each subunit contributes to the lining of the chloride channel pore.

$GABA_A$ Subunit Compositions

In some embodiments, the preferred subunit composition comprises at least one alpha subunit or at least one beta subunit. In other embodiments, the preferred subunit composition comprises at least one alpha subunit and at least one beta subunit. In specific embodiments, the preferred subunit compositions may be (i) $\alpha 1$, $\beta 3$, $\gamma 2$; (ii) $\alpha 2$, $\beta 3$, $\gamma 2$; (iii) $\alpha 3$, $\beta 3$, $\gamma 2$; (iv) $\alpha 4$, $\beta 3$, $\gamma 2$; (v) $\alpha 5$, $\beta 3$, $\gamma 2$; (vi) $\alpha 6$, $\beta 3$, $\gamma 2$; (vii) $\alpha 1$, $\beta 1$, $\gamma 2$; (viii) $\alpha 1$, $\beta 2$, $\gamma 2$; (ix) $\alpha 4$, $\beta 3$; (x) $\alpha 4$, $\beta 3$, $\delta$; (xi) $\alpha 6$, $\beta 3$; (xii) $\alpha 6$, $\beta 3$, $\delta$; (xiii) $\alpha 1$, $\beta 2$; (xiv) $\alpha 3$, $\beta 3$; (xv) $\alpha 1$, $\beta 2$, $\delta$; (xvi) $\alpha 4$, $\beta 2$, $\delta$; (xvii) $\alpha 3$, $\beta 3$, $\ominus$; or (xviii) $\alpha 3$, $\beta 3$, $\epsilon$.

Promoters

In some embodiments, the vector comprises a promoter operably linked to a nucleic acid encoding an exogenous alpha or beta subunit of a $GABA_A$ receptor in DRG neurons. The promoter may be a neuron-specific promoter. In some embodiments, the promoter is a DRG-specific promoter. Specific gene expression in a selected cell type can be achieved by using a cell-specific promoter.

Neuron-specific promoters may be any nucleotide sequence that functions to activate transcription of operably linked sequences within neurons or neuronal cells and substantially not in other cell types. A promoter does not substantially activate transcription if the levels of transcription of operably linked sequences in any of those cell types are sufficiently low so as not to affect physiological functioning of the cell.

Neuron-specific promoters may include promoters for neuronal genes such as Synapsin I, Neuron-specific enolase, Neurofilament-L and Neuropeptide Y and promoters specific for particular types of neuronal cells. In some embodiments, the neuron-specific promoter is Platelet-derived growth factor $\beta$-chain (PDGF $\beta$) promoter, advillin, mouse calcium/calmodulin-dependent protein kinase II, tubulin alpha I, neuron-specific enolase, neurofilament, receptor tyrosine kinase, G-protein-coupled receptor MRGPRB4, tyrosine-hydroxylase, tropomyosin receptor kinase B, or tropomyosin receptor kinase C. In a specific embodiment, the neuron-specific promoter is human PDGF $\beta$ promoter. Other neuron-specific promoters will be known to persons skilled in the art.

A neuron-specific promoter comprises at least one nucleotide sequence capable of activating neuronal cell specific expression of operably linked sequences and in some embodiments the nucleotide sequence will retain the minimum binding site(s) for transcription factor(s) required for the sequence to act as a promoter. In some embodiments, the vector comprises multiple copies of the same sequence or two or more different nucleotide sequences each of which is effective to activate transcriptional activity. For various promoters which may be used, transcription factor binding sites may be known or identified by one of ordinary skill using methods known in the art as described above. Suitable promoter/enhancer constructs may be readily determined by standard expression assay.

The transcriptional activity of a promoter in some instances may be weak, providing a less than ideal level of expression of therapeutic gene sequences. In various embodiments, the promoter may be operably linked to an enhancer. As would be understood by a skilled person, an "enhancer" is any nucleotide sequence capable of increasing the transcriptional activity of an operably linked promoter and, in the case of a neuron-specific promoter, of selectively increasing the transcriptional activity of the promoter in neuronal cells. A number of enhancers are known and a person skilled in the art would also know how to screen for novel enhancer sequences, for instance, by screening nucleotide sequences capable of increasing the transcription of a reporter gene, for instance, through functional mapping.

A first nucleic acid sequence is operably linked with a second nucleic acid sequence when the sequences are placed in a functional relationship. For example, a coding sequence is operably linked to a promoter if the promoter activates the transcription of the coding sequence. Similarly, a promoter and an enhancer are operably linked when the enhancer increases the transcription of operably linked sequences. Enhancers may function when separated from promoters and as such, an enhancer may be operably linked to a promoter even though it is not contiguous to the promoter. Generally, however, operably linked sequences are contiguous.

In different embodiments, the enhancer may be a heterologous enhancer, meaning a nucleotide sequence which is not naturally operably linked to a promoter and which, when so operably linked, increases the transcriptional activity of the promoter. Reference to increasing the transcriptional activity is meant to refer to any detectable increase in the level of transcription of an operably linked sequence compared to the level of the transcription observed with a promoter alone, as may be detected in standard transcriptional assays, including those using a reporter gene construct.

Routes of Gene Therapy Administration

Intrathecal Delivery

A nucleic acid encoding an exogenous alpha or beta subunit in DRG neurons in a subject may be administered into the cerebrospinal fluid surrounding the spinal cord via intrathecal delivery. The vectors are administered preferably by intrathecal injection in an amount sufficient to achieve the desired result. In some embodiments, the intrathecal administration of the composition does not result in substantial adverse effects in the subject.

Intrathecal administration of the recombinant vector into DRG cerebrospinal fluid may be accomplished by a relatively minimally invasive technique. The nucleic acid vector encoding an exogenous alpha or beta subunit under the control of a neuron-specific promoter can be delivered to the cells in the DRG. The site of administration may be tailored to the desired treatment. In some embodiments, the site of administrations is the lumbar region. Injections into the lumbar region are considered to be relatively safe as the subarachnoid space is relatively large in this area.

Effective amounts of vectors can be given repeatedly, depending upon the effect of the initial treatment regimen. Administrations are typically given periodically, while monitoring any response. It will be recognized by a skilled person that lower or higher dosages may be given, according to the administration schedules and routes selected.

When administered to a human patient, for example, the vectors are administered in an effective amount and for a sufficient time period to achieve a desired result. For example, the vectors may be administered in quantities and dosages necessary to deliver a therapeutic gene, the product of which functions to alleviate, improve, mitigate, ameliorate, stabilize, prevent the spread of, slow or delay the progression of or cure a peripheral neuronal neuropathy.

The effective amount to be administered to a patient can vary depending on many factors such as, among other things, the pharmacodynamic properties of the therapeutic gene product, the mode of administration, the age, health and weight of the subject, the nature and extent of the disorder or disease state, the frequency of the treatment and the type of concurrent treatment, if any. In embodiments employing viral vectors, the effective amount may also depend on the virulence and titre of the virus.

One of skill in the art can determine the appropriate amount based on the above factors. Vectors may be administered initially in a suitable amount that may be adjusted as required, depending on the clinical response of the patient. The effective amount of a vector can be determined empirically and depends on the maximal amount of the vector that can be safely administered. In some embodiments, the vector may have little cytotoxicity in vertebrates and may be administered in large amounts.

However, the amount of vectors administered should be the minimal amount that produces the desired result.

Intraperitoneal Delivery

A nucleic acid encoding an exogenous alpha or beta subunit in DRG neurons in a subject may be administered via intraperitoneal delivery. The vectors are administered preferably by intraperitoneal injection in an amount sufficient to achieve the desired result. In some embodiments, the intraperitoneal administration of the composition does not result in substantial adverse effects in the subject.

Effective amounts of vectors can be given repeatedly, depending upon the effect of the initial treatment regimen. Administrations are typically given periodically, while monitoring any response. It will be recognized by a skilled person that lower or higher dosages may be given, according to the administration schedules and routes selected.

When administered to a human patient, for example, the vectors are administered in an effective amount and for a sufficient time period to achieve a desired result. For example, the vectors may be administered in quantities and dosages necessary to deliver a therapeutic gene, the product of which functions to alleviate, improve, mitigate, ameliorate, stabilize, prevent the spread of, slow or delay the progression of or cure a peripheral neuronal neuropathy.

The effective amount to be administered to a patient can vary depending on many factors such as, among other things, the pharmacodynamic properties of the therapeutic gene product, the mode of administration, the age, health and weight of the subject, the nature and extent of the disorder or disease state, the frequency of the treatment and the type of concurrent treatment, if any. In embodiments employing viral vectors, the effective amount may also depend on the virulence and titre of the virus.

One of skill in the art can determine the appropriate amount based on the above factors. Vectors may be administered initially in a suitable amount that may be adjusted as required, depending on the clinical response of the patient. The effective amount of a vector can be determined empirically and depends on the maximal amount of the vector that can be safely administered. In some embodiments, the vector may have little cytotoxicity in vertebrates and may be administered in large amounts. However, the amount of vectors administered should be the minimal amount that produces the desired result.

EXAMPLES

Mouse Models of ASD Exhibit Aberrant Innocuous Touch Sensitivity

Mouse models of syndromic and non-syndromic forms of ASD were examined to determine if they exhibit deficits in texture discrimination and tactile sensitivity. Mecp2 null mice and mice with an arginine-to-cysteine missense mutation in Mecp2 (Mecp2R$^{306C}$), a common mutation found in human RTT patients, were examined. Mice harboring mutations in Shank3 and Fmr1, which in humans are associated with forms of ASD and Fragile X Syndrome, respectively, were also analyzed. Six week-old male Mecp2$^{-/Y}$, Mecp2$^{R306C}$, Shank3B$^{+/-}$, and Fmr1$^{-/y}$ mice and control littermates were subjected to tactile-based tasks to assess mechanosensory behaviors and sensitivity.

Figure 9A:
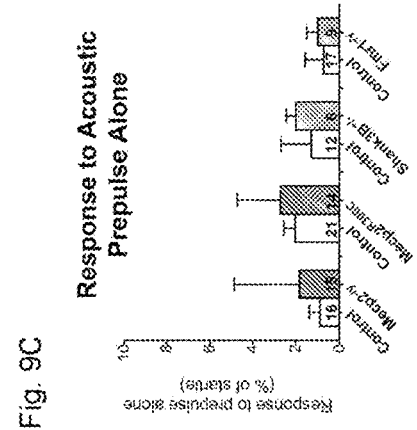
FIGS. 9A-9C show additional behavioral analyses of Mecp2, Shank3B, and Fmr1 mutant mice.

Textured NORT was developed to assess glabrous skin tactile discrimination abilities in mice. Textured NORT utilizes 4 cm long cubes that differ only in texture (rough or smooth, FIGS. 1A, 1B, 8, see Experimental Procedures). While control mice preferentially explored the cube with novel texture in the textured NORT assay, Mecp2$^{-/y}$, Mecp2$^{R306C}$, Shank3B$^{+/-}$ and Fmr1$^{-/y}$ mice did not (FIG. 1C). The deficits are specific for textured NORT, and not a general lack of novelty-seeking behavior, as mutant mice performed comparably to control mice on a control NORT in which objects differed in color and shape, but not texture, when the retention period was five minutes (FIG. 1D). Moreover, the amount of time spent investigating objects during NORT did not differ between genotypes (FIG. 9A). Mutant mice did not exhibit an aversion to the objects, nor did they avoid tactile exploration. Mecp2$^{-/y}$, Mecp2$^{R306C}$, Shank3B$^{+/-}$ and Fmr1$^{-/y}$ mice did not show a preference for novel colored or shaped objects, however, when the retention period was increased to 1 hour (FIG. 1E).

A novel tactile PPI assay was used to investigate whether Mecp2$^{-/y}$, Mecp2$^{R306C}$ Shank3B$^{+/-}$ and Fmr1$^{-/y}$ mice exhibit abnormalities in hairy skin tactile sensitivity and/or tactile sensorimotor gating. For tactile PPI, the 'prepulse' is a light air puff (0.9 PSI) applied to back hairy skin, and this prepulse is followed by a broadband white noise acoustic startle 'pulse' of 125 decibels (dB) to elicit an acoustic startle reflex. Air puffs were administered to the backs of mice at various times (inter-stimulus intervals (ISIs)) prior to the acoustic startle pulse to assess both hairy skin sensitivity and sensorimotor gating (FIG. 1F). A light air puff prepulse robustly reduces the magnitude of an acoustic startle response in control mice (FIG. 1G, FIG. 1H). Tactile PPI is mediated by cutaneous sensory neuron detection of the tactile prepulse because it is abolished when back hairy skin is pretreated with lidocaine to silence cutaneous sensory nerve fibers or when the air puff stimulus is pointed away from the mouse (FIG. 1G, FIG. 1H, FIG. 8I, and FIG. 8J).

Figure 9B:
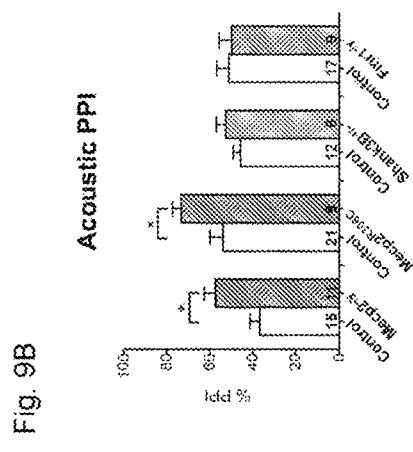
Figure 9C:
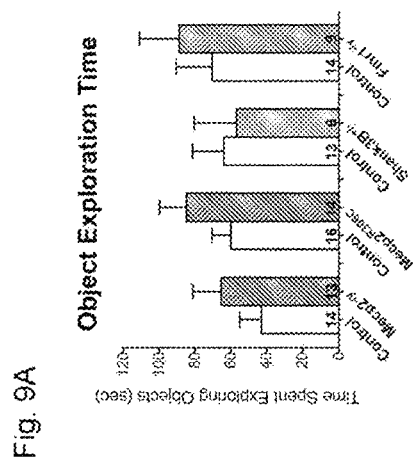

Mecp2$^{-/y}$, Mecp2$^{R306C}$, Shank3B$^{+/-}$ and Fmr1$^{-/y}$ mice all exhibited enhanced tactile PPI responses, compared to control littermates (FIG. 1J). For comparison, all ASD and control mice were also tested on an acoustic version of PPI, with varying acoustic prepulse intensities. Mecp2$^{-/y}$ and Mecp2$^{R306C}$ mice exhibited an increase in acoustic PPI at a prepulse intensity 15 dB above background, while the other mutant lines tested showed no acoustic PPI deficits (FIG. 9B). Mecp2$^{-/y}$ and Mecp2$^{R306C}$ mice also startled significantly less to the 125 dB startle noise, indicative of motor impairments (FIG. 1I). Tactile PPI alterations in the mutants are at least in part due to hypersensitivity to the air puff prepulse stimulus itself, as Mecp2$^{-/y}$, Mecp2$^{R306C}$, Shank3B$^{+/-}$, and Fmr1$^{-/y}$ mutant mice displayed significantly increased responses to the air puff alone (FIG. 1K), but not to an acoustic prepulse alone (FIG. 9C), compared to control littermates.

Figure 2B:
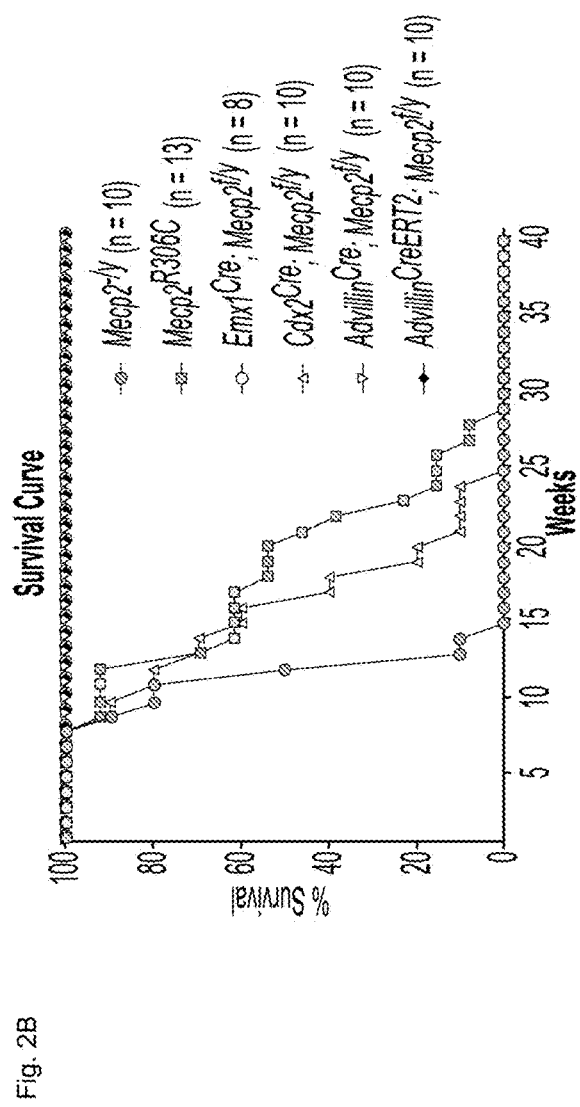

Somatosensory Neuron Deletion of Mecp2 in Either Development or Adulthood Leads to Aberrant Tactile Sensitivity Cellular locus of tactile sensory dysfunction in Mecp2 mutants was identified using a conditional Mecp2 allele. Crossing Mecp2 floxed (Mecp2$^{f/y}$) mice with mice expressing Cre recombinase in specific cell types allowed for Mecp2 deletion and loss of MECP2 protein in either excitatory neurons in the forebrain (Emx1$^{Cre}$; Mecp2$^{f/y}$), all cells that are caudal to cervical level 2 (Cdx2$^{Cre}$; Mecp2$^{f/y}$), or all DRG and trigeminal somatosensory neurons (Advillin$^{Cre}$; Mecp2$^{f/y}$) (FIG. 2A). Deletion of Mecp2 in cells below the neck (Cdx2$^{Cre}$; Mecp2$^{f/y}$) recapitulated the reduced lifespan observed in Mecp2$^{-/y}$ and Mecp2$^{R306C}$ mutant mice; the majority of these mice did not survive beyond 16 weeks (FIG. 2B), likely due to respiratory and/or cardiovascular deficits. Similar to Mecp2$^{-/y}$ mice, Cdx2$^{Cre}$; Mecp2$^{f/y}$ mutants also displayed abnormal breathing patterns, decreased respiratory tidal volume and rate, and decreased $CO_2$ expiration as measured by plethysmography (FIGS. 10E-10H). Cdx2$^{Cre}$; Mecp2$^{f/y}$ mutants also exhibited reduced body weight, a hindlimb clasping phenotype, motor deficits as measured using an accelerating rotarod, but not reduced brain size (FIGS. 10D, 9I, 9J). In contrast, mice lacking Mecp2 exclusively in somatosensory neurons (Advillin$^{Cre}$; Mecp2$^{f/y}$) exhibited normal body weight, brain size, hindlimb extension, motor performance, respiration (FIGS. 10D-10J), and lifespan (FIG. 2B). Thus, Mecp2 deletion in primary somatosensory neurons does not lead to overt RTT phenotypes.

To ask whether Mecp2 in excitatory neurons of the forebrain, SC, and/or peripheral somatosensory neurons contribute to tactile perception deficits, we next subjected Emx1$^{Cre}$; Mecp2$^{f/y}$, Cdx2$^{Cre}$; Mecp2$^{f/y}$ and Advillin$^{Cre}$; Mecp2$^{f/y}$ mice to textured and control NORT, and tactile and acoustic PPI. Cdx2$^{Cre}$; Mecp2$^{f/y}$ and Advillin$^{Cre}$; Mecp2$^{f/y}$ mice, but not Emx1$^{Cre}$; Mecp2$^{f/y}$ mice, had a significant deficit in textured NORT. Both conditional mutants were able to discriminate between objects that differ in color and shape in both the 5 minute and 1 hour retention period tests (FIGS. 2C-2E). Females with heterozygous deletion of Mecp2 in somatosensory neurons (Advillin$^{Cre}$; Mecp2$^{f/+}$) also exhibited deficits in textured NORT (FIG. 2C). We did not observe any differences in object exploration time in any condition or genotype tested (FIG. 10A). Similarly, deletion of Mecp2 in neurons below the neck or in primary somatosensory neurons led to tactile hypersensitivity in hairy skin, as measured by the tactile PPI assay (FIG. 2G). These changes are at least in part due to hypersensitivity to tactile stimuli applied to hairy skin because Cdx2$^{Cre}$; Mecp2$^{f/y}$, Advillin$^{Cre}$; Mecp2$^{f/y}$, and Advillin$^{Cre}$; Mecp2$^{f/+}$ mutants exhibited enhanced responses to air puff alone (FIG. 2H), but not to acoustic PPI (FIG. 10B) or an acoustic pre-pulse (FIG. 10C), compared to control littermates. Cdx2$^{Cre}$; Mecp2$^{f/y}$ mice showed a significant reduction in startle amplitude compared to control littermates (FIG. 2F). Mice with deletion of Mecp2 in excitatory forebrain neurons (Emx1$^{Cre}$; Mecp2$^{f/y}$) performed similarly to control littermates on the tactile PPI assay, and did not show increased responsiveness to air puff stimuli alone (FIGS. 2G, 2H).

We also addressed whether Mecp2 expression in primary somatosensory neurons is required in adulthood for normal tactile discrimination and sensitivity. For this, Mecp2$^{f/y}$ mice were crossed to an Advillin$^{CreERT2}$ mouse line, which enables excision of floxed alleles in primary somatosensory neurons of adult mice following treatment with tamoxifen. Administration of 1 mg tamoxifen per day for 5 days beginning at P28 resulted in deletion of Mecp2 in >90% of DRG neurons, whereas Mecp2 expression in the SC and brain was unaltered (FIG. 2A). Adult deletion of Mecp2 in primary somatosensory neurons (in either males or heterozygous females) recapitulated the tactile behavioral deficits observed in the developmental Mecp2 mutants; both textured NORT and tactile PPI were impaired (FIGS. 2C-H). Thus, Mecp2 expression in primary somatosensory neurons is necessary for both normal glabrous skin tactile discrimination and hairy skin sensitivity.

Sensory Neuron Deletion of Mecp2 Leads to a Decrease in GABRB3 in the Dorsal Horn, and Gabrb3 Expression in Sensory Neurons is Required for Tactile Sensitivity While there are multiple etiologies of ASD, one common observation among ASD animal models is a deficit in GABAergic signaling. Indeed, mutations in the GABA$_A$ receptor subunit β3 (Gabrb3) gene are associated with ASD in humans, and mice harboring a Gabrb3 mutation (Gabrb3$^{+/-}$) exhibit social behavior deficits, hypersensitivity to both thermal and mechanical stimuli, and sensorimotor impairments. Therefore, we asked whether GABRB3 is localized to synapses between LTMR subtypes and their postsynaptic partners in the SC dorsal horn. We found that GABRB3-containing GABA$_A$ receptors are indeed localized to presynaptic compartments of Aβ- and Aδ-LTMR central terminals in the dorsal horn (FIG. 3A). GABRB3 puncta are also found on presynaptic primary sensory neuron terminals associated with PSDC projection neurons. SC sections from Cdx2$^{Cre}$; Gabrb3$^{f/f}$ mutant mice revealed a 75% loss in the number of GABRB3 puncta, compared to control tissue, in the dorsal horn of these mutants (FIGS. 11A, 11B). Importantly, GABRB3 puncta associated with axonal fibers emanating from DRG sensory neurons were completely absent in Advillin$^{Cre}$; Gabrb3$^{f/f}$ mice (FIGS. 11C, 11D), demonstrating both antibody specificity and primary somatosensory neurons as the cellular source of most dorsal horn GABRB3 puncta.

Mecp2 deficiency leads to decreased expression of Gabrb3 in brains of both humans and mice. To determine whether tactile perception abnormalities in Mecp2 mutants are associated with a loss of GABRB3-containing GABA$_A$ receptors on primary somatosensory neuron terminals in the dorsal horn, GABRB3 immunohistochemistry (IHC) was done using SC sections of Mecp2 mutant mice and control littermates. Mecp2 null mice exhibited >80% reduction in GABRB3 puncta associated with vGlut1+terminals in the dorsal horn (FIGS. 3B, 3C). Strikingly, Advillin$^{Cre}$; Mecp2$^{f/y}$ mutant mice exhibited ~70% loss of GABRB3 puncta associated with vGlut1+terminals in the dorsal horn (FIGS. 3D, 3E), indicating a reduction in GABRB3-containing GABA$_A$ receptors on presynaptic terminals of primary somatosensory neurons.

Our findings suggested a model in which tactile perception abnormalities in Mecp2 mutants arise due to a reduction in presynaptic GABA$_A$ receptors on LTMR terminals in the dorsal horn and thus a lack of presynaptic inhibition (PSI) of LTMR inputs to the CNS. If this is the case, then deletion of the ASD-associated gene Gabrb3 should recapitulate the Mecp2 mutant tactile behavior phenotype. Indeed, as with Mecp2 mutants, Gabrb3$^{+/-}$ mice exhibited deficits in both glabrous skin tactile discrimination and hairy skin sensitivity (FIGS. 3F-3K). We next generated Advillin$^{Cre}$; Gabrb3$^{f/+}$, Advillin$^{Cre}$; Gabrb3$^{f/f}$ and Advillin$^{CreERT2}$; Gabrb3$^{f/+}$ mutant mice, using a Gabrb3 floxed mouse line, to ask whether reduced Gabrb3 expression selectively in somatosensory neurons during development and in adulthood leads to tactile response abnormalities in adults. Advillin$^{Cre}$; Gabrb3$^{f/+}$, Advillin$^{Cre}$; Gabrb3$^{f/f}$ and Advillin$^{CreERT2}$; Gabrb3$^{f/+}$ mice exhibited a deficit in textured NORT, while no impairments were observed in control versions of NORT (FIGS. 3F-3H, FIG. 11E). Moreover, Gabrb3 conditional mutant mice from each group exhibited enhanced responses to air puff stimuli alone and enhanced tactile PPI, but were not different from control littermates in acoustic PPI performance (FIGS. 3I-3K, FIG. 11F, and FIG. 11G). These findings show that mice lacking Gabrb3 in primary somatosensory neurons phenocopy mice lacking Mecp2 in somatosensory neurons, implicating a functional link between these ASD-associated genes.

Sensory Neuron Deletion of Either Mecp2 or Gabrb3 Induces A-Fiber Synapse Hyperexcitability Our behavioral and anatomical findings led us to hypothesize that loss of GABA$_A$ receptor-dependent PSI of LTMR inputs in the dorsal horn causes excessive LTMR excitatory drive onto postsynaptic SC neurons and thus increased responsiveness to tactile stimuli in both Mecp2 and Gabrb3 mutant mice. This hypothesis was tested using both SC slice (FIG. 4) and intact isolated SC (FIG. 5) electrophysiological measurements. We recorded from retrogradely labeled PSDC projection neurons in SC slices with dorsal roots attached, which enabled direct electrical stimulation of the roots to evoke postsynaptic responses in PSDCs (FIG. 4A). To selectively monitor quantal events from primary somatosensory neurons onto PSDCs, as opposed to global miniature excitatory postsynaptic currents (mEPSCs) that reflect both primary afferent and other, non-primary afferent synaptic inputs, we replaced calcium in the extracellular recording solution with strontium and evoked asynchronous quantal EPSCs (qEPSCs) from stimulated sensory afferents. Using this approach, we reliably triggered qEPSCs in PSDCs following dorsal root stimulation at an intensity that selectively activates A-fibers (100 µA, 0.1 ms). Strikingly, qEPSC frequency, but not amplitude or decay time, was increased in slices from Advillin$^{Cre}$; Mecp2$^{f/y}$ mutants compared to slices from age-matched controls (FIGS. 4B-4H). These results suggest that enhanced presynaptic release probability, and not a change in the number and/or biophysical properties of postsynaptic glutamate receptors, accounts for increased synaptic transmission between mechanosensory afferents lacking Mecp2 and PSDCs. A similar finding of enhanced presynaptic release probability was observed in recordings from slices obtained from Advillin$^{Cre}$; Gabrb3$^{f/+}$ mice compared with controls (FIGS. 4B-H). These findings suggest a model in which neurotransmitter release probability is significantly enhanced at A-fiber synapses in the SC dorsal horn of mice lacking Mecp2 due to a loss of GABA-mediated PSI at these terminals.

Sensory Neuron Deletion of Either Mecp2 or Gabrb3 Leads to Loss of PSI in the SC Dorsal in the Dorsal Horn of both Advillin$^{Cre}$; Mecp2$^{f/y}$ and Advillin$^{Cre}$; Gabrb3$^{f/+}$ Mutant Mice Using an Isolated SC Preparation In the SC dorsal horn, PSI of LTMRs is predominantly mediated through primary afferent depolarization (PAD).

Figure 5A:
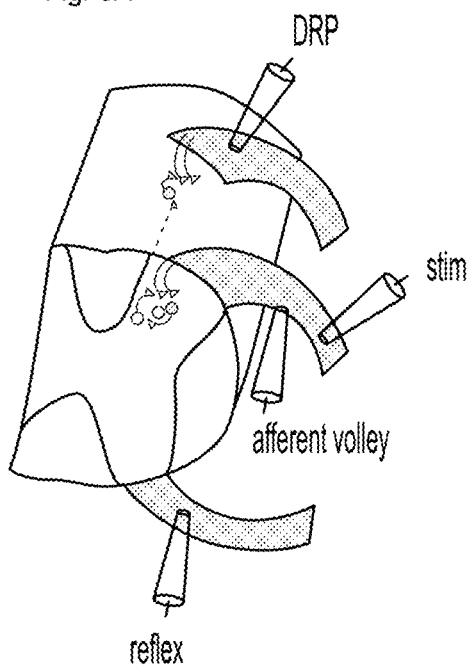
Figure 5B:
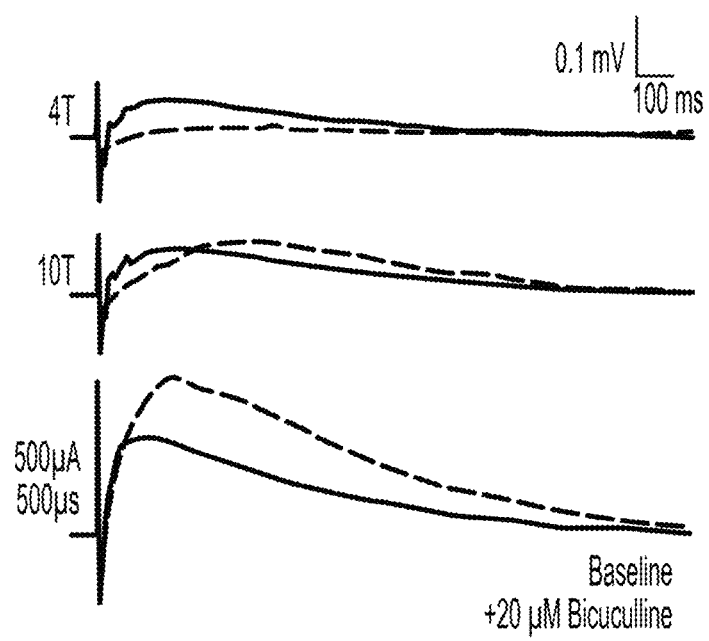

PAD is believed to be generated through a trisynaptic circuit in which primary afferents innervate dorsal horn glutamatergic interneurons, which then innervate GABAergic interneurons that form axo-axonic synapses onto primary afferent terminals (FIG. 5A). Due to the relatively depolarized chloride reversal potential of primary somatosensory neurons, GABA acting on primary afferent terminals leads to their depolarization, which in turn reduces action potential-evoked transmitter release from sensory neuron terminals in the dorsal horn. PAD can be measured as a back-propagating depolarization of the dorsal root, or dorsal root potential (DRP). Activity-dependent PSI can thus be assessed by electrically stimulating one dorsal root and recording a DRP on an adjacent dorsal root (FIG. 5A). By stimulating at low intensity (here, defined as less than or equal to 4 times the threshold of afferent volley recruitment), a low-threshold DRP was readily elicited in control mice (FIG. 5B). This DRP is almost entirely inhibited by the $GABA_A$ receptor blocker bicuculline (FIG. 5B). As stimulus intensity increases, a greater number and variety of afferents are recruited, and DRPs increase in magnitude. At maximal intensity, DRPs are no longer solely $GABA_A$ receptor dependent (FIG. 5B). Evoked DRPs were greatly diminished in both $Advillin^{Cre}$; $Mecp2^{f/y}$ and $Advillin^{Cre}$; $Gabrb3^{f/+}$ mice, with Mecp2 mutants being most affected (FIGS. 5C-5E). At low threshold stimulus intensity, DRPs in these mice were virtually non-existent, and as stimulus intensity increased, small DRPs were observed. As $GABA_A$ receptors on SC interneurons are likely to be unaffected in $Advillin^{Cre}$; $Mecp2^{f/y}$ and $Advillin^{Cre}$; $Gabrb3^{f/+}$ mice, we hypothesized that motor reflexes, as recorded electrophysiologically from ventral roots, would be unchanged. Indeed, motor reflexes were unaffected in both $Advillin^{Cre}$; $Mecp2^{f/y}$ and $Advillin^{Cre}$; $Gabrb3^{f/+}$ mutants (data not shown), and $GABA_A$ receptor modulation of these reflexes was comparable to that of control mice (FIG. 5F, FIG. 5G). These findings indicate that primary somatosensory neuron deletion of either Mecp2 or Gabrb3 increases sensitivity to light touch due to a deficiency of $GABA_A$ receptors on somatosensory neuron terminals and a loss of $GABA_A$ receptor-mediated PSI.

Figure 6B:
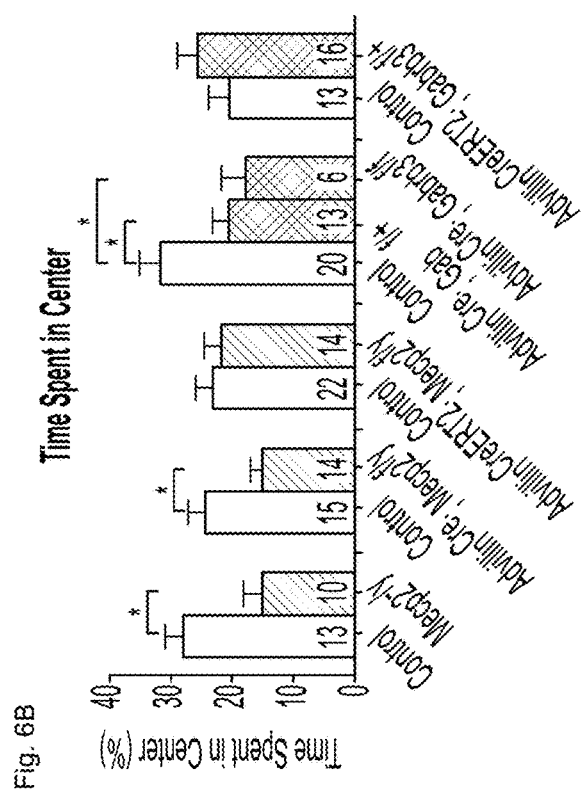
FIGS. 6A-6I shows that primary somatosensory neuron deletion of either Mecp2 or Gabrb3 leads to deficits in cognitive and social behaviors.
Figure 6A:
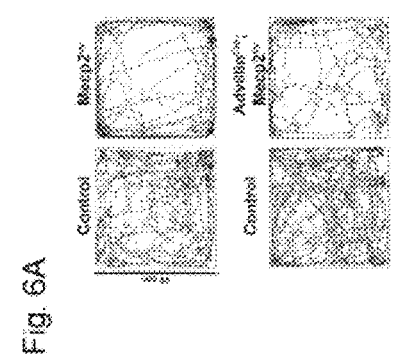
Figure 6D:
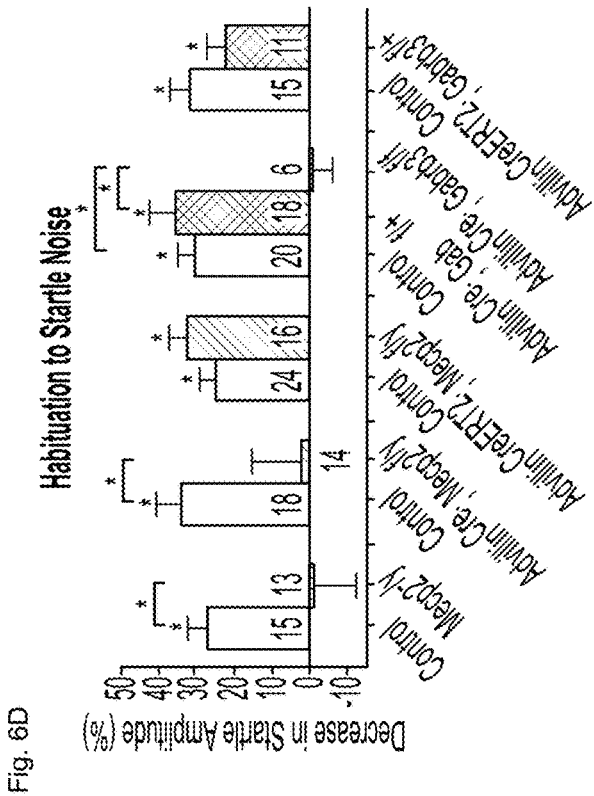
Figure 6C:
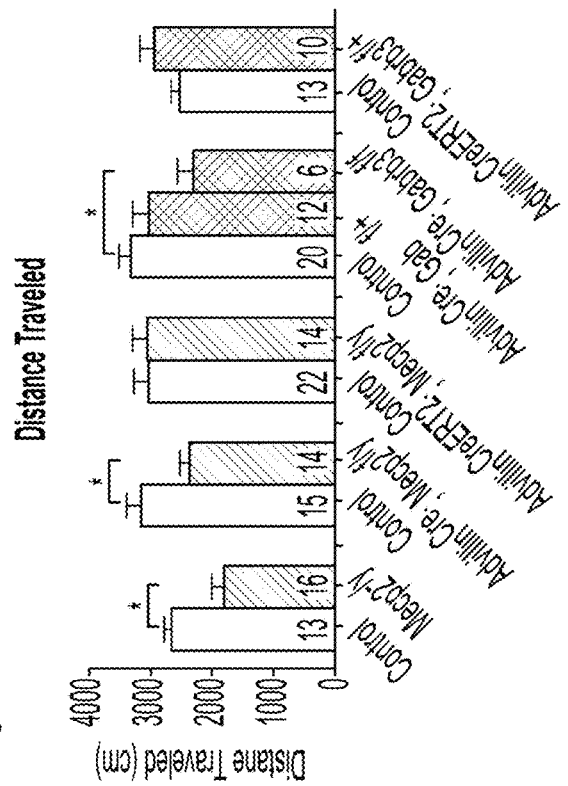
Figure 6E:
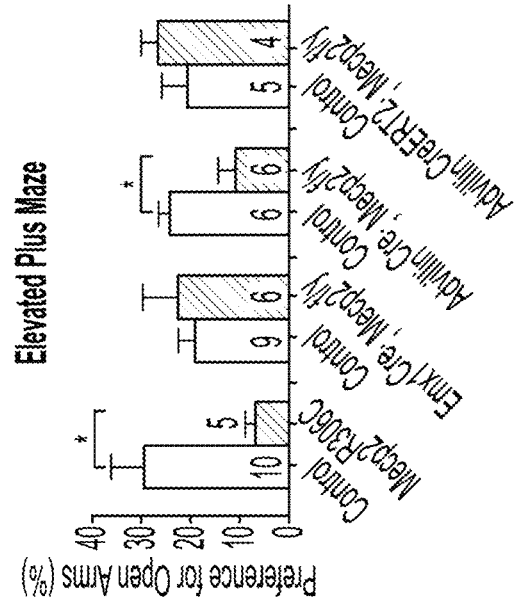

Primary Somatosensory Neuron Deletion of Either Mecp2 or Gabrb3 Leads to Deficits in Cognitive and Mouse Social Behaviors We next asked whether mice harboring developmental or adult deletions of either Mecp2 or Gabrb3 in primary somatosensory neurons exhibit anxiety-like behavior, deficits in nest building and/or social interactions. Mutant and control mice were first subjected to a 10-minute open field (OF) test; mice with anxiety-like behavior spend less time exploring the center of the chamber and travel shorter distances. $Mecp2^{-/y}$ and $Gabrb3^{+/-}$ mutant mice exhibited a decrease in both the percentage of time spent in the center of the chamber and total distance traveled during the OF test (FIGS. 6A-6C, FIG. 12B, and FIG. 12C). Mice lacking either Mecp2 or Gabrb3 exclusively in primary somatosensory neurons during development ($Advillin^{Cre}$; $Mecp2^{f/y}$w, $Advillin^{Cre}$; $Gabrb3^{f/f}$ and $Advillin^{Cre}$; $Gabrb3^{f/+}$ mice), but not mice in which Mecp2 or Gabrb3 was deleted in somatosensory neurons in adulthood ($Advillin^{CreERT2}$; $Mecp2^{f/y}$ or $Advillin^{CreERT2}$; $Gabrb3^{f/+}$), also exhibited anxiety-like behavior compared to control littermates (FIGS. 6A-6C, FIGS. 12A-12C). A second correlate of anxiety-like behavior in both humans and rodents is abnormal habituation to aversive stimuli. In normal humans and mice, the startle response to loud acoustic stimuli decreases over time, whereas humans and rodents with anxiety show less habituation to an aversive startle stimulus. To assess habituation to acoustic startle noises, acoustic startle trials were performed before and after the PPI trials described above. Across genotypes, control mice exhibited ~30% reduction in the acoustic startle response at the end of the session compared to responses measured at the beginning of the session (FIG. 6D, FIG. 12D). $Advillin^{Cre}$; $Mecp2^{f/y}$ and $Advillin^{Cre}$; $Gabrb3^{f/f}$, as well as germline Mecp2 and Gabrb3 mutants, failed to habituate to the acoustic startle noise (FIG. 6D, FIG. 12D). In contrast, mice in which either Mecp2 or Gabrb3 was deleted in primary somatosensory neurons in adulthood ($Advillin^{CreERT2}$; $Mecp2^{f/y}$ or $Advillin^{CreERT2}$; $Gabrb3^{f/+}$) exhibited normal decreases in their startle responses over time (FIG. 6D). A subset of the mouse lines were tested on a third measure of anxiety-like behavior in rodents, the elevated plus maze (EPM). $Mecp2^{R306C}$ and $Advillin^{Cre}$; $Mecp2^{f/y}$ mutant mice spent significantly less time in the open arms of the EPM compared to littermate controls, indicative of increased anxiety-like behavior in these mice (FIG. 6E). Conversely, $Emx1^{Cre}$; $Mecp2^{f/y}$ and $Advillin^{CreERT2}$; $Mecp2^{f/y}$ exhibited normal behavior in this test (FIG. 6E). Thus, primary somatosensory neuron deletion of either Mecp2 or Gabrb3 during development, but not in adulthood, leads to anxiety-like behavior in mice.

Both Mecp2 and Gabrb3 mutant mice display deficits in nest building, a socially relevant tactile behavior of adult rodents. Adult mice were placed in individual cages and provided nestlets 30 minutes before the start of the dark cycle. Fourteen to sixteen hours later, nest construction was scored as previously described using a 5-point scale. Mice with either embryonic or adult deletion of Mecp2 or Gabrb3 in primary somatosensory neurons showed impairments in nest building behavior, compared to control littermates, although these nesting deficits were not as severe as those of $Mecp2^{-/y}$ and $Mecp2^{R306C}$ mutant mice (FIG. 12E, FIG. 12F).

Figure 6F:
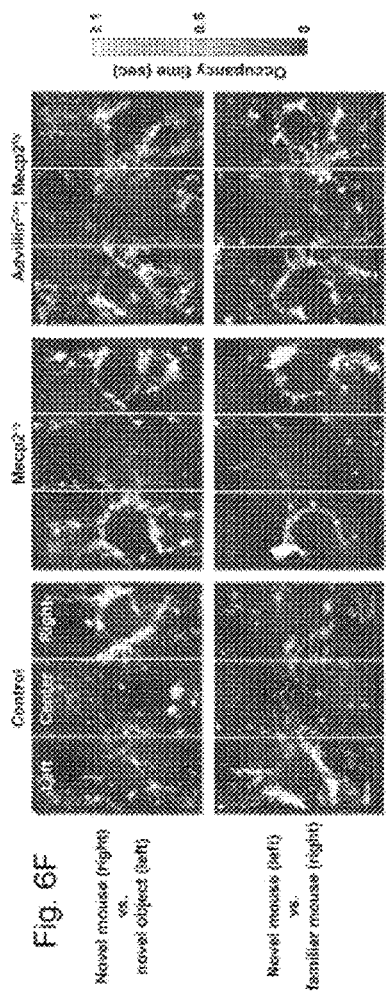
Figure 6G:
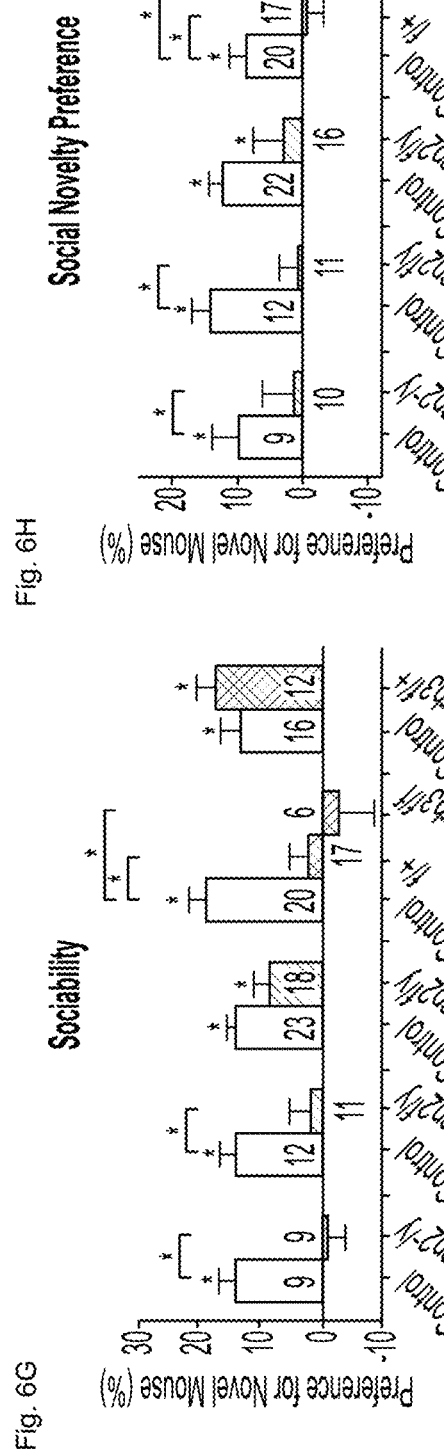
Figure 6H:

The three-chamber social interaction test was implemented. It is used to assess both sociability and social recognition/preference in rodents, and mouse models of ASD display altered behaviors in this assay. Control mice with normal social preferences show more time exploring a novel mouse in both the sociability and social novelty preference tests. In contrast, several mouse models of ASD, including $Gabrb3^{+/-}$ mice, display a reduced amount of time exploring the novel mouse in this assay. $Mecp2^{-/y}$, $Mecp2^{R306C}$ and $Gabrb3^{+/-}$ mice exhibit impairments in both sessions of this test, as they did not prefer a novel mouse compared to an empty cup (sociability test) nor did they prefer a novel mouse to a familiar mouse (social novelty preference test) (FIGS. 6F-6H, FIGS. 12G-12I). Mice with primary somatosensory neuron deletion of either Mecp2 ($Advillin^{Cre}$; $Mecp2^{f/y}$) or Gabrb3 ($Advillin^{Cre}$; $Gabrb3^{f/f}$ and $Advillin^{Cre}$; $Gabrb3^{f/+}$) displayed comparable deficits in both sociability and social novelty preference (FIGS. 6F-6H). On the other hand, mice in which either Mecp2 or Gabrb3 was deleted in adulthood ($Advillin^{CreERT2}$; $Mecp2^{f/y}$ or $Advillin^{CreER12}$; $Gabrb3^{f/+}$) displayed significant preference for the novel mouse during the sociability test, although these mice did not display a preference for a novel mouse compared to a familiar mouse during the social novelty preference test (FIG. 6G, FIG. 6H).

Figure 6I:
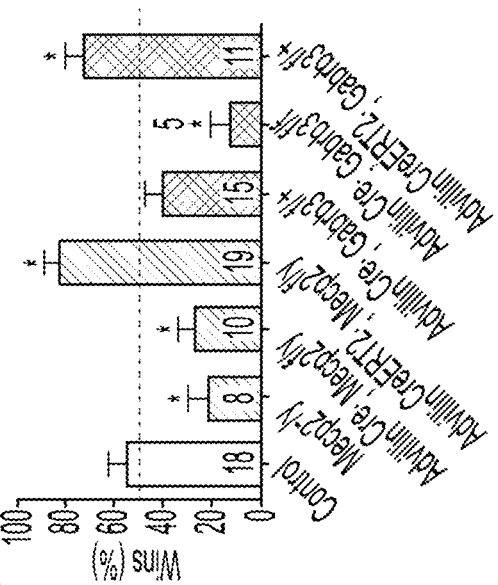

To further evaluate social interactions, mice were subjected to a tube dominance test, which allows for assessment of social approach/avoidance behavior as well as an evaluation of dominance hierarchies in mice, and can be used to assess social impairments in ASD mouse models. $Mecp2^{-/y}$, Mecp2$^{R306C}$ and Gabrb3$^{+/-}$ mutant mice exhibit decreased social dominance and aggression, as they lost the majority of matches against control mice (FIG. 6I, FIG. 12J). Similarly, Cdx2$^{Cre}$; Mecp2$^{f/y}$, Advillin$^{Cre}$; Mecp2$^{f/y}$, and Advillin$^{Cre}$; Gabrb3$^{f/f}$ mutant mice were all significantly more submissive and lost the majority of their matches (FIG. 6I, FIG. 12). In contrast, mice in which either Mecp2 or Gabrb3 was deleted in somatosensory neurons in adulthood demonstrated increased dominance, as these mice won the majority of their matches (FIG. 6I). Mice with deletion of Mecp2 in excitatory forebrain neurons were neither submissive nor dominant in this assay. Mecp2 and Gabrb3 are developmentally required in primary somatosensory neurons for the acquisition of certain cognitive and social behaviors in mice.

Figure 7B:
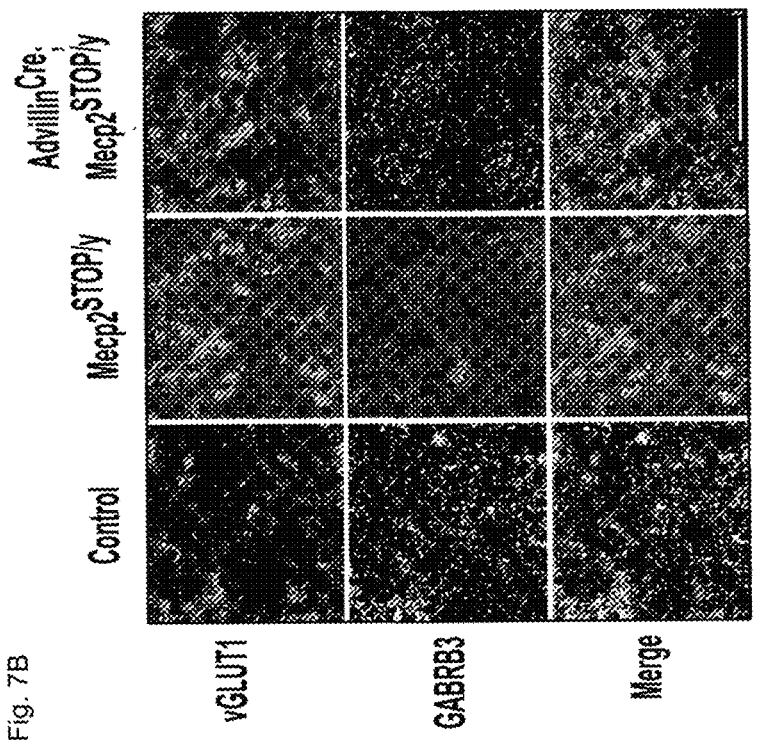
FIG. 7B is a series of IHC images of lamina III of the SC dorsal horn, co-labeled for vGLUT1 and GABRB3 to visualize GABRB3 puncta associated with presynaptic terminals of Aβ- and Aδ-LTMRs.
Figure 7A:
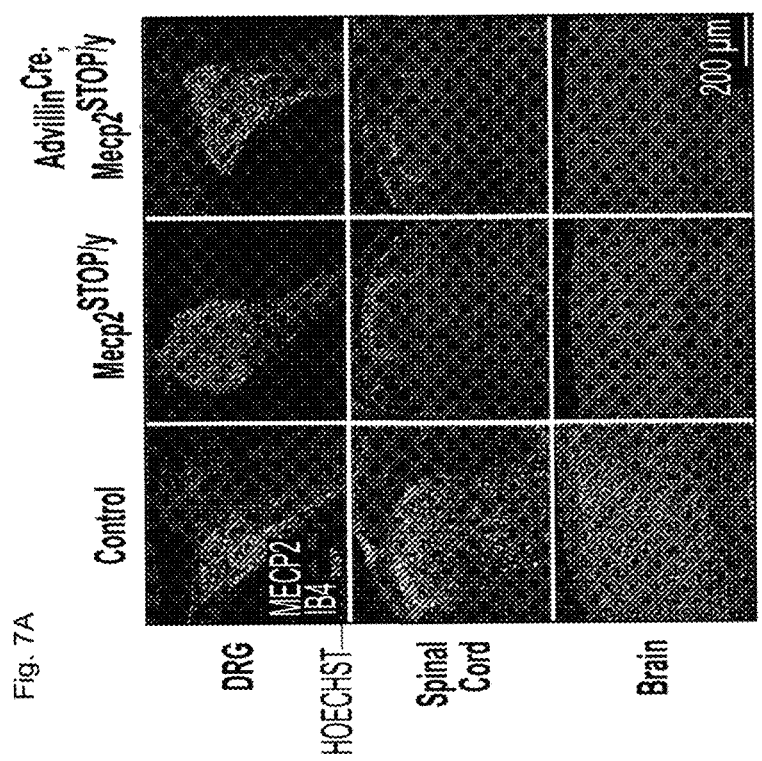

Mecp2 Expression in Primary Somatosensory Neurons is Sufficient for Normal Tactile Discrimination, PSI, and Certain Cognitive and Social Behaviors Whether Mecp2 in primary somatosensory neurons is sufficient for normal tactile function was addressed by restoring Mecp2 expression exclusively in the peripheral somatosensory neurons in a Mecp2 null background. A Mecp2$^{STOP/y}$ mouse line was utilized, in which Mecp2 is expressed only in cells following Cre-mediated excision of a STOP codon (FIG. 7A). Expression of Mecp2 exclusively in primary somatosensory neurons in an otherwise Mecp2 null background (Advillin$^{Cre}$; Mecp2$^{STOP/y}$, FIG. 7A) rescued the deficits in textured NORT (FIG. 7D), hypersensitivity to air puff and alterations in tactile PPI (FIG. 7E, FIG. 7F) observed in Mecp2 null mutants. Mecp2 expression in primary somatosensory neurons alone is sufficient to rescue expression of GABRB3 at presynaptic sensory neuron terminals (FIG. 7B, FIG. 7C) and in supporting GABA$_A$ receptor-mediated PSI of somatosensory input to the dorsal horn (FIG. 7G, FIG. 7H).

Figure 13G:
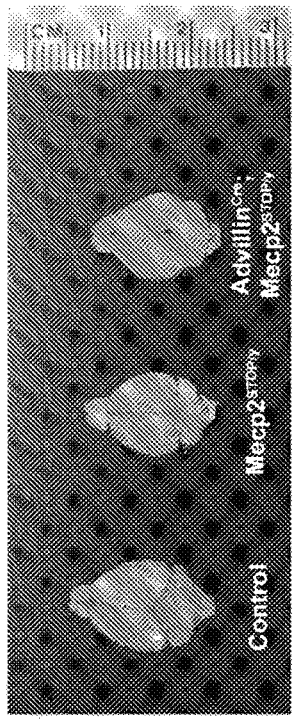
Figure 13I:
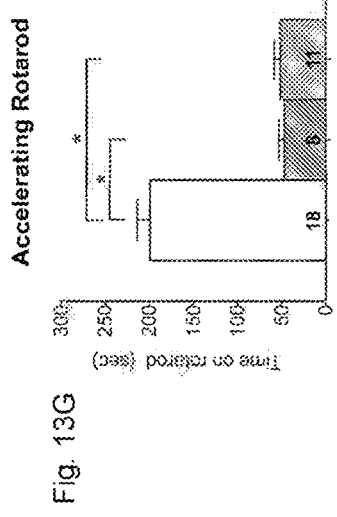
Figure 13H:
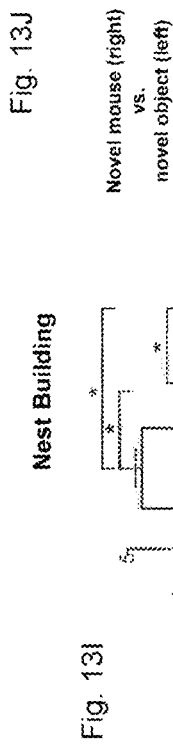
Figure 13J:
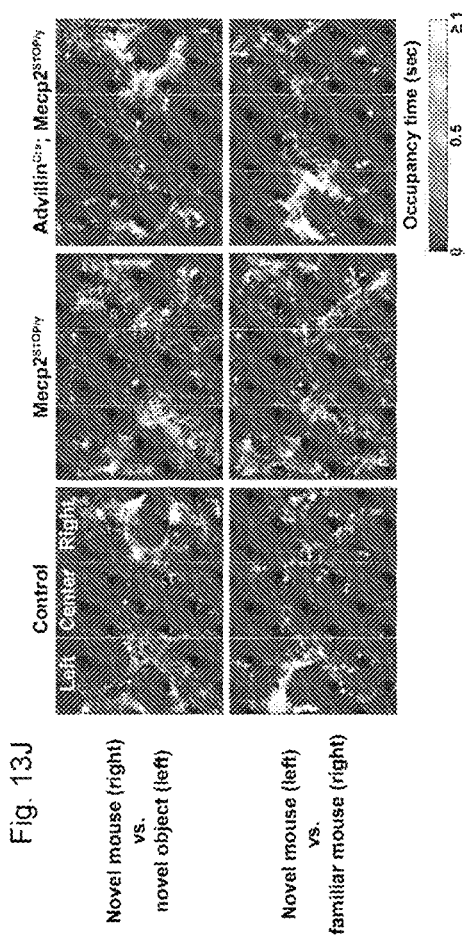

Behavioral analyses of mice with expression of Mecp2 exclusively in primary somatosensory neurons revealed normal levels of anxiety-like behaviors, assessed by their performances in the OF test, habituation to acoustic startle noises, as well as EPM, whereas Mecp2$^{STOP/y}$ mutants showed increased anxiety-like behavior in each of these tests (FIGS. 7I-7M). Moreover, although Advillin$^{Cre}$; Mecp2$^{STOP/y}$ mice displayed lower nest building scores than controls, their values were improved relative to Mecp2$^{STOP/y}$ mutants (FIG. 13I). Advillin$^{Cre}$; Mecp2$^{STOP/y}$ mice also performed no differently than controls in either portion of the three-chamber social interaction test (FIG. 7N, FIG. 7O, and FIG. 13J), and they exhibited neither submissive nor dominant behavior in the tube dominance assay (FIG. 7P). However, expression of Mecp2 exclusively in primary somatosensory neurons did not rescue decreased brain size, memory, motor or acoustic PPI abnormalities (FIGS. 13A-13J). Thus, Mecp2 expression in primary somatosensory neurons in an otherwise Mecp2 null mouse rescues tactile behavioral deficits, deficits in GABRB3 expression associated with LTMR terminals, abnormalities in tactile PPI, anxiety-like behaviors, and a subset of the social behavior deficits observed in Mecp2 null mutants.

Figure 14A:
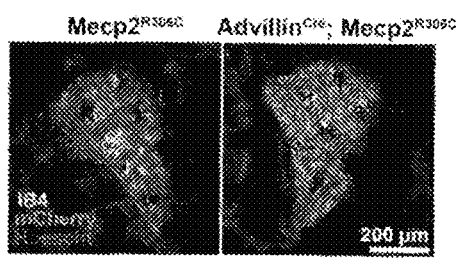
FIG. 14A is an image showing restoration of Gabrb3 expression only in peripheral somatosensory neurons, beginning at P5, allows for robust transduction of DRG neurons in animals that have been intraperitoneally injected at P5 with AAV-FLEX-Synapsin-Gabrb3-T2A-mCherry (20 µl of sterile PBS containing 2.0×10$^{12}$ viral particles).
Figure 14B:
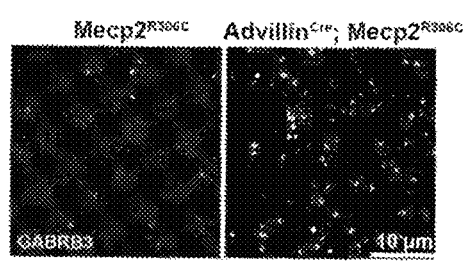
FIG. 14B is an image showing restoration of Gabrb3 expression only in peripheral somatosensory neurons, beginning at P5, allows for increased expression of GABRB3 in the dorsal horn of the SC in animals that have been intraperitoneally injected at P5 with AAV-FLEX-Synapsin-Gabrb3-T2A-mCherry (20 µl of sterile PBS containing 2.0×10$^{12}$ viral particles).
Figure 14C:
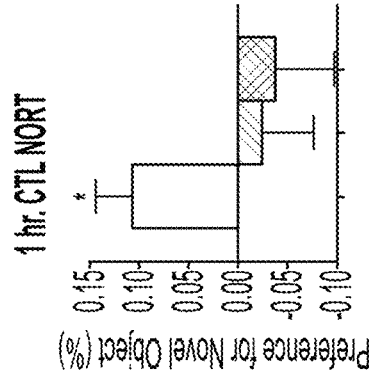
FIGS. 14O-14E are a series of bar graphs showing postnatal expression of Gabrb3 in peripheral somatosensory neurons significantly improves texture discrimination which is retained short term, but does not improve long-term memory deficits.
FIG. 14F is a bar graph showing postnatal expression of Gabrb3 in peripheral somatosensory neurons does not improve decreased startle amplitude.
FIG. 14G is a bar graph showing postnatal expression of Gabrb3 in peripheral somatosensory neurons improves tactile hypersensitivity in the tactile PPI assay.
FIG. 14H is a bar graph showing postnatal expression of Gabrb3 in peripheral somatosensory neurons improves tactile hypersensitivity in the air puff assay.
FIG. 14I is a bar graph showing postnatal expression of Gabrb3 in peripheral somatosensory neurons does not normalize performance on acoustic PPI.
FIG. 14J is a bar graph showing the response to a non-startling 80 dB noise.
FIGS. 14K and 14L are graphs showing DRG transduction efficiency and expression of GABRB3 at A62 and Aδ LTMR LTMR presynaptic terminals in the dorsal horn of the spinal cord inversely correlated with response to a light air puff stimulus, indicating a relationship between improved GABRB3 expression and improvement of tactile hypersensitivity in hairy skin.
FIG. 14M is a bar graph showing postnatal expression of Gabrb3 in peripheral somatosensory neurons significantly improves anxiety-like behaviors as measured by time spent in the center in the open field test.
FIG. 14N is a bar graph showing postnatal expression of Gabrb3 in peripheral somatosensory neurons significantly improves anxiety-like behaviors as measured by distance traveled in the open field test.
FIG. 14P is a bar graph showing postnatal expression of Gabrb3 in peripheral somatosensory neurons significantly improves anxiety-like behaviors as measured by time spent in the open arms in the elevated plus maze.
Figure 14D:
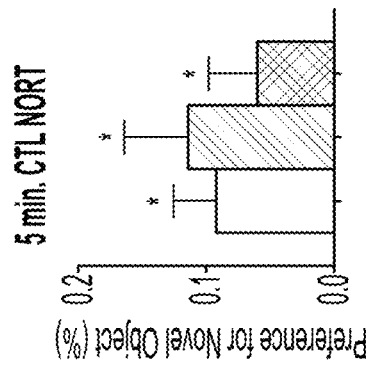
Figure 14E:
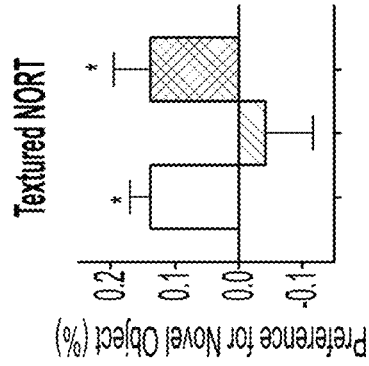
Figure 14F:
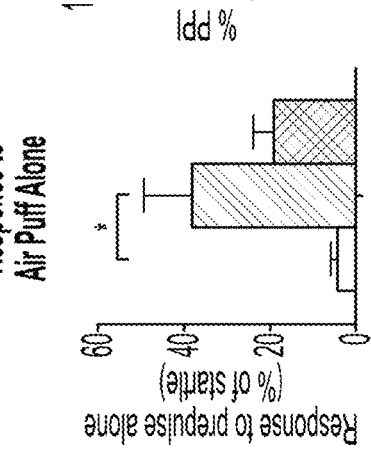
Figure 14G:
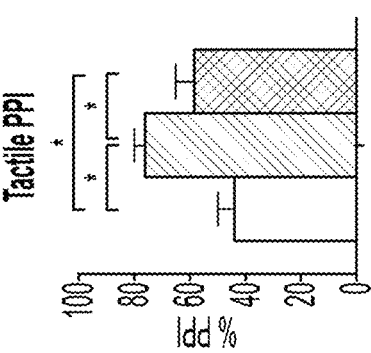
Figure 14H:
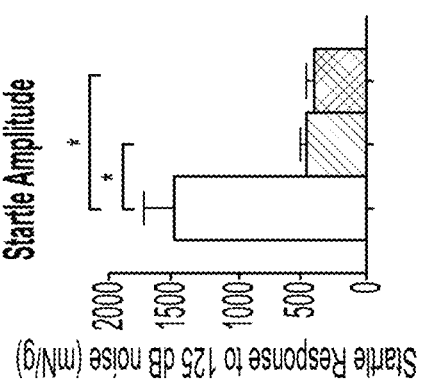
Figure 14I:
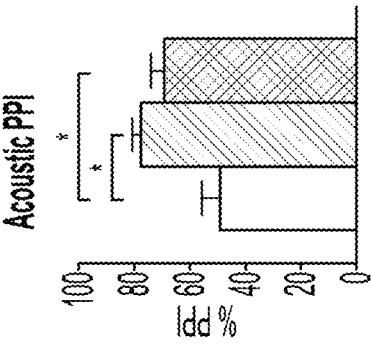

Viral Rescue of GABRB3 by Intraperitoneal Injections of AAV2/9 Improves Tactile Dysfunction and Anxiety-Like Behaviors Restoration of Gabrb3 expression only in peripheral somatosensory neurons, beginning at P5, allows for robust transduction of DRG neurons (FIG. 14A) and increased expression of GABRB3 in the dorsal horn of the SC (FIG. 14B). Postnatal expression of Gabrb3 in peripheral somatosensory neurons significantly improves texture discrimination (FIG. 14C), which is retained short term (FIG. 14D), but does not improve long-term memory deficits (FIG. 14E). Postnatal expression of Gabrb3 in peripheral somatosensory neurons also improves tactile hypersensitivity (FIGS. 14G, 14H), but does not improve decreased startle amplitude (FIG. 14F) or normalize performance on acoustic PPI (FIG. 14I). Postnatal expression of Gabrb3 in peripheral somatosensory neurons do not show increased sensitivity to acoustic pre-pulse alone (FIG. 14J), indicating their hypersensitivity is specific to tactile stimuli (FIG. 14H). DRG transduction efficiency and expression of GABRB3 at Aβ and Aδ LTMR presynaptic terminals in the dorsal horn of the spinal cord inversely correlated with response to a light air puff stimulus (FIGS. 14K, 14L), indicating a relationship between improved GABRB3 expression and improvement of tactile hypersensitivity in hairy skin. Postnatal expression of Gabrb3 in peripheral somatosensory neurons significantly improves anxiety-like behaviors as measured in the open field test (FIGS. 14M, 14N), habituation to startle noise (FIG. 14O), and elevated plus maze (FIG. 14P).

Acute Intraperitoneal Injections of GABA$_A$ Agonists Improve Tactile Dysfunction and Anxiety-Like Behaviors Midazolam injected animals show a trend toward decreased startle amplitude, compared to animals treated with vehicle (FIG. 15A). Vehicle-treated Advillin$^{Cre}$; Mecp2$^{f/y}$ mutant mice exhibit increased performance on the tactile PPI assay, compared to vehicle treated control littermates (FIG. 15B). Both Midazolam- and Isoguvacine injected Advillin$^{Cre}$; Mecp2$^{f/y}$ mutant mice exhibit a trend toward normalized responses in the tactile PPI assay, and are not different than control littermates with the same drug treatment (FIG. 15B). Vehicle-treated Advillin$^{Cre}$; Mecp2$^{f/y}$ mutant mice exhibit increased response to an air puff stimulus alone, compared to vehicle treated control littermates (FIG. 15C). Both Midazolam or Isoguvacine treatment in Advillin$^{Cre}$; Mecp2$^{f/y}$ mutant mice decreased response to an air puff stimulus alone, and animals with these treatments did not show increased responses compared to control littermates (FIG. 15C).

Shank3 is Required in Peripheral Sensory Neurons for Normal Tactile Behaviors, as Well as Other ASD-Related Behaviors It remained unknown if peripheral sensory neurons and/or spinal cord (SC) neurons were abnormal in ASD mouse models other than the Mecp2 and Gabrb3 mutant mice. We therefore sought to determine whether Shank3 is required in cells below the neck, or specifically peripheral somatosensory neurons, for normal tactile behaviors. Shank3$^{+/-}$ mice are appropriate for these studies because this mouse line is a well-accepted model of ASD, and Shank3 is expressed during development in peripheral somatosensory neurons and SC neurons (Allen Brain Atlas). We utilized a conditional Shank3 knock-in mouse with a Flexed and inverted PDZ binding domain (Shank3$^{FX}$). This mouse line enables conditional manipulation of the Shank3 gene at its endogenous locus such that in the absence of Cre, Shank3$^{FX/FX}$ mice function as Shank3 knockout mice and the majority of SHANK3 protein isoforms are absent. In the presence of Cre, the Flexed PDZ domain is re-oriented and SHANK3 protein expressed is restored.

Figure 16A:
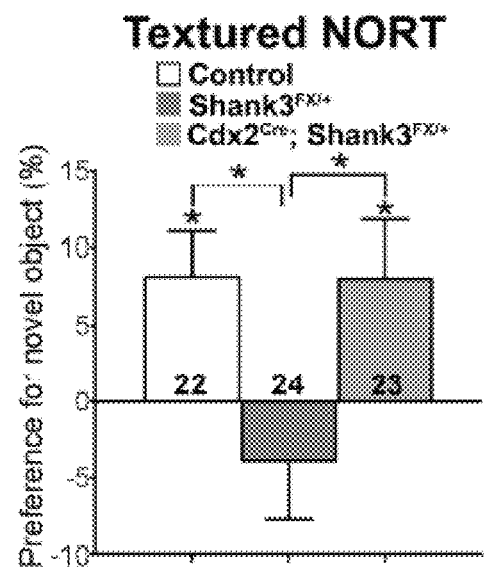
FIGS. 16A-16D show the improvements observed in Shank3 heterozygous mice with restoration of Shank3 expression in all cells below the neck.
Figure 16B:
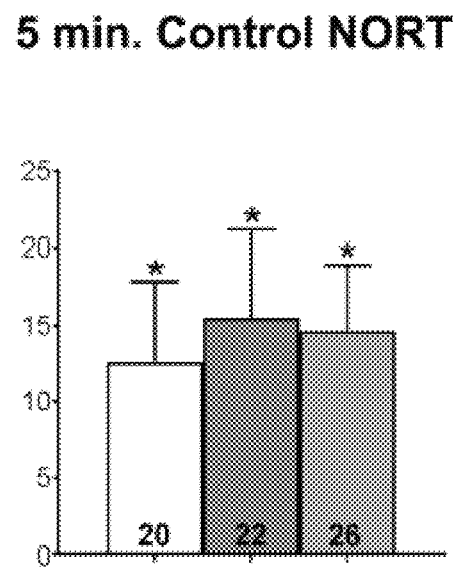
Figure 16C:
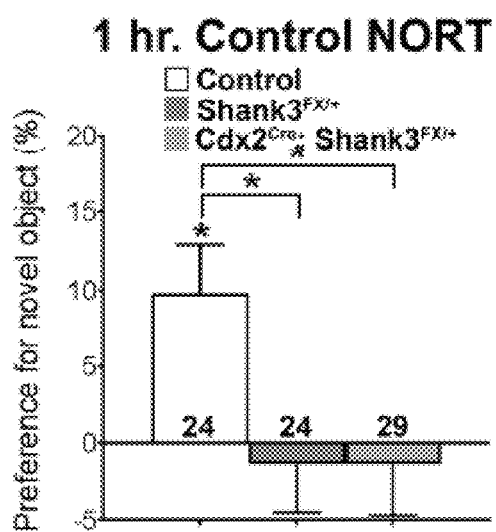
Figure 16D:
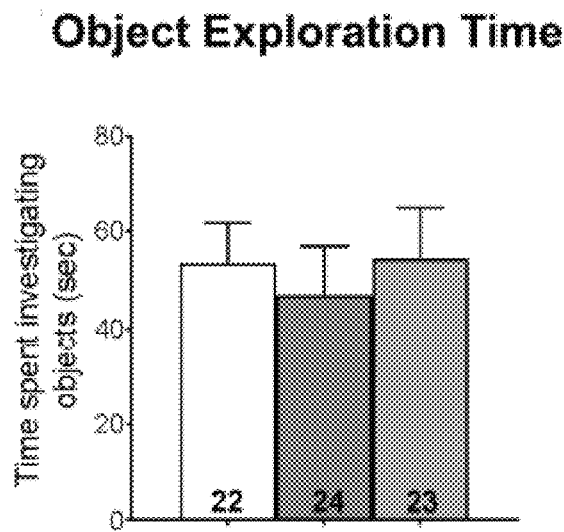
Figure 17A:
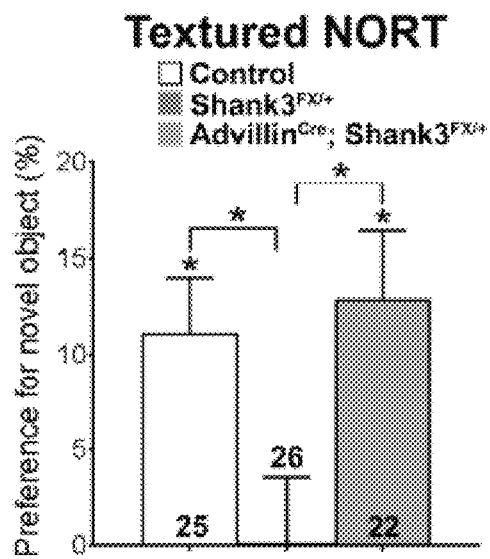
FIGS. 17A-17D show improvements in texture discrimination deficits observed in Shank3 heterozygous mutant mice having restored Shank3 expression in peripheral somatosensory neurons.
Figure 17B:
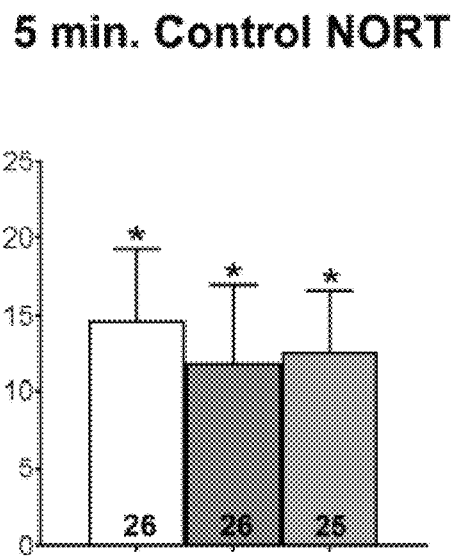
Figure 17C:
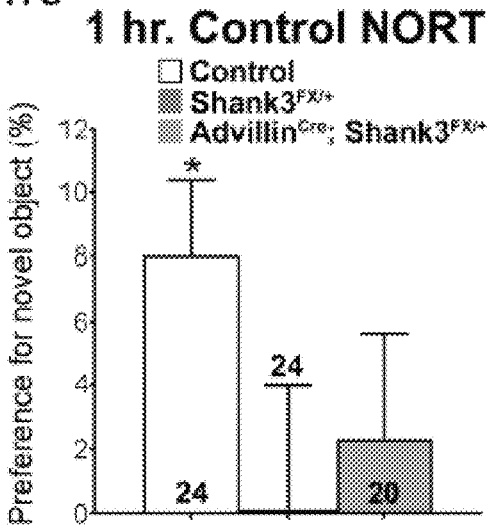
Figure 17D:
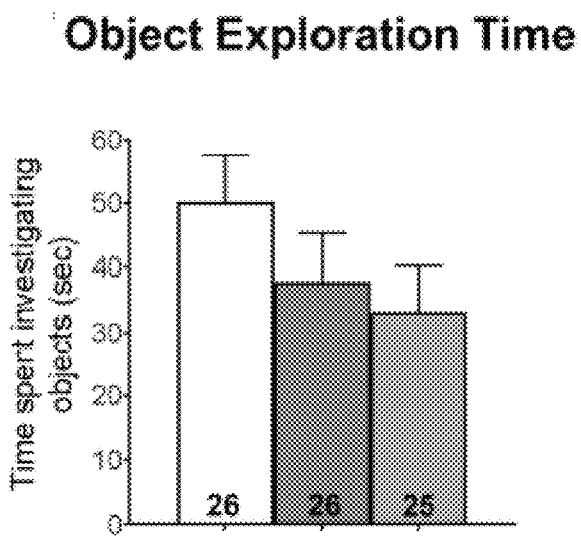
Figure 20A:
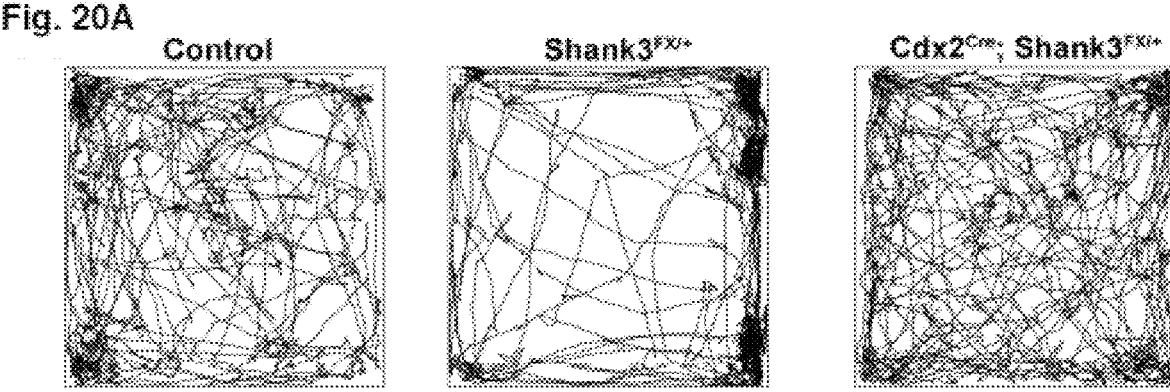
FIGS. 20A-20C show improvements in anxiety-like behaviors observed in Shank3 heterozygous mutant mice with restored Shank3 expression in all cells below the neck.
Figure 20B:
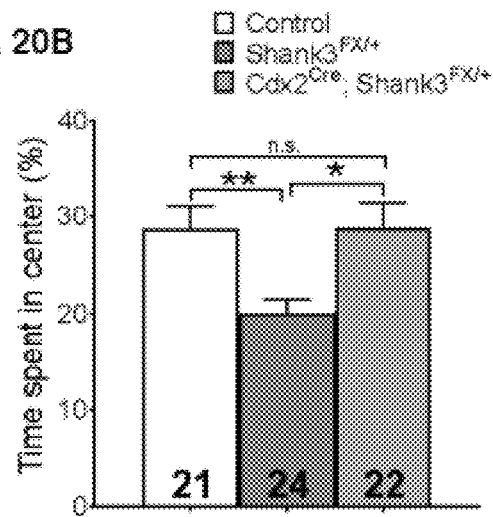
Figure 20C:
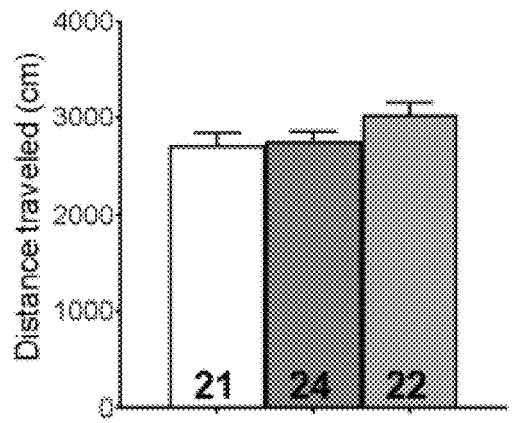
Figure 21A:
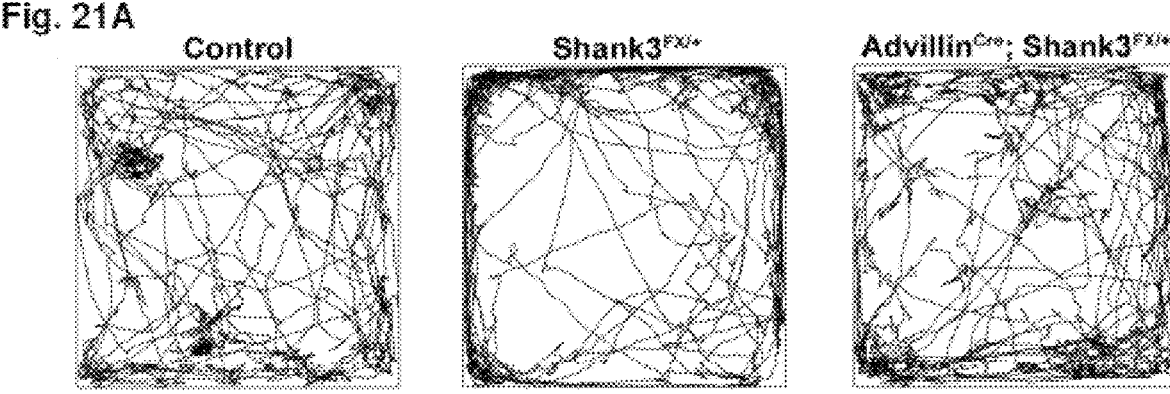
FIGS. 21A-21C show improvements in anxiety-like behaviors observed in Shank3 heterozygous mutant mice having restored Shank3 expression in peripheral sensory neurons.
Figure 21B:
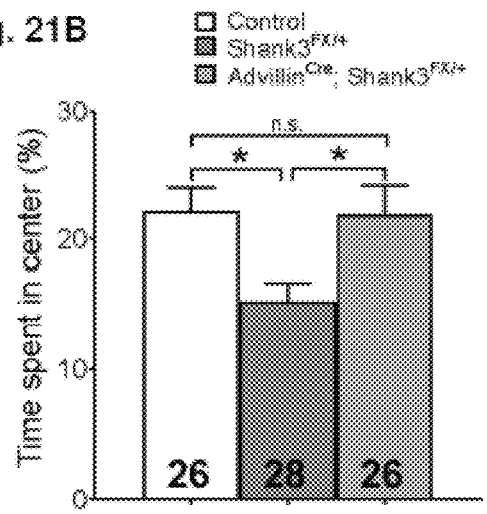
Figure 21C:
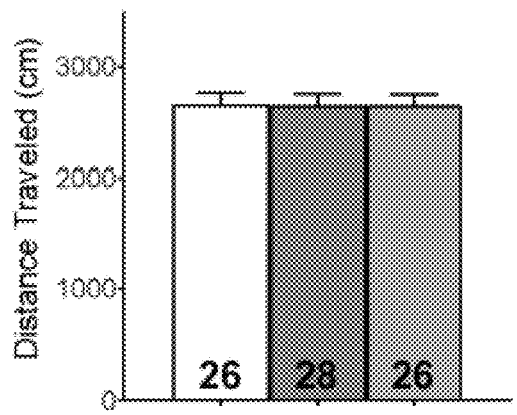

Crossing Shank3FX mice to mice expressing Cre recombinase in specific cell types allowed for normal Shank3 expression in either all cells caudal to cervical level 2 ($Cdx2^{Cre}$; $Shank3^{FX/+}$) or all peripheral somatosensory neurons ($Advillin^{Cre}$; $Shank3^{FX/+}$), while cells not expressing Cre remained heterozygous for Shank3. We then assessed hairy skin sensitivity in Shank3 heterozygous mice ($Shank3^{FX/+}$), mutant rescue mice ($Cdx2^{Cre}$; $Shank3^{FX/+}$ or $Advillin^{Cre}$; $Shank3^{FX/+}$) or their control littermates using our textured NORT and tactile PPI assays. Shank3Fx⁴ mice from both crosses exhibited deficits in textured NORT and 1-hour retention NORT, as well as enhanced performance in tactile PPI and increased responsivity to an air puff stimulus, compared to control littermates (FIGS. 16A, 17A, 18B-18C and 19B-19C). Shank3 heterozygous mice, however, performed comparable to controls on the color/shape version of NORT (FIGS. 16B and 17B) and spent similar amounts of time exploring the objects in each of the NORT versions (FIGS. 16D and 17D). $Shank3^{FX/+}$ mice also showed no abnormalities in acoustic PPI or responsivity to a non-startling acoustic stimulus (FIGS. 18D-18E and 19D-19E). Surprisingly, mice with restoration of Shank3 either below the neck ($Cdx2^{Cre}$; $Shank3^{FX/+}$) or exclusively in peripheral somatosensory neurons ($Advillin^{Cre}$; $Shank3^{FX/+}$) exhibited normal tactile behaviors in both the textured NORT (FIGS. 16A and 17A) and tactile PPI assays (FIGS. 18B-18C and 19B-19C), and their performances were not different than control littermates. Both $Cdx2^{Cre}$; $Shank3^{FX/+}$ and $Advillin^{Cre}$; $Shank3^{FX/+}$ did not show a preference for the novel object in the 1-hour retention NORT, indicating that these mice exhibited long-term memory deficits consistent with those observed in Shank3 heterozygous mice. Taken together, these results indicate that Shank3 function in peripheral sensory neurons is sufficient to support normal texture discrimination and tactile sensitivity.

Because we found that Shank3 is also required in peripheral somatosensory neurons for normal tactile behaviors, we asked whether Shank3 expression in peripheral somatosensory neurons might improve anxiety-like behaviors and social interaction deficits observed in Shank3 heterozygous mice ($Shank3^{FX/+}$). Remarkably, restoration of Shank3 either below the neck ($Cdx2^{Cre}$; $Shank3^{FX/+}$) or exclusively in peripheral somatosensory neurons ($Advillin^{Cre}$; $Shank3^{FX/+}$) improved anxiety-like behaviors normally observed in $Shank3^{FX/+}$ mice: both rescue groups exhibited a habituation to startling noises (FIGS. 18F and 19F), as well as an increase in the time spent in the center of a chamber during the open field test (FIGS. 20A-20B and 21A-21B). Furthermore, while Shank3 heterozygous mice exhibit impairments in sociability and social novelty preference during the three-chamber social interaction test, both $Cdx2^{Cre}$; $Shank3^{FX/+}$ and $Advillin^{Cre}$; $Shank3^{FX/+}$ mice exhibited a significant preference for the novel mouse compared to a novel object in the sociability portion of the test (FIGS. 22-23). Together, these results demonstrate that Shank3 expression in peripheral somatosensory neurons in an otherwise Shank3 heterozygous background is sufficient for normal tactile behaviors, improves anxiety-like behaviors and social interaction deficits observed in Shank3 heterozygous mice.

Loss of Shank3 in Peripheral Sensory Neurons leads to Reduction in HCN1 Expression, Impaired $I_h$ Currents and Increased Excitability of Low Threshold Mechanoreceptor Neurons We hypothesize that ASD-associated genes function cell autonomously in peripheral somatosensory neurons to control excitatory drive onto SC neurons, either through controlling $GABA_A$ receptor-mediated PSI or LTMR excitability. Decreased HCN expression causes hyperexcitability because the current mediated by HCN channels, In, displays an inherent negative-feedback property that imparts a stabilizing effect on neuronal excitability. HCN1 protein is concentrated on presynaptic terminals of medium- and large-diameter somatosensory neurons in the spinal cord (SC) dorsal horn. Shank3 mutations may therefore cause a decrease in HCN1 expression in peripheral somatosensory neurons, leading to increased excitability of primary afferents and hypersensitivity to tactile stimuli.

Figure 24A:
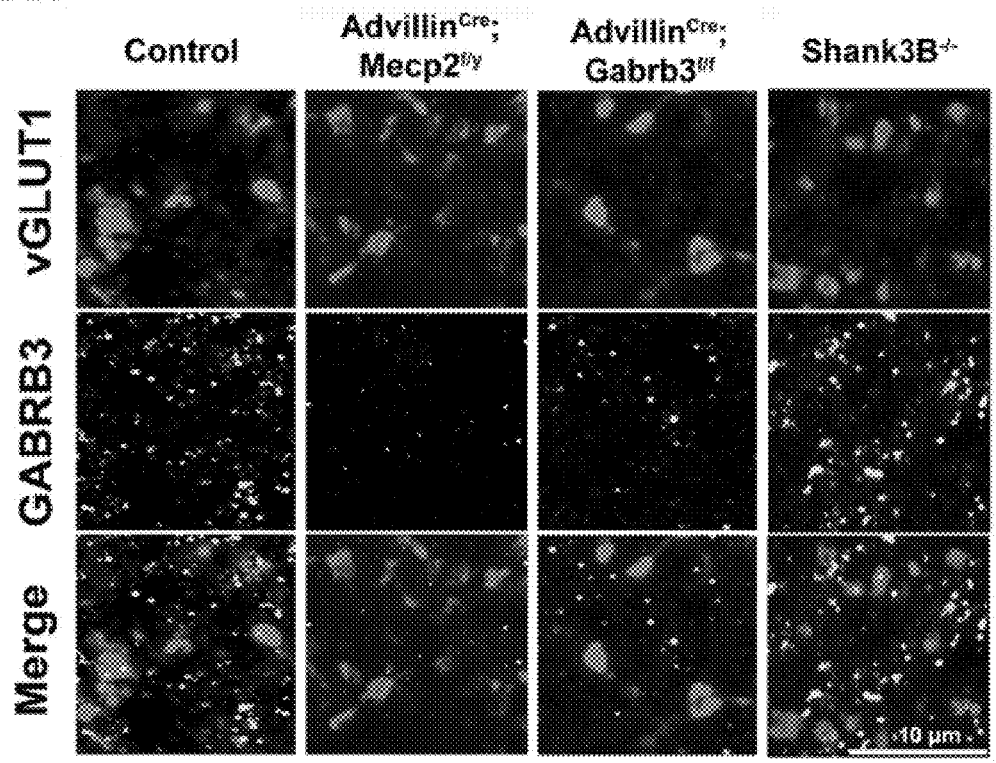
FIGS. 24A-24C show that GABRB3 expression is reduced at presynaptic terminals of low-threshold mechanoreceptor neurons in the spinal cord dorsal horn of Mecp2 and Gabrb3 mutant mice, but not in Shank3 mutant mice.
Figure 24B:
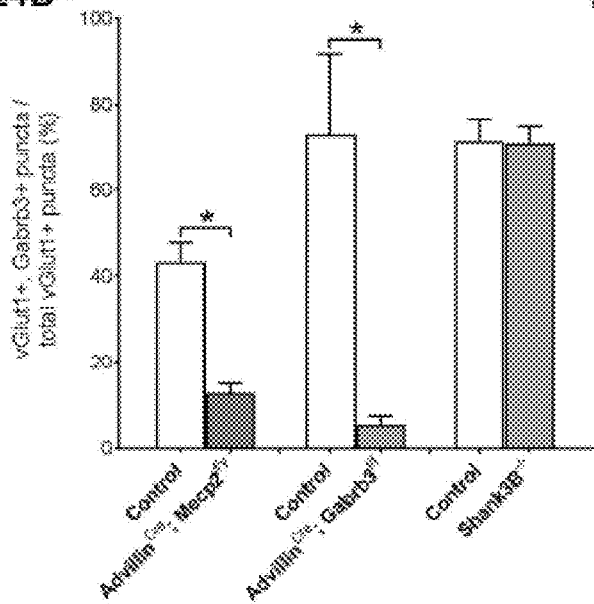
Figure 24C:
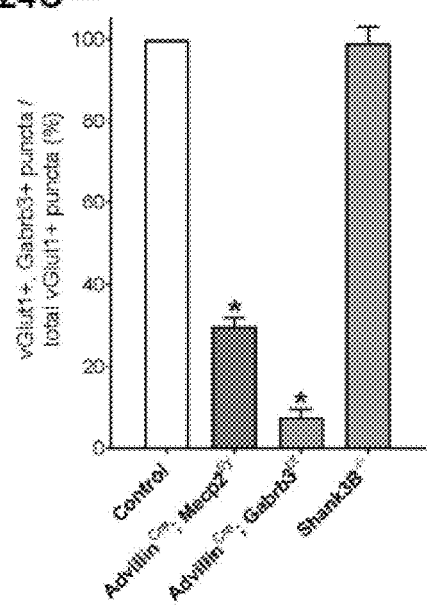
Figure 25A:
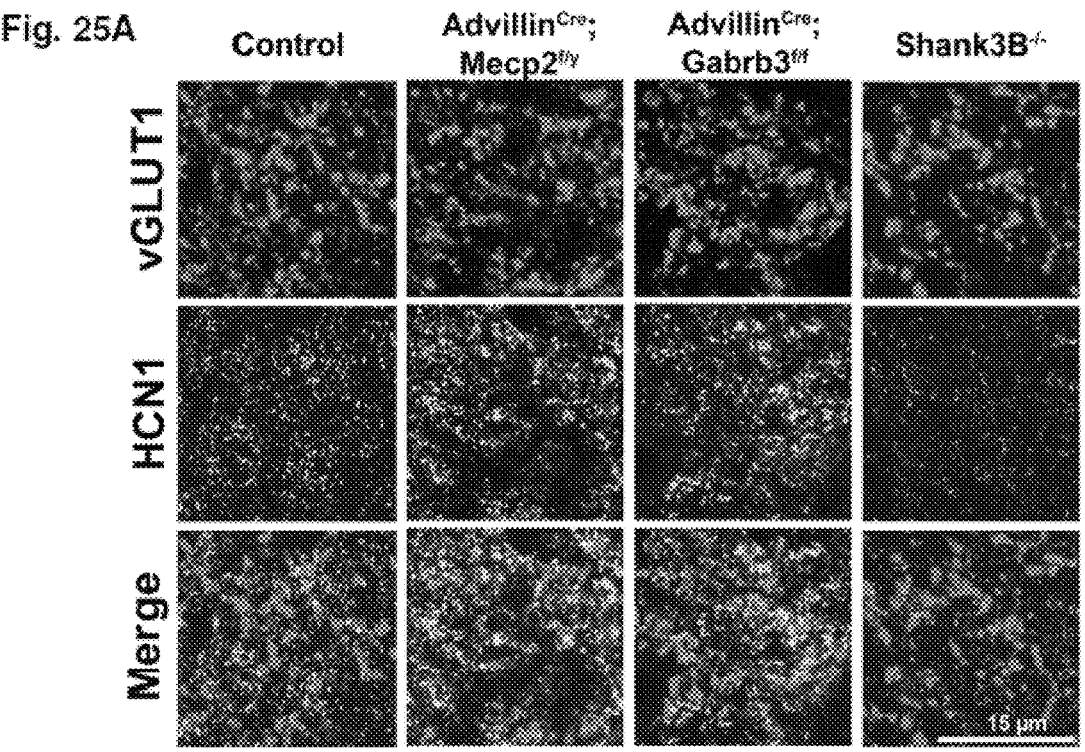
FIGS. 25A-25C show that HCN1 expression is reduced at presynaptic terminals of low-threshold mechanoreceptor neurons in the dorsal horn of Shank3 mutant mice, but not Mecp2 or Gabrb3 mutant mice.
Figure 25B:
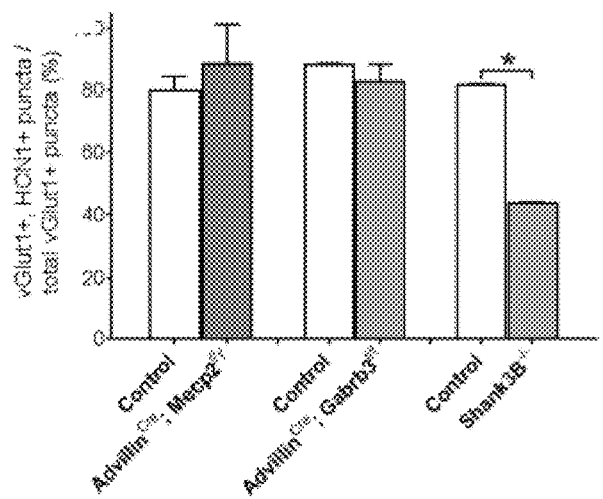
Figure 25C:
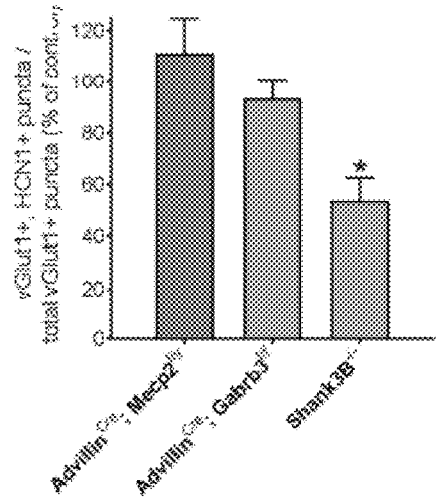
Figure 31A:
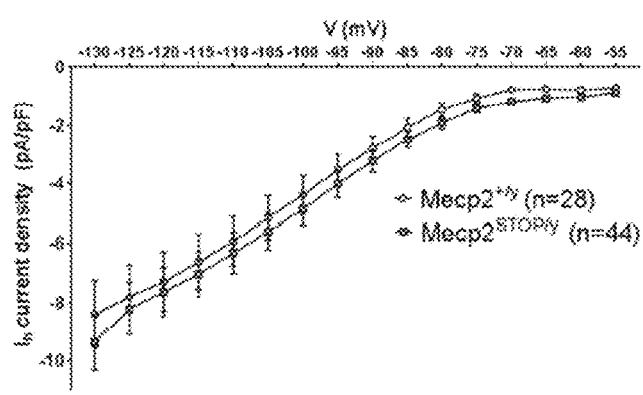
FIGS. 31A-31D show that large diameter primary sensory neurons from Mecp2 mutant mice exhibit no deficits in In currents, but do show increased excitability.
Figure 31B:
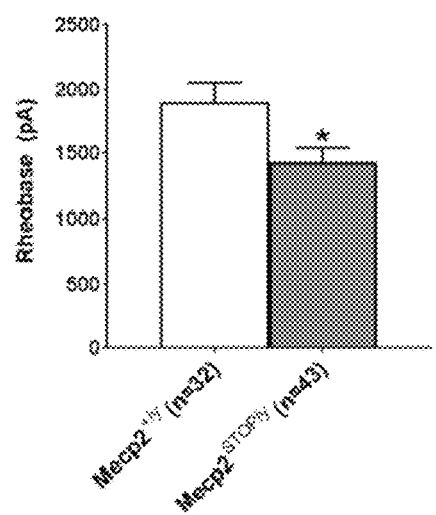
Figure 31C:
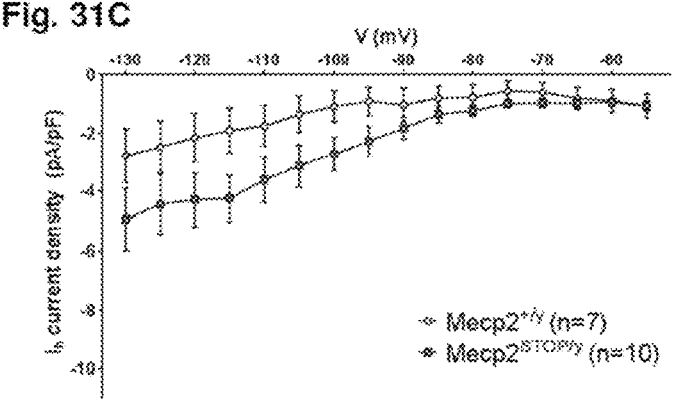
Figure 31D:
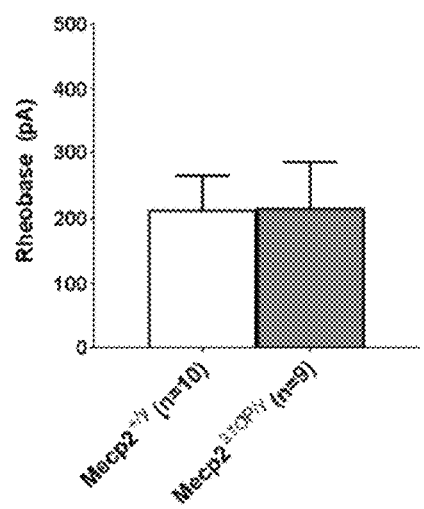

Our findings indicate that while GABRB3 expression is unaltered, HCN1 expression is greatly reduced at presynaptic terminals of Aβ and Aδ LTMRs in lamina III/IV of the SC dorsal horn of $Shank3^{+/-}$ mice (FIGS. 24-26). HCN1-containing channels mediate somatosensory neuron excitability, which can be measured physiologically by action potential firing rates and direct assessment of In currents. We cultured neurons from dorsal root ganglia of $Shank3B^{+/+}$ and $Shank3B^{+/-}$ mice, and recorded physiological properties from both large and small diameter neurons, 24-48 hours post culture. Large diameter $Shank3B^{+/-}$ neurons exhibit a significant decrease in resting membrane potential, and an increase in input resistance, compared to large diameter neurons cultured from control littermates (Table 2). However, no differences in resting membrane potential or input resistance were observed between small diameter neurons of $Shank3B^{+/-}$ mutant and $Shank3B^{+/+}$ control mice (Table 3).

TABLE 2

Electrophysiological properties of cultured large diameter dorsal root ganglion neurons from Shank3B+/+ and Shank3B+/− mice.

| Parameter | Shank3B+/+ | Shank3B+/− | t-test (p-value) |
|---|---|---|---|
| Cm (pF) | 132.10 ± 10.16 | 131.75 ± 13.73 | 0.98 |
| Rm (MΩ) | 66.15 ± 10.12 | 96.97 ± 11.20* | 0.04 |
| Ra (MΩ) | 12.89 ± 0.74 | 14.52 ± 1.22 | 0.27 |
| τ (msec) | 1.17 ± 0.09 | 1.07 ± 0.11 | 0.50 |
| Vrest (mV) | −62.42 ± 2.56 | −67.83 ± 0.87* | 0.04 |
| Diameter (μm) | 49.25 ± 0.88 | 47.80 ± 0.65 | 0.22 |
| N number (# neurons) | 51 | 59 | |

TABLE 3

Electrophysiological properties of cultured small diameter dorsal root ganglion neurons from Shank3B+/+ and Shank3B+/− mice.

| Parameter | Shank3B+/+ | Shank3B+/− | t-test (p-value) |
|---|---|---|---|
| Cm (pF) | 52.71 ± 114.83 | 44.25 ± 20.14 | 0.73 |
| Rm (MΩ) | 75.12 ± 118.07 | 86.18 ± 29.25 | 0.74 |
| Ra (MΩ) | 27.14 ± 4.65 | 29.71 ± 10.75 | 0.82 |
| τ (msec) | 0.70 ± 0.19 | 0.71 ± 0.39 | 0.99 |
| Vrest (mV) | −53.83 ± 2.17 | −54.71 ± 1.99 | 0.77 |
| Diameter (μm) | 27.64 ± 1.09 | 27.33 ± 1.21 | 0.85 |
| N number (# neurons) | 9 | 7 | |

Large diameter $Shank3B^{+/-}$ neurons also exhibited a significant decrease in $I_h$ density (FIG. 27), as well as a significant decrease in the amount of minimal current required to produce an action potential (rheobase) in these neurons, compared to large diameter neurons cultured from control (Shank3B$^{+/+}$) mice (FIG. 28). In contrast, no differences in I$_h$ or rheobase in small diameter neurons cultured from Shank3B$^{+/-}$ or Shank3B$^{+/+}$ mice were observed (FIGS. 29-30).

These results are distinct from those observed in Mecp2 mutants, as mutations in Mecp2 lead to a significant reduction in GABRB3 expression at presynaptic terminals of Aβ and Aδ LTMRs in lamina III/IV of the SC dorsal horn of Advillin$^{Cre}$;Mecp2$^{f/y}$ mice, but HCN1 expression is unaltered compared to control littermates (FIGS. 24-25). Furthermore, I$_h$ currents are not affected in cultured large diameter neurons of Advillin$^{Cre}$; Mecp2$^{f/y}$ mice, although mutant neurons do exhibit a decrease in rheobase compared to control neurons (FIG. 31). Interestingly, no differences in physiological properties were found in small diameter neurons cultured from Advillin$^{Cre}$; Mecp2$^{f/y}$, compared to controls (FIG. 31).

Together, these findings indicate that Shank3$^{+/-}$ large diameter DRG neurons exhibit hyperexcitability, a dramatic loss of I$_h$ currents, and reduced rheobase (FIGS. 24-30), while large diameter DRG neurons cultured from Advillin$^{Cre}$; Mecp2$^{f/y}$ exhibited hyperexcitability but no changes in I$_h$. Loss of Mecp2 also leads to significant deficits in GABA$_A$ receptor-mediated presynaptic inhibition (PSI), which leads to tactile hypersensitivity. Thus, we propose that at least two distinct mechanisms can underlie tactile hypersensitivity in ASD mouse models: loss of PSI of LTMR inputs to the SC and hyperexcitability of LTMRs.

ASD-Related Gene Mutations in Peripheral Somatosensory Neurons Lead to Aberrant Brain Development We found that the number of PV-positive neurons in primary trunk somatosensory cortex (S1) is increased in Mecp2 null (Mecp2$^{STOP/y}$) mice, compared to control littermates (FIGS. 26A-26B). PV-positive neurons in this region of cortex of Mecp2 null mice were also significantly smaller than PV-positive neurons in control littermates, suggesting significantly altered inhibitory circuits in Mecp2 mutant mice (FIGS. 26A-26C). Remarkably, restoration of Mecp2 expression only in somatosensory neurons (Advillin$^{Cre}$; Mecp2$^{STOP/y}$) normalized the increased density and decreased soma size of PV-positive neurons in primary somatosensory cortex that is observed in Mecp2$^{STOP/y}$ mice (FIG. 26). In line with this, conditional deletion of Mecp2 only in primary sensory neurons (Advillin$^{Cre}$; Mecp2$^{f/y}$) causes an increase in PV-positive neuron number in primary somatosensory cortex, compared to control littermates (FIG. 40).

We also chose to investigate whether expression of Mecp2 only in peripheral somatosensory neurons would affect PV-positive neuron properties in brain regions associated with anxiety-like behaviors or social interactions. Our findings indicate that while Mecp2 null mice exhibit a decreased BLA size and number of PV-positive neurons in the BLA, expression of Mecp2 only in peripheral sensory neurons improves PV-positive neuron number and size abnormalities observed in the BLA of Mecp2 null mice (FIG. 37).

Figure 38A:
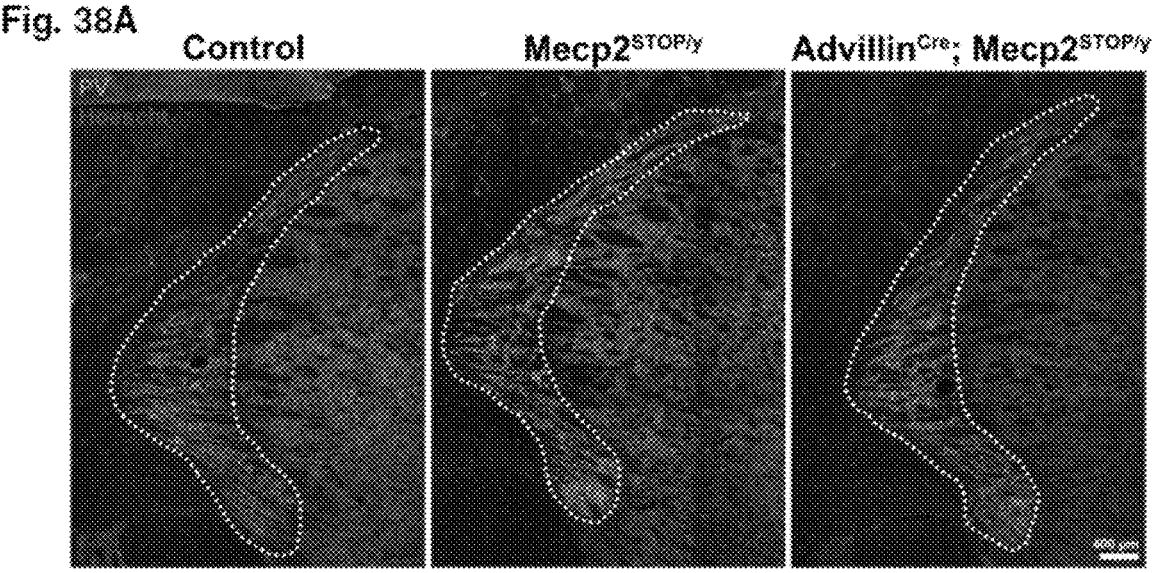
FIGS. 38A-38C show that restoration of Mecp2 only in peripheral sensory neurons of Mecp2 mutant mice does not affect PV-positive neuronal properties in the thalamic reticular nucleus.
Figure 38B:
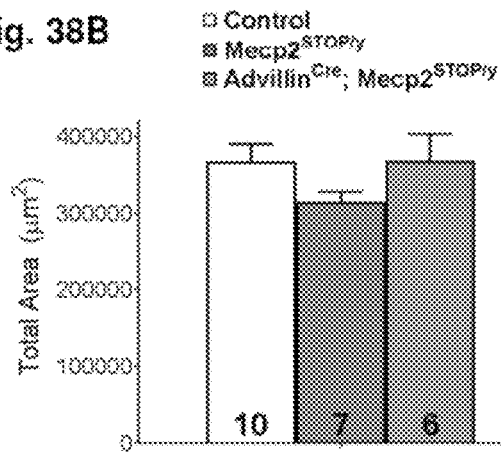
Figure 38C:
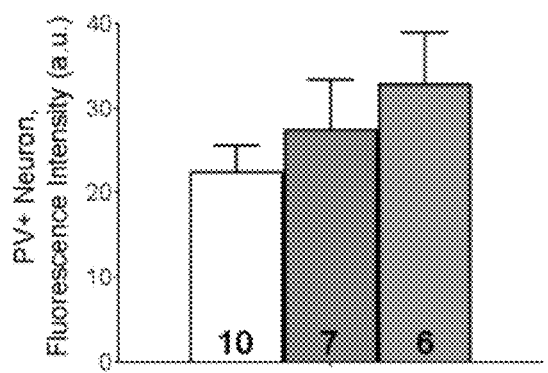
Figure 39A:
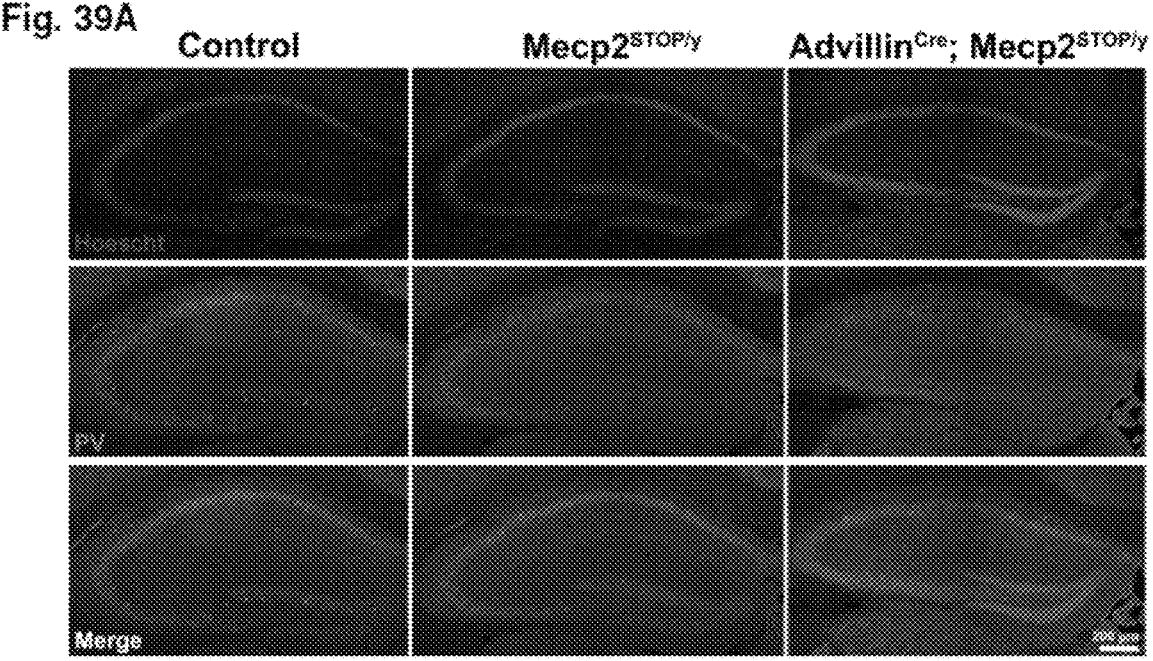
FIGS. 39A-39D show that restoration of Mecp2 only in peripheral sensory neurons of Mecp2 mutant mice does not improve PV-positive neuronal impairments in hippocampus.
Figure 39B:
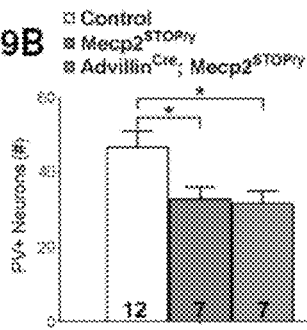
Figure 39C:
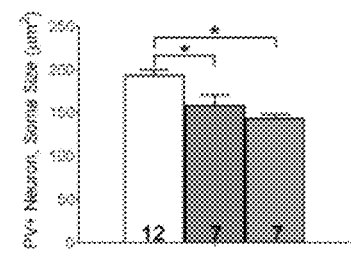
Figure 39D:
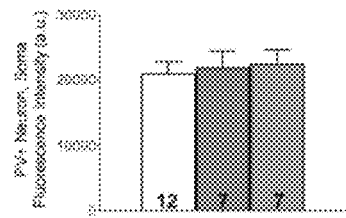
Figure 40A:
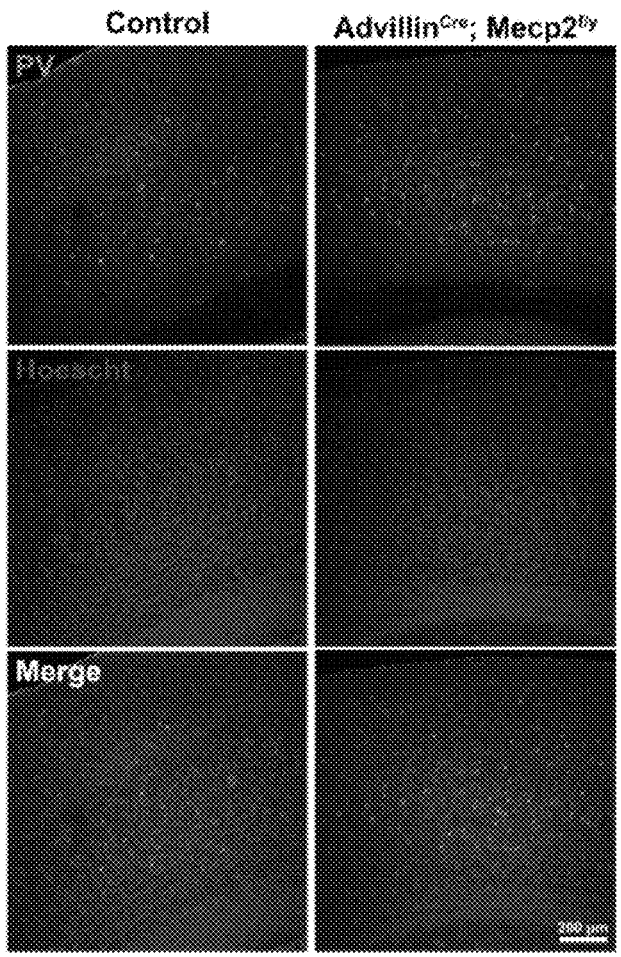
FIGS. 40A-40D show that deletion of Mecp2 only in peripheral sensory neurons leads to an increased number of PV-positive neurons in the primary somatosensory cortex.
Figure 40B:
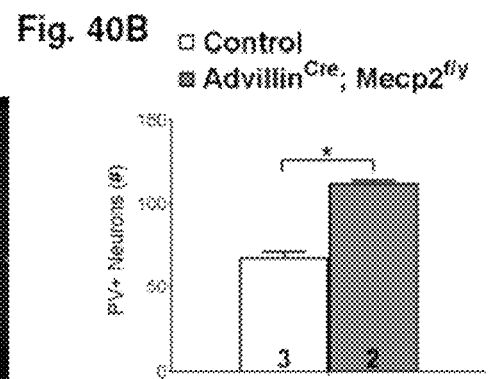
Figure 40C:
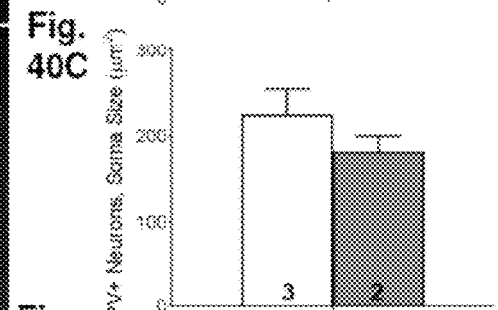
Figure 40D:
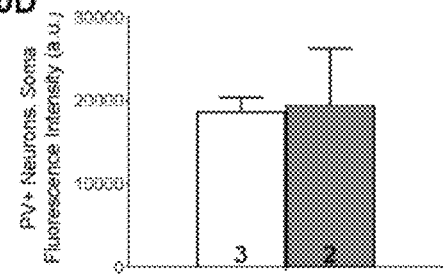
Figure 49B:
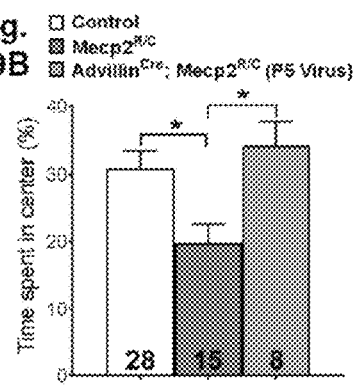
Figure 49C:
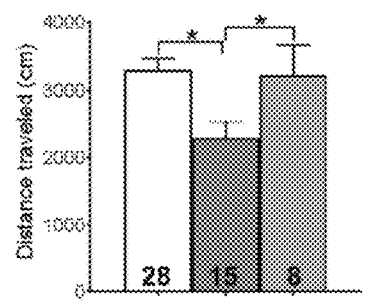
Figure 50A:
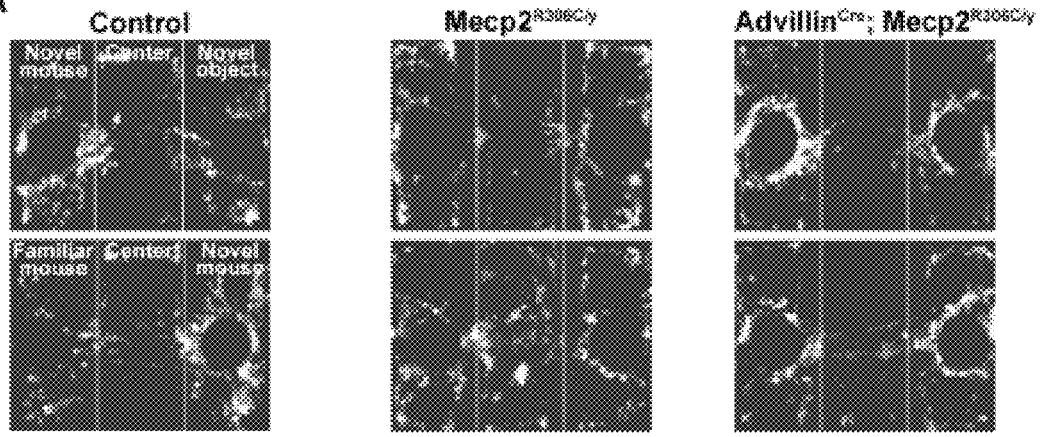
FIGS. 50A-50D show that increased expression of GABRB3 in peripheral sensory neurons beginning at P5 improves some social behaviors in male Mecp2$^{R306C}$ mutant mice.
Figure 50B:
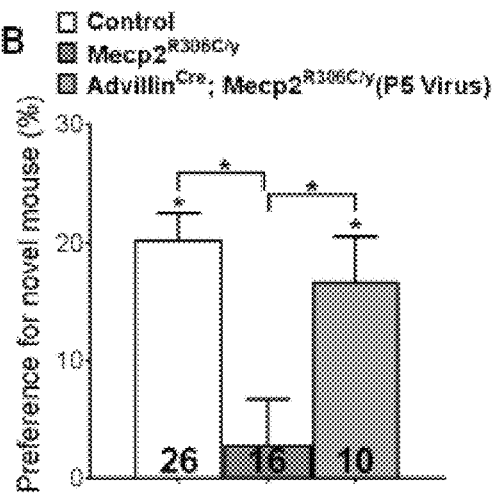
Figure 50C:
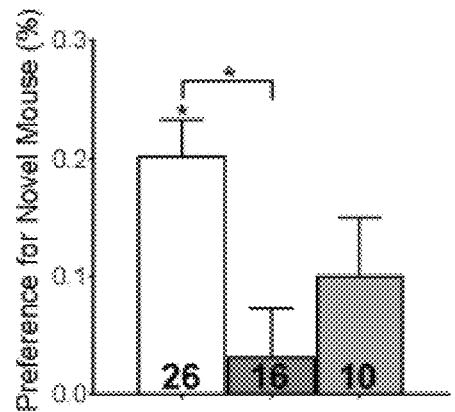
Figure 50D:
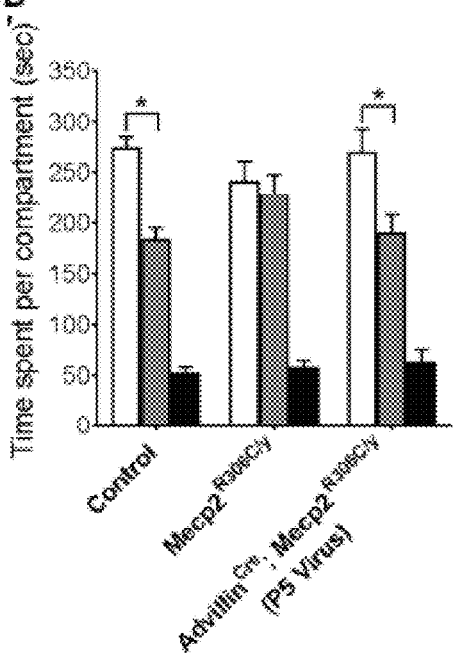
Figure 50E:
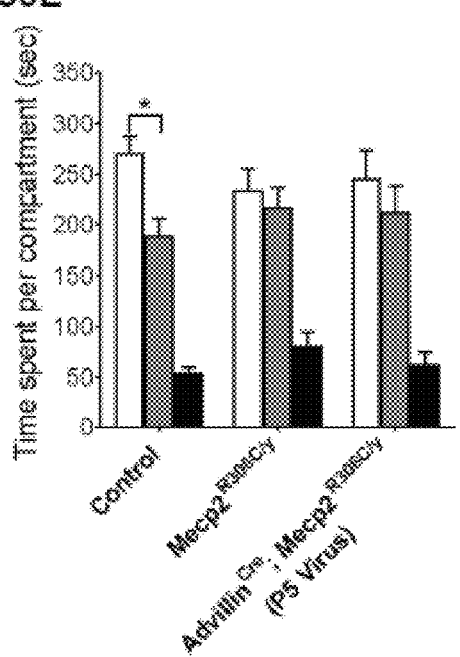
FIG. 50E is a bar graph of Average time spent (seconds) in each of the three chambers during the "Social Novelty Preference" portion of the 3-chamber social interaction test for the indicated groups. Comparisons between time spent in each chamber, per genotype: repeated measures two-way ANOVA with post-hoc Tukey's test: *, p<0.05.
Figure 51A:
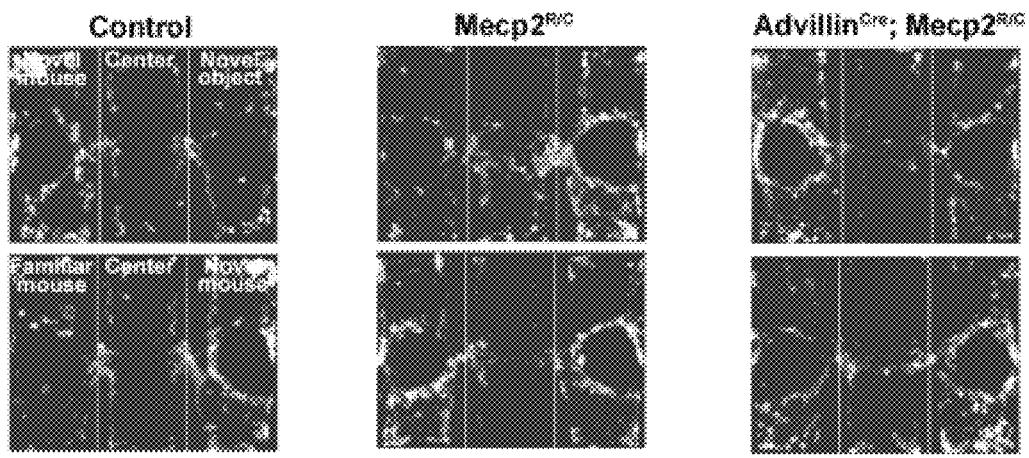
FIGS. 51A-51E show that increased expression of GABRB3 in peripheral sensory neurons beginning at P5 normalizes social behaviors in female Mecp2$^{R306C}$ mutant mice during the three chamber social interaction test.
Figure 51B:
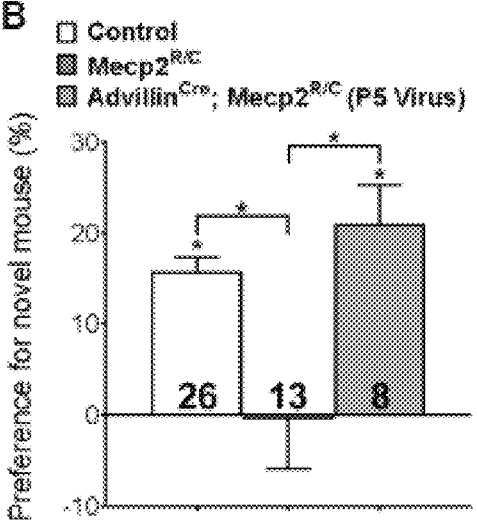
Figure 51C:
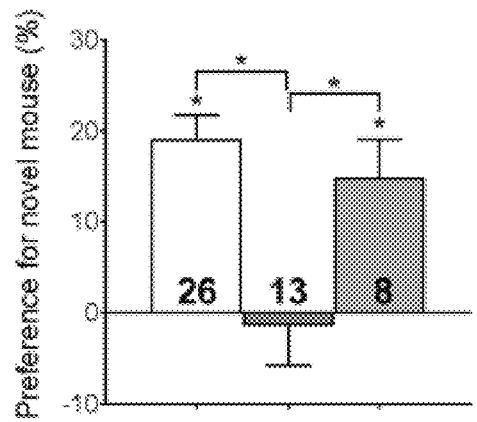
Figure 51D:
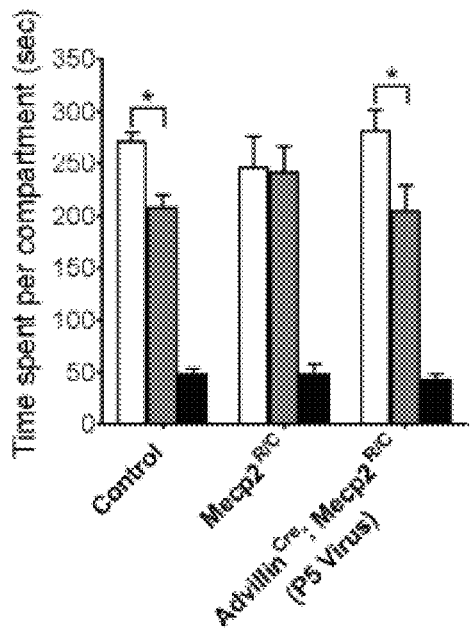
Figure 51E:
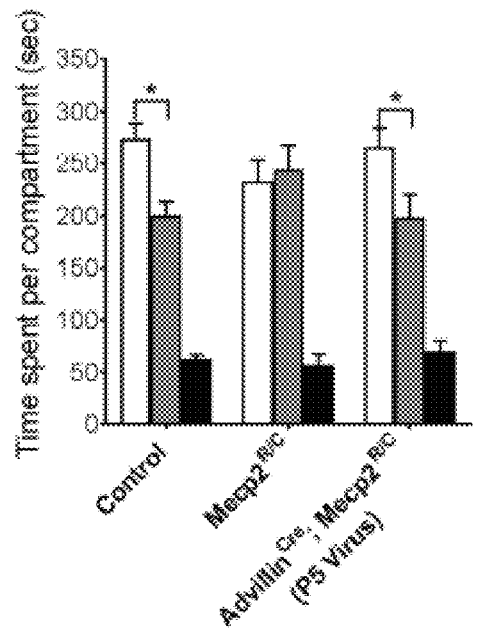
Figure 52A:
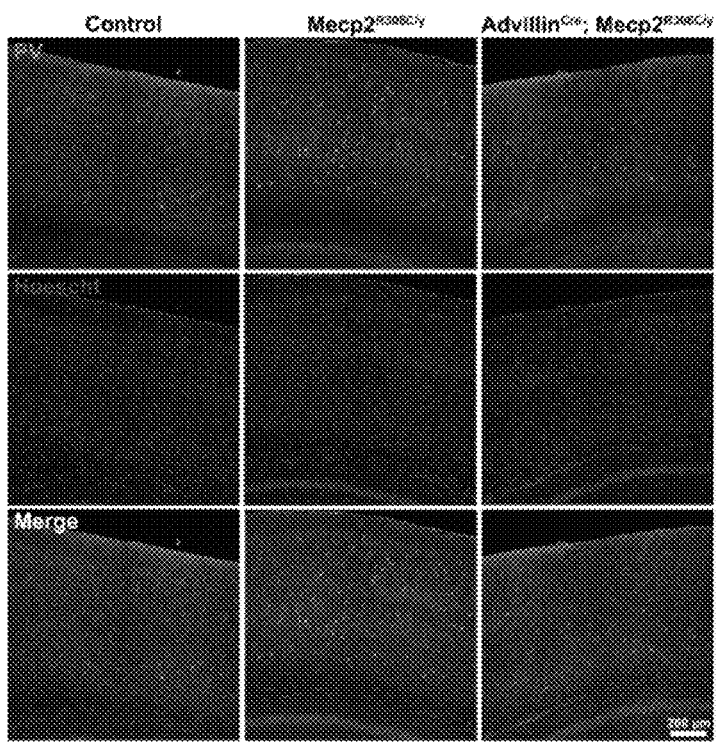
FIGS. 52A-52D shows that expression of GABRB3 only in peripheral somatosensory neurons beginning at P5 improves PV-positive neuronal impairments in the primary somatosensory cortex of Mecp2$^{R306C}$ mutant mice.
Figure 52B:
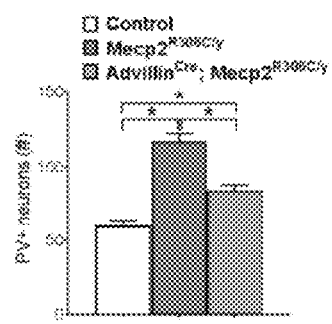
Figure 52C:
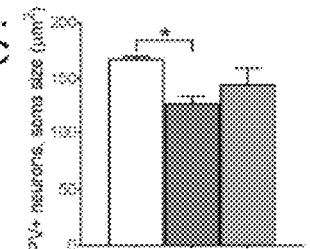
Figure 52D:
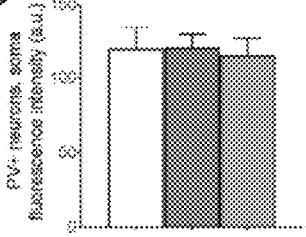
Figure 53A:
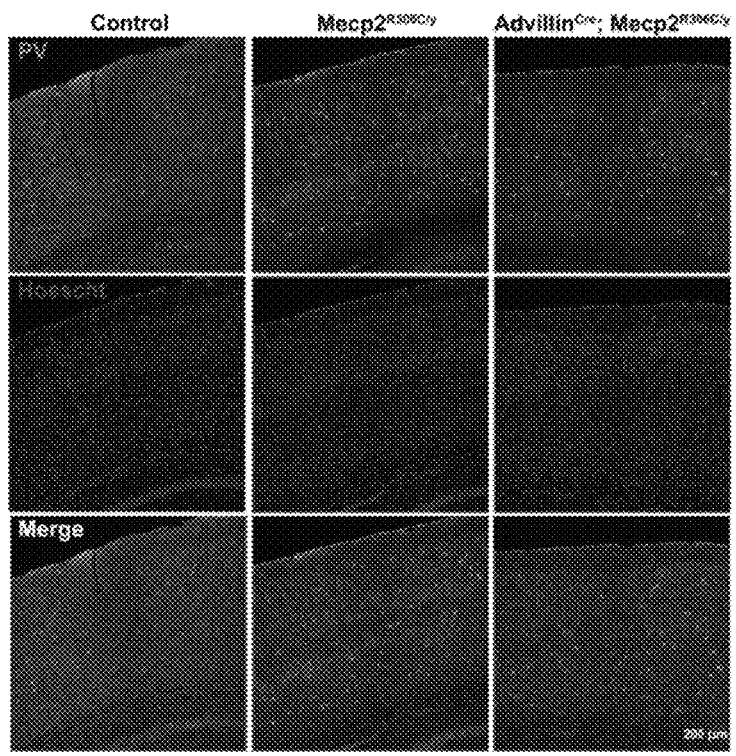
FIGS. 53A-53D show that expression of GABRB3 only in peripheral somatosensory neurons beginning at P5 does not improve PV-positive neuronal impairments in the primary visual cortex of Mecp2$^{R306C}$ mutant mice.
Figure 53B:
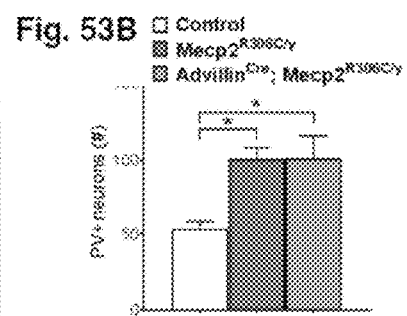
Figure 53C:
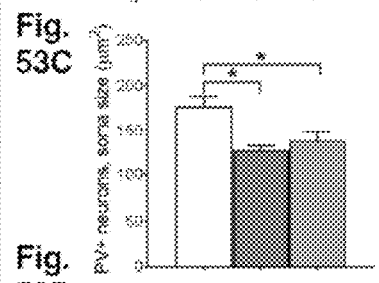
Figure 53D:
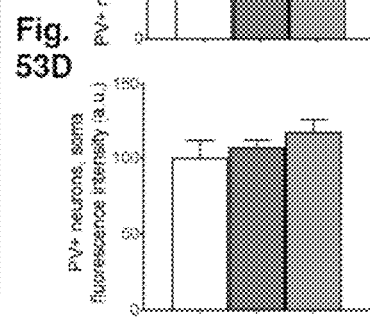
Figure 54A:
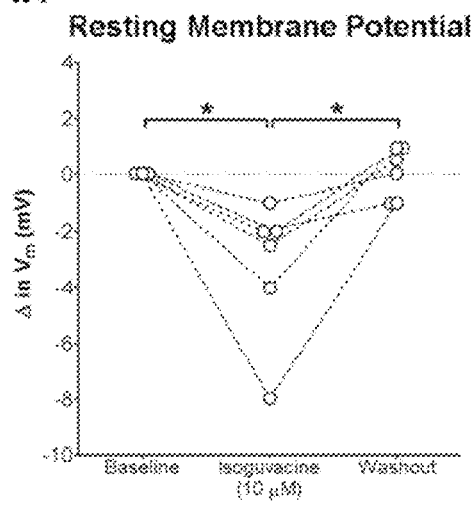
FIGS. 54A-54D shows that isoguvacine treatment reduces resting membrane potential and decreases excitability of large diameter cultured primary sensory neurons.
Figure 54B:
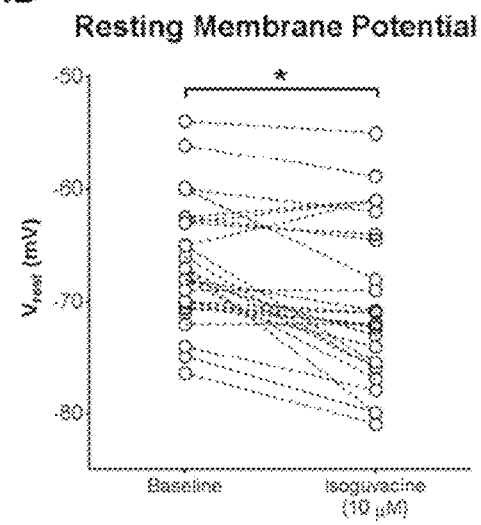
Figure 54C:
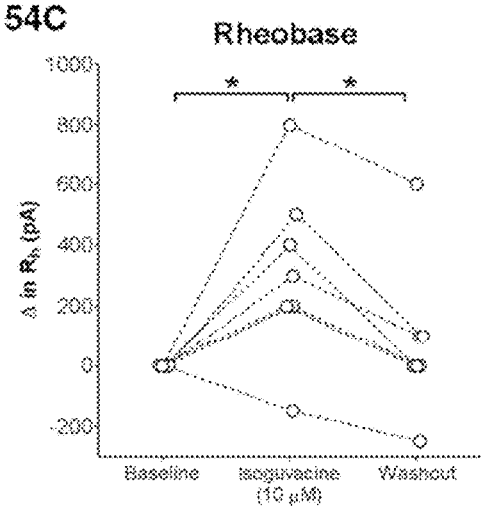
Figure 54D:
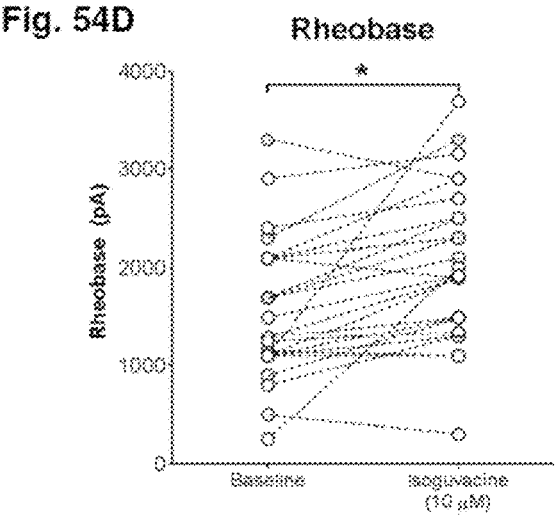
Figure 55A:
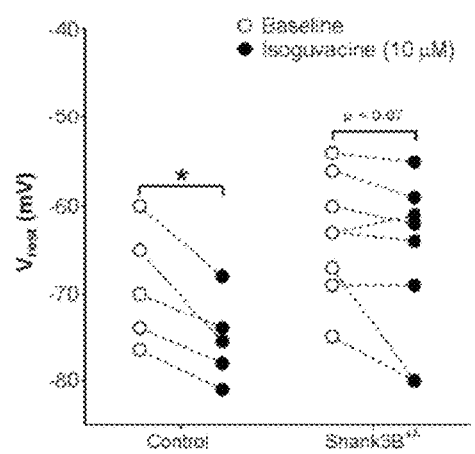
FIGS. 55A-55D show that Isoguvacine treatment reduces resting membrane potential and decreases excitability of large diameter cultured primary sensory neurons from Shank3 and Mecp2 mutant mice.
Figure 55B:
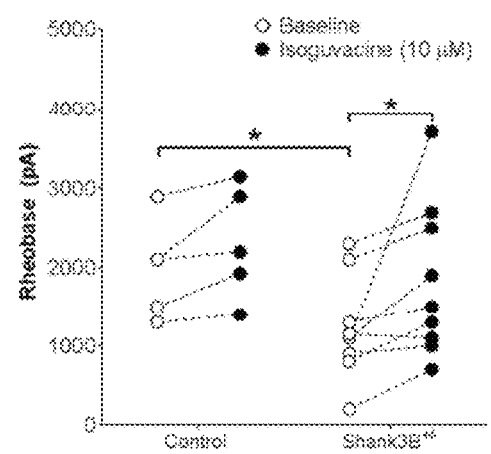
Figure 55C:
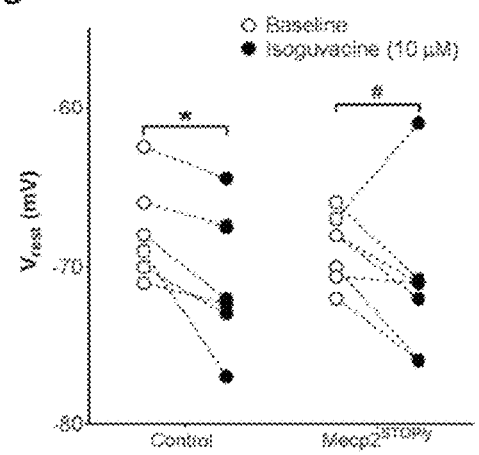
Figure 55D:
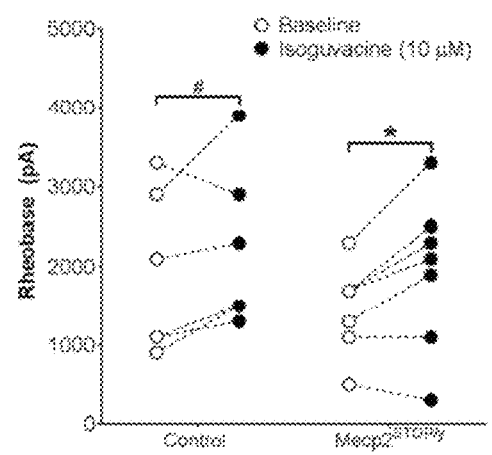
Figure 56A:
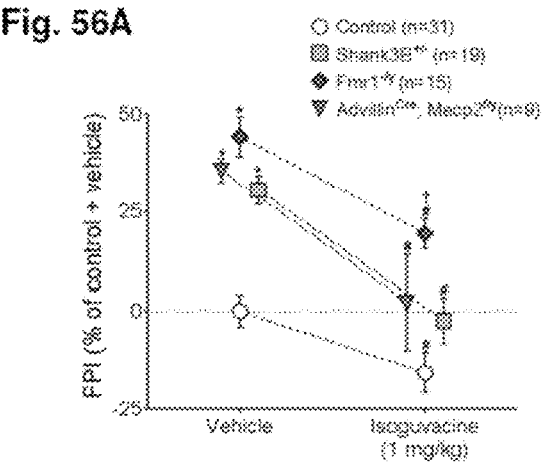
FIGS. 56A-56D show that isoguvacine treatment significantly reduces tactile hypersensitivity in multiple mouse models of ASD.
Figure 56B:
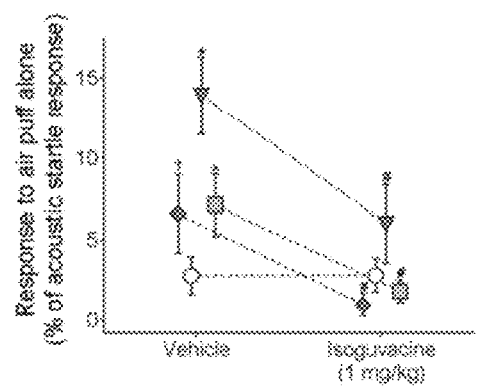
Figure 56C:
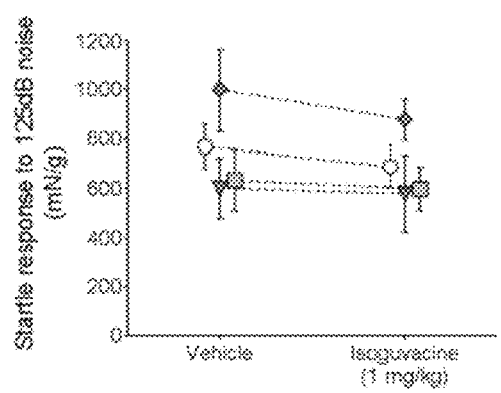
Figure 56D:
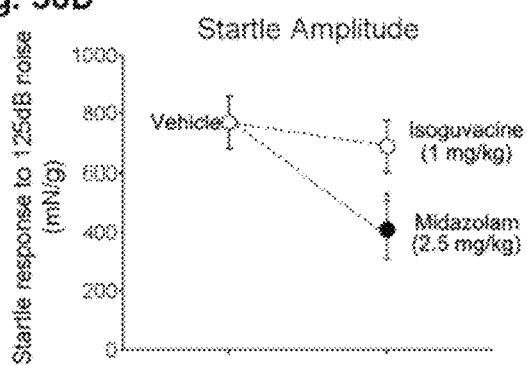
Figure 56E:
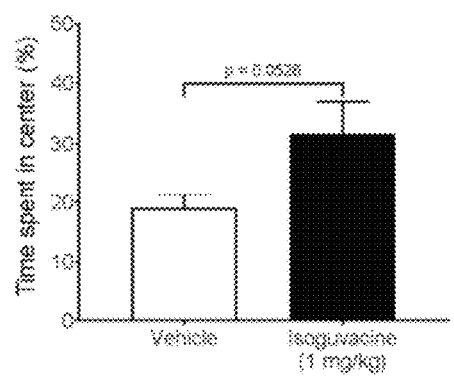
FIG. 56E is a graph of percentage of time spent in the center of the chamber during an open field test. Experiments were performed in mice, 30 minutes after an intraperitoneal (i.p.) of either saline (vehicle) or isoguvacine (1 mg/kg).
Figure 56F:
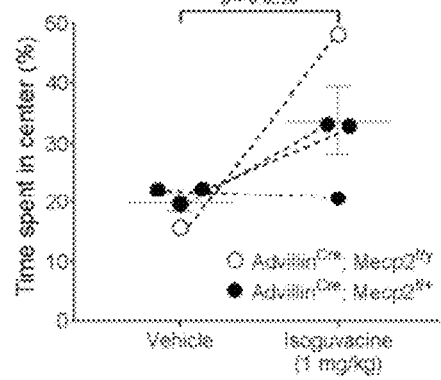
FIG. 56F is a graph of percentage of time spent in the center of the chamber during an open field test. Experiments were performed in Advillin$^{Cre}$; Mecp2$^{fl/y\ or\ fl/+}$ mutant mice, 30 minutes after an intraperitoneal (i.p.) of either saline (vehicle) or isoguvacine (1 mg/kg).

Expression of Mecp2 only in peripheral sensory neurons did not improve PV-positive neuron phenotypes observed in the hippocampus: both Mecp2$^{STOP/y}$ and Advillin$^{Cre}$; Mecp2$^{STOP/y}$ exhibited a decrease in PV-positive neuron number and soma size in the hippocampus, compared to littermate controls (FIG. 39). Furthermore, no changes in the reticular nucleus of the thalamus were observed in any of the conditions (FIG. 38).

Abnormalities in PV-positive neuron properties have also been observed in the cortex of Shank3 mutant mice. In agreement with this, we found that the number of PV-positive neurons was significantly decreased in 51 of Shank3$^{FX/+}$ mice, compared to control littermates (FIG. 41). Restoration of Shank3 expression only in peripheral sensory neurons improved this deficit in PV-positive neuron numbers, and the number of PV-positive neurons in S1 of Advillin$^{Cre}$; Shank3$^{FX/+}$ mice was not different then controls (FIG. 41). While Shank3$^{FX/+}$ mice exhibited a significant decrease in the number of PV-positive neurons in the BLA, Advillin$^{Cre}$; Shank3$^{FX/+}$ mice displayed an increase in PV-positive neurons in this region (FIG. 42). Additionally, conditional deletion of Shank3 only in peripheral somatosensory neurons also lead to a decrease in the number of PV-positive neurons in S1 of Advillin$^{Cre}$; Shank3$^{f/+}$ mice, compared to control littermates (FIG. 43).

Taken together, our findings indicate that ASD-related gene deletion only in peripheral somatosensory neurons leads to abnormal development of PV-positive cortical circuits, which may lead to changes in sensory processing, anxiety-like behaviors and social interactions. Furthermore, restoration of either Mecp2 or Shank3 exclusively in peripheral somatosensory neurons was sufficient to improve deficits in PV-positive neuron properties in both S1 and BLA. These findings indicate that perturbations in peripheral sensory neuron properties during development lead to changes in brain development which may contribute to ASD-like behaviors in mice, and targeting peripheral sensory neurons during early development periods may improve both brain development and behavioral outcomes related to ASD.

A Therapeutic Time Window for Rescue of Tactile, Anxiety-Like and Social Interaction Deficits in Mouse Models of ASD Symptoms of ASD emerge at 2-3 years of age in human patients. We therefore sought to determine the optimal age of replacement of ASD genes in somatosensory neurons for the acquisition of normal tactile and other ASD-related behaviors in mice.

Figure 34A:
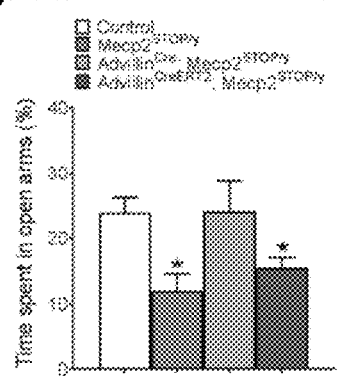
FIGS. 34A-34C show a critical time window for expression of Mecp2 exclusively in peripheral sensory neurons for the improvement of anxiety-like behavior in the elevated plus maze.
Figure 34B:
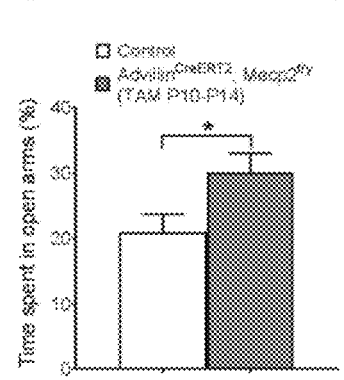
Figure 34C:
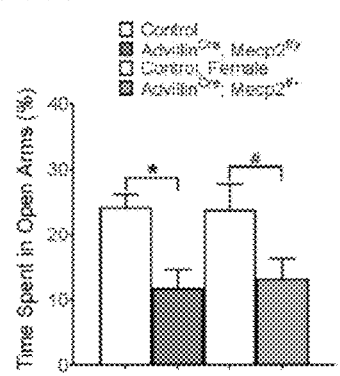
Figure 35A:
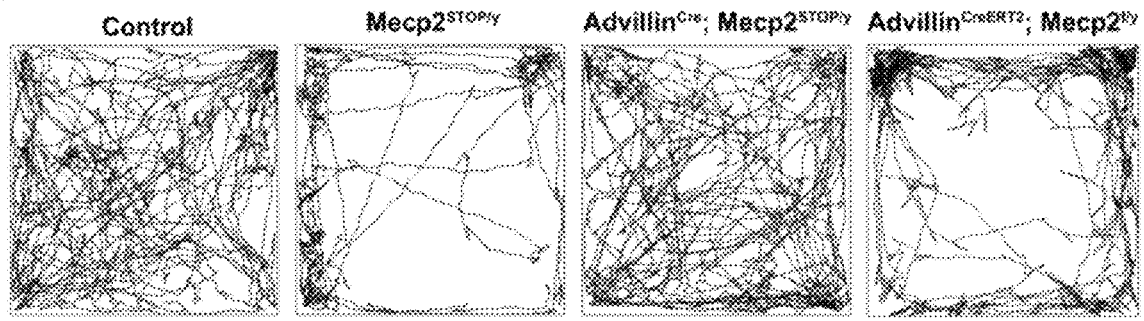
FIGS. 35A-35E show a critical time window for expression of Mecp2 exclusively in peripheral sensory neurons for the improvement of anxiety-like behavior in the open field test.
Figure 35B:
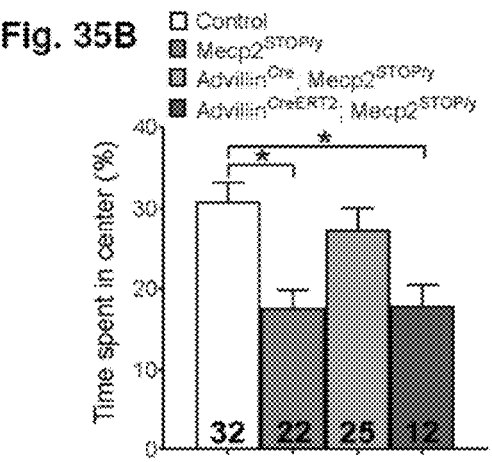
Figure 35C:
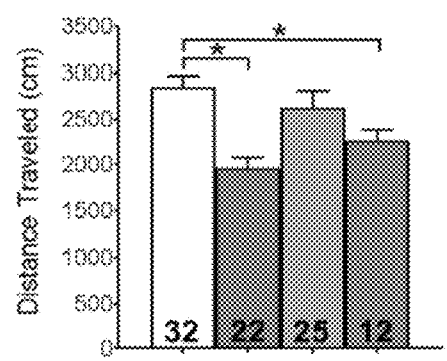
Figure 35D:
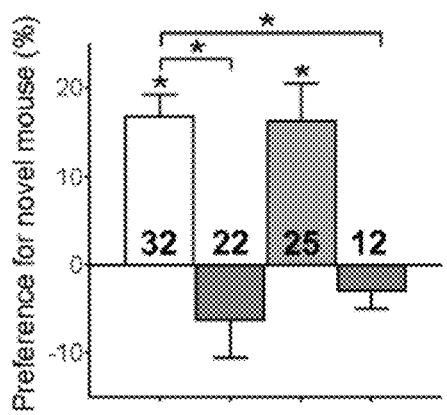
Figure 35E:
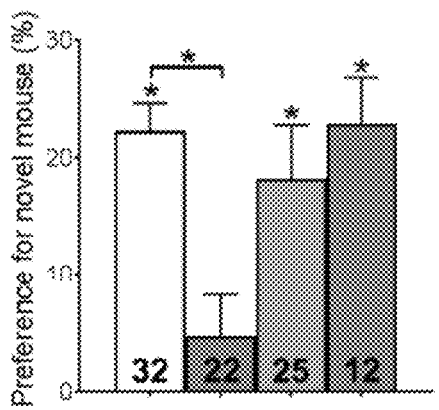
Figure 37A:
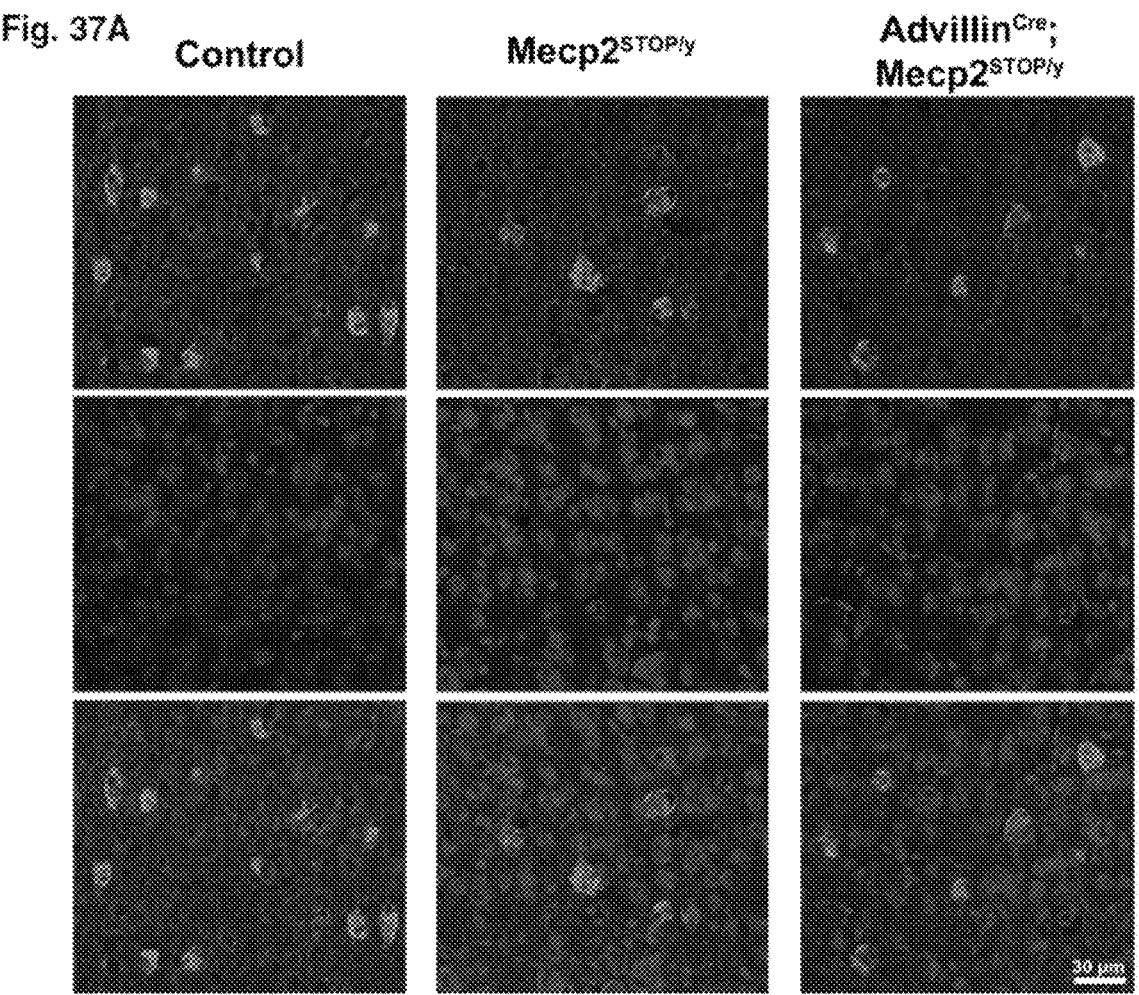
FIGS. 37A-37D show that restoration of Mecp2 only in peripheral sensory neurons of Mecp2 mutant mice improves PV-positive neuronal impairments in basolateral amygdala.
Figure 37B:
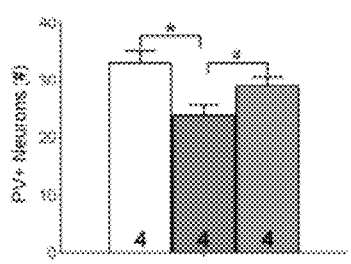
Figure 37C:
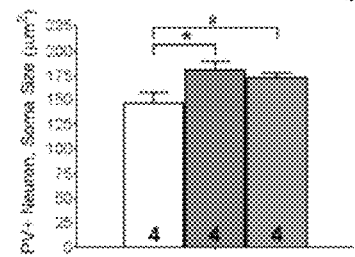
Figure 37D:
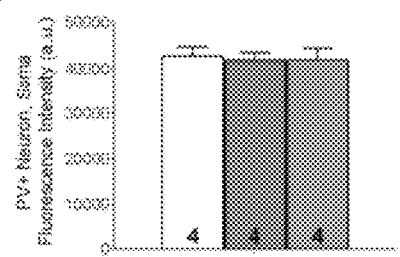

While expression of Mecp2 in somatosensory neurons beginning at P28 of Advillin$^{CreERT2}$; Mecp2$^{STOP/y}$ mice rescued tactile deficits, these mutant mice continued to exhibit increased anxiety-like behaviors that were similar to Mecp2 null mice (Mecp2$^{STOP/y}$), and had more mild social behavior deficits (FIGS. 32, 34, and 35). These findings indicate a developmental requirement of Mecp2 in somatosensory neurons for the acquisition of normal tactile sensitivity, anxiety-like behavior, and some social behaviors, and that the critical window for acquisition of these behaviors closes prior to P28.

Viral Restoration of GABRB3 Improves Behavioral Deficits in an Mecp2 Mouse Model of ASD To first determine whether genetic restoration of Gabrb3 expression in peripheral somatosensory neurons can improve ASD outcomes, we used a combination of mouse genetics and Cre-dependent adeno-associated viruses (AAV) to express Gabrb3 exclusively in peripheral somatosensory neurons of Mecp2$^{R306C}$ mice. Mecp2$^{R306C}$ mutant mice harbor an arginine-to-cysteine missense mutation in Mecp2 (mecp2$^{R306C}$, a common mutation found in human RTT patients. Crossing Mecp2R$^{306C}$ C mice to Advillin$^{Cre}$ mice enabled expression of virally-delivered Cre-dependent alleles exclusively in dorsal root ganglia (DRG) and trigeminal somatosensory neurons. Advillin$^{Cre}$; Mecp2$^{R306C}$ mice, mutant Mecp2$^{R306C}$ mice (without Cre transgene), or wild-type control littermates were injected intraperitoneally (i.p.) at P5 with the Cre-dependent viral delivery vector, AAV-FLEX-Synapsin-Gabrb3-T2A-mCherry. We found that viral delivery at P5 provided robust transduction of DRG neurons (FIGS. 47A-47C) and increased expression of GABRB3 in somatosensory endings in the SC dorsal horn (FIGS. 47D-47E). Remarkably, this postnatal restoration of Gabrb3 expression in peripheral somatosensory neurons of Mecp2$^{R306C}$ mice reduced their texture discrimination deficits and tactile hypersensitivity (FIGS. 44-46) as well as anxiety-like behaviors measured in the open field test and elevated plus maze (FIGS. 38-39) and improved social behaviors assessed in the three chamber social interaction test (FIGS. 40 and 41). Remarkably, while Mecp2$^{R306C}$ mutant mice exhibited an increase in PV-positive neuron number and decrease in PV-positive soma size in primary somatosensory and visual cortices, viral delivery of Gabrb3 at P5 in Advillin$^{Cre}$; mecp2$^{R306C}$ mice significantly improved the PV-positive neuron abnormalities in primary somatosensory cortex, but not visual cortex (FIGS. 42 and 43).

It is important to note that the amount of viral transduction of DRG neurons, as well as the percentage of GABRB3 puncta at peripheral somatosensory neuron terminals in the dorsal horn of the SC both negatively correlated with responsivity to an air puff stimulus, indicating a relationship between GABA$_A$ receptor signaling on primary afferents and tactile sensitivity. Furthermore, while male Advillin$^{Cre}$; Mecp2$^{R306C/y}$ mice showed significant improvements tactile sensitivity, anxiety-like behaviors and social interactions, female Advillin$^{Cre}$; Mecp2$^{R/C}$ mice with heterozygous mutations in Mecp2 showed a complete rescue of these behaviors and were not different than control littermates.

Peripherally-restricted GABAA Receptor Agonists Improve Tactile Hypersensitivity in Multiple ASD Mouse Models These exciting findings prompted us to ask whether peripherally restricted GABA$_A$ receptor agonists could also be used to ameliorate tactile hypersensitivity and other behavioral deficits in ASD models. We utilized a peripherally restricted GABA$_A$ receptor agonist, isoguvacine, to determine whether augmenting GABA$_A$ receptor signaling at DRG cell bodies could reduce excitability of primary somatosensory afferents. Application of 10 μM isoguvacine to cultured large diameter DRG neurons caused a decrease in resting membrane potential, and an increase in the amount of minimal current required to produce an action potential (rheobase, FIG. 54). These findings suggest that isoguvacine can act directly on the cell bodies of dorsal root ganglion (DRG) neurons.

We next determined whether isoguvacine could improve electrophysiological deficits observed in large diameter peripheral somatosensory neurons cultured from Shank3 and Mecp2 mutant mice. Application of 10 μM isoguvacine to large diameter DRG neurons cultured from Shank3B$^{+/-}$ or Mecp2$^{STOP/Y}$ mice lead to a significant decrease in resting membrane potential, as well as an increase in rheobase (FIG. 55). The application of isoguvacine decreased excitability of large diameter peripheral somatosensory neurons from both Shank3B$^{+/-}$ and Mecp2$^{STOP/Y}$ mice, such that rheobase was no longer different than neurons cultured from control littermates in each condition (FIG. 55).

These findings indicate that GABA$_A$ receptor agonists could reduce excitability of somatosensory primary afferents and hence decrease tactile hypersensitivity in mouse models of ASD. Indeed, we found that acute administration of the peripherally restricted GABA$_A$ receptor agonist isoguvacine (1 mg/kg, i.p.) significantly reduces tactile hypersensitivity, as measured by the tactile PPI assay, in Mecp2, Shank3 and Fmr1 mutant mice (FIG. 56). We speculate that enhanced GABA$_A$ receptor signaling attenuates hyperexcitability and augmented mechanosensory neuron inputs to the SC in all ASD mouse models, not only in those models in which the primary deficit is in GABA$_A$ receptor-dependent PSI, because GABA attenuates the firing of mechanosensory neurons. As tactile hypersensitivity contributes to the genesis of anxiety-like behaviors and social impairments, a reduction in tactile sensitivity through augmenting GABAA receptor signaling on peripheral somatosensory neurons may also improve these other ASD-related behaviors. In line with this, administration of isoguvacine (1 mg/kg, i.p.) also enhanced the time spent in the center of a chamber during the open field test, including Advillin$^{Cre}$; Mecp2$^{floxed}$ mutant mice that normally exhibit increased anxiety-like behavior in this assay (FIGS. 41E-41F). Taken together, these data suggest that peripherally restricted GABA$_A$ receptor agonists may represent a novel therapeutic target for the treatment of tactile hypersensitivity, anxiety and social impairments in ASD.

Experimental Procedures

Mouse Lines

Mice were group housed with littermates in standard housing on a 12-hour light/dark cycle. Mecp2$^{-/y}$, mecp2$^{R306C}$, Mecp2$^{f/y}$, Mecp2$^{STOP}$, Shank3B$^{+/-}$, Fmr1$^{-/y}$, Gabrb3$^{+/-}$, Gabrb3$^{f/f}$, Ella$^{Cre}$, Emx1$^{Cre}$, Cdx2$^{Cre}$, Advillin$^{Cre}$, and Advillin$^{CreERT2}$ mouse lines have been described previously, and references are included in the Extended Experimental Procedures. For all behavioral, electrophysiological and histological analyses, experimenters were blinded to genotype.

Behavioral Testing

Male and female mice were of mixed genetic backgrounds (C57BL/6J and 129/SvEv) except for Mecp2 null and Mecp2$^{R306C}$ mice, which were on a C57BL/6J background. Testing began at 6 weeks of age, and in most cases, was completed by 8 weeks of age. The OF test, NORT, startle reflex/PPI, EPM, plethysmography, rotarod, tube dominance test, nest building, and 3-chamber social interaction tests are described in Extended Experimental Procedures.

Electrophysiological Recordings

P14-P19 acute SC slices with dorsal roots attached were used for whole cell patch clamp recordings of PSDCs. Quantal EPSCs were recorded in ACSF with 4 mM strontium replacing Ca$^{2+}$ using a holding potential of −70 mV, and induced by dorsal root stimulation at A-fiber strength (100 μA, 0.1 ms). For DRP measurements, isolated spinal cords with spinal roots attached were prepared. Bipolar glass suction electrodes (inner diameter 80-120 μm) were used to stimulate the T11-L1 dorsal root; recording from the same root to measure afferent recruitment, from an adjacent dorsal root to measure DRPs, and from ventral roots to measure spinal reflexes.

Histological Analyses

IHC of tissue sections were performed using standard procedures. For GABRB3 puncta analysis, Z-stack images of SC slices were taken on a Zeiss LSM 700 confocal microscope using a 63× oil-immersion lens (Zeiss; Plan-Apochromat 63×/NA 1.40).

Statistical Analyses

All data are expressed as the mean±SEM. Unless otherwise stated in the figure legend, data were analyzed using Student's t-test. Animal numbers per group are shown in the bars or legends of each panel.

Mouse Lines and Genotyping

Mice were group housed with littermates in standard housing on a 12-hour light/dark cycle. Tail biopsies were taken at weaning (P21, +/−2 days), which were used for genetic identification.

Mecp2 null mice were obtained from Michael Greenberg (also available from the Jackson Laboratory, 003890), were previously described (Guy et al., 2001). The following primers were used to identify the null allele: common forward 5'AAA TTG GGT TAC ACC GCT GA-3'; mutant reverse 5'CCA CCT AGC CTG CCT GTA CT-3'; and wild type reverse 5'-CTG TAT CCT TGG GTC AAG CTG-3'. Mecp2$^{R306C}$ mice were obtained from Michael Greenberg, and were previously described. The following primers were used to identify the mutant allele: forward 5'-GGA TTG TGG AAA AGC CAG-3'; and reverse 5'-ATG ACC TGG GCA GAT GTG GTA G-3'.

Shank3B null mice were obtained from the Jackson Laboratory (17688), and were previously described. The following primers were used to identify the null allele: common forward 5'- GAG ACT GAT CAG CGC AGT TG-3'; wild type reverse 5'-TGA CAT AAT CGC TGG CAA AG-3'; mutant reverse 5'-GCT ATA CGA AGT TAT GTC GAC TAG G-3'. Fmr1 null mice were obtained from the Jackson Laboratory (003025), and were previously described. The following primers were used to identify the null allele: mutant forward 5'- CAC GAG ACT AGT GAG ACG TG-3'; wild type forward 5'-TGT GAT AGA ATA TGC AGC ATG TGA-3'; common reverse 5'-CTT CTG GCA CCT CCA GCT T-3'.

Mecp2 floxed mice were obtained from the Jackson Laboratory (006847). The floxed Mecp2 sequence was identified using the following primers: forward 5'-TGG TAA AGA CCC ATG TGA CCC AAG-3' and reverse 5'-GGC TTG CCA CAT GAC AAG AC-3'. The following primers were used to identify the null allele (post Cre excision), as well as to check for off-target Cre expression in Advillin$^{Cre}$ mice: forward 5'-TGG TAA AGA CCC ATG TGA CCC AAG-3'; and post-cre excision reverse 5'-TCC ACC TAG CCT GCC TGT ACT TTG-3'. Mecp2$^{STOP}$ mice were obtained from the Jackson Laboratory (006849), and were previously described. The following primers were used to identify the mutant allele: forward common 5'-AAC AGT GCC AGC TGC TCT TC-3' and wildtype reverse 5'-CTG TAT CCT TGG GTC AAG CTG-3' and mutant reverse 5'- GCC AGA GGC CAC TTG TGT AG-3'. Gabrb3 floxed mice were obtained from the Jackson Laboratory (008310), and were previously described. The floxed Gabrb3 sequence was identified using the following primers: forward 5'- ATT CGC CTG AGA CCC GAC T-3' and reverse 5'-GTT CAT CCC CAC GCA GAC-3'.

Ella$^{Cre}$ mice were obtained from the Jackson Laboratory (003314), and were previously described. The Cre transgene was identified using generic Cre primers (The Jackson Laboratory): transgene forward 5'-GCG GTC TGG CAG TAA AAA CTA TC-3'; transgene reverse 5'-GTG AAA CAG CAT TGC TGT CAC TT-3'; internal positive control forward 5'-CTA GGC CAC AGA ATT GAA AGA TCT-3'; and internal positive control reverse 5'-GTA GGT GGA AAT TCT AGC ATC C-3'. Emx1$^{Cre}$ mice were obtained from the Jackson Laboratory (005628), and were previously described. The Cre transgene was identified using generic Cre primers (The Jackson Laboratory). Cdx2$^{Cre}$ mice were obtained from Eric Fearon, and described previously. Advillin$^{Cre}$ mice were obtained from Fan Wang (Duke University), and were previously described. The Advillin$^{Cre}$ transgene was identified using the following primers: forward 5'-CCC TGT TCA CTG TGA GTA GG-3'; and reverse 5'-AGT ATC TGG TAG GTG CTT CCA G-3'. Advillin$^{CreERT2}$ mice were obtained from John Wood, and were described previously. (The Jackson Laboratory, 026516). The Advillin$^{CreERT2}$ transgene was identified using the following primers: 5'- CCC TGT TCA CTG TGA GTA GG-3'; 5'-AGT ATC TGG TAG GTG CTT CCA G-3'; and 5'- GCG ATC CCT GAA CAT GTC AT C-3'.

Proper expression of the Advillin$^{Cre}$ transgene was assessed using PCR and histological verification. Animals with post-Cre excision expression in tail biopsy tissue, or animals with transgene expression and recombination in the spinal cord or brain were excluded from analyses.

Tamoxifen Administration

Tamoxifen was administered to Advillin$^{CreERT2}$ mice to promote excision of floxed alleles (either Mecp2 floxed or Gabrb3 floxed) in primary somatosensory neurons of adult mice. Intraperitoneal injections of tamoxifen (1 mg per day; Toronto Research Chemicals) were administered to mice for 5 consecutive days, from P28-32. All mice in this study shown for Advillin$^{CreERT2}$ mouse lines, including Advillin$^{CreERT2}$ and Mecp2 floxed controls in these groups, received this tamoxifen regimen, and no changes in health or behaviors were observed in either sets of controls compared to non-tamoxifen treated animals.

Behavioral Testing

Male and female mice of mixed genetic backgrounds (C57BL/6J and 129/SvEv) were used for behavioral analyses. The only exceptions were Mecp2 null mice and Mecp2$^{R306C}$ mice, which were on a pure C57BL/6J background, in which animals were backcrossed for at least 5 generations. Testing was done beginning at 6 weeks of age, and in most cases, behavioral testing was completed by 8 weeks of age. All behavioral testing performed in female mice was completed prior to the start of the estrous cycle. Mice were weaned and ear notched for genotyping at P21 (+/−2 days). All animals were group housed, with control and mutant animals in the same litters and cages. Mecp2$^{f/y}$, Mecp2$^{f/+}$, Gabrb3$^{f/f}$, Gabrb3$^{f/f}$, Emx1$^{Cre}$, Cdx2$^{Cre}$, Advillin$^{Cre}$, and Advillin$^{CreERT2}$ mice were used as controls in addition to wild type animals. Littermates from the same genetic crosses were used as controls for each group, to control for variability in mouse strains/backgrounds. No differences were observed between wild type animals and any floxed or Cre positive groups for any of the tests performed. Prior to any behavioral testing, animals were brought into the procedure room and allowed to habituate to the room for 30 minutes. Animal numbers per group for behavioral tests are indicated in figures. All behavioral analyses were done by observers who were blinded to genotype.

Ear Notching

Ear notching was employed as the method of identification for all animals used in behavioral experiments, as toe tagging or metal ear tags can affect animals' ambulatory behavior. Ear notching was performed using an ear punch device (Kent Scientific) on mice at weaning age (P21+/−2 days). For this, mice were restrained by the scruff and the ear punch was used to create holes and/or notches in the ears, following the "Universal Mouse Numbering System". This method of identification allowed experimenters to identify mice without unnecessary handling of the mouse.

Whisker Plucking

Bilateral removal of all mystacial pad vibrissae was performed 3 days prior to the start of experiments. Mice were placed under isoflourane anesthesia and all mystacial vibrissae were plucked with tweezers. Whisker removal caused a small but significant increase in grooming time during a 20-minute open field test, but no differences in speed of movement, ambulatory time or jump time were observed following whisker removal (FIGS. 8A-8D). Animals with and without whiskers also performed comparably on the textured NORT test, but removal of whiskers did promote object investigation using the glabrous skin on paws over whisking/nose poke investigations (FIG. 8E-8G). Whisker removal also caused no changes in anxiety-like behavior, as measured by time spent in the open arms of an elevated plus maze (FIG. 8H). Whiskers begin to regrow 8-12 days after plucking. NORT was completed in the first week following whisker removal, and therefore whiskers were only plucked once. Whiskers were allowed to regrow thereafter, and animals had regrown whiskers by the time social behavior tests were performed.

Open Field Test

On the first day of behavioral testing, animals were subjected to the open field test. During this test, an animal was placed in an empty plexiglass arena (40 cm×40 cm×40 cm) and allowed to explore for 10 minutes, under dim lighting. The outside walls of the chamber were opaque, while the inner dividers were clear plexiglass. The position of the mouse was tracked using custom Matlab scripts. A portion of videos were blindly hand-scored to verify accuracy. Distance traveled and time spent away from walls (time in center) were analyzed per 10-minute video.

Novel Object Recognition Test (NORT)

NORT was performed in the same plexiglass arena used for open field testing. The cube-shaped objects were designed to promote climbing, which enhances novel object recognition performance requiring texture discrimination via glabrous skin on the paws (FIG. 1A). In this test, mice were first habituated to an open field chamber by allowing free exploration of an empty chamber for 10 minutes during each of two consecutive days (FIG. 1B). (The first day of habituation was used as the open field test, see above for details).

Each of the three subsequent testing days included two sessions. In the first session (learning phase), the mouse was placed in the testing arena, equidistant to, and facing away from, the two identical objects placed in the center of the arena. The two objects were positioned equidistant from the center of the arena, and equidistant from the walls of the arena. Each mouse was allowed to explore the objects for 10 minutes. Animals were then removed from the testing arena and placed in a transport cage for 5 minutes. During this time, the arena was cleaned with 70% ethanol, and one of the objects was replaced with a novel object. The mouse was then placed back into the chamber and allowed to explore objects for 10 minutes (testing phase). The amount of time the mouse spent physically investigating (touching) each of the objects was assessed during both the learning and testing phases. If an animal did not physically touch both objects during the learning phase, it was excluded from NORT analysis.

On the third day, a texture-specific NORT (textured NORT) was performed: in the learning phase, an animal was presented with two cubes of identical texture and was allowed to freely explore the objects for ten minutes. After a 5 minute retention period in a separate holding cage, the animal was placed back into the test chamber, with one of the objects exchanged for a novel textured object. Since mice prefer novel stimuli, an animal that can discriminate between the textures on the objects spends more time investigating the novel textured object, whereas an animal that cannot discriminate between the textures is expected to investigate the objects equally. Animals were also subjected to a 'control' NORT on the fourth day, where the test objects differed in color and shape, but not texture, also using a 5 minute retention period (5 min. shape NORT). Lastly, a second control NORT was implemented, but with a one-hour retention period between exploration and testing phases to assess memory performance (1 hr. Shape NORT; FIG. 1 B).

For textured NORT, one object was replaced with a second, novel object that differed only in texture. Textured objects (either smooth or rough) were 4 cm on each side and constructed of plexiglass. All sides of the textured objects had ridges etched into the plexiglass using a laser cutter. For rough objects these ridges faced outwardly, while for smooth objects, the ridges pointed inward so that the objects appear visually identical but differed only in their textures. For the 5 minute and 1 hour control NORTs, small wooden blocks were utilized. Blocks differed in shape, size and color, but overall volumes were similar (~6 cm×3 cm×3 cm). For each test, the placement and object used as the novel object was psuedorandomized and counterbalanced between groups.

To avoid confounding whisker movements and sensations, whiskers were plucked three days prior to the start of habituation (See above section on whisker plucking). Under these conditions, animals showed no adverse behavioral effects and used glabrous skin on their paws during more than 90% of object exploration (FIGS. 8A-8H).

The position of the mouse was tracked using custom Matlab scripts. Whisking, nose pokes and investigation using the paws were all included in the time spent investigating objects, though over 90% of the time investigating objects was performed using the glabrous skin on paws (FIG. 8G). All three versions of NORT were analyzed using the same object exploration criteria. Over 25 percent of the videos were also blindly hand-scored to verify investigation times and the average difference in reported preference values was 2.6%.

Startle Reflex/Prepulse Inhibition (PPI)

The response of mice to tactile and acoustic startle stimuli, and the ability of a tactile or acoustic stimulus to inhibit startle to a loud acoustic stimulus was measured using a San Diego Instruments startle reflex system (SR-LAB™ Startle Response System). While the startle response to tactile stimuli has been previously investigated, we sought to determine whether mice exhibit specific tactile sensorimotor gating deficits by employing a PPI assay in which the pre-stimulus is an air puff (0.9 PSI, 50 ms), followed by a startle tone stimulus (125 dB, 20 ms). Air puffs were administered to the back of the mouse to assess hairy skin sensitivity. The 0.9 PSI prepulse stimulus strength was chosen because control animals showed a minimal, but statistically significant response to the stimulus alone, compared to baseline movement in the chamber without any stimulus (average response in controls, 5.89%+/−2.15). In addition, this prepulse intensity was chosen because it produced significant inhibition of startle reflex at multiple (ISIs). A tone pre-stimulus (ranging from 68 dB to 80 dB, for 20 ms), followed by startle tone stimulus (120 dB, 20 ms) version of the PPI assay (acoustic PPI) was used as a control to determine particular tactile perception deficits.

For testing sessions, animals were placed into a ventilated, cylindrical holder on a platform within a soundproof chamber. Protocols consisted of an acclimation phase, block I, block II, block III and block IV trials. Each time an animal was tested, it first underwent an acclimation phase to acclimate to the animal holder, startle box and background noise. Each mouse was placed in the chamber for a 5 minute acclimation period, during which constant background noise of broadband white noise was presented. Background noise for the acoustic PPI testing sessions was 65 dB. Background noise for the tactile PPI testing sessions was increased to 75 dB, to ensure that that the animal could not hear the air puff prepulse.

Block I consisted of 5 startle stimuli alone (120 or 125 dB broadband white noise for acoustic and tactile PPI testing sessions, respectively), to measure the initial startle reflex. Block II consisted of 5 prepulse stimuli alone (either 80 dB broadband white noise or a 0.9 PSI air puff for acoustic and tactile PPI testing sessions, respectively), to measure response to the prepulse stimulus alone. Block III incorporated prepulse/pulse, pulse alone and no stimulation trials that were pseudo randomized. Acoustic PPI and tactile PPI sessions were run on separate days. Block IV consisted of 5 startle stimuli alone, to measure habituation to the startle stimuli over the testing session. Intertrial intervals were varied from 10 seconds to 50 seconds (average 30 seconds) between each trial.

For acoustic PPI, the prepulse was 20 ms in duration and presented 100 ms before the startle pulse (inter-stimulus interval, ISI). For tactile PPI, the prepulse intensity remained constant (0.9 PSI, 20 ms), and the ISI was varied from 50 ms to 1 second in duration. Whole body flinch, or startle reflex, was quantitated using an accelerometer sensor measuring the amplitude of movement of the animal, within the cylindrical holder.

Elevated Plus Maze

The elevated plus maze was used to measure anxiety-like behavior in rodents. The elevated plus maze was a custom-built acrylic chamber. The arms were each 30 cm long×5 cm wide, with two of the opposing arms having walls that were 15 cm high. The maze stood 40 cm above the ground. Testing occurred in a dimly lit room with a camera overhead for tracking animal movement. The animal was placed into the center of the maze and allowed to freely explore for 10 minutes. The time spent in either the center, closed arms or open arms of the maze during each test session was quantified using custom Matlab scripts. The percentage of time each mouse spent in the open arms, compared to the closed arms and center of the chamber was calculated and expressed as a percent time spent in the open arms of the maze.

3-Chamber Social Interaction Test

The 3-chamber social interaction assay is a commonly used method of assessing both sociability and social recognition/preference in rodents, and is often used to measure ASD-like behavioral deficits in mice. Testing occurred in three sessions within a three-chambered box with openings between the chambers (each compartment is 20 cm wide×40 cm long×22 cm high). The outside walls of the chamber were opaque, while the inner dividers were clear plexiglass. After a 5 minute habituation period in the empty chamber, the test mouse was moved into the empty center chamber with partitions in place. A wire mesh cup containing a novel mouse was placed on one side of the chamber and an empty mesh cup was placed on the other side during the "sociability" session. The partitions were then lifted, and the test mouse was free to explore all three sections of the chamber. After 10 minutes, the test mouse was moved into the empty center chamber with partitions in place. A second novel mouse was placed under the empty cup, partitions were removed, and the test mouse was allowed to freely explore the chamber during the "social novelty preference" session for 10 minutes. The time spent in each of the three chambers during each test session was quantified using custom Matlab scripts. A portion of the videos was also blindly hand scored to ensure accuracy of automated tracking. Control mice show a significant preference for the chamber containing the novel mouse in each portion of the test, indicating a preference for novel mice compared to novel objects as well as a preference (and recognition of) a novel mouse versus a familiar mouse.

Nest Building

Nest building was performed as previously described. Briefly, mice were singly housed 30 minutes before the dark cycle began, and put into clean cages with 4 pieces of pressed cotton nestlets placed in the front of the cage (2cm×2cm per square). The next day (14-16 hours later), nests were photographed and any un-shredded material was weighed. Nests were scored blindly based on a 5-point nest-rating scale.

Tube Dominance Test

The tube dominance test is a commonly used assay to determine aggression levels and social dominance in mice, without allowing mice to injure each other by fighting. In this test, a test mouse was placed into one end of a clear, plexiglass tube (30 inches in length, 3.5 inches in diameter). Additional plexiglass sections (smaller, flat pieces) were inserted into the tube, depending on the size of the mice.

Both mice were able to move forward and backward with ease in the tube, but the tube was tight enough such that they could not climb on top of each other, nor could they turn around in the tube. A non-littermate control mouse of similar body weight (+/−3 grams), age and of the same cross was placed in the opposite side of the tube, and both mice were released at the same time and moved to the center of the tube. The more dominant mouse aggressively forced his opponent mouse out of the tube, and the first mouse to place all four feet outside of the tube was identified as the loser. Each mouse was given a break between trials (greater than fifteen minutes) and the test was repeated three times with different control mice for each trial.

Rotarod

Rotarod was performed using a MedAssociates accelerating rotarod. Mice were placed on an elevated rotarod initially rotating at 3.0 rpm. The rotarod accelerated to 30 rpm over a period of five minutes. A fall was recorded when an animal fell off the rotarod or if the animal rotated twice around the rod without recovering. Each mouse was subjected to three trials, with at least 15 minutes between each trial. The average latency to fall (in seconds) was calculated per mouse.

Plethysmography

Animals were 8-10 weeks old when subjected to plethysmographic recordings for respiratory analysis. Plethysmographic recordings of mouse breathing patterns were obtained as previously described. Briefly, breathing patterns were recorded in unrestrained mice by whole-body barometric plethysmography. The animal was placed in a reference chamber immersed in a temperature-regulated water bath maintained at 26-28° C. For each mouse, continuous plethysmographic measurements were taken until the animal was quiet, without any head, limb or body movements, and only these periods were used for analysis. Analyses were performed on ten separate stretches for ten seconds each of continuous, quiet breath per animal.

Immunohistochemistry

For histology, mutant and control littermates were sacrificed in pairs or groups. Mice (P84-P160) were anesthetized with isofluorane and transcardially perfused with 20 mL of PBS, following by 25 mL of 4% paraformaldehyde (PFA) in PBS at room temperature (RT). Brains, spinal cords and dorsal root ganglia (DRG) were dissected from perfused mice and post-fixed overnight in 4% PFA at 4° C. Tissue was then washed 3 times in 1×PBS for 1-2 hours each, then brain, spinal cord and attached DRGs were finely dissected out of the vertebral column. Tissue was cryoprotected in 30% sucrose in 1×PBS overnight at 4° C., then embedded in NEG50 and frozen at −20° C. Tissue was stored at −70° C. until it was sectioned at 30 μm using a cryostat.

Sections on slides were dried at RT for 1 hour, then washed 3×10 minutes in 1×PBS. Tissue was then blocked for 1-2 hours in 1×PBS containing 0.3% Triton-X 100 and 5% normal donkey serum (Jackson Immuno, 005-000-121). Sections were incubated with primary antibodies diluted in blocking solution (5% normal donkey serum, no detergent) at 4° C. for 1-2 days. After which, sections were washed with 1×PBS containing 0.02% Tween 20 (PBST) and then incubated with secondary antibodies diluted 1:500 in blocking solution, at room temperature for 2 hours. IB4 was diluted at 1:500 and applied with secondary antibodies when needed. Following secondary antibody incubation, tissue was washed 3×10 minutes with PBST. One wash of PBST contained a 1:10,000 dilution of Hoechst solution. Sections were washed one more time with PBST, then mounted with fluoromount-G (Southern Biotech). Primary antibodies used: rabbit anti-DsRed (632496, Clontech, 1:1000); goat anti-GABRB3 (PA5-19060, Life Technologies, 1:250); rabbit anti-MECP2 (provided by Michael Greenberg, 1:1000); guinea pig anti-vGLUT1 (AB5905, Millipore, 1:1000); and Alexa 647-conjugated IB4 (16520-100, Life Technologies, 1:1000). Secondary antibodies included: Alexa 488, 546 or 647 conjugated donkey anti-rabbit antibodies; Alexa 488, 546 or 647 conjugated donkey anti-goat antibodies; and Alexa 488, 546 or 647 conjugated donkey anti-guinea pig antibodies. All secondary antibodies were purchased from Life Technologies or Jackson ImmunoResearch and used at a 1:500 dilution.

Puncta Analysis

Z-stack images of spinal cord slices were taken on a Zeiss LSM 700 confocal microscope using a 63× oil-immersion lens (Zeiss; Plan-Apochromat 63×/NA 1.40). Images were taken in lamina III of the dorsal horn, which was identified by immunostaining with IB4 to delineate lamina IIi. The percent of GABRB3 puncta that were colocalized with vGLUT1 puncta were analyzed using NIH ImageJ software with a custom ImageJ plugin. Colocalization was analyzed per one micron section thickness of tissue, with a total of ten continuous sections. At least five images from three to five animals per genotype were analyzed for each experiment.

Spinal Cord Slice Preparation

Cholera toxin subunit B (CTB) was injected into the dorsal column at cervical level 1 and acute spinal cord slices with dorsal roots attached at P14-P19 were prepared. Mice were briefly anesthetized with Isoflurane, and intracardially perfused with ice-cold artificial cerebrospinal fluid (ACSF) prior to spinal cord removal. The isolated spinal cord was embedded in low-melting agarose (Sigma Aldrich), and transverse slices (300 μm) were prepared from lumbar levels (L4-L6) using a Leica vibrating blade microtome (Leica VT1200S). Spinal cord slices were prepared in ice cold ACSF containing: 1 mM kynurenic acid, 2.5 mM KCl, 0.5 mM $CaCl_2$, 7 mM $MgCl_2$ $6H_2O$, 26 mM $NaHCO_3$, 11 mM dextrose (glucose), 1.3 mM NaAscorbate, and 248 mM sucrose. Slices were allowed to recover for a minimum of 60 min at room temperature in a submerged holding chamber containing oxygenated (95% $O_2$, 5% $CO_2$) ACSF consisting of: 86 mM NaCl, 2.5 mM KCl, 1.2 mM $NaH_2PO_4$, 35 mM $NaHCO_3$, 20 mM Hepes, 25 mM glucose, 5mM NaAscorbate, 2 mM Thio Urea, 3 mM Na Pyruvate, 1 mM $MgSO_4$ $7H_2O$, 2 mM $CaCl_2$ (pH 7.3, osm 305).

Spinal Cord Slice Electrophysiological Recordings

Spinal cord slices were stored in a submerged recording chamber at room temperature and continuously perfused with ACSF containing 2.5mM $CaCl_2$, 1 mM $NaH_2PO_4$, 119 mM NaCl, 2.5 mM KCl, 1.3 mM $MgSO_4$ $7H_2O$, 26 mM $NaHCO_3$, 25 mM dextrose, and 1.3 mM Na ascorbate, saturated with 95% $O_2$, 5% $CO_2$ at a rate of ~2 ml/min. Cells were visualized using infrared differential interference contrast and fluorescence microscopy. Whole cell voltage-clamp recordings from retrogradely labeled PSDCs in laminae IV-V were obtained under visual guidance using a 40× objective. Patch electrodes (5.5-6.5 MΩ) were filled with a KCl-based internal solution containing 125 mM KCl, 2.8 mM NaCl, 2 mM $MgCl_2$, 2 mM ATP-$Mg^{2+}$, 0.3 mM GTP-Na+, 0.6 mM EGTA, and 10 mM HEPES, and neurons were voltage clamped at −70 mV. Quantal excitatory post-synaptic currents (qEPSCs) were recorded at −70 mV in ACSF with 4 mM strontium replacing $Ca^{2+}$, and induced with dorsal root stimulation at A-fiber strength (100 µA, 0.1 ms). Eight stimuli at 40 Hz were used to elicit asynchronously released strontium mEPSCs (Morishita and Alger, 1997), and quantal EPSCs were measured in the 400 ms period following the synchronous event elicited by the train using Mini Analysis program (Synaptosoft). Input resistance and access resistance were monitored continuously throughout each experiment and cells were excluded from analysis if these values changed by more than 10% during the experiment. At the end of each experiment, 6-Cyano-7-nitroquinoxaline-2,3-dione (CNQX; 10 µM) was bath-applied to block AMPA receptors and confirm the glutamatergic nature of the A-fiber evoked qEPSCs. Data were acquired using a Multiclamp amplifier, a Digidata 1440A acquisition system, and pClamp10 software (Molecular Devices). Sampling rate was 10 kHz, and data were low-pass filtered at 3 kHz. No correction for junction potential was applied. All electrophysiological measurements were done by observers who were blinded to genotype.

Isolated Spinal Cord Preparation

Mice postnatal day 11-17 were briefly anesthetized with Isoflurane, and intracardially perfused with ice-cold low calcium, high-magnesium ACSF containing: 128 mM NaCl, 1.9 mM KCl, 1.2 mM $KH_2PO_4$, 26 mM $NaHCO_3$, 0.85 mM $CaCl_2$, 6.5 mM $MgSO_4$, and 10 mM d-glucose (pH of 7.4) prior to decapitation and vertebral removal. A ventral vertebrectomy and laminectomy and an off-centered sagittal hemisection (adjacent to the contralateral dorsal column) were performed using insect pins to maximally expose the deep dorsal horn to the ACSF while keeping the dorsal column intact. A dorsal laminectomy was then performed, and surrounding tissue removed to retain only the isolated spinal cord and spinal roots. The perfusion solution was then switched to oxygenated regular ACSF (128 mM NaCl, 1.9 mM KCl, 1.2 mM $KH_2PO_4$, 26 mM $NaHCO_3$, 2.4 mM $CaCl_2$, 1.3 mM $MgSO_4$, and 10 mM D-glucose). Mutants and littermate or age-matched controls were recorded on the same or adjacent days to minimize fluctuations of the recording electrodes. At the end of some experiments, bicuculline methiodide (10-20 µM; Sigma) was added to the ACSF and recordings resumed after 10 minutes.

Isolated Spinal Cord Electrophysiological Recordings

Bipolar glass suction electrodes (inner diameter 80-120 µm) were used to both record slow potentials in spinal roots and stimulate the adjacent dorsal root. Teflon insulated and chlorided silver ground wires were wrapped around the outside of the glass to reduce fluctuations in the DC recordings and minimize current spread. A T11-L1 dorsal root was stimulated, and recording electrodes placed proximally on the same root to record afferent recruit, on the ventral root to record reflexes, and on an adjacent dorsal root to record DRPs. Stimulus threshold (T) was determined at 100 µs and gradually increasing current amplitude until a volley was observed (usually 3-7µA). DRPs and reflexes were recorded at 4 times T, 10T, 20T, and supramaximally at 500 µA, 500 µs, with 10-30 s between sweeps and 10 sweeps per intensity. Due to the immaturity of the neurons at these ages, recruitment of afferents was observed at each stimulus intensity, and at no time were C-fibers recruited at 4T. DC recordings were acquired using an AC/DC differential amplifier and mini headstage (A-M systems, Model 3000), a Digidata 1440A acquisition system, and pClamp10 software (Molecular Devices). Sampling rate was 10 kHz with no filtering. A custom built MATLAB program was used to subtract the baseline values prior to the stimulus, average 10 sweeps at each intensity, low-pass filter the response at 100 Hz, find the onset of the evoked DRP, its peak amplitude, and the integral under the filtered response from onset to offset (defined as the time at which the slow potential decayed to 20% of peak amplitude, with a 1 s hard time cap). Ventral root recordings were rectified and integrated at 3 intervals: 2-8 ms, 8-30 ms, and 30-150 ms post stimulus, and values averaged across the 10 sweeps.

Statistical Methods

Data are expressed as the mean values+/−standard error of the mean (SEM). Bartlett's test for equal variance was applied to all data sets, and the variances among groups were not shown to be statistically different from each other. The number of animals per group used in each experiment is denoted within the bar for that group in each panel. Unless otherwise stated in the figure legend, a Student's t-test was used to compare a group to chance performance, or to compare mutants to their control littermates.

For NORT, three-chamber social interaction tests, tube dominance tests, and some PPI tests (FIGS. 1G-1H, FIG. 8I), each group was analyzed compared to a chance level using a Student's t-test (chance level: 0% preference in NORT and three-chamber; 0% response above baseline in PPI; and, 50% wins in tube dominance). If these values were statistically significantly above chance, significance was denoted by asterisk direction above that bar.

Comparisons between control littermates and mutants in each group for all experiments were performed using Student's t-test (in the case of two groups in one condition), one-way ANOVA (in the case of three or more groups in one condition), or two-way ANOVA (in the case of at least two groups in multiple conditions). If significant differences between mutants and control littermates were observed, this was indicated by an asterisk over the indicated groups. Asterisks indicate p values for Student's t-tests, unless otherwise noted in the figure legends. Main effects from one-way and two-way ANOVAs are expressed as an F-statistic and P-value within brackets. For one-way and two-way ANOVAs, post-hoc comparisons were performed using the post-hoc test indicated in the figure legend. The p values of post-hoc comparisons between groups are represented with asterisks above brackets over the indicated groups using a bracketed line in the figures. For nesting behavior, Mann-Whitney tests for non-parametric data were performed for simple group comparisons with no within-subjects factors. All statistics were performed using GraphPad Prism.

From the foregoing description, one skilled in the art can easily ascertain the essential characteristics of this invention; can make various changes and modifications of the invention to adapt it to various usages and conditions.

What is claimed is:

1. A method of reducing anxiety in a subject diagnosed with Autism Spectrum Disorders (ASD), Rett Syndrome (RTT), or Fragile X Syndrome, by administering to the subject a therapeutically effective amount of a peripherally-restricted $GABA_A$ agent, wherein the $GABA_A$ agent is not isonipecotic acid, gamma-amino butyric acid (GABA), isoguvacine, homotaurine, acetylaminopropane sulfonate, trans-amino-4-crotonic acid (TACA), 4,5,6,7-tetrahydroisoxazolo[5,4-c]pyridine-3-ol (THIP), 5-oxo-zaleplon, tiagabine, 3-((aminoiminomethyl) thio)-2-propenoic acid (ZAPA), L-838,417, or stiripentol.

2. The method of claim 1, wherein the $GABA_A$ agent is a $GABA_A$ receptor agonist.

3. The method of claim 1, wherein the $GABA_A$ agent is a positive allosteric modulator of the $GABA_A$ receptor.

4. The method of claim 1, wherein said subject is a human.

5. The method of claim 1, wherein the $GABA_A$ agent is trans-aminocyclopentane-3-carboxylic acid.

6. The method of claim 2, wherein the $GABA_A$ receptor agonist is N-methyl isoguvacine, acetylaminopropane sulfonate, homohypotaurine, β-guanidinopropionic acid, trans-aminocyclopentane-3-carboxylic acid, or a pharmaceutically acceptable salt thereof.

7. The method of claim 2, wherein the $GABA_A$ receptor agonist is a compound of Formula (I):

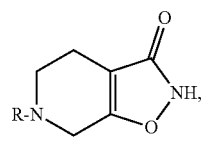

(I)

or a pharmaceutically acceptable salt or tautomer thereof; wherein R is selected from the group consisting of acetyl, or a group of the general Formula (Ia):

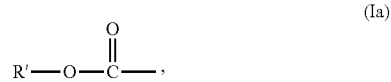

(Ia)

where R' is $C_1$-$C_8$ alkyl, phenyl, phenyl substituted in the 4 position with halogen, $C_1$-$C_4$ alkoxy, or $C_1$-$C_4$ alkyl; or phenylalkyl in which the phenyl group may be substituted in the 4-position with halogen, $C_1$-$C_4$ alkoxy, or $C_1$-$C_4$ alkyl.

8. The method of claim 3, wherein the positive allosteric modulator of the $GABA_A$ receptor is selected from the group consisting of 5-nitro-alpha-oxo-N-(1R)-phenylethyl1-1H-indole-3-acetamide (TCS 1205), 5-nitro-alpha-oxo-N-(1R)-phenylethyl1-1H-indole-3-acetamide, 5-oxo-zaleplon, homo-β-proline, 5-fluoro-2-[4-fluoro-3-[8-fluoro-7-(2-hydroxypropan-2-yl)imidazo[1,2-a]pyridin-3-yl]phenyl]benzonitrile (TP 003), and [1-[(Z)-2-chloro-2-(2,4-dichlorophenyl)vinyl]-1H-1,2,4-triazole] (loreclezole).

9. The method of claim 1, wherein the subject has been diagnosed with ASD.

10. The method of claim 1, wherein the subject has been diagnosed with RTT.

11. The method of claim 1, wherein the subject has been diagnosed with Fragile X Syndrome.

12. The method of claim 1, wherein the subject is characterized as having a deficiency in Mecp2, Gabrb3, or Shank3.

13. The method of claim 1, wherein the subject is characterized has having abnormal habituation to aversive stimuli.

* * * * *

UNITED STATES PATENT AND TRADEMARK OFFICE
CERTIFICATE OF CORRECTION

PATENT NO. : 12,201,631 B2  
APPLICATION NO. : 17/845961  
DATED : January 21, 2025  
INVENTOR(S) : Lauren L. Orefice et al.

It is certified that error appears in the above-identified patent and that said Letters Patent is hereby corrected as shown below:

In the Claims

In Claim 8, at Column 80, Lines 32-40, the text:
"The method of claim 3, wherein the positive allosteric modulator of the $GABA_A$ receptor is selected from the group consisting of 5-nitro-alpha-oxo-N-(1R)-phenylethyl1-1H-indole-3-acetamide (TCS 1205), 5-nitro-alpha-oxo-N-(1R)-phenylethyl1-1H-indole-3-acetamide, 5-oxo-zaleplon, homo-β-proline, 5-fluoro-2-[4-fluoro-3-[8-fluoro-7-(2-hydroxypropan-2-yl)imidazo[1,2-a]pyridin-3-yl]phenyl]benzonitrile (TP 003), and [1-[(Z)-2-chloro-2-(2,4-dichlorophenyl)vinyl]-1H-1,2,4-triazole] (loreclezole)."
Should be replaced with:
-- The method of claim 3, wherein the positive allosteric modulator of the $GABA_A$ receptor is selected from the group consisting of 5-nitro-alpha-oxo-N-(1R)-phenylethyl]-1H-indole-3-acetamide (TCS 1205), homo-β-proline, 5-fluoro-2-[4-fluoro-3-[8-fluoro-7-(2-hydroxypropan-2-yl)imidazo[1,2-a]pyridin-3-yl]phenyl]benzonitrile (TP 003), and [1-[(Z)-2-chloro-2-(2,4-dichlorophenyl)vinyl]-1H-1,2,4-triazole] (loreclezole). --.

Signed and Sealed this  
Twenty-second Day of July, 2025

Coke Morgan Stewart  
*Acting Director of the United States Patent and Trademark Office*

SEQUENCE LISTING

<160> NUMBER OF SEQ ID NOS: 25

<210> SEQ ID NO 1
<211> LENGTH: 20
<212> TYPE: DNA
<213> ORGANISM: Mus musculus

<400> SEQUENCE: 1
aaattgggtt acaccgctga                                                   20

<210> SEQ ID NO 2
<211> LENGTH: 20
<212> TYPE: DNA
<213> ORGANISM: Mus musculus

<400> SEQUENCE: 2
ccacctagcc tgcctgtact                                                   20

<210> SEQ ID NO 3
<211> LENGTH: 21
<212> TYPE: DNA
<213> ORGANISM: Mus musculus

<400> SEQUENCE: 3
ctgtatcctt gggtcaagct g                                                 21

<210> SEQ ID NO 4
<211> LENGTH: 18
<212> TYPE: DNA
<213> ORGANISM: Mus musculus

<400> SEQUENCE: 4
ggattgtgga aaagccag                                                     18

<210> SEQ ID NO 5
<211> LENGTH: 22
<212> TYPE: DNA
<213> ORGANISM: Mus musculus

<400> SEQUENCE: 5
atgacctggg cagatgtggt ag                                                22

<210> SEQ ID NO 6
<211> LENGTH: 20
<212> TYPE: DNA
<213> ORGANISM: Mus musculus

<400> SEQUENCE: 6
gagactgatc agcgcagttg                                                   20

<210> SEQ ID NO 7
<211> LENGTH: 20
<212> TYPE: DNA
<213> ORGANISM: Mus musculus

<400> SEQUENCE: 7
tgacataatc gctggcaaag                                                   20

<210> SEQ ID NO 8
<211> LENGTH: 25
<212> TYPE: DNA
<213> ORGANISM: Mus musculus

-continued

```
<400> SEQUENCE: 8
gctatacgaa gttatgtcga ctagg                                         25

<210> SEQ ID NO 9
<211> LENGTH: 20
<212> TYPE: DNA
<213> ORGANISM: Mus musculus

<400> SEQUENCE: 9
cacgagacta gtgagacgtg                                               20

<210> SEQ ID NO 10
<211> LENGTH: 24
<212> TYPE: DNA
<213> ORGANISM: Mus musculus

<400> SEQUENCE: 10
tgtgatagaa tatgcagcat gtga                                          24

<210> SEQ ID NO 11
<211> LENGTH: 19
<212> TYPE: DNA
<213> ORGANISM: Mus musculus

<400> SEQUENCE: 11
cttctggcac ctccagctt                                                19

<210> SEQ ID NO 12
<211> LENGTH: 24
<212> TYPE: DNA
<213> ORGANISM: Mus musculus

<400> SEQUENCE: 12
tggtaaagac ccatgtgacc caag                                          24

<210> SEQ ID NO 13
<211> LENGTH: 20
<212> TYPE: DNA
<213> ORGANISM: Mus musculus

<400> SEQUENCE: 13
ggcttgccac atgacaagac                                               20

<210> SEQ ID NO 14
<211> LENGTH: 24
<212> TYPE: DNA
<213> ORGANISM: Mus musculus

<400> SEQUENCE: 14
tccacctagc ctgcctgtac tttg                                          24

<210> SEQ ID NO 15
<211> LENGTH: 20
<212> TYPE: DNA
<213> ORGANISM: Mus musculus

<400> SEQUENCE: 15
aacagtgcca gctgctcttc                                               20

<210> SEQ ID NO 16
<211> LENGTH: 20
<212> TYPE: DNA
```

<213> ORGANISM: Mus musculus

<400> SEQUENCE: 16
gccagaggcc acttgtgtag                                               20

<210> SEQ ID NO 17
<211> LENGTH: 19
<212> TYPE: DNA
<213> ORGANISM: Mus musculus

<400> SEQUENCE: 17
attcgcctga gacccgact                                                19

<210> SEQ ID NO 18
<211> LENGTH: 18
<212> TYPE: DNA
<213> ORGANISM: Mus musculus

<400> SEQUENCE: 18
gttcatcccc acgcagac                                                 18

<210> SEQ ID NO 19
<211> LENGTH: 23
<212> TYPE: DNA
<213> ORGANISM: Mus musculus

<400> SEQUENCE: 19
gcggtctggc agtaaaaact atc                                           23

<210> SEQ ID NO 20
<211> LENGTH: 23
<212> TYPE: DNA
<213> ORGANISM: Mus musculus

<400> SEQUENCE: 20
gtgaaacagc attgctgtca ctt                                           23

<210> SEQ ID NO 21
<211> LENGTH: 24
<212> TYPE: DNA
<213> ORGANISM: Mus musculus

<400> SEQUENCE: 21
ctaggccaca gaattgaaag atct                                          24

<210> SEQ ID NO 22
<211> LENGTH: 22
<212> TYPE: DNA
<213> ORGANISM: Mus musculus

<400> SEQUENCE: 22
gtaggtggaa attctagcat cc                                            22

<210> SEQ ID NO 23
<211> LENGTH: 20
<212> TYPE: DNA
<213> ORGANISM: Mus musculus

<400> SEQUENCE: 23
ccctgttcac tgtgagtagg                                               20

<210> SEQ ID NO 24
<211> LENGTH: 22

```
<212> TYPE: DNA
<213> ORGANISM: Mus musculus

<400> SEQUENCE: 24
agtatctggt aggtgcttcc ag                                              22

<210> SEQ ID NO 25
<211> LENGTH: 22
<212> TYPE: DNA
<213> ORGANISM: Mus musculus

<400> SEQUENCE: 25
gcgatccctg aacatgtcca tc                                              22
```